United States Patent
Wu et al.

(10) Patent No.: US 11,753,619 B2
(45) Date of Patent: Sep. 12, 2023

(54) ENGINEERED CELLS AND METHODS OF USE

(71) Applicant: THE SCRIPPS RESEARCH INSTITUTE, La Jolla, CA (US)

(72) Inventors: Peng Wu, San Diego, CA (US); Jie Li, San Diego, CA (US); Yiran Zhou, San Diego, CA (US); Mingkuan Chen, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 764 days.

(21) Appl. No.: 16/482,497

(22) PCT Filed: Feb. 1, 2018

(86) PCT No.: PCT/US2018/016503
§ 371 (c)(1),
(2) Date: Jul. 31, 2019

(87) PCT Pub. No.: WO2018/144769
PCT Pub. Date: Aug. 9, 2018

(65) Prior Publication Data
US 2020/0010795 A1  Jan. 9, 2020

Related U.S. Application Data

(60) Provisional application No. 62/578,721, filed on Oct. 30, 2017, provisional application No. 62/453,922, filed on Feb. 2, 2017.

(51) Int. Cl.
| | |
|---|---|
| *C12N 5/00* | (2006.01) |
| *C12N 9/10* | (2006.01) |
| *A61P 35/00* | (2006.01) |
| *C07K 16/32* | (2006.01) |
| *A61K 47/69* | (2017.01) |
| *C12N 5/0783* | (2010.01) |
| *A61K 47/54* | (2017.01) |
| *C12N 5/0784* | (2010.01) |
| *C07K 16/28* | (2006.01) |
| *A61K 47/68* | (2017.01) |
| *C12N 5/10* | (2006.01) |

(52) U.S. Cl.
CPC .......... *C12N 5/0006* (2013.01); *A61K 47/549* (2017.08); *A61K 47/6849* (2017.08); *A61K 47/6855* (2017.08); *A61K 47/6901* (2017.08); *A61P 35/00* (2018.01); *C07K 16/2827* (2013.01); *C07K 16/2854* (2013.01); *C07K 16/32* (2013.01); *C12N 5/0636* (2013.01); *C12N 5/0639* (2013.01); *C12N 5/0646* (2013.01); *C12N 5/10* (2013.01); *C12N 9/1051* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,925,796 | A | 5/1990 | Bergh et al. |
| 5,516,665 | A | 5/1996 | Wong et al. |
| 2004/0052770 | A1 | 3/2004 | Klingemann et al. |
| 2008/0241856 | A1 | 10/2008 | Wong et al. |
| 2011/0257376 | A1 | 10/2011 | Wong et al. |
| 2012/0114620 | A1 | 5/2012 | Braughler et al. |
| 2015/0190529 | A1 | 7/2015 | Peterson et al. |
| 2016/0356779 | A1 | 12/2016 | Wu et al. |

FOREIGN PATENT DOCUMENTS

WO    2016077526 A1    5/2016

OTHER PUBLICATIONS

Mahal, et al. (2001) "A Small-Molecular Modulator of Poly-α2,8-Sialic Acid Expression on Cultured Neurons and Tumor Cells", Science, 294: 380-82. (Year: 2001).*
Parmar, et al. (2015) "Ex vivo fucosylation of third-party human regulatory T cells enhances anti-graft-versus-host disease potency in vivo", Blood, 125(9): 1502-06. (Year: 2015).*
Armstrong, et al. (2016) "Strategies for cell membrane functionalization" Experimental Biology and Medicine, 241(10): 1098-106. (Year: 2016).*
Li, et al. (2018) "A Single-Step Chemoenzymatic Reaction for the Construction of Antibody-Cell Conjugates", ACS Central Science, 4: 1633-41. (Year: 2018).*
International Search Report and Written Opinion for International application No. PCT/US18/16503 dated Jun. 15, 2018; 17 pages.
Besanceney-Webler et al., "Increasing the Efficacy of Bioorthogonal Click Reactions for Bioconjugation: A Comparative Study," Angew. Chem. Int. Ed., 2011; 50:8051-8056.
Srivastava et al., "Enzymatic Transfer of a Preassembled Trisaccharide Antigen to Cell Surfaces Using a Fucosyltransferase," The Journal of Biological Chemistry, 1992; 267(31):22356-22361.
Sackstein, et al., Ex vivo Glycan Engineering of CD44 Programs Human Multipotent Mesenchymal Stromal Cell Trafficking to Bone, Nature Medicine, Feb. 2008, pp. 181-187, vol. 14, No. 2.
Srivastava, et al., Enzymatic Transfer of a Preassembled Trisaccharide Antigen to Cell Surfaces Using a Fucosyltransferase, The Journal of Biological Chemistry, Nov. 5, 1992, pp. 22356-22361, vol. 267, No. 31.

(Continued)

*Primary Examiner* — Robert M Kelly
(74) *Attorney, Agent, or Firm* — Hugh Wang; Thomas Fitting

(57) ABSTRACT

Provided herein are engineered cells, comprising: a chemical or biological moiety covalently bound to a cell surface glycan, wherein the chemical or biological moiety is selected from the group consisting of small molecule, polynucleotide, polypeptide, and antibody. Also provided are compositions comprising these engineered cells and methods of making and using the same.

7 Claims, 77 Drawing Sheets

(56) References Cited

OTHER PUBLICATIONS

Wang, et al., Chemoenzymatic Synthesis of GDP-L-Fucose and the Lewis X Glycan Derivatives, PNAS, Sep. 22, 2009, pp. 16096-16101, vol. 106, No. 38.

Xia, et al., Surface Fucosylation of Human Cord Blood Cells Augments Binding to P-selectin and E-selectin and Enhances Engraftment in Bone Marrow, Blood, Nov. 15, 2004, pp. 3091-3096, vol. 104, No. 10.

Zheng, et al., Tracking N-Acetyllactosamine on Cell-Surface Glycans In Vivo, Angewendte Chemie, 2011, pp. 4113-4118, vol. 50.

\* cited by examiner

*One-pot reaction scheme*

*One-pot one-step reaction scheme*

A (B)

(C)

Before fucosylation

| Sample Name | Subset Name | Count | Median : PE-A |
|---|---|---|---|
| day21 | CD451+ | 90.0 | 553 |
| day14 | CD451+ | 20165 | 992 |
| day7 | CD451+ | 11022 | 4465 |
| day-5 | CD451+ | 8415 | 1857 |
| naive OT-1/CD45.1 CD8+T cells | CD451+ | 10103 | 9.70 |

After fucosylation

| Sample Name | Subset Name | Count | Median : PE-A |
|---|---|---|---|
| day21 | CD451+ | 168 | 254 |
| day14 | CD451+ | 20337 | 158 |
| day7 | CD451+ | 11613 | 1605 |
| day-5 | CD451+ | 9257 | 300 |
| naive OT-1/CD45.1 CD8+T cells | CD451+ | 10125 | 7.98 |

(A)

(B)

| Sample Name | Subset Name | Count | Median : Comp-PE-A |
|---|---|---|---|
| day6_SAMP+.fcs | Q2: CD4+, CD25+ | 6476 | 1176 |
| day6_SAMP-.fcs | Q2: CD4+, CD25+ | 6487 | 653 |

| Sample Name | Subset Name | Count | Median : Comp-PE-A |
|---|---|---|---|
| day6_AKR+.fcs | Q2: CD4+, CD25+ | 8347 | 1337 |
| day6_AKR-.fcs | Q2: CD4+, CD25+ | 8545 | 673 |

A

B

C

D

| Sample Name | Subset Name | Count | Median : RL1-A |
|---|---|---|---|
| unfucosylation | Lymphocytes | 15969 | 367 |
| fucosylation | Lymphocytes | 14981 | 1206 |

E

| Sample Name | Subset Name | Count | Median : RL1-A |
|---|---|---|---|
| unfucosylation | Lymphocytes | 17949 | 1566 |
| fucosylation | Lymphocytes | 17146 | 1156 |

(A)

(B)

(C)

A

B

C

D

E a-CLA Binding

E-selectin Binding

Galectin-1 Binding

| Sample Name | Median : RL1-A |
|---|---|
| NON-Fu-CTLA-4-CTLA-4.fcs | 380 |
| Fu-IgG-CTLA-4.fcs | 371 |
| Fu-CTLA-4-CTLA-4.fcs | 1799 |

| Sample Name | Median : RL1-A |
|---|---|
| Fu-CTLA-4-CTLA-4.fcs | 2581 |
| Fu-IgG-CTLA-4.fcs | 1848 |
| non-fu-CTLA-4.fcs | 638 |

— OT-1 CD8+
▩▩ OT-1 CD8+/B-α-PD-L1
▩▩ OT-1 CD8+/B-α-PD-L1/C-α-PD-L1

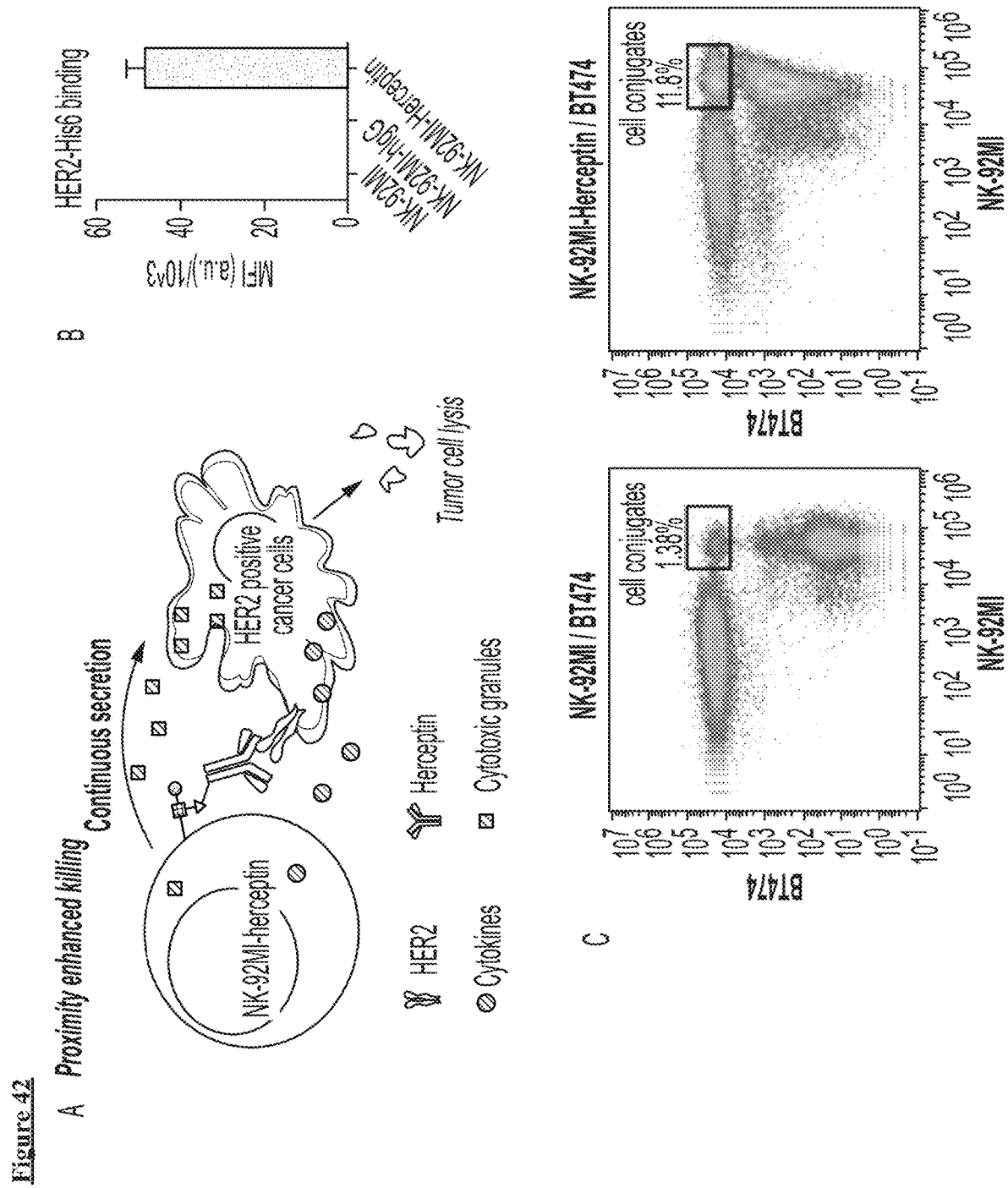

A

B

C

D

ENGINEERED CELLS AND METHODS OF USE

CROSS-REFERENCE TO RELATED APPLICATIONS

This application claims the benefit of priority to U.S. Provisional Patent Application Ser. No. 62/453,922 filed Feb. 2, 2017, and U.S. Provisional Patent Application Ser. No. 62/578,721 filed on Oct. 30, 2017, the entire contents of each of which are incorporated herein by reference.

STATEMENT OF GOVERNMENT LICENSE RIGHTS

This invention was made with government support under grant numbers GM113046 and GM093282 awarded by The National Institutes of Health. The government has certain rights in the invention.

FIELD OF THE INVENTION

The present disclosure relates to engineered and modified cells, specifically in the field of medicine.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer is a leading cause of death in the United States and worldwide. Recently, immunotherapy has emerged as a fourth weapon besides surgery, radiation, and chemotherapy deployed for the treatment of cancer. Cancer immunotherapy aims to harness the body's own immune system to fight cancer. While good results have been achieved in adoptive cell therapy (ACT) and checkpoint blockade therapy, the cancer fighting properties of the T-cells infused in the patients remain to be improved, including their migratory potentials and capabilities to counteract the immune-suppressive signals in the tumor microenvironment. Natural killer (NK) cells play a crucial role in innate immunity against malignant cells, yet also being developed as an effective cancer killer in cancer immunotherapy. However, one challenge of NK cell based therapy is the difficulty of obtaining sufficient numbers of active NK cells from a patient's blood. NK-92, a highly cytotoxic natural killer (NK) cell line established from patients with clonal NK-cell lymphoma, can be employed to generate larger numbers of cytotoxic NK cells in GMP-grade. Specific targeting is a gold standard for a good cancer therapy. However, NK-92 cells do not express Fc receptors for ADCC effects to target specific cells, which limit its wide applications.

Likewise, dendritic cells (DCs) have long been considered as the central players in cancer immunotherapy. The migratory ability of DCs has profound impact on the outcome of the DC-based immunotherapy. However, it was shown that only a small portion (1-2%) of total administered DCs reached secondary lymphatic organs to activate T cells, limiting the practical application of this vaccination approach.

Thus there remains a need in the art for new compositions and methods that can effectively label antigen specific antibody onto a cell surface which in turn directs these cells to kill specific antigen expression in diseased cells and effectively treat diseases.

SUMMARY OF THE DISCLOSURE

Various embodiments disclosed herein include an engineered cell, comprising a chemical or biological moiety covalently bound to a cell surface glycan present on the surface of the cell, wherein the chemical or biological moiety is selected from the group consisting of small molecule, polynucleotide, polypeptide, and antibody. In one embodiment, the engineered cell is an immune cell. In one embodiment, the engineered cell is a T-cell or a natural killer (NK) cell. In one embodiment, the T cell is a CD8+ or a CD4+ T cell. In one embodiment, the cell is a Dendritic Cell (DC). In one embodiment, the small molecule is a small drug molecule or a pharmaceutically acceptable salt or a co-crystal thereof. In one embodiment, the antibody is a single chain variable fragment (scFv), fragment antigen binding (Fab) fragment, or a full length antibody. In one embodiment, the antibody is an immunoglobulin G (IgG) antibody. In one embodiment, the IgG is a full length IgG. In one embodiment, the chemical or biological moiety attached to the engineered cell is a biological marker and/or probe. In one embodiment, the chemical or biological moiety is a biotin probe, a fluorescent probe, a biorthogonal reaction handle, and/or a dye labeled single strand DNA. In one embodiment, the dye is FAM. In one embodiment, the fluorescent probe is Cy3. In one embodiment, the biorthogonal reaction handle is tetrazine. In one embodiment, the fucose derivative is a GDP-fucose. In one embodiment, the engineered cell is a chimeric antigen receptor (CAR)-T cell. In one embodiment, the CAR-T cell comprises a genetically modified T-cell with the cell surface GlcNAc covalently bound to a GDP-Fucose bearing a new motif. In one embodiment, the CAR comprises three domains: scFv, Fab, and/or mature ligands that engage their cognate receptor. In one embodiment, the cell surface glycan is N-acetylglucosamine (GlcNAc). In one embodiment, the chemical or biological moiety is covalently bound to the GlcNAc via a fucose derivative. In one embodiment, the cell surface glycan is Sialic acid (NeuAc).

Various embodiments disclosed herein also include a composition comprising: an antibody-cell conjugate, wherein one or more antibodies are covalently bound to one or more glycan moiety on the surface of a cell. In one embodiment, the cell is immune cell. In one embodiment, the cell is a primary human T cell, a natural killer (NK) cell, a CD4+ cell, and/or primary CD8+OT-1 T cells. In one embodiment, the NK cell is NK-92MI cell. In one embodiment, the cell is a Dendritic Cell (DC). In one embodiment, the antibody is Trastuzumab. In one embodiment, the cell is NK-92MI and at least one antibody is Trastuzumab. In one embodiment, more than one type of antibody is conjugated on the surface of the cell. In one embodiment, the glycan moiety is N-acetylglucosamine (GlcNAc). In one embodiment, the antibody is covalently bound to the GlcNAc via a fucose derivative. In one embodiment, the glycan moiety is Sialic acid (NeuAc). In one embodiment, the composition is a pharmaceutical composition. In one embodiment, the pharmaceutical composition further comprises a pharmaceutically acceptable carrier or excipient. In one embodiment, the pharmaceutical composition is for the treatment of a disease in a subject. In one embodiment, the antibody-cell conjugate enables firm binding on inflammation sites (anti-E-selectin), target specific cancer cells (anti-HER2), and/or block the immune checkpoint (anti-PD-L1).

Various embodiments disclosed herein further include a method of treating a disease in a subject comprising: providing a pharmaceutical composition comprising an engineered cell and a pharmaceutically acceptable carrier; and treating the disease by administering a therapeutically effective dosage of the pharmaceutical composition to the subject, wherein the engineered cell comprises a chemical or biological moiety covalently bound to a glycan moiety present on its surface, and wherein the chemical or biological moiety is selected from the group consisting of small molecule, polynucleotide, polypeptide, and antibody. In one embodiment, the antibody is an immunoglobulin G (IgG) antibody. In one embodiment, the antibody is an anti-PD-L1 antibody. In one embodiment, the antibody is an anti-E-selectin antibody. In one embodiment, the antibody is an anti-HER2 antibody. In one embodiment, the antibody is Trastuzumab. In one embodiment, more than one chemical or biological moiety is covalently bound to the surface of the cell to target more than one disease at the same time. In one embodiment, the cell is a dendritic cell. In one embodiment, the cell is an immune cell. In one embodiment, the cell is a primary human T cell, a natural killer (NK) cell, a CD4+ cell, and/or primary CD8+OT-1 T cells. In one embodiment, the NK cell is NK-92MI cell. In one embodiment, the glycan moiety is N-acetylglucosamine (GlcNAc). In one embodiment, the chemical or biological moiety is covalently bound to the GlcNAc via a fucose derivative. In one embodiment, the fucose derivative comprises fucose-alkyne. In one embodiment, the glycan moiety is Sialic acid (NeuAc). In one embodiment, the disease is cancer. In one embodiment, treating the disease comprises reducing the size of a cancerous tumor in the subject. In one embodiment, the cancer is a breast cancer.

Embodiments of the present disclosure also include a method of treating, decreasing, inhibiting, or reducing cancer in a subject, comprising: administering to the subject a therapeutically effective dosage of a pharmaceutical composition comprising an engineered cell, having an antibody covalently bound to a glycan moiety present on its surface. In one embodiment, the cancer is breast cancer. In one embodiment, the antibody is Trastuzumab. In one embodiment, the cell is NK-92MI. In one embodiment, more than one antibody is conjugated on the surface of the cell to target more than one cancer at the same time.

Embodiments of the instant disclosure further include a method of making an engineered cell, comprising: making a fucose derivative or GDP-fucose derivative comprising a chemical or biological moiety covalently bound to a fucose or GDP-fucose; making the engineered cell by incubating a cell with a composition comprising (a) the fucose derivative and/or GDP-Fucose derivative and (b) a fucosyltransferase enzyme. In another embodiment, disclosed herein is a method of making an engineered cell, comprising: generating CMP-sialic acid conjugated with an antibody (CS-IgG) by reacting an antibody bearing a TCO moiety with CS-Az-Tz or CS-Poc-Tz; and making the engineered cell by incubating a naturally occurring cell with a composition comprising (a) CS-IgG and (b) a sialyltransferase. In one embodiment, the fucosyltransferase enzyme is α-1,3-fucosyltransferase. In one embodiment, the α-1,3-fucosyltransferase is H. pylori α-1,3-fucosyltransferase. In one embodiment, the α-1,3-fucosyltransferase is recombinantly prepared. In one embodiment, the sialyltransferase is selected from the group consisting of ST6Gal1, Pasteurella multocida α(2,3) sialyltransferase M144D mutant (Pm2, 3ST-M144D), and Photobacterium damsel α(2,6) sialyltransferase (Pd2,6ST). In one embodiment, the chemical or biological moiety is selected from the group consisting of small drug molecules, biomolecules, probe molecules, fluorophores, polynucleotides, polypeptides, and whole IgG, or combinations thereof. In one embodiment, the biomolecule is Trastuzumab. In one embodiment, the cell is an immune cell. In one embodiment, the cell is a primary human T cell or a natural killer (NK) cell. In one embodiment, the NK cell is NK-92MI cell. In one embodiment, the T cell is a CD4+ cell, or a CD8+ T cells. In one embodiment, the chemical or biological moiety is covalently attached via a fucose derivative to LacNAc, a universal unit of N-glycans, on the surface of the cell. In one embodiment, the fucose modified biomolecule and/or GDP-fucose modified biomolecule comprises a fucose-alkyne and/or GDP-fucose azide. In one embodiment, the biomolecule-cell conjugate is further modified with a chemical or biological moiety using ligand accelerated and biocompatible copper(I)-catalyzed alkyne-azide cycloaddition (CuAAC) reaction.

Various embodiments disclosed herein also include a one-pot method of making an engineered cell adapted to attach a molecule on its surface comprising: preparing GDP-fucose analog by combining a fucose analog with a mixture comprising ATP, GTP, L-fucokinase/GDP-fucose pyrophosphorylase (FKP), $Mg^{2+}$ or $Mn^{2+}$, and inorganic pyrophosphate (PPase); and making the engineered cell by adding a naturally occurring cell to a composition comprising the crude product from step (a) and H. pylori α-1,3-fucosyltransferase. In one embodiment, disclosed herein is a one-pot, one-step method of making an engineered cell adapted to attach a molecule on its surface comprising: incubating a cell with a composition comprising a fucose analog, ATP, GTP, L-fucokinase/GDP-fucose pyrophosphorylase (FKP), $Mg^{2+}$ or $Mn^{2+}$, inorganic pyrophosphate (PPase) and H. pylori α-1,3-fucosyltransferase. In one embodiment, the fucose analog comprises a fucose conjugated with a chemical or biological moiety. In one embodiment, the fucose analog comprises a fucose-alkyne. In one embodiment, the engineered cell comprises a chemical or biological moiety attached to a glycan on the surface of the cell. In one embodiment, the product from step (a) is further modified through a Copper-Catalyzed Azide-Alkyne Cycloaddition (CuACC) reaction to generate GDP-fucose analogs conjugated to a small molecule, polynucleotide, polypeptide, and/or antibody.

Further embodiments of the instant disclosure include a one pot in-situ fucosylation strategy to convert cell surface LacNAc or SLacNAc into LeX or sLeX comprising: preparing GDP-fucose analogs by combining a fucose analog with a mixture comprising ATP, GTP, FKP, $Mg^{2+}$ or $Mn^{2+}$, and inorganic pyrophosphate (PPase); and converting cell surface LacNAc or SLacNAc into LeX or sLeX by adding a naturally occurring cell to a composition comprising the crude product from step (a) and H. pylori α-1,3-fucosyltransferase.

Various embodiments disclosed herein also include a kit comprising: GDP-fucose derivative and H. pylori α-1,3-fucosyltransferase.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
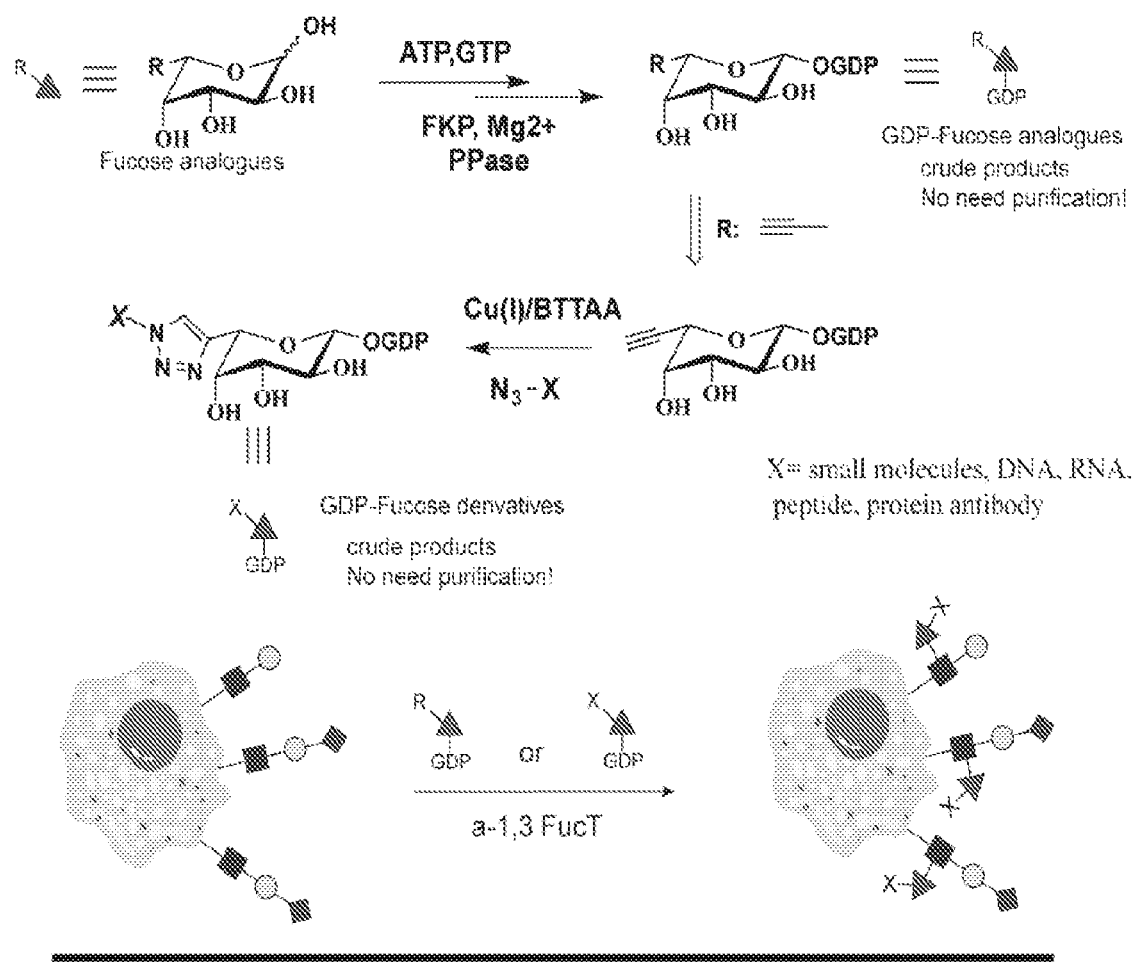
FIG. 1 depicts, in accordance with embodiments herein, in situ one-pot fucosylation reagents preparation and cell-surface reaction scheme.
Figure 1:
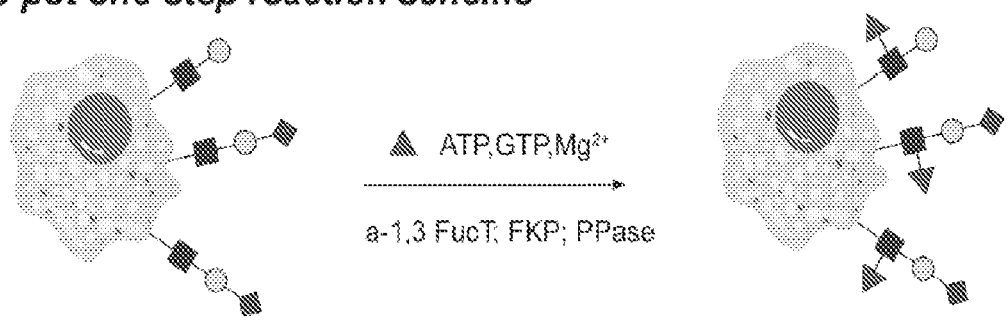

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "fucosyltransferase," as used herein, refers to an enzyme that transfers a fucose sugar from a GDP-fucose (guanosine diphosphate-fucose) donor substrate to an acceptor substrate. The acceptor substrate can be another sugar such as the transfer of a fucose to a core GlcNAc (N-acetylglucosamine) sugar as in the case of N-linked glycosylation, or to a protein, as in the case of O-linked glycosylation produced by 0-fucosyltransferase.

The terms "peptide," "polypeptide" and "protein" are used interchangeably to refer to an isolated polymer of amino acid residues, and are not limited to a minimum length unless otherwise defined. Peptides, oligopeptides, dimers, multimers, and the like, are also composed of linearly arranged amino acids linked by peptide bonds, and whether produced biologically and isolated from the natural environment, produced using recombinant technology, or produced synthetically typically using naturally occurring amino acids. In some aspects, the polypeptide or protein is a "modified polypeptide" comprising non-naturally occurring amino acids. In some aspects, the polypeptides comprise a combination of naturally occurring and non-naturally occurring amino acids, and in some embodiments, the peptides comprise only non-naturally occurring amino acids. The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C-terminus modification, peptide bond modification, backbone modification, and/or side chain modification.

The term "antibody" as used herein contemplates a polypeptide or a protein complex that specifically binds an epitope of an antigen or mimetope thereof. An antibody includes an intact antibody, or a binding fragment thereof that competes with the intact antibody for specific binding and includes chimeric, humanized, fully human, and bispecific antibodies. Binding fragments include, but are not limited to, Fab, Fab', F(ab')2, Fv, and single-chain antibodies. In some embodiments, an antibody is referred to as an immunoglobulin and include the various classes and isotypes, such as IgA (IgA1 and IgA2), IgD, IgE, IgM, and IgG (IgG1, IgG3 and IgG4) etc. in some embodiments the term "antibody" as used herein refers to polyclonal and monoclonal antibodies and functional fragments thereof. An antibody includes modified or derivatised antibody variants that retain the ability to specifically bind an epitope. Antibodies are capable of selectively binding to a target antigen or epitope. Antibodies may include, but are not limited to polyclonal antibodies, monoclonal antibodies (mAbs), humanized and other chimeric antibodies, single chain antibodies (scFvs), Fab fragments, F(ab')2 fragments and disulfide-linked Fvs (sdFv) fragments. In some embodiments, the antibody is from any origin, such as mouse or human, including a chimeric antibody thereof. In some embodiments, the antibody is humanized.

Examples of antibodies include, but are not limited to, 3F8, 8H9, Abagovomab, Abciximab (ReoPro), Abituzumab, Abrilumab, Actoxumab, Adalimumab (Humira), Adecatumumab, Aducanumab, Afasevikumab, Afelimomab, Afutuzumab, Alacizumab pegol, ALD518, Alemtuzumab (Lemtrada, Campath), Alirocumab (Praluent), Altumomab pentetate (Hybri-ceaker), Amatuximab, Anatumomab mafenatox, Anetumab ravtansine, Anifrolumab, Anrukinzumab, Apolizumab, Arcitumomab (CEA-Scan), Ascrinvacumab, Aselizumab, Atezolizumab (Tecentriq), Atinumab, Atorolimumab, Avelumab (Bavencio), Bapineuzumab, Basiliximab (Simulect), Bavituximab, Bectumomab (LymphoScan), Begelomab, Belimumab (Benlysta), Benralizumab, Bertilimumab, Besilesomab (Scintimun), Bevacizumab (Avastin), Bezlotoxumab (Zinplava), Biciromab (FibriScint), Bimagrumab, Bimekizumab, Bivatuzumab mertansine, Bleselumab, Blinatumomab (Blincyto), Blontuvetmab (Blontress), Blosozumab, Bococizumab, Brazikumab, Brentuximab vedotin (Adcentris), Briakinumab, Brodalumab (Siliz), Brolucizumab, Brontictuzumab, Burosumab, Cabiralizumab, Canakinumab (Ilaris), Cantuzumab mertansine, Cantuzumab ravtansine, Caplacizumab, Capromab pendetide (Prostascint), Carlumab, Carotuximab, Catumaxomab (Removab), cBR96-doxorubicin immunoconjugate, Cedelizumab, Cergutuzumab amunaleukin, Certolizumab pegol (Cimzia), Cetuximab (Erbitux), Citatuzumab bogatox, Cixutumumab, Clazakizumab, Clenoliximab, Clivatuzumab tetraxetan (hPAM4-Cide), Codrituzumab, Coltuximab ravtansine, Conatumumab, Concizumab, Crenezumab, Crotedumab, CR6261, Dacetuzumab, Daclizumab (Zenapax), Dalotuzumab, Dapirolizumab pegol, Daratumumab (Darzalex), Dectrekumab, Demcizumab, Denintuzumab mafodotin, Denosumab (Prolia), Depatuxizumab mafodotin, Derlotuximab biotin, Detumomab, Dinutuximab (Unituxin), Diridavumab, Domagrozumab, Dorlimomab aritox, Drozitumab, Duligotumab, Dupilumab (Dupixent), Durvalumab (Imfinzi), Dusigitumab, Ecromeximab, Eculizumab (Soliris), Edobacomab, Edrecolomab (Panorex), Efalizumab (Raptiva), Efungumab (Mycograb), Idelumab, Elgemtumab, Elotuzumab (Repatha), Elsilimomab, Emactuzumab, Emibetuzumab, Emicizumab, Enavatuzumab, Enfortumab vedotin, Enlinomab pegol, Enoblituzumab, Enokizumab, Enoticumab, Ensituximab, Epitumomab cituxetan, Epratuzumab, Erenumab, Erlizumab, Ertumaxomab (Rexomun), Etaracizumab (Abegrin), Etrolizumab, Evinacumab, Evolocumab (Repatha), Exbivirumab, Fanolesomab (NeutroSpec), Faralimomab, Farletuzumab, Fasinumab, FB TAOS (Lymphomun), Felvizumab, Fezakinumab, Fibatuzumab, Ficlatuzumab, Figitumumab, Firivumab, Flanvotumab, Fletikumab, Fontolizumab (HuZAF), Foralumab, Foravirumab, Fresolimumab, Fulranumab, Futuximab, Galcanezumab, Galiximab, Ganitumab, Gantenerumab, Gavilimomab, Gemtuzumab ozogamicin (Mylotarg), Gevokizumab, Girentuximab (Rencarex), Glembatumumab vedotin, Golimumab (Simponi), Gomiliximab, Guselkumab, Ibalizumab, Ibritumomab tiuxetan (Zevalin), Icrucumab, Idarucizumab (Praxbind), Igovomab (Indimacis-125), IMAB362, Imalumab, Imciromab (Myoscint), Imgatuzumab, Inclacumab, Indatuximab ravtansine, Indusatumab vedotin, Inebilizumab, Infliximab (Remicade), Intetumumab, Inolimomab, Inotuzumab ozogamicin, Ipilimumab, Iratumumab, Isatuximab, Itolizumab, Ixekizumab (Taltz), Keliximab, Labetuzumab (CEA-Cide), Lampalizumab, Lanadelumab, Landogrozumab, Laprituximab emtansine, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, MABp1 (Xilonix), Mapatumumab, Margetuximab, Maslimomab, Mavrilimumab, Matuzumab, Mepolizumab (Bosatria), Metelimumab, Milatuzumab, Minretumomab, Mirvetuximab soravtansine, Mitumomab, Mogamulizumab, Monalizumab, Morolimumab, Motavizumab (Numax), Moxetumomab pasudotox, Muromonab-CD3 (Orthoclone OKT3), Nacolomab tafenatox, Namilumab, Naptumomab estafenatox, Naratuximab emtansine, Narnatumab, Natalizumab (Tysabri), Navicixizumab, Navivumab, Nebacumab, Necitumumab (Portrazza), Nemolizumab, Nerelimomab, Nesvacumab, Nimotuzumab (Theracim, Theraloc), Nivolumab (Opdivo), Nofetumomab merpentan (Verluma), Obiltoxaximab, Obinutuzumab (Gazyva), Ocaratuzumab, Ocrelizumab (Ocrevus), Odulimomab, Ofatumumab (Arzerra), Olaratumab (Lartruvo), Olokizumab, Omalizumab (Xolair), Onartuzumab, Ontuxizumab, Opicinumab, Oportuzumab monatox, Oregovomab (OvaRex), Orticumab, Otelixizumab, Otlertuzumab, Oxelumab, Ozanezumab, Ozoralizumab, Pagibaximab, Palivizumab (Synagis, Abbosynagis), Pamrevlumab, Panitumumab (Vectibix), Pankomab, Panobacumab, Parsatuzumab, Pascolizumab, Pasotuxizumab, Pateclizumab, Patritumab, Pembrolizumab (Keytruda), Pemtumomab (Theragyn), Perakizumab, Pertuzumab (Omnitarg), Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab (Cyramza), Ranibizumab (Lucentis), Raxibacumab, Refanezumab, Regavirumab, Reslizumab, Rilotumumab, Rinucumab, Risankizumab, Rituximab (MabThera, Rituxan), Rivabazumab pegol, Robatumumab, Roledumab, Romosozumab, Rontalizumab, Rovalpituzumab tesirine, Rovelizumab (LeukArrest), Ruplizumab (Antova), Sacituzumab govitecan, Samalizumab, Sapelizumab, Sarilumab, Satumomab pendetide, Secukinumab (Cosentyx), Seribantumab, Setoxaximab, Sevirumab, Sibrotuzumab, SGN-CD19A, SGN-CD33A, Sifalimumab, Siltuximab (Sylvant), Simtuzumab, Siplizumab, Sirukumab, Sofituzumab vedotin, Solanezumab, Solitomab, Sonepcizumab, Sontuzumab, Stamulumab, Sulesomab (LeukoScan), Suvizumab, Tabalumab, Tacatuzumab tetraxetan (AFP-Cide), Tadocizumab, Talizumab, Tamtuvetmab (Tactress), Tanezumab, Taplitumomab paptox, Tarextumab, Tefibazumab (Aurexis), Telimomab aritox, Tenatumomab, Teneliximab, Teplizumab, Teprotumumab, Tesidolumab, Tetulomab, Tezepelumab, TGN1412, Ticilimumab (tremelimumab), Tildrakizumab, Tigatuzumab, Timolumab, Tisotumab vedotin, TNX-650, Tocilizumab (Actemra, RoActemra), Toralizumab, Tosatoxumab, Tositumomab (Bexxar), Tovetumab, Tralokinumab, Trastuzumab (Herceptin), Trastuzumab emtansine (Kadcyla), TRBS07 (Ektomab), Tregalizumab, Tremelimumab, Trevogrumab, Tucotuzumab celmoleukin, Tuvirumab, Ublituximab, Ulocuplumab, Urelumab, Urtoxazumab, Ustekinumab (Stelara), Utomilumab, Vadastuximab talirine, Vandortuzumab vedotin, Vantictumab, Vanucizumab, Vapaliximab, Varlilumab, Vatelizumab, Vedolizumab (Entyvio), Veltuzumab, Vepalimomab, Vesencumab, Visilizumab (Nuvion), Vobarilizumab, Volociximab, Vorsetuzumab mafodotin, Votumumab (HumaSPECT), Xentuzumab, Zalutumumab (HuMax-EGFr), Zanolimumab (HuMax-CD4), Zatuximab, Ziralimumab, and Zolimomab. In one preferred embodiment, the antibody is Trastuzumab (Herceptin).

The term "antibody" as used herein also contemplates the biosimilar or second generation version of the monoclonal antibodies described herein.

The term "polynucleotide," or "nucleotide" as used herein, refer generally to linear polymers of natural or modified nucleosides, including deoxyribonucleosides, ribonucleosides, alpha-anomeric forms thereof, and the like, usually linked by phosphodiester bonds or analogs thereof ranging in size from a few monomeric units, e.g. 2-4, to several hundreds of monomeric units. When a polynucleotide is represented by a sequence of letters, such as "ATGCCTG," it will be understood that the nucleotides are in 5'→3' order from left to right. Polynucleotide as used herein also includes abasic, sugar-phosphate or sugar-phosphorothioate polymers.

The term "small molecule" as used herein refers generally to a low molecular weight compound, usually less than 900 daltons.

The term "click chemistry" or "Copper-Catalyzed Azide-Alkyne Cycloaddition reaction" or "CuACC reaction" as used herein, refers to the copper(I)-catalyzed [3+2]-Huisgen 1,3-dipolar cyclo-addition of terminal alkynes and azides leading to 1,2,3-triazoles. It may also refer to a copper free variant of this reaction that might also be used. (J. M. Baskin, J. A. Prescher, S. T. Laughlin, N. J. Agard, P. V. Chang, I. A. Miller, A. Lo, J. A. Codelli, C. R. Bertozzi, Proc. Natl. Acad. Sci. U.S.A. 2007, 104, 16793.).

As described herein, in accordance with the various embodiments herein, the inventors have developed a novel cell engineering technology by which molecules are covalently attached on the glycans present on a cell surface. Such molecules may be small chemical moieties, or larger biological moieties such as proteins, polynucleotides, and/or antibodies. The applications of the engineered cells disclosed herein are numerous—illustrative examples include boosting the activity of immune cells for adoptive cell therapy (ACT); and/or conjugating small molecules, proteins or antibodies to the cell-surface for novel immunotherapy strategies.

In one embodiment, disclosed herein is a non-naturally occurring engineered cell, comprising: a chemical or biological moiety covalently bound to a glycan present on the surface of a cell via a fucose derivative. A variety of chemical and biological moieties can be attached to the cell surface glycan, as disclosed throughout this disclosure. Examples include, but are not limited to, drugs (e.g., pharmaceuticals), catalysts, antibiotics, antibodies, antimycotics, carbohydrates, cytokines, enzymes, glycoproteins, lipids, nucleic acids, nucleotides, oligonucleotides, polynucleotides, proteins, peptides, ligand, cells, ribozymes, probe molecules, or combinations thereof. Similarly the chemical or biological moieties may be attached to different types of glycans present on the cell surface—non-limiting examples include Gal (Galactin), GlcNAc (N-Acetylglucosamine), LacNAc, and/or NeuAc (Sialic acid). In one embodiment, this technique for making engineered cells by covalently attaching molecules covalently on the glycans present on the cell surface is done in one pot, without the need for purification. In another embodiment, this technique is done in one pot, one step, and in-situ.

In one aspect, the present disclosure provides an engineered cell, comprising a chemical or biological moiety covalently bound to a cell surface glycan present on the surface of the cell, wherein the chemical or biological moiety is selected from the group consisting of small molecule, polynucleotide, polypeptide, and antibody. In one embodiment, the engineered cell is an immune cell. In one embodiment, the engineered cell is a T-cell, a Dendritic Cell (DC), or a natural killer (NK) cell. In one embodiment, the T cell is a CD8+ or a CD4+ T cell. In one embodiment, the small molecule is a small drug molecule or a pharmaceutically acceptable salt or a co-crystal thereof. In one embodiment, the antibody is a single chain variable fragment (scFv), fragment antigen binding (Fab) fragment, or a full length antibody, such as a full length immunoglobulin G (IgG) antibody. In one embodiment, the chemical or biological moiety attached to the engineered cell is a biological marker and/or probe. In one embodiment, the chemical or biological moiety is a biotin probe, a fluorescent probe, a biorthogonal reaction handle, and/or a dye labeled single strand DNA. In one embodiment, the dye is FAM. In one embodiment, the fluorescent probe is Cy3. In one embodiment, the biorthogonal reaction handle is tetrazine. In one embodiment, the fucose derivative is a GDP-fucose. In one embodiment, the engineered cell is a chimeric antigen receptor (CAR)-T cell. In one embodiment, the CAR-T cell comprises a genetically modified T-cell with the cell surface GlcNAc covalently bound to a GDP-Fucose bearing a new motif. In one embodiment, the CAR comprises three domains: scFv, Fab, and/or mature ligands that engage their cognate receptor. In one embodiment, the cell surface glycan is N-acetylglucosamine (GlcNAc). In one embodiment, the chemical or biological moiety is covalently bound to the GlcNAc via a fucose derivative. In one embodiment, the cell surface glycan is Sialic acid (NeuAc).

In one embodiment, the present disclosure provides a composition comprising: an antibody-cell conjugate, wherein one or more antibodies are covalently bound to one or more glycan moiety on the surface of a cell. In one embodiment, the cell is immune cell. In one embodiment, the cell is a primary human T cell, a natural killer (NK) cell, a CD4+ cell, and/or primary CD8+OT-1 T cells. In one embodiment, the NK cell is NK-92MI cell. In one embodiment, the cell is a Dendritic Cell (DC). In one embodiment, the antibody is Trastuzumab. In one embodiment, the cell is NK-92MI and at least one antibody is Trastuzumab. In one embodiment, more than one type of antibody is conjugated on the surface of the cell. In one embodiment, the glycan moiety is N-acetylglucosamine (GlcNAc). In one embodiment, the antibody is covalently bound to the GlcNAc via a fucose derivative. In one embodiment, the glycan moiety is Sialic acid (NeuAc). In one embodiment, the composition is a pharmaceutical composition. In one embodiment, the pharmaceutical composition further comprises a pharmaceutically acceptable carrier or excipient. In one embodiment, the pharmaceutical composition is for the treatment of a disease in a subject. In one embodiment, the antibody-cell conjugate enables firm binding on inflammation sites (anti-E-selectin), target specific cancer cells (anti-HER2), and/or block the immune checkpoint (anti-PD-L1).

Cancer immunotherapy, which harnesses the body's own immune system to fight cancer, has emerged as a fourth way of treating cancer, besides surgery, radiation, and chemotherapy. While good results have been achieved in adoptive cell therapy (ACT) and checkpoint blockade therapy, the cancer fighting properties of the T-cells infused in the patients remain to be improved. Likewise, dendritic cells (DCs) have long been considered as the central players in cancer immunotherapy. However, it was shown that only a small portion (1-2%) of total administered DCs reached secondary lymphatic organs to activate T cells, limiting the practical application of this vaccination approach.

In one embodiment, the engineered cells and methods disclosed herein provides an attractive way of overcoming these limitations. In one embodiment, the present disclosure provides a method of treating a disease in a subject comprising: providing a pharmaceutical composition comprising an engineered cell and a pharmaceutically acceptable carrier; and treating the disease by administering a therapeutically effective dosage of the pharmaceutical composition to the subject, wherein the engineered cell comprises a chemical or biological moiety covalently bound to a glycan moiety present on its surface, and wherein the chemical or biological moiety is selected from the group consisting of small molecule, polynucleotide, polypeptide, and antibody. In one embodiment, the antibody is an immunoglobulin G (IgG) antibody. In one embodiment, the antibody is an anti-PD-L1 antibody. In one embodiment, the antibody is an anti-E-selectin antibody. In one embodiment, the antibody is an anti-HER2 antibody. In one embodiment, the antibody is Trastuzumab. In one embodiment, more than one chemical or biological moiety is covalently bound to the surface of the cell to target more than one disease at the same time. In one embodiment, the cell is a dendritic cell. In one embodiment, the cell is an immune cell. In one embodiment, the cell is a primary human T cell, a natural killer (NK) cell, a CD4+ cell, and/or primary CD8+OT-1 T cells. In one embodiment, the NK cell is NK-92MI cell. In one embodiment, the glycan moiety is N-acetylglucosamine (GlcNAc). In one embodiment, the chemical or biological moiety is covalently bound to the GlcNAc via a fucose derivative. In one embodiment, the fucose derivative comprises fucose-alkyne. In one embodiment, the glycan moiety is Sialic acid (NeuAc). In one embodiment, the disease is cancer. In one embodiment, treating the disease comprises reducing the size of a cancerous tumor in the subject. In one embodiment, the cancer is a breast cancer.

In another embodiment, the present disclosure provides a method of treating, decreasing, inhibiting, or reducing cancer in a subject, comprising: administering to the subject a therapeutically effective dosage of a pharmaceutical composition comprising an engineered cell, having an antibody covalently bound to a glycan moiety present on its surface. In one embodiment, the cancer is breast cancer. In one embodiment, the antibody is Trastuzumab. In one embodiment, the cell is NK-92MI. In one embodiment, more than one antibody is conjugated on the surface of the cell to target more than one cancer at the same time.

The present disclosure further provides a variety of methods for making the engineered cells disclosed herein. In one embodiment of the present disclosure, a method is provided for making an engineered cell, comprising: making a fucose derivative or GDP-fucose derivative comprising a chemical or biological moiety covalently bound to a fucose or GDP-fucose; making the engineered cell by incubating a cell with a composition comprising (a) the fucose derivative and/or GDP-Fucose derivative and (b) a fucosyltransferase enzyme. In another embodiment of the present disclosure, a method is provided for making an engineered cell, comprising: generating CMP-sialic acid conjugated with an antibody (CS-IgG) by reacting an antibody bearing a TCO moiety with CS-Az-Tz or CS-Poc-Tz; and making the engineered cell by incubating a naturally occurring cell with a composition comprising (a) CS-IgG and (b) a sialyltransferase. In one embodiment, the fucosyltransferase enzyme is α-1,3-fucosyltransferase. In one embodiment, the α-1,3-fucosyltransferase is *H. pylori* α-1,3-fucosyltransferase. In one embodiment, the α-1,3-fucosyltransferase is recombinantly prepared. In one embodiment, the sialyltransferase is selected from the group consisting of ST6Gal1, *Pasteurella multocida* α(2,3) sialyltransferase M144D mutant (Pm2, 3ST-M144D), and *Photobacterium damsel* α(2,6) sialyltransferase (Pd2,6ST). In one embodiment, the chemical or biological moiety is selected from the group consisting of small drug molecules, biomolecules, probe molecules, fluorophores, polynucleotides, polypeptides, and whole IgG, or combinations thereof. In one embodiment, the biomolecule is Trastuzumab. In one embodiment, the cell is an immune cell. In one embodiment, the cell is a primary human T cell or a natural killer (NK) cell. In one embodiment, the NK cell is NK-92MI cell. In one embodiment, the T cell is a CD4+ cell, or a CD8+ T cells. In one embodiment, the chemical or biological moiety is covalently attached via a fucose derivative to LacNAc, a universal unit of N-glycans, on the surface of the cell. In one embodiment, the fucose modified biomolecule and/or GDP-fucose modified biomolecule comprises a fucose-alkyne and/or GDP-fucose azide. In one embodiment, the biomolecule-cell conjugate is further modified with a chemical or biological moiety using ligand accelerated and biocompatible copper(I)-catalyzed alkyne-azide cycloaddition (CuAAC) reaction.

In one embodiment, disclosed herein is a one-pot method of making an engineered cell adapted to attach a molecule on its surface comprising: preparing GDP-fucose analog by combining a fucose analog with a mixture comprising ATP, GTP, L-fucokinase/GDP-fucose pyrophosphorylase (FKP), $Mg^{2+}$ or $Mn^{2+}$, and inorganic pyrophosphate (PPase); and making the engineered cell by adding a naturally occurring cell to a composition comprising the crude product from step (a) and *H. pylori* α-1,3-fucosyltransferase. In one embodiment, disclosed herein is a one-pot, one-step method of making an engineered cell adapted to attach a molecule on its surface comprising: incubating a cell with a composition comprising a fucose analog, ATP, GTP, L-fucokinase/GDP-fucose pyrophosphorylase (FKP), $Mg^{2+}$ or $Mn^{2+}$, inorganic pyrophosphate (PPase) and *H. pylori* α-1,3-fucosyltransferase. In one embodiment, the fucose analog comprises a fucose conjugated with a chemical or biological moiety. In one embodiment, the fucose analog comprises a fucose-alkyne. In one embodiment, the engineered cell comprises a chemical or biological moiety attached to a glycan on the surface of the cell. In one embodiment, the product from step (a) is further modified through a Copper-Catalyzed Azide-Alkyne Cycloaddition (CuACC) reaction to generate GDP-fucose analogs conjugated to a small molecule, polynucleotide, polypeptide, and/or antibody.

In one embodiment, disclosed herein is a one pot in-situ fucosylation strategy to convert cell surface LacNAc or SLacNAc into LeX or sLeX comprising: preparing GDP-fucose analogs by combining a fucose analog with a mixture comprising ATP, GTP, FKP, $Mg^{2+}$ or $Mn^{2+}$, and inorganic pyrophosphate (PPase); and converting cell surface LacNAc or SLacNAc into LeX or sLeX by adding a naturally occurring cell to a composition comprising the crude product from step (a) and *H. pylori* α-1,3-fucosyltransferase.

In one embodiment, disclosed herein is a composition comprising an engineered cell is adapted to attach a molecule on its surface. In one embodiment, the engineered cell is an immune cell. In one embodiment, the engineered cell is a T-cell. In one embodiment, the molecule attached to the cell surface is a small molecule drug, an antibody, a therapeutic cell, a polypeptide and/or a polynucleotide. In one embodiment, the antibody is a full length antibody. An antibody used in accordance with this disclosure may be a polyclonal, monoclonal, chimeric, mouse, humanized or fully human. In one embodiment, the molecule attached to the engineered cell is a single-chain variable fragment (scFv). In one embodiment, the molecule attached to the engineered cell is a fragment antigen-binding (Fab) fragment. In one embodiment, the molecule attached to the engineered cell is a biological marker and/or probe. In one embodiment, the biological marker and/or probe is a fluorescent dye. In one embodiment, the engineered cell is a chimeric antigen receptor (CAR)-T cell wherein the CAR-T cell comprises a genetically modified T-cell with the cell surface glycans covalently bound to a GDP-Fucose bearing a new motif. In one embodiment, the CAR molecule comprises 3 domains: scFv, Fab, and/or mature ligands that engage their cognate receptor.

The present disclosure describes a one-pot in situ fucosylation strategy to modify cell-surface glycans. The applications include (1) boost the activity of immune cells for adoptive cell therapy (ACT); (2) conjugate small molecules, proteins or antibodies to the cell-surface for novel immunotherapy strategies.

Almost all key cell-surface molecules involved in the innate and adaptive immune systems are glycosylated. Glycosylated molecules play essential roles in the immune cell differentiation and trafficking. The interaction between the glycan ligand sialyl Lewis X ($sLe^X$) with the selectin family of glycan binding proteins (P-selectin and E-selectin) mediates the tethering and rolling of circulating leukocytes on the vascular cell wall, which promotes subsequent extravasation and migration of leukocytes through the endothelium into the surrounding tissue. However, the inventors have discovered that many activated immune cells with therapeutic potential such as lymphocytes or myeloid cells have very low levels of $sLe^X$.

The inventors have solved this problem by disclosing herein a one-pot in situ fucosylation strategy to convert cell-surface N-acetyllactosamine (LacNAc, Galβ1,4 GlcNAc) or its sialylated form (sLacNAc) into the Lewis X ($Le^X$) or sialyl Lewis X ($sLe^X$) epitopes. Converting cell-surface LacNAc and sLacNAc residues into $sLe^X$ ex vivo on the surface of immune cells via this strategy serve as a "two birds, one stone" approach to boost the efficacy of cell-based immunotherapy. The sLe$^X$ epitope created on the surface of immune cells directs the homing, engraftment and retention of therapeutic cells to diseased tissues where they are needed most. Furthermore, by converting LacNAc and sLacNAc residues into sLe$^X$, galectin-LacNAc interactions are inhibited, which in turn suppresses galectin-mediated immune cell apoptosis. Using this one-pot in situ fucosylation approach, biomacromolecules such as an antibody can be directly attached onto the cell surface of immune cells for immunotherapy.

Accordingly, in one embodiment, disclosed herein is a one-pot method of making an engineered cell adapted to attach a molecule on its surface comprising: preparing GDP-fucose analog by combining a fucose analog with a mixture comprising ATP, GTP, FKP, MgSO4, and inorganic pyrophosphate (PPase), and making the engineered cell by adding the crude product from step (a) and α-1,3-FucT to a cell. In one embodiment, disclosed herein is a one-pot, one-step method of making an engineered cell adapted to attach a molecule on its surface comprising: incubating a cell with a fucose analog, ATP, GTP, FKP, MgSO4, inorganic pyrophosphate (PPase) and α-1,3-FucT. In one embodiment, the engineered cell comprises a molecule attached to a glycan on the surface of the cell. In one embodiment, the fucose analog comprises a fucose-alkyne. In one embodiment, the product from step (a) is further modified through a CuACC reaction to generate GDP-fucose analogs conjugated to a small molecule, polynucleotide, polypeptide, and/or antibody. In one embodiment, disclosed herein is a one pot in-situ fucosylation strategy to convert cell surface LacNAc or SLacNAc into Le$^X$ or sLe$^X$ comprising: Preparing GDP-fucose analogs by combining a fucose analog with a mixture comprising ATP, GTP, FKP, MgSO4, and inorganic pyrophosphate (PPase); and Making the engineered cell by adding to a cell a composition comprising the crude product from step (a) and *H. pylori* α-1,3-FucT. While the inventors have generally used α-1,3-FucosylTransferase enzyme derived from the organism *H. pylori*, it will be apparent to one of skill in the art that any fucosyltransferase enzyme, irrespective of the source, may be used for the methods, compositions, and kits described herein.

In one embodiment, provided herein is a method of treating a disease in a subject comprising providing an engineered cell adapted to attach a molecule on its surface, and treating the disease by administering to the subject the engineered cell. In one embodiment, provided herein is a method of treating cancer in a subject comprising: providing an engineered cell wherein an anti-PD-L1 antibody is covalently linked to the cell surface LacNAc molecule of an immune cell; administering to the subject the engineered cell, wherein the antibody in the engineered cell recognizes a specific antigen on cancer cells; and treating cancer in the subject, by contacting the engineered cell with a cancer cell. In one embodiment, the engineered cell comprises a molecule attached to a glycan on the surface of the cell. In one embodiment, the fucose comprises fucose-alkyne. In one embodiment, the product from the first step is further modified through a CuACC reaction to generate GDP-fucose analogs conjugated to a small molecule, polynucleotide, polypeptide, and/or antibody. In one embodiment, the size of the cancerous tumor in the patient decreases upon administration of the engineered cell to the patient.

Engineering the immune cell surface from the outside is an efficient approach to improve cell-based therapy, which would have the potential to compete with the genetic manipulation due to its low risk of lymphocyte transformation and genome mutation, or may be used as an alternative approach, at least. Cell surface glycans are positioned most outside of the cell surface and therefore are excellent targets to be engineered. They could be efficiently modified through the metabolic engineering or chemoenzymatic engineering. As discussed throughout this disclosure, the inventors have developed a one-pot in-situ fucosylation strategy to convert cell-surface LacNAc or its sialylated form sLacNAc into the Le$^X$ or sLe$^X$ epitopes. This method has been widely used to boost cell therapy efficiency, such as stem cell, regulatory cell and cord blood cell based therapy. The inventors extended the one-pot fucosylation strategy to install different functionalities, ranging from small molecules to biomacromolecules, like whole IgG antibody, onto cell surface. The process catalyzed by *H. pylori* α-1,3 fucosyltransferase is fast and efficient, even using a big substrate such as a protein conjugated to GDP-fucose. Taken together, the inventors have developed a totally new method for engineering immune cells, which is biocompatible and base on the natural epitope mimics, and also open the door of playing games with different combinations of small molecules drugs, antibodies and therapeutic cells.

For example, T cells can be genetically engineered to express special receptors on their surface called chimeric antigen receptors (CARs). CARs are proteins that allow the T cells to recognize a specific protein (antigen) on tumor cells. These engineered CAR T cells are then grown ex vivo until they number in the billions. The expanded population of CAR T cells is then infused into the patient. After the infusion, if all goes as planned, the T cells multiply in the patient's body and, with guidance from their engineered receptor, recognize and destroy cancer cells that harbor the antigen on their surfaces. A CAR may consist of three domains, i.e. antigen binding domain, transmembrane domain and cytosolic signal activation domain. The antigen binding domain falls in 3 general categories: (a) single-chain variable fragment (scFv) derived from antibodies; (b) Fab fragment antigen-binding (Fab) selected from libraries; or (c) nature ligands that engage their cognate receptor. CAR-Ts have showed promising efficacy in treating blood cancers, however, disappointing results were observed in the treatment of solid tumors due to the presence of suppressive mechanisms in the tumor microenvironment.

The one-pot strategy can be applied to install small molecules, scFv, Fab or full-length antibodies targeting checkpoint inhibitors onto the surface of CAR-Ts, ex vivo expanded tumor infiltrating lymphocytes or other types of immune cells to boost their activities. For example, using this strategy, the inventors can introduce antibodies blocking checkpoint inhibitors, e.g. (Programmed Death ligand 1 PD-L1) and (Cytotoxic T Lymphocyte-Associated Antigen 4) CTAL-4, onto the surface of CAR-T cells (or ex vivo expanded tumor infiltrating lymphocytes). Similarly, the inventors can use the same strategy to introduce antibodies against CTAL-4 onto the surface of ex vivo maturated, antigen-loaded dendritic cells to boost their anti-tumor or anti-viral activities. Furthermore, using this strategy, the inventors can install two or more different molecules onto cell-surface, e.g. anti-PD-L1 and anti-Tim 3 to inhibit more than one checkpoint inhibitors. The same strategy can be used to install biomolecules other than antibodies onto cell surface. For example, Programmed cell death protein 1 can be conjugated to regulatory T cells to enhance their immune suppressive functions.

Conjugating an antibody such as anti-PD-L1 to the cell surface of T cells for combination immunotherapy can significantly reduce the quantity of the antibody to be administered. In clinic trials, anti-PD-L1 antibody is administered intravenously (at escalating doses ranging from 0.3 to 10 mg per kilogram of body weight) to patient every 14 days in 6-week cycles for up to 16 cycles. By administrating anti-PD-L1 conjugated T cells, 10 to 100 fold less anti-PD-L1 would be used.

Thus, as disclosed herein, the inventors developed a novel method to engineer cells by construction of antibody-cell conjugates for enhanced cell therapy via one-step enzymatic glycoengineering. As described herein, in accordance with the various embodiments herein, the inventors have described a novel one-pot in situ fucosylation strategy to label antigen specific antibody onto a natural killer (NK) cell surface, which direct NK cells to kill specific antigen expressing cancer cells. Using Her2+ expressing cancer model, the inventors have demonstrated that enzymatic conjugation of Herceptin to NK cells enhanced killing of Her2+ expressing cancer cells in vitro and in vivo. The method is much easier and more efficient than genetic approaches.

In one embodiment, the present disclosure provides a composition comprising: an antibody-cell conjugate, wherein one or more antibodies are covalently attached to one or more glycan molecules on the surface of the cell. In one embodiment, the cell is immune cell. In one embodiment, the cell is a primary human T cell, a natural killer (NK) cell line, and/or primary CD8+OT-1 T cells. In one embodiment, the NK cell line is NK-92MI. In one embodiment, the antibody-cell conjugate is as described in FIG. 1B. In one embodiment, the antibody is Trastuzumab (Herceptin). In one embodiment, more than one type of antibody is conjugated on the surface of the cell. In one embodiment, the cell is NK-92MI and at least one antibody is Trastuzumab (Herceptin). In one embodiment, the antibody-cell conjugate enables firm binding on inflammation sites (anti-E-selectin), target specific cancer cells (anti-HER2), and/or block the immune checkpoint (anti-PD-L1).

In one embodiment, the instant disclosure provides a pharmaceutical composition comprising: an antibody-cell conjugate as described above, and a pharmaceutically acceptable carrier or excipient. In one embodiment, the pharmaceutical composition is for the treatment of a disease in a subject. In one embodiment, provided herein is a method of treating, decreasing, inhibiting, or reducing cancer in a subject, comprising: administering to the subject a therapeutically effective dosage of a pharmaceutical composition comprising an antibody-cell conjugate as disclosed herein. In one embodiment, the cancer is breast cancer. In one embodiment, more than one antibody is conjugated on the surface of the cell to target more than one cancer at the same time.

In one embodiment, disclosed herein is a method of making a biomolecule-cell conjugate, comprising: incubating a cell with a composition comprising (a) one or more fucose modified biomolecules and/or GDP-Fucose modified biomolecules and (b) a fucosyltransferase enzyme. In one embodiment, the fucosyltransferase enzyme is α-1,3-fucosyltransferase. In one embodiment, the α-1,3-fucosyltransferase is obtained from H. pylori. In one embodiment, the α-1,3-fucosyltransferase is recombinantly prepared. In one embodiment, the biomolecules are probe molecules, fluorophores, polynucleotides, polypeptides, whole IgG, or combinations thereof. In one embodiment, the biomolecule is Trastuzumab (Herceptin). In one embodiment, the cell is an immune cell. In one embodiment, the cell is a primary human T cell, a natural killer (NK) cell line, and/or primary CD8+OT-1 T cells. In one embodiment, the cell is NK-92MI. In one embodiment, the biomolecule is covalently attached to LacNAc, a universal unit of N-glycans, on the surface of the cell. In one embodiment, the fucose modified biomolecule and/or GDP-fucose modified biomolecule comprises a fucose-alkyne and/or GDP-fucose azide. In one embodiment, the biomolecule-cell conjugate is further modified with a chemical or biological moiety using ligand accelerated and biocompatible copper(I)-catalyzed alkyne-azide cycloaddition (CuAAC) reaction. In one embodiment, the chemical or biological moiety is a biotin probe, a fluorescent probe Cy3, a biorthogonal reaction handle tetrazine, and/or a dye (FAM) labeled single strand DNA.

In one embodiment, using chemoenzymatic method to labeling antibodies to NK-92 cell surface provide a significant financial advantage and time saving procedure. NK-92 cells do not express Fc receptors for ADCC effects to target specific cells, which limit its wide applications. Genetic methods are used to install high affinity CD16 onto NK cells which can be used for in vivo treatment combined large dose of antibody injection. Using the chemoenzymatic labeling method, antibody conjugated NK cells can be produced within hours and only consume low quantity of antibody.

In one embodiment, the one-pot approach to transfer fucose linked antibody to the cell surface provides a unique, specific and biocompatible way to label two or more antibodies at the same time. Using the chemoenzymatic labeling system, two or more kinds of antigen specific antibodies can be installed onto the same NK cell, which facilitated NK cells target different cancers at the same time, while genetic expression of two or more antibodies in the same cell is very difficult.

In one embodiment, the composition disclosed herein is a pharmaceutical composition. In various embodiments, the pharmaceutical compositions according to the present disclosure may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 21$^{st}$ edition, Williams & Wilkins PA, USA) (2005).

Typical dosages of an effective composition can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

In one embodiment disclosed herein is a kit comprising GDP-fucose derivative and *H. pylori* α-1,3-fucosyltransferase. The kit is useful for practicing the inventive method of making an engineered cell adapted to attach a molecule on its surface. The kit is an assemblage of materials or components, including at least one of the inventive compositions. Thus, in some embodiments the kit contains a composition including a GDP-fucose derivative and *H. pylori* α-1,3-fucosyltransferase, as described above.

The exact nature of the components configured in the inventive kit depends on its intended purpose. For example, some embodiments are configured for the purpose of treating cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to make an engineered cell. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in the chemical or biotechnological field. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing GDP-fucose derivative and *H. pylori* α-1,3-fucosyltransferase. The packaging material generally has an external label which indicates the contents and/or purpose of the kit and/or its components.

Embodiments of the present disclosure are further described in the following examples. The examples are merely illustrative and do not in any way limit the scope of the invention as claimed.

EXAMPLES

Example 1

Cell engineers are continuously working with great effort on training cells to be living therapeutics. The past several years have witnessed spectacular results in patients treated with adoptive cell transfer (ACT). Most notably, Kymriah® (tisagenlecleucel) (a Registered trademark of Novartis), a chimeric antigen receptor T-cell (CAR-T) therapy, is approved as the first cell-based gene therapy in the United States most recently. Genetic engineering serves as a common and robust approach to engineer cells with novel functionalities. However, genetic engineering has showed limited success due to several technical challenges and safety concerns (e.g. viral transduction resistance of primary cells, heterogeneous expression levels and potential of endogenous gene disruption). To break through these limitations, engineering cell surfaces from "outside" via biochemical, biophysical or enzymatic methods has emerged as versatile and general applicable approaches. The modification sites of non-genetic methods from "outside" could be glycans, proteins or lipids on cell surface, among which glycans are positioned at the interface between cells and the extracellular milieu and therefore serve as excellent targets. In cell surface glycoengineering, a two-step method has been developed for coupling metabolic oligosaccharide engineering (MOE) with bioorthogonal chemistry. The advantages of high efficiency and good biocompatibility make it one of the most widely used cell surface engineering approaches.

Figure 39:
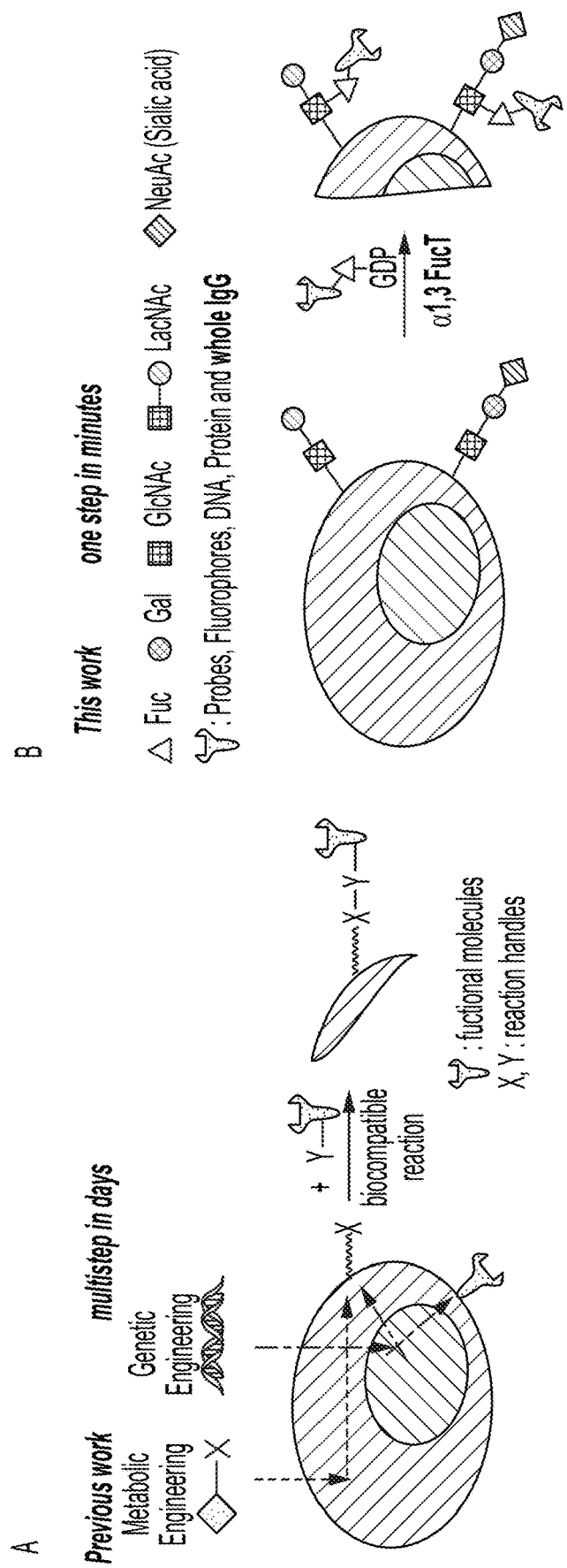
FIG. 39 depicts, in accordance with embodiments herein, a one-step enzymatic fucosylation based strategy for cell-surface engineering. (A) Two conventionally used cell-surface engineering approaches. Metabolic engineering is used to install a reaction handle (X) onto the cell surface, which can react with a complementary handle (Y) on a molecule of interest. Genetic engineering is powerful and robust, which could install functional molecules and reaction handles on cell surface. These two approaches usually have multistep and last several days. (B) An enzymatic glycoengineering approach capable of transferring a variety of functional molecules to the cell surface in one-step. The reaction between cell surface LacNAc/sialylLacNAc and GDP-Fuc derivatives is enabled by a α1,3FucT from *H. pylori*, which could tolerate modifications as large as whole IgG at the C6 position of the fucose. (C) One-pot synthesis protocol for GF-Al and GF-Az derivatives is described. Shown functionalities (Z) include bioorthogonal handles (tetrazine, Tz), biophysical probes (biotin, Cy3), and biomaterials (ssDNA).
Figure 39:
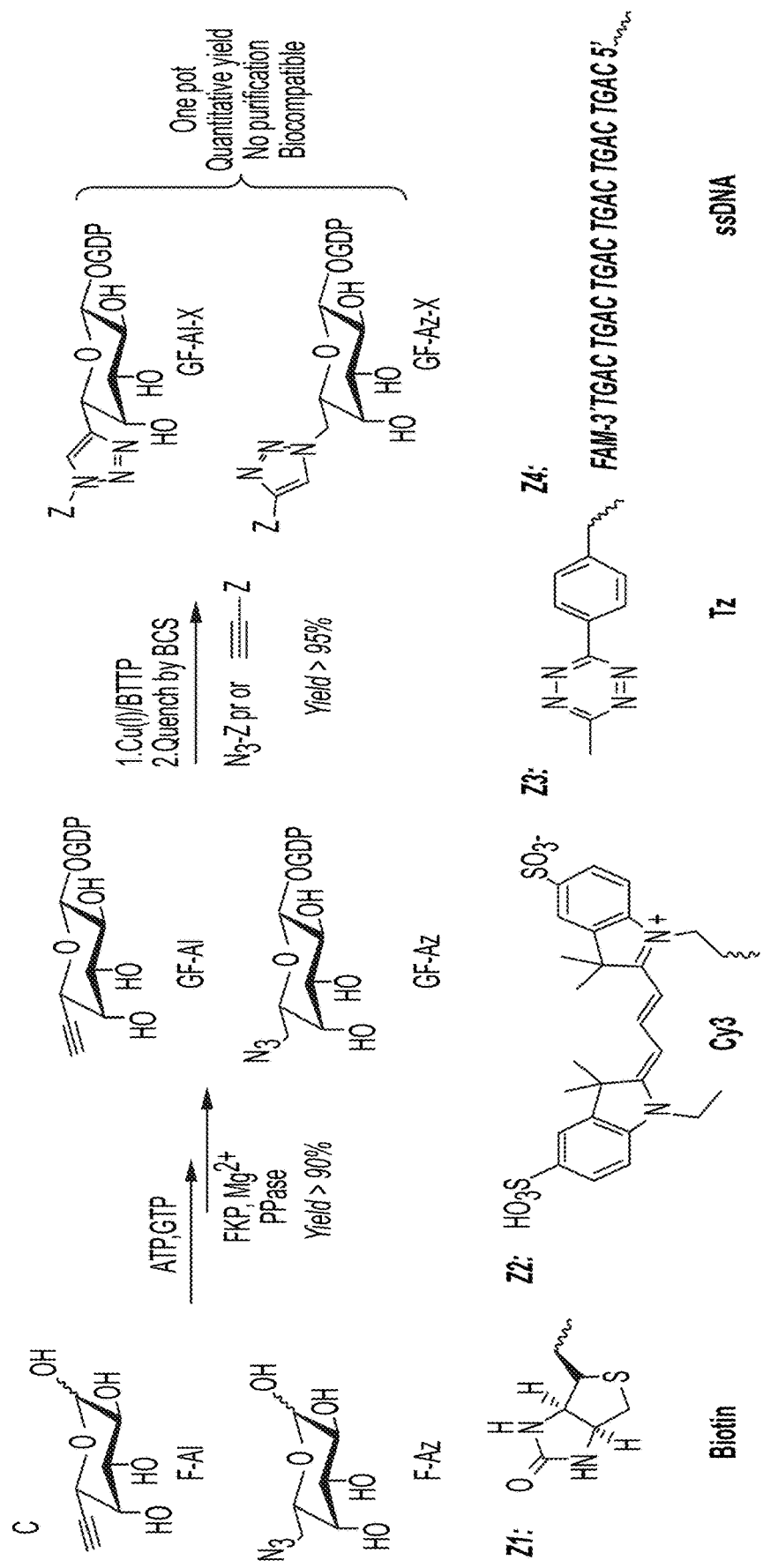

Preparation of therapeutic cells in clinical practice usually needs ex vivo isolation, activation and large-scale expansion of specific cells. Both genetic and metabolic engineering start in the early stages of cells preparation (e.g. during activation) and might interfere with these procedures. Moreover, these approaches are often completed through multi-steps in several days, sometimes followed by subsequent chemical reactions, which need more cell processing and quality control outside of the body (FIG. 39A). Their complexity in procedures could slow down the clinical translation. In contrast, enzymatic engineering of cell surface glycans as disclosed herein could be easily achieved in one-step just before infusion to human body. One impressive example of enzymatic engineering is ex vivo fucosylation of cells (e.g. stem cells and regulatory T cells) with GDP-fucose (GDP-Fuc or GF) and exogenous α(1,3)-fucosyltransferase (FucT or FT) could promote or improve the process of adhesion, homing or engraftment in adoptive transfer, which is currently under several clinical trials. However, transferring natural donor substrates to cell surface in glycoengineering has a narrow range of applications. To enrich the applications of cell surface enzymatic glycoengineering, expanding substrates scope to install versatile functionalities is highly desired.

Previously Palcic and co-workers described a method of decorating erythrocytes of blood type O with a blood group B trisaccharide antigen, by taking advantage of the relaxed substrates specificity of a human α1,3FucT that could recognize GDP-Fuc derivatives. (See Srivastava, G.; Kaur, K. J.; Hindsgaul, O.; Palcic, M. M. J. Biol. Chem. 1992, 267, 22356.) While this protocol provided an important development—most notably enzymatic transfer of diversified unnatural functional molecules to cell surface; several key drawbacks remained, which made the method not useful for therapeutic applications.

The presently disclosed in-situ fucosylation or sialylation strategy provides an attractive alternative. The reaction system disclosed herein is more efficient than previously disclosed methods, it is more biocompatible, and can be used to transfer large molecules, such as proteins, polypeptides, polynucleotides, and antibodies to a cell.

In one embodiment, the present disclosure provides sialyltransferases and fucosyltransferases that efficiently and site-specifically installs functionalities like bioorthogonal handles, fluorescent probes or preassembled oligosaccharide on live cell surface for glycan detection, glycoprotein analysis or glycan architectures remodeling. Although novel applications have appeared, the moieties that could be enzymatically transferred are still chemical synthesized small molecules or oligomers. Further, as disclosed herein, complex and biologically important macromolecules can be installed on a cell surface, and the resulting engineered cell would be broadly applicable in cell therapy. For example, monoclonal antibodies (mAbs) have shown great efficacy in treating disease like cancer or autoimmune. Making antibody-drug conjugates (ADC) would further enhance the potency of mAbs in cancer therapy. In one embodiment, enzymatic transfer of mAbs to therapeutic cell surface would transiently alter the functions of cells through remodeling cell-cell interactions, blocking signaling pathways or generating synergetic therapeutic effects.

In one embodiment, disclosed herein is a novel strategy for constructing antibody-cell conjugates (ACC) using α1,3FucT from $H. pylori$, which could transfer a whole IgG antibody modified with GDP-Fuc derivatives to LacNAc (Galβ1,4GlcNAc), a universal unit of N-glycans, on live cell surface in several minutes. Meanwhile, a one-pot protocol coupling chemoenzymatic reactions with bioorthogonal chemistry was also invented to produce GDP-Fuc derivatives modified biomaterials from easily synthesized fucose analogues, which makes this engineering approach more general applicable and cost effective. In one embodiment, using this methodology, three cases of ACC on immune cells were established, including primary human T cells, natural killer cell lines (NK-92MI) and primary CD8+OT-1 T cells. Monoclonal antibodies conjugated on cell surfaces help these immune cells to enhance firm binding on inflammation sites (anti-E-selectin), target specific cancer cells (anti-HER2) or block the immune checkpoint (anti-PD-L1), which might improve adoptive cell therapies in different stages.

Example 2

FIG. 1 illustrates one embodiment of the two step one-pot reaction, and the one step one-pot reaction.

Two Step One-Pot Reactions:

Reactions were typically carried out in a 1.5-mL Eppendorf tube with 1.0 mL buffer (pH 7.5) containing L-fucose or its C-5 substituted analogs (final concentration, 10 mM), ATP (10 mM), GTP (10 mM), MgSO4 (10 mM), inorganic pyrophosphatase (90 units, endotoxin free), and FKP (9 units, endotoxin free). The reaction mixture was incubated at 37° C. for 5-6 h with shaking (225 rpm). The reaction progress was monitored by TLC, using 10 mM tetrabutylammonium hydroxide in 80% aqueous acetonitrile as the developing solvent (p-anisaldehyde sugar stain). After the disappearance of fucose or fucose analogs, the crude product could be used directly on cell-surface fucosylation. If fucose-alkyne or azide were used, the crude product could be further modified through CuAAC reaction to generate GDP-fucose conjugates. For example, the crude GDP-fucose-alkyne sample (5 mM) were reacted with azide probes (5 mM) in the presence of Cu/BTTAA (100 uM) and sodium ascorbate (2 mM) at 37° C. for 1 h. After reaction finished, BCS (1 mM) were added to quench the reaction. The crude one-pot product, either before or after click reaction, could be directly used for the subsequent fucosylation reaction on the cell surface without purification. $10^6$ live cells were washed 3×times with PBS and re-suspended in 100 μL HBSS buffer containing 20 mM MgSO4, 3 mM HEPES, 0.1% FBS, 200 μM GDP-Fuc (or GDP-Fuc-conjugates), 30 mU α(1,3)FucT. After the incubation at 37° C. for 20 min, the cells were washed 3×times and then blocked in PBS with 2% FBS for 30 min for further application or analysis.

One-Step One-Pot Reaction:

Reagents were prepared in a 1.5-mL Eppendorf tube with 100 uL buffer (pH 7.8) containing L-fucose or its C-5 substituted analogs (final concentration, 1 mM), ATP (10 mM), GTP (10 mM), MgSO4 (20 mM), inorganic pyrophosphatase (90 units, endotoxin free), FKP (9 units, endotoxin free) and 30 mU *H. pylori* α(1,3)FucT (endotoxin free). Live cells (1×10$^6$) were then added to the reaction mixtures. After the incubation at 37° C. for 60 min, the cells were washed three times and then blocked in PBS with 2% FBS for 30 min for further application or analysis.

Example 3

Figure 2:
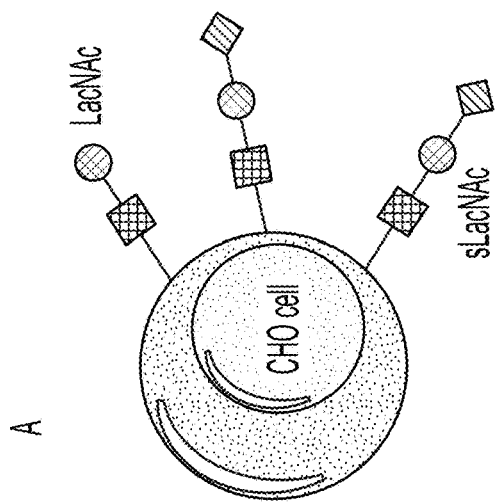
FIG. 2 depicts, in accordance with embodiments herein, in situ one-pot fucosylation of cultured Chinese Hamster Ovary (CHO) cells using crude one-pot GDP-fucose.
Figure 2:
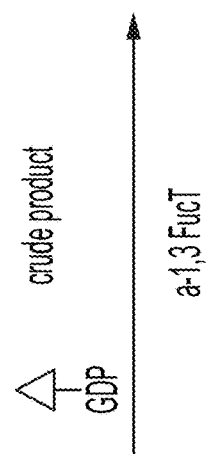
Figure 2:
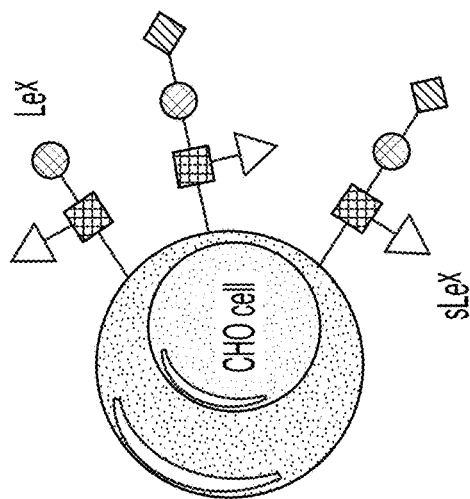
Figure 2:
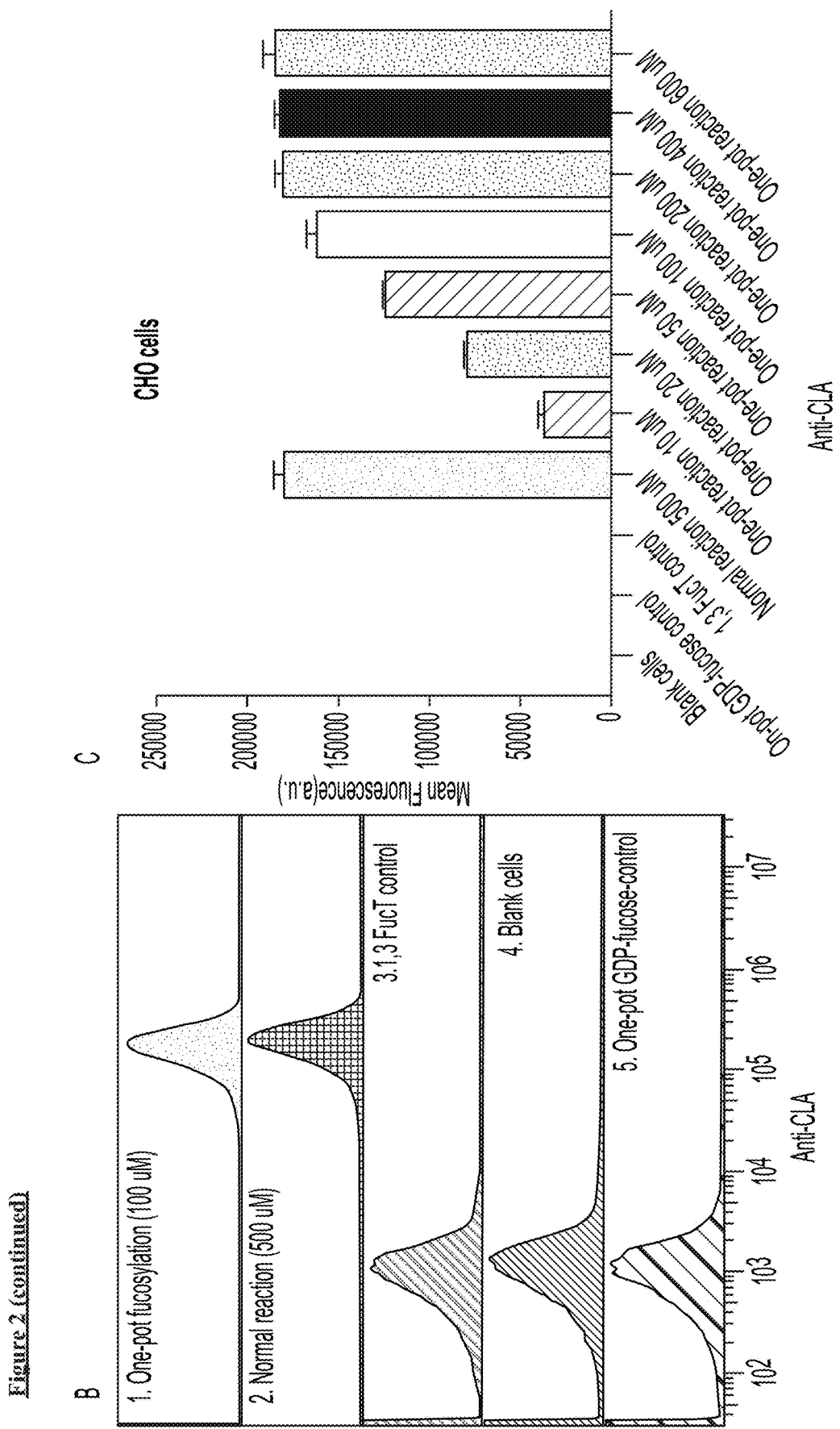
Figure 2:
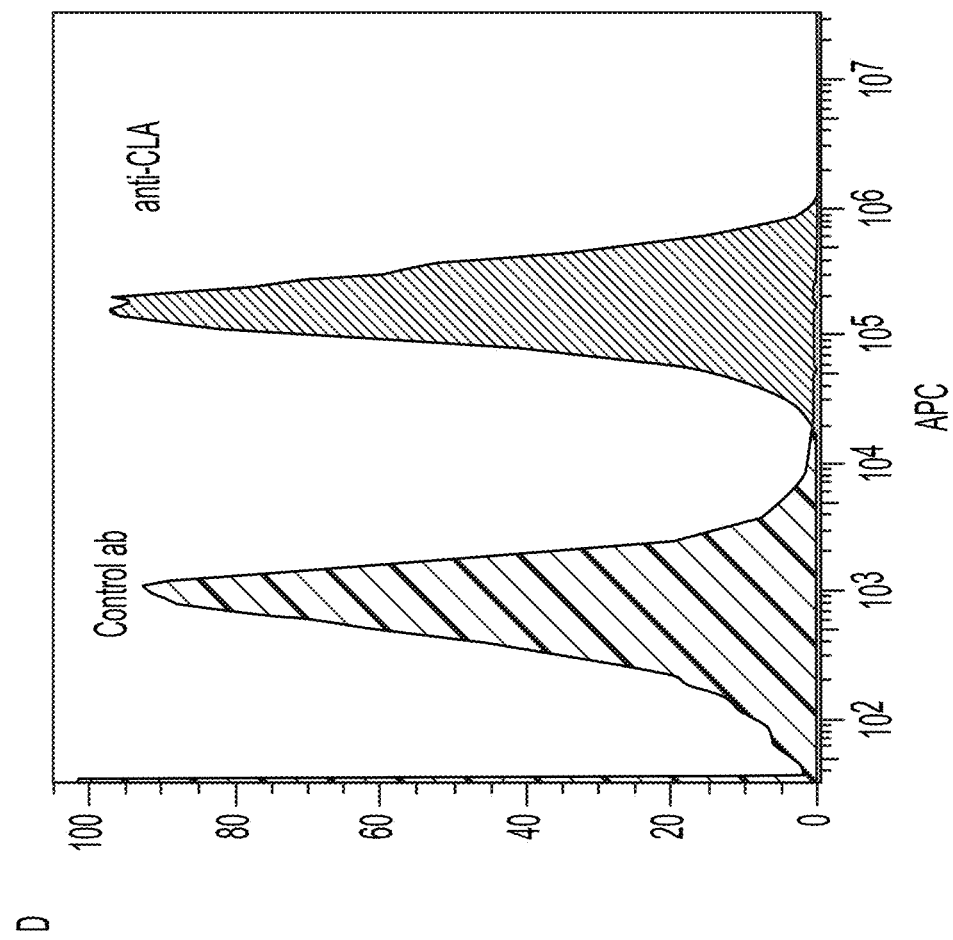

As illustrated in FIG. 2, in one embodiment, one-pot fucosylation reaction was performed on cultured CHO cells. After fucosylation, the cell surface sLacNAc were converted into sLe$^X$, which could be detected through APC conjugated anti-CLA antibody (FIG. 2A). Live CHO cells were washed 3 times with PBS and resuspended in 100 µL fucosylation buffer (containing *H. pylori* α-1,3-FucT) with either purified GDP-fucose (indicates as normal reaction in the figure) or one-pot GDP-fucose. After the incubation at 37° C. for 20 min, the cells were washed, blocked and then stained with APC-anti-CLA. After washing, the samples were analyzed in flow cytometry. As shown in FIGS. 2B and 2C, the fucosylation reaction runs well with one-pot GDP-fucose. The concentration titration indicates that the reaction could be saturated using 100 uM one-pot GDP-fucose, which is identical to purified GDP-fucose according to the results disclosed herein. Control experiments were also characterized without *H. pylori* α-1,3-FucT or GDP-fucose (FIG. 2B), which indicates that the reaction needs both of the reagents. The control antibody staining was shown in FIG. 2D. (FIG. 2C, One-way ANOVA test, between columns, P<0.0001)

Example 4

Figure 3:
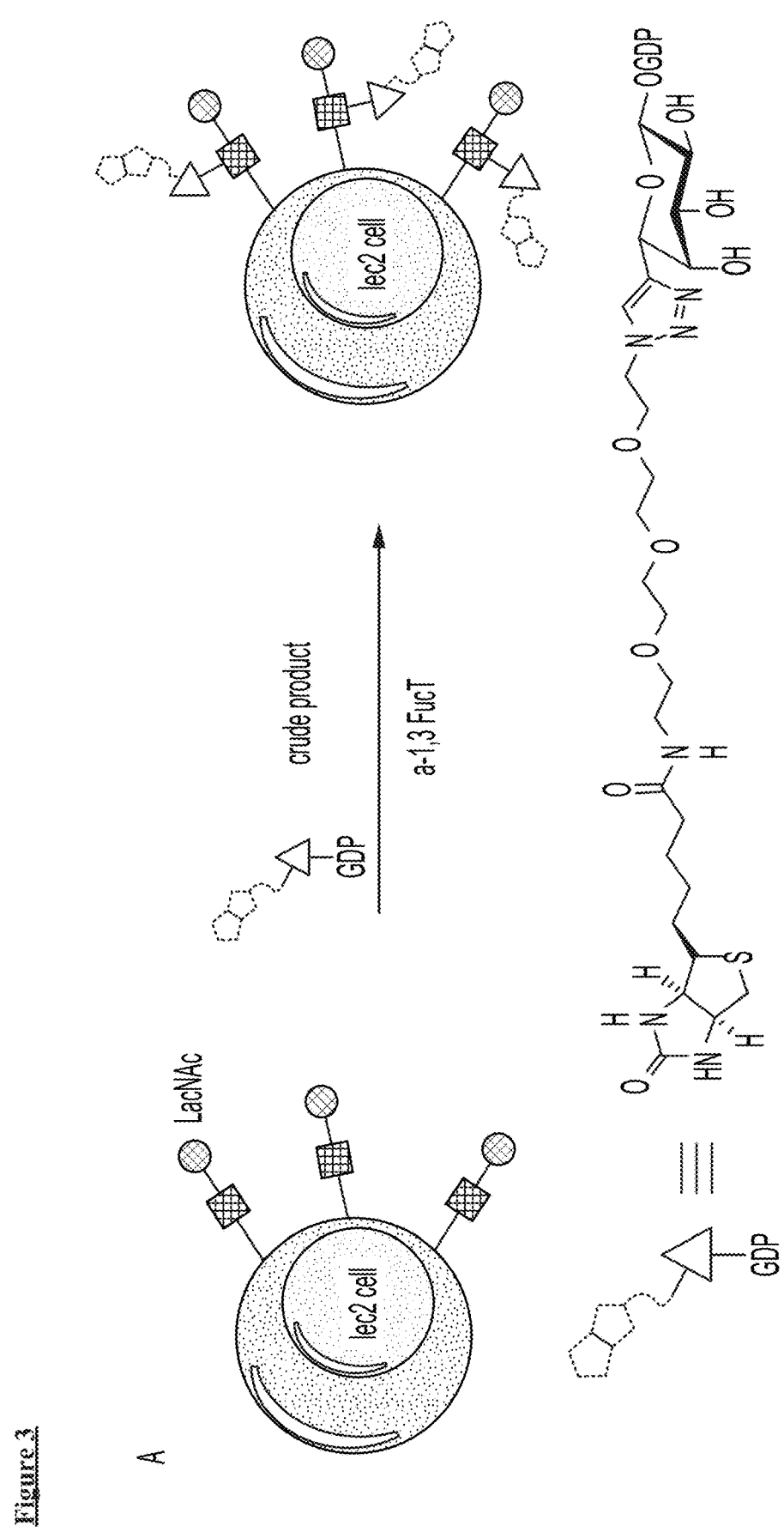
FIG. 3 depicts, in accordance with embodiments herein, modification of cultured Lec2 CHO cell surface using crude one-pot GDP-fucose-biotin.
Figure 3:
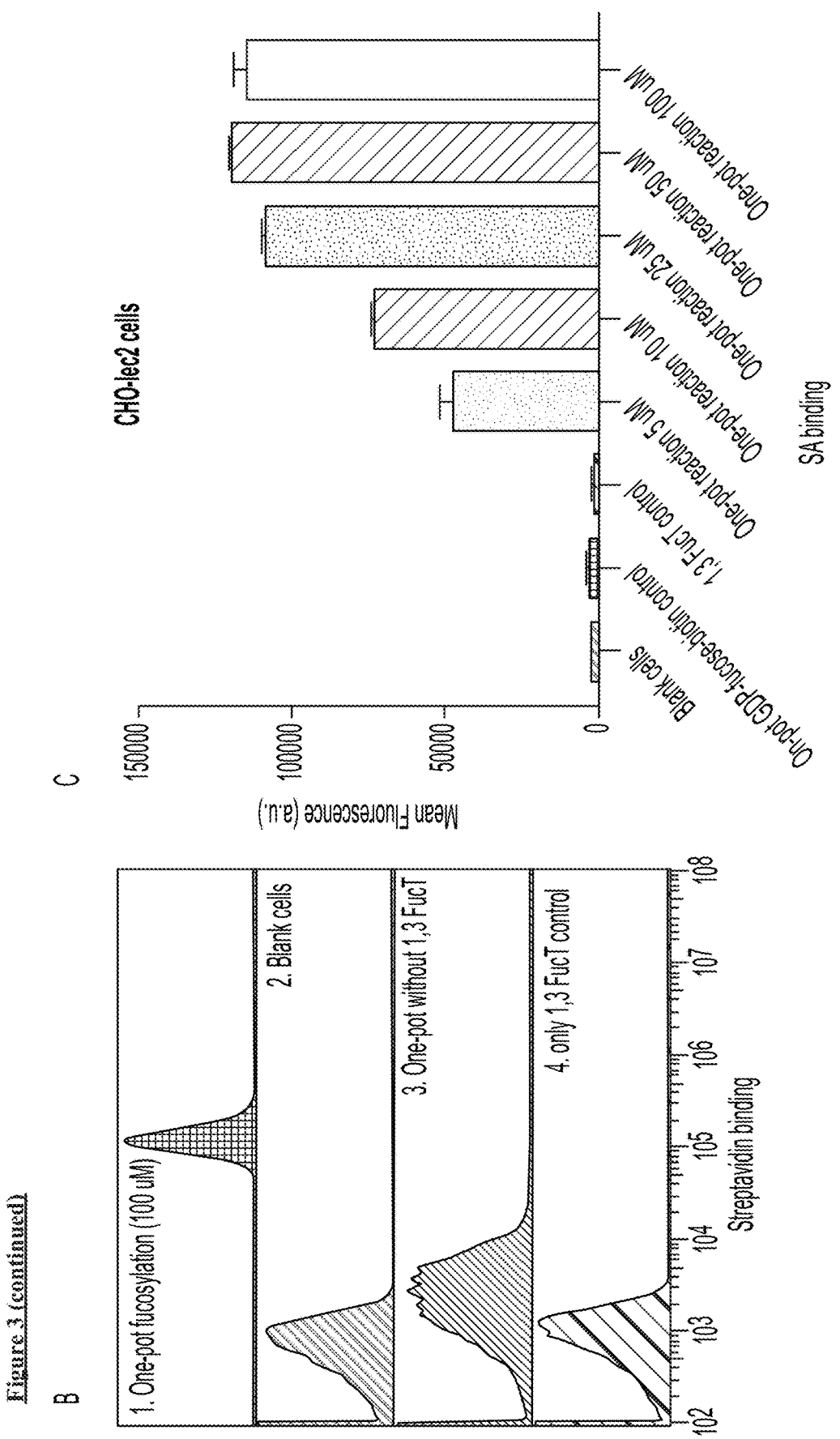
Figure 3:
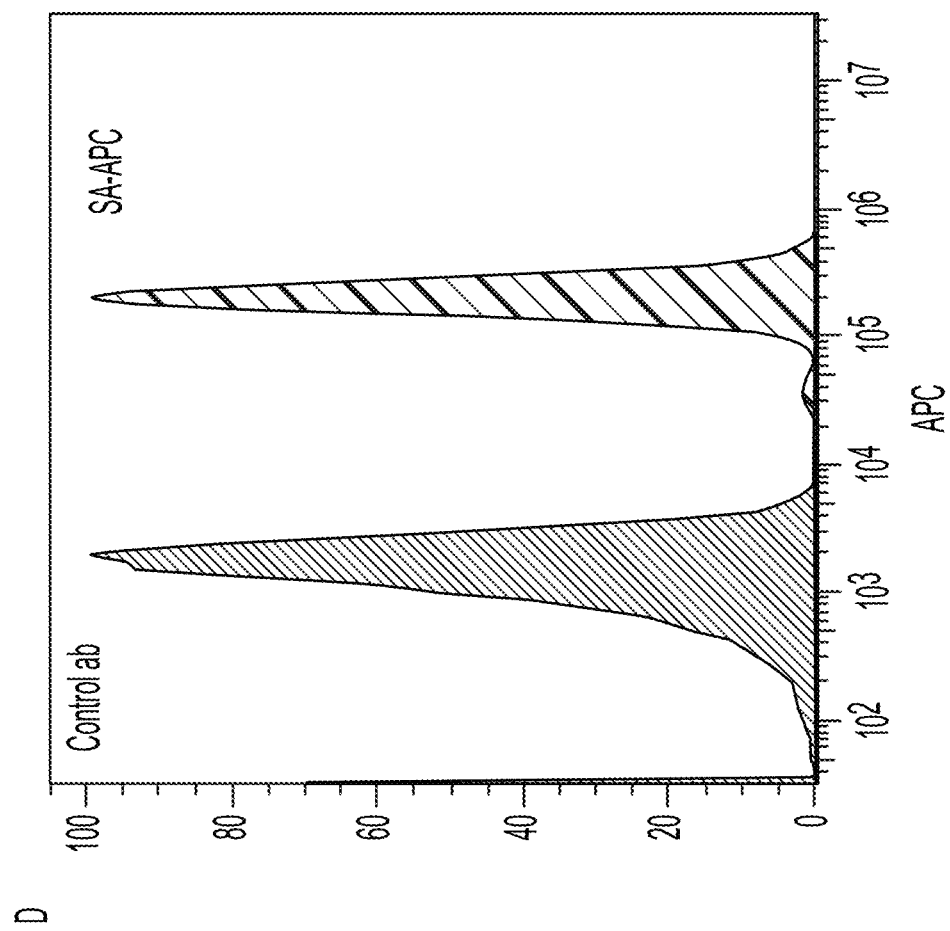

As illustrated in FIG. 3, in one embodiment, one-pot fucosylation reaction was used to modify Lec2 CHO cells (with high level of LacNAc expression) within biotin probe. The GDP-fucose-biotin derivative was synthesized in one-pot according to the procedure in Example 1. One-pot fucosylation reaction was used to modify Lec2 CHO cells (with high level of LacNAc expression) with biotin probe. Using GDP-fucose-biotin as the substrate, the cell surface was fucosylated with biotin molecule, which is specifically located on LacNAc (FIG. 3A). Live lec2 cells were washed 3 times with PBS and resuspended in 100 µL fucosyaltion buffer (containing *H. pylori* α-1,3-FucT) with one-pot GDP-fucose-biotin. After the incubation at 37° C. for 20 min, the cells were washed, blocked and then stained with APC-streptavidin (APC-SA). After washing, the samples were analyzed in flow cytometry. As shown in FIGS. 3B and 3C, the lec2 cells were efficiently labeled with biotin after fucosylation reaction using the one-pot synthesized GDP-fucose-biotin. The concentration titration indicates that saturation concentration is reached when using 50 uM one-pot GDP-fucose-biotin. Control experiments were also characterized without *H. pylori* α-1,3-FucT or GDP-fucose-biotin (FIGS. 3B, 3 and 4), which indicates that the reaction needs both of the reagents. The control antibody staining was shown in FIG. 3D. Other GDP-fucose derivatives could also been synthesized and used to modify cells using the same protocol. This is a general approach to modify cell surface specifically on LacNAc. (FIG. 3C, One-way ANOVA test, between columns, P<0.0001) The biotinylated cells could be further functionalized with SA-conjugated moieties.

Example 5

As illustrated in FIGS. 4-8, cell surfaces may be modified using the one-pot fucosylation reaction strategy disclosed herein.

Figure 4:
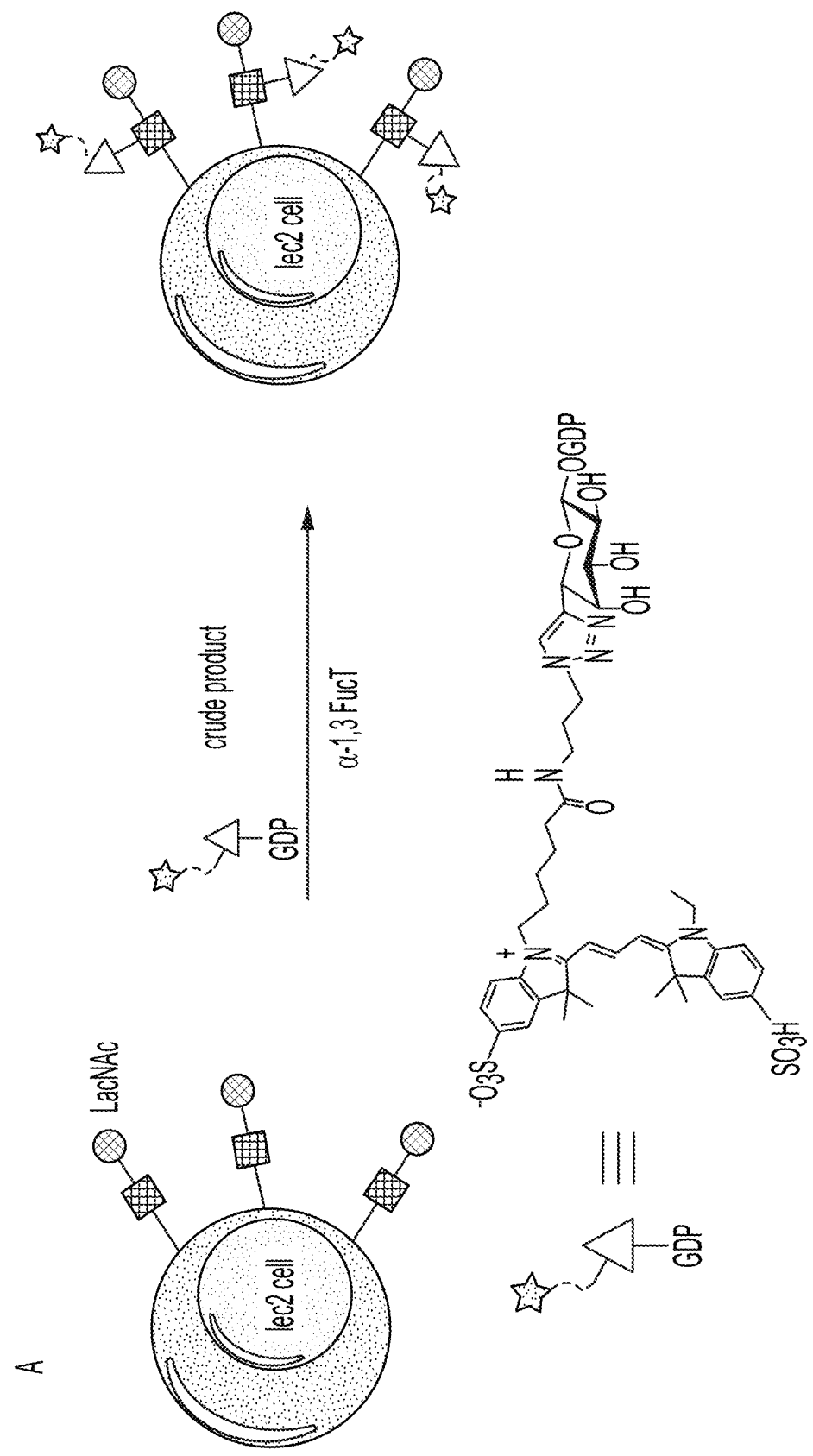
FIG. 4 depicts, in accordance with embodiments herein, modification of cultured Lec2 CHO cell surface using crude one-pot GDP-fucose-Cy3.
Figure 4:
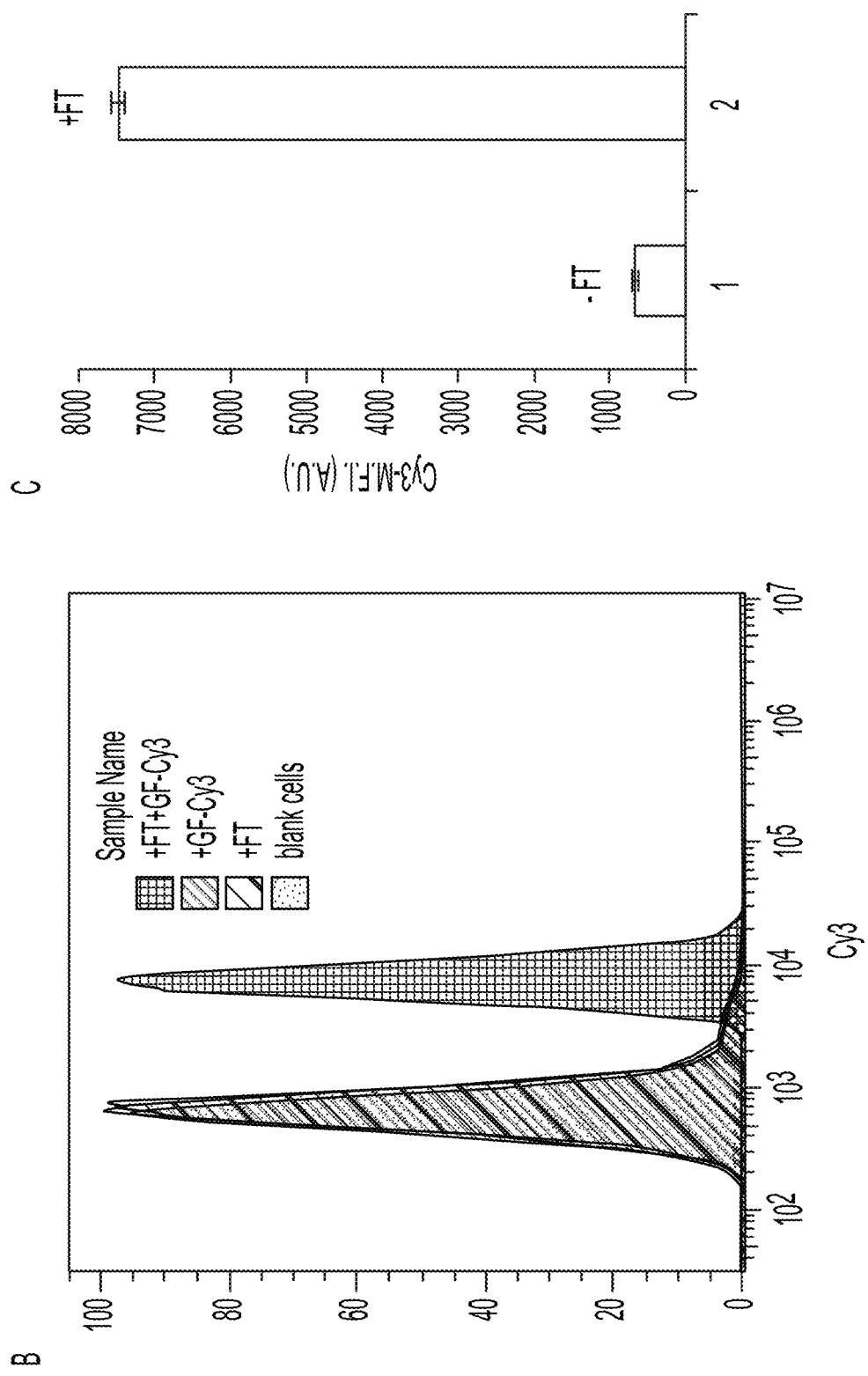

In one embodiment, FIG. 4 illustrates modification of cultured Lec2 CHO cell surface using crude one-pot GDP-fucose-Cy3. In one embodiment, the one-pot fucosylation reaction was used to modify Lec2 CHO cells with fluorescent dye Cy3. GDP-fucose-Cy3 derivatives were synthesized by the one-pot procedure disclosed herein. Using GDP-fucose-Cy3 as substrates, the cell surface was modified with Cy3 probe specifically on LacNAc, which could be directly detected (FIG. 4A). After fucosylation, the samples were analyzed in flow cytometry. As shown in FIGS. 4B and 4C, the Lec2 cells were efficiently labeled with Cy3 probe. Control experiments were also characterized without *H. pylori* α-1,3-FucT or GDP-fucose-Cy3 (FIG. 4B), which indicates that the reaction needs both of the reagents. The Cy3 labeled LacNAc on cell surface could be in situ tracked using confocal microscope.

Example 6

Figure 5:
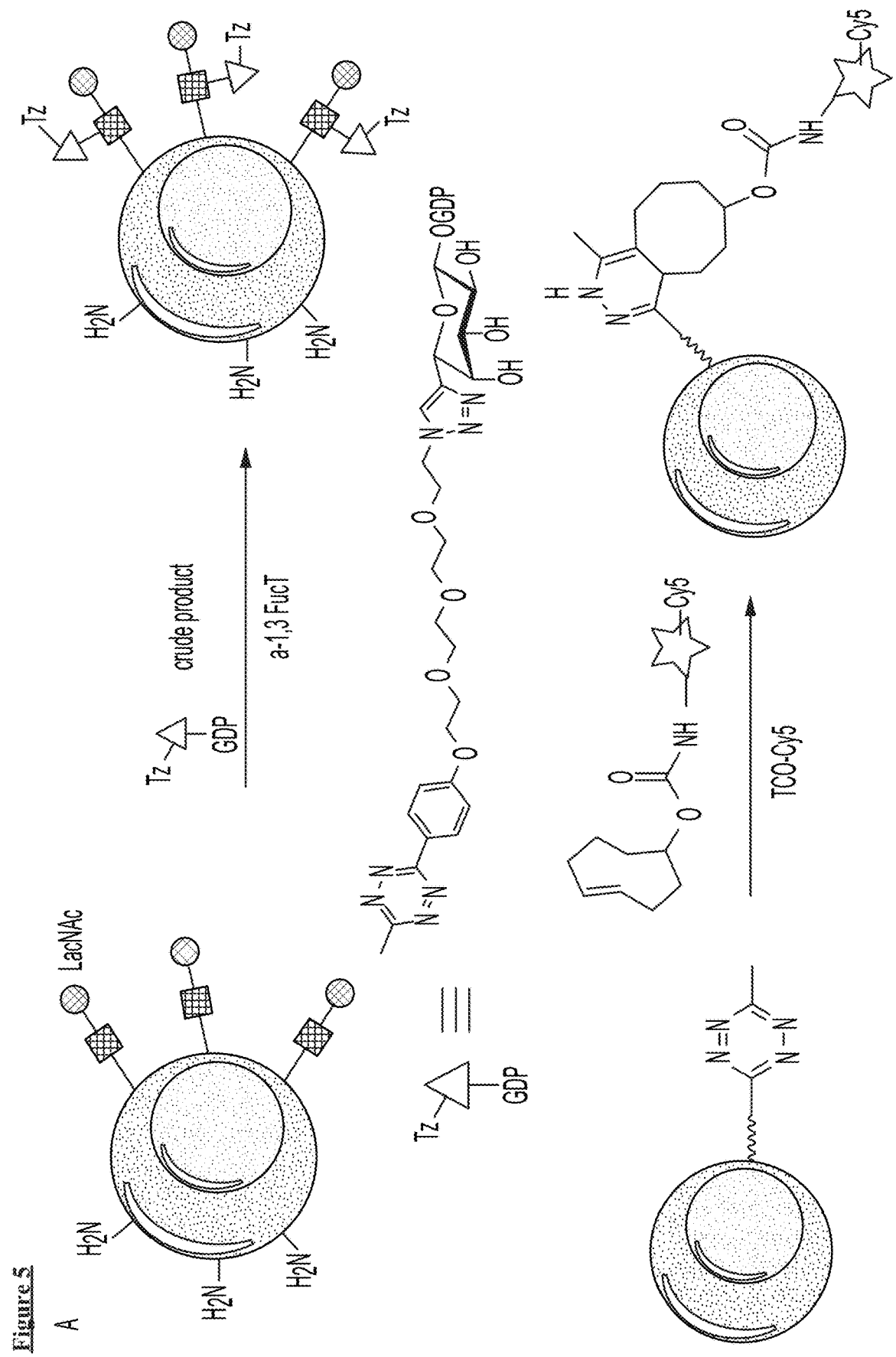
FIG. 5 depicts, in accordance with embodiments herein, modification of cultured Lec2 CHO cell surface using crude one-pot GDP-fucose-tetrazine.
Figure 5:
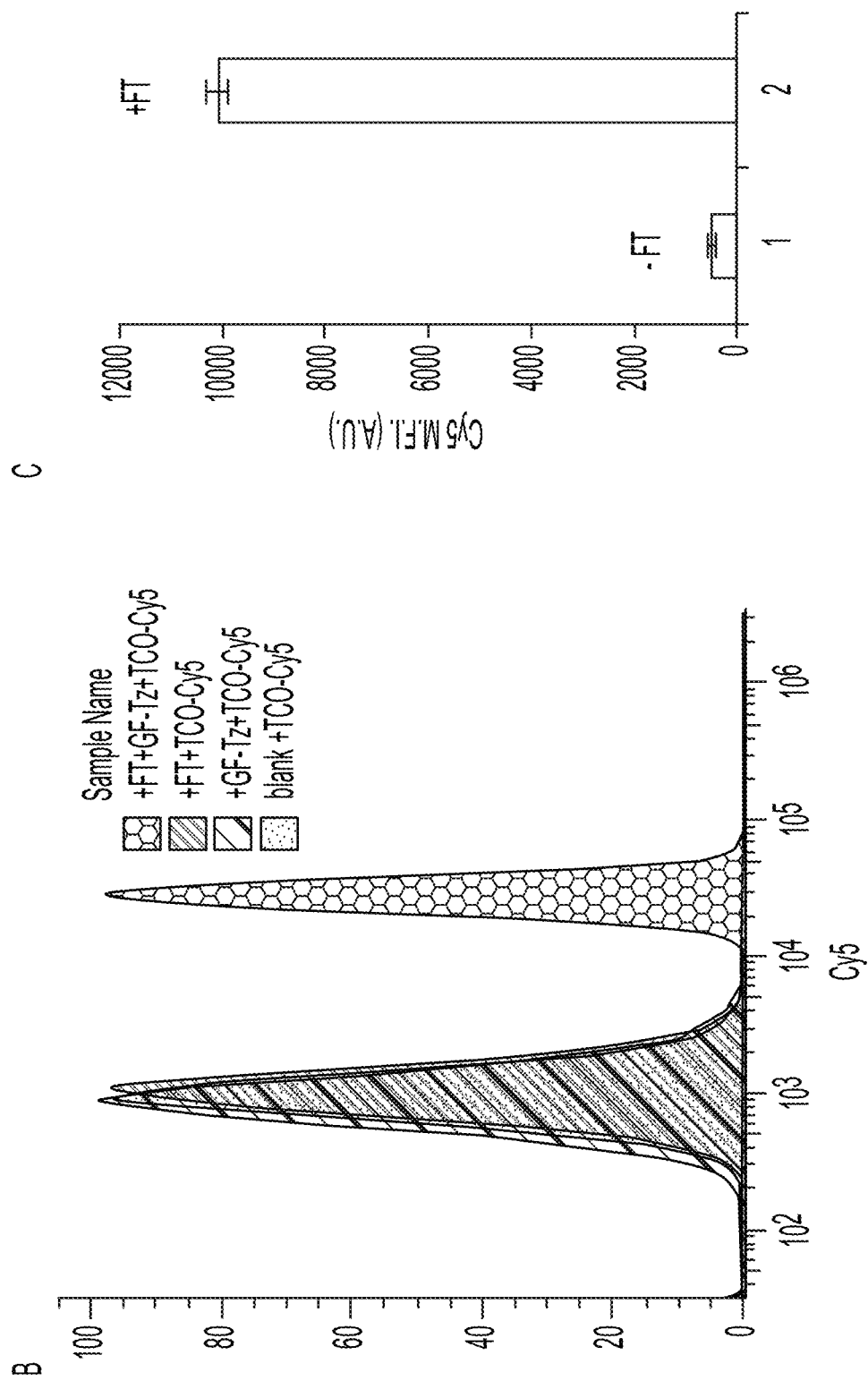

In one embodiment, FIG. 5 illustrates modification of cultured Lec2 CHO cell surface using crude one-pot GDP-fucose-tetrazine. One-pot fucosylation reaction was used to modify CHO-lec 2 cells with the efficient bioorthogonal group, tetrazine (Tz). GDP-fucose-tetrazine derivatives were synthesized by the one-pot procedure according to the procedure in Example 1. Using GDP-fucose-Tz as substrates, the cell surface was functionalized with tetrazine group specifically on LacNAc, which could be further efficiently conjugated with trans-cyclooctene (TCO) through the inverse-electron demand Diels-Alder reaction (inv DA) (FIG. 5A). The fucosylation protocol is the same as in Example 3. After fucosylation, the samples were conjugated with TCO-Cy5 probe for the detection of tetrazine group and then analyzed in flow cytometry. As shown in FIGS. 5B and 5C, the Lec2 cells were efficiently labeled with Cy5 probe. Control experiments were also characterized without 1, 3 FucT or GDP-fucose-Tz (FIG. 5B), which indicates that the reaction needs both of the reagents.

Example 7

Figure 6:
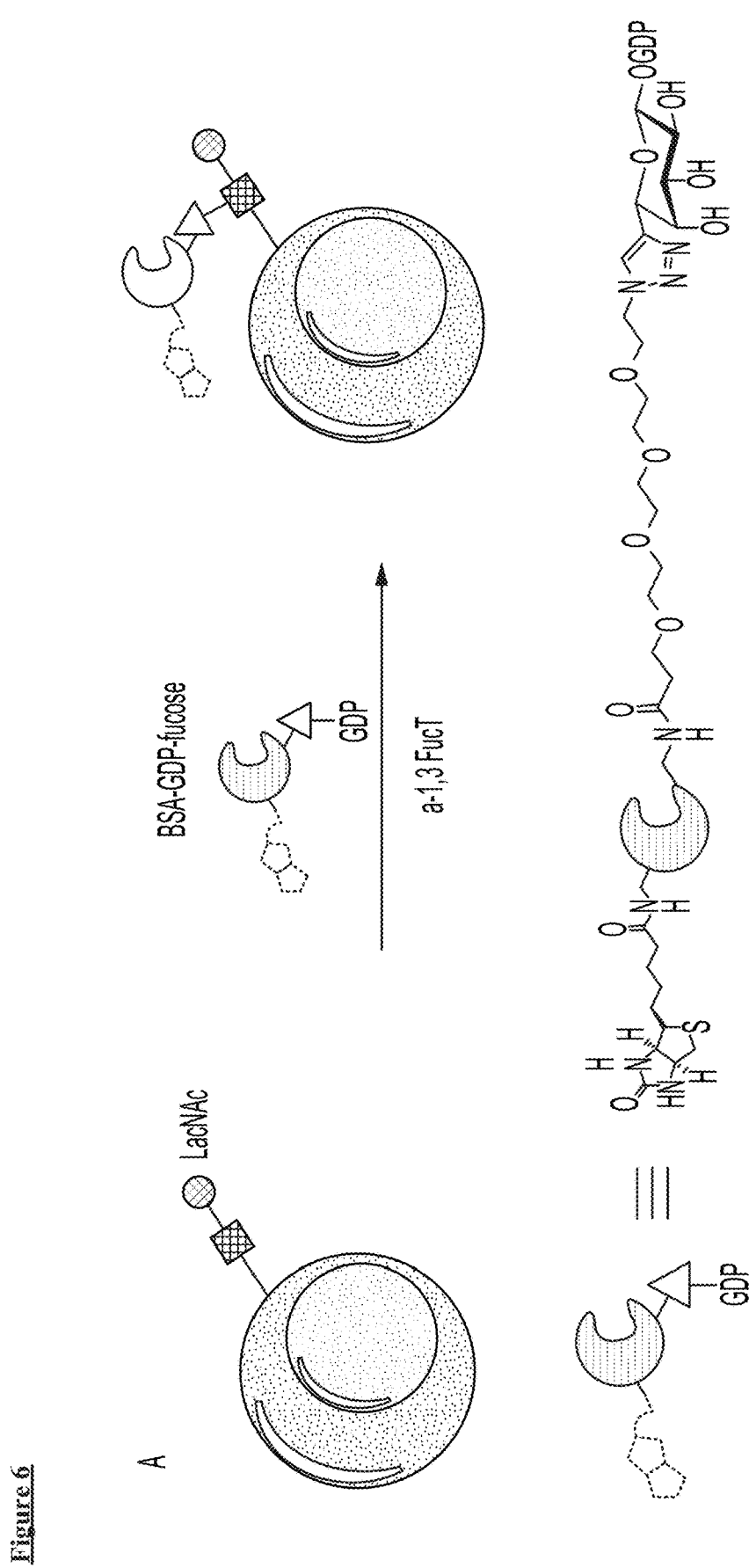
FIG. 6 depicts, in accordance with embodiments herein, modification of cultured Lec2 CHO cell surface using crude one-pot GDP-fucose-BSA.
Figure 6:
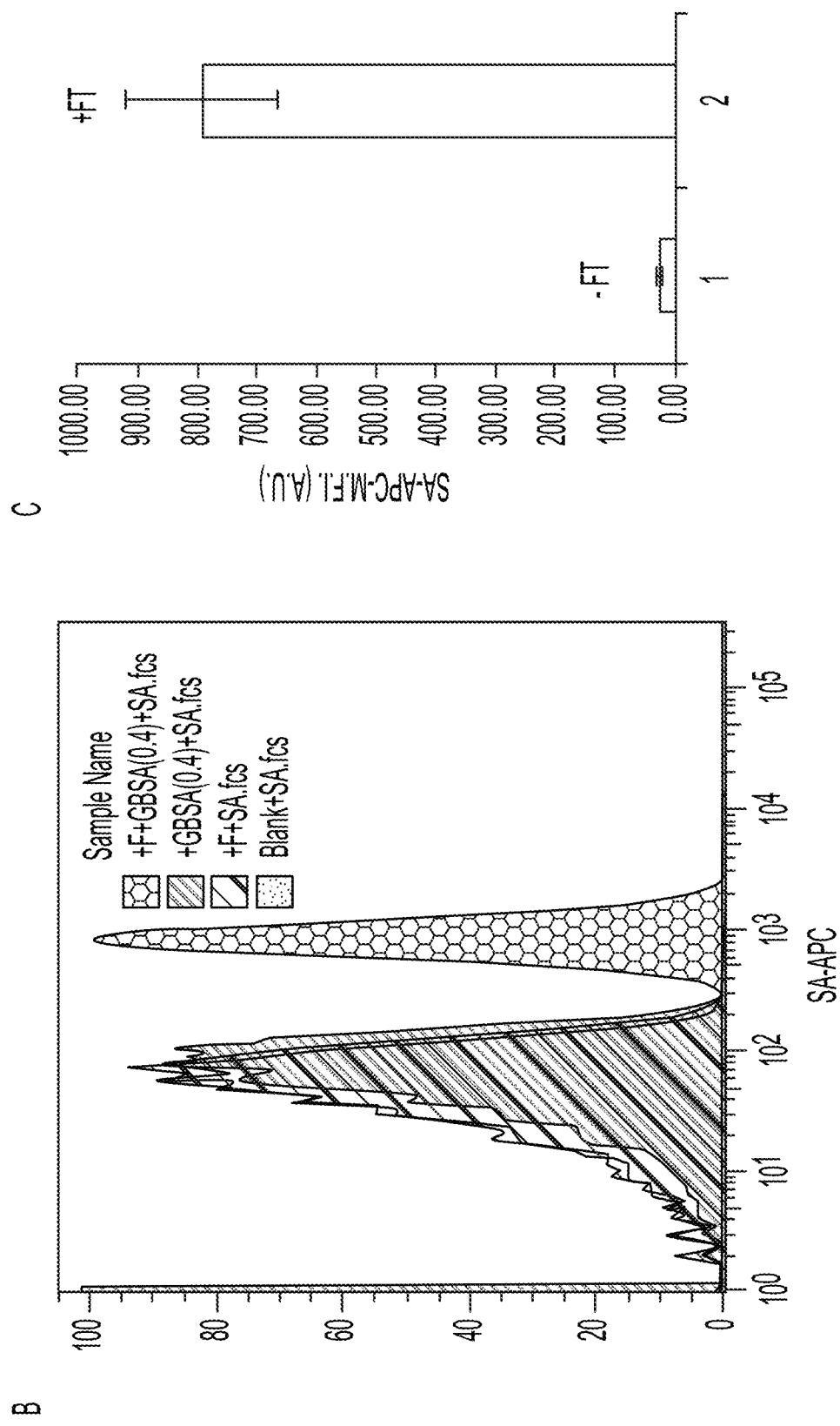

In one embodiment, FIG. 6 illustrates modification of cultured Lec2 CHO cell surface using crude one-pot GDP-fucose-BSA. One-pot fucosylation reaction was used to modify CHO-lec 2 cells with model BSA protein. BSA protein was first reacted with the NHS-biotin and NHS-azide probe. The azide groups on the BSA protein were then reacted with GDP-fucose-alkyne probes through CuAAC reaction. After reaction, the mixture was quenched with BCS and then desalted. Using GDP-fucose-BSA as substrates, the cell surface was conjugated with BSA protein specifically on LacNAc (FIG. 6A). GDP-fucose-BSA concentration was 0.4 mg/ml in this example. After fucosylation, the samples were stained with APC-SA to detect the biotin probe on BSA protein and then analyzed in flow cytometry. As shown in FIGS. 6B and 6C, the lec2 cells were efficiently labeled with BSA protein. Control experiments were also characterized without *H. pylori* α-1,3-FucT or GDP-fucose-BSA (FIG. 6B), which indicates that the reaction needs both of the reagents.

Example 8

Figure 7:
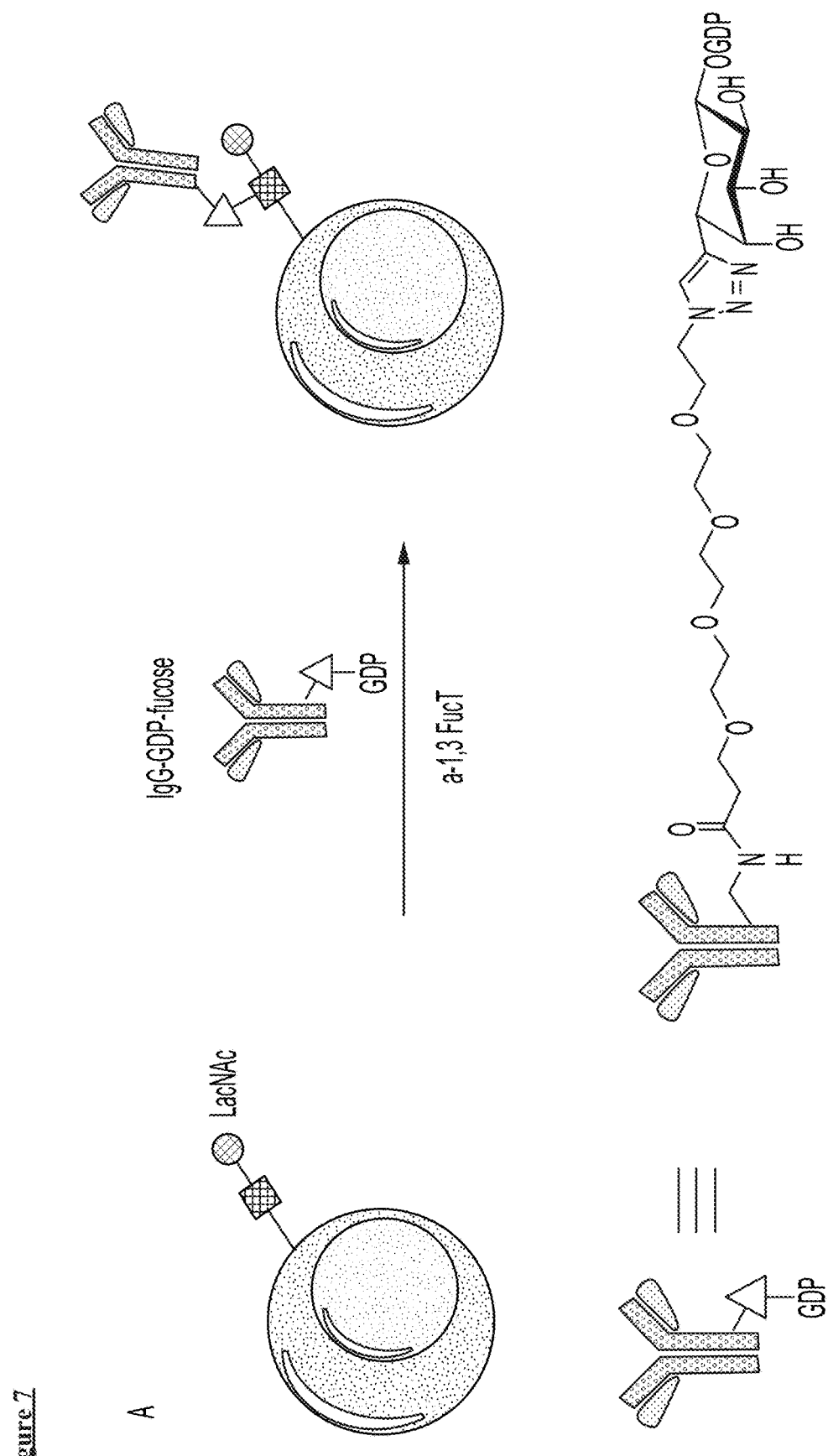
FIG. 7 depicts, in accordance with embodiments herein, modification of cultured Lec2 CHO cell surface using crude one-pot GDP-fucose-antibody.
Figure 7:
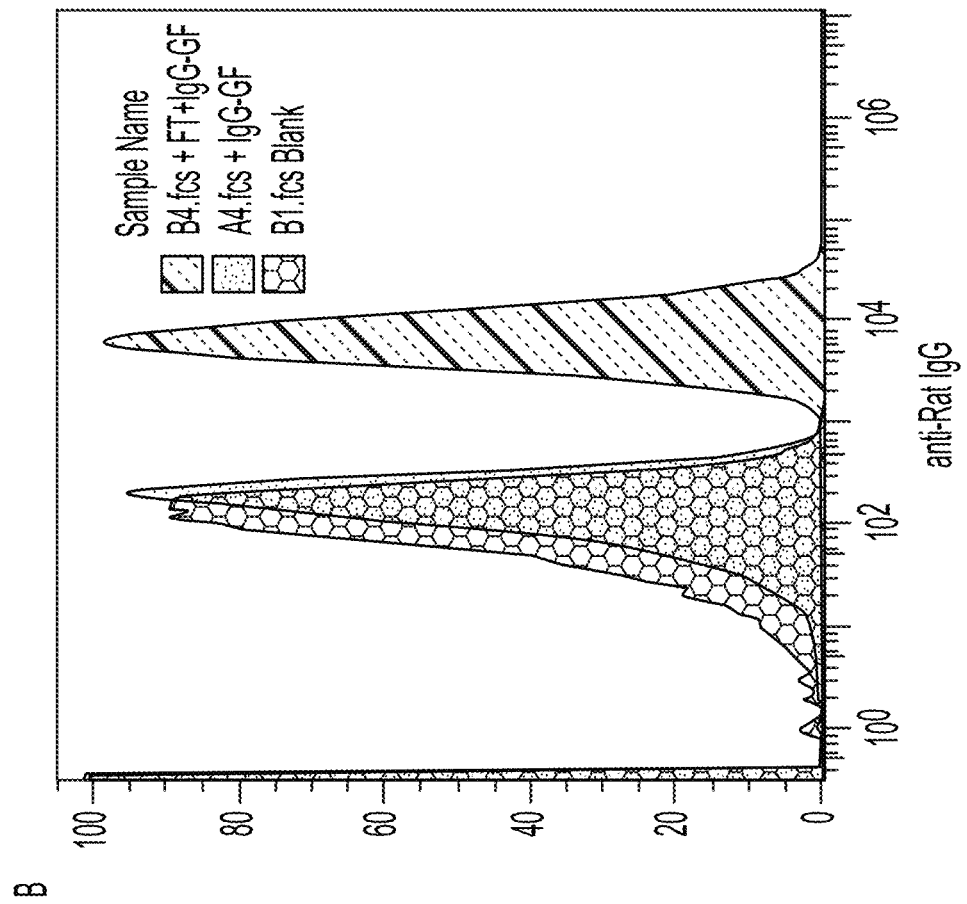

In one embodiment, FIG. 7 illustrates modification of cultured Lec 2 CHO cell surface using crude one-pot GDP-fucose-antibody. One-pot fucosylation reaction was used to modify Lec 2 CHO cells with antibodies. The rat IgG was first reacted with the NHS-azide probe. The azide groups on the rat IgG were then reacted with GDP-fucose-alkyne probes through CuAAC reaction. After reaction, the mixture was quenched with BCS and then desalted. Using GDP-fucose-IgG as substrates, the cell surface was conjugated with rat IgG specifically on LacNAc (FIG. 7A). GDP-fucose-IgG concentration is 0.2 mg/ml in this example. After fucosylation, the samples were stained with APC-anti-Rat IgG to detect the rat IgG and then analyzed in flow cytometry. As shown in FIGS. 7B and 7C, the lec2 cells were efficiently labeled with rat-IgG. Control experiments were also characterized without *H. pylori* α-1,3-FucT (FIG. 6B).

Example 9

Figure 8:
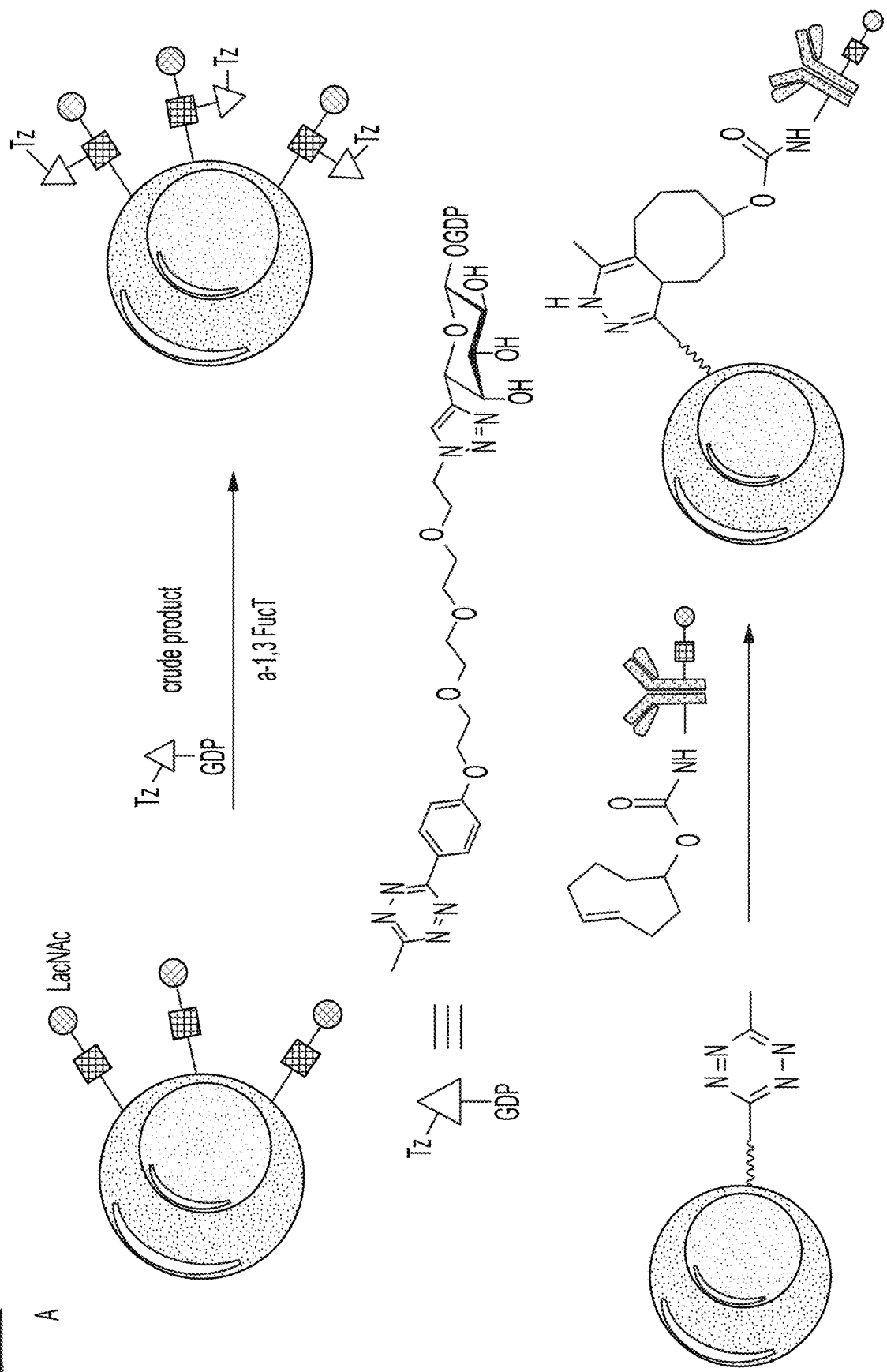
FIG. 8 depicts, in accordance with embodiments herein, modification of cultured Lec2 CHO cell surface using crude one-pot GDP-fucose-Tz and subsequent TCO-antibody.
Figure 8:
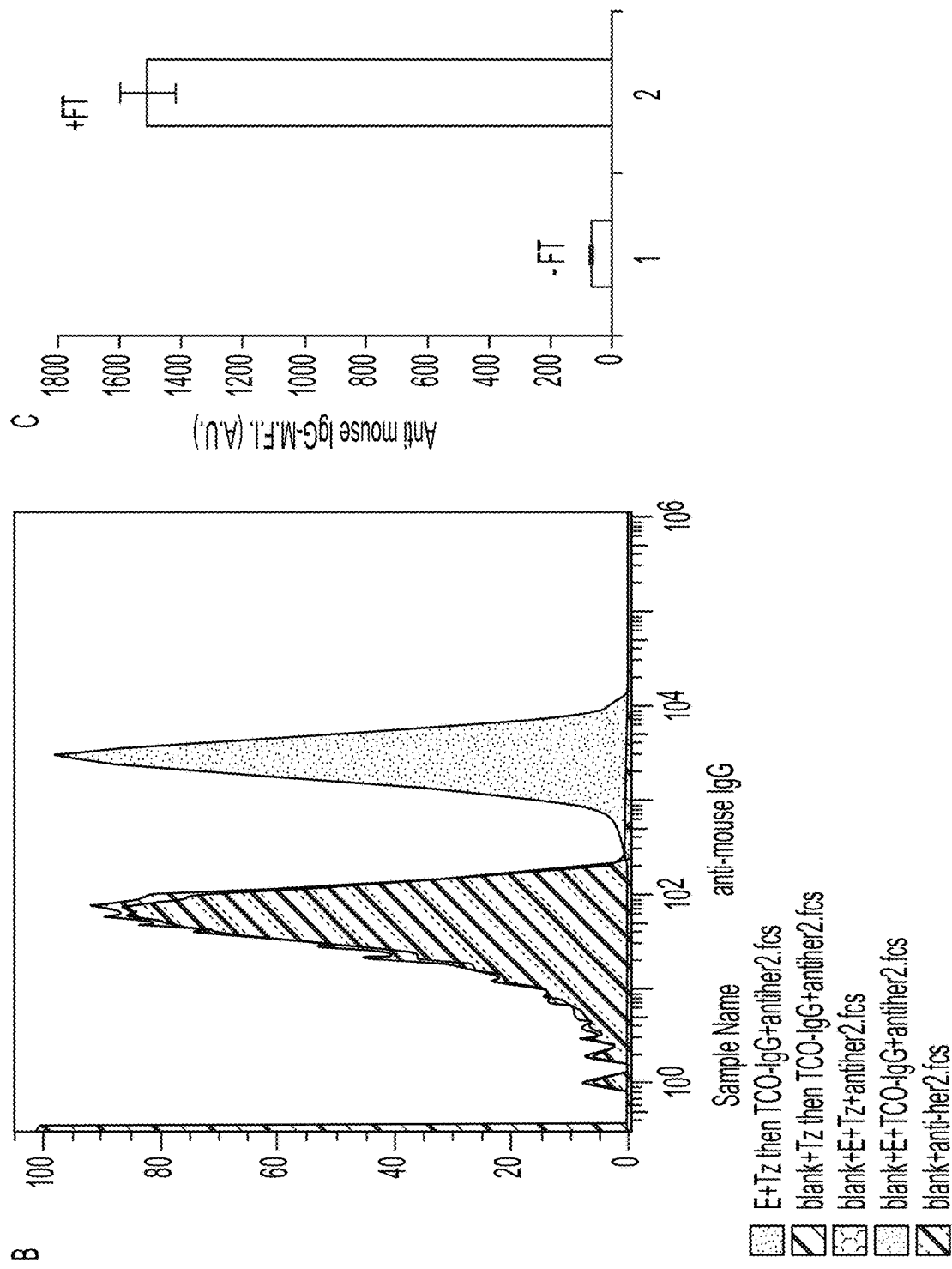

In one embodiment, FIG. 8 illustrates modification of cultured Lec2 CHO cell surface using crude one-pot GDP-fucose-Tz and subsequent TCO-antibody. As described above in Example 5, the CHO cell surface was functionalized with tetrazine group specifically on LacNAc. After fucosylation, the samples were reacted with 0.1 mg/ml TCO-mouse IgG for 20 min in room temperature (FIG. 8A). The TCO-IgG protein was first prepared by label IgG with NHS-TCO group. After conjugated with mouse IgG antibody, the cells were stained with APC-anti-mouse IgG and then analyzed by FACS. As shown in FIGS. 8B and 8C, the lec2 cells were efficiently labeled with mouse IgG. Control experiments were also characterized without *H. pylori* α-1,3-FucT or GDP-fucose-Tz (FIG. 5B), which indicated that the reaction needs both of the reagents. This example shows that the cells functionalized with tetrazine can be easily modified by TCO-moieties.

Example 10

As illustrated in FIGS. 9-14, cell surfaces may be modified using the one-pot fucosylation reaction strategy disclosed herein.

Figure 9:
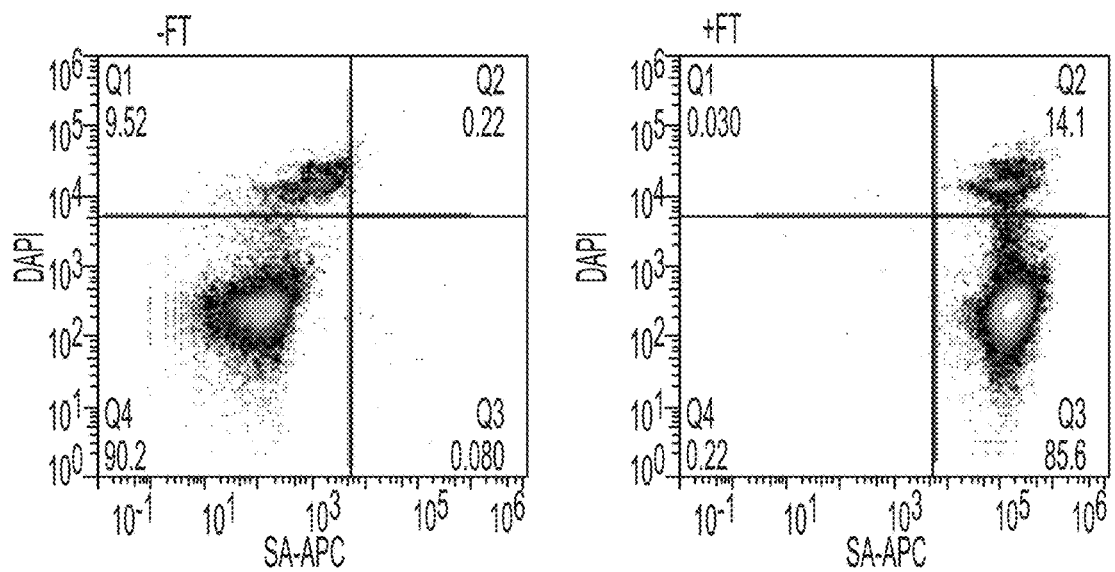
FIG. 9 depicts, in accordance with embodiments herein, modification of cultured wild type CHO cells surface using crude one-pot GDP-fucose-biotin.

In one embodiment, FIG. 9 illustrates modification of cultured wild type CHO cells surface using crude one-pot GDP-fucose-biotin. To illustrate the general applicability, one-pot fucosylation reaction was used to modify wild type CHO cells with biotin probe using the protocol disclosed in Example 3. After fucosylation and staining with SA-APC, the samples were analyzed in flow cytometry. As shown in FIG. 9, the CHO cells were efficiently labeled with biotin.

Example 11

Figure 10:
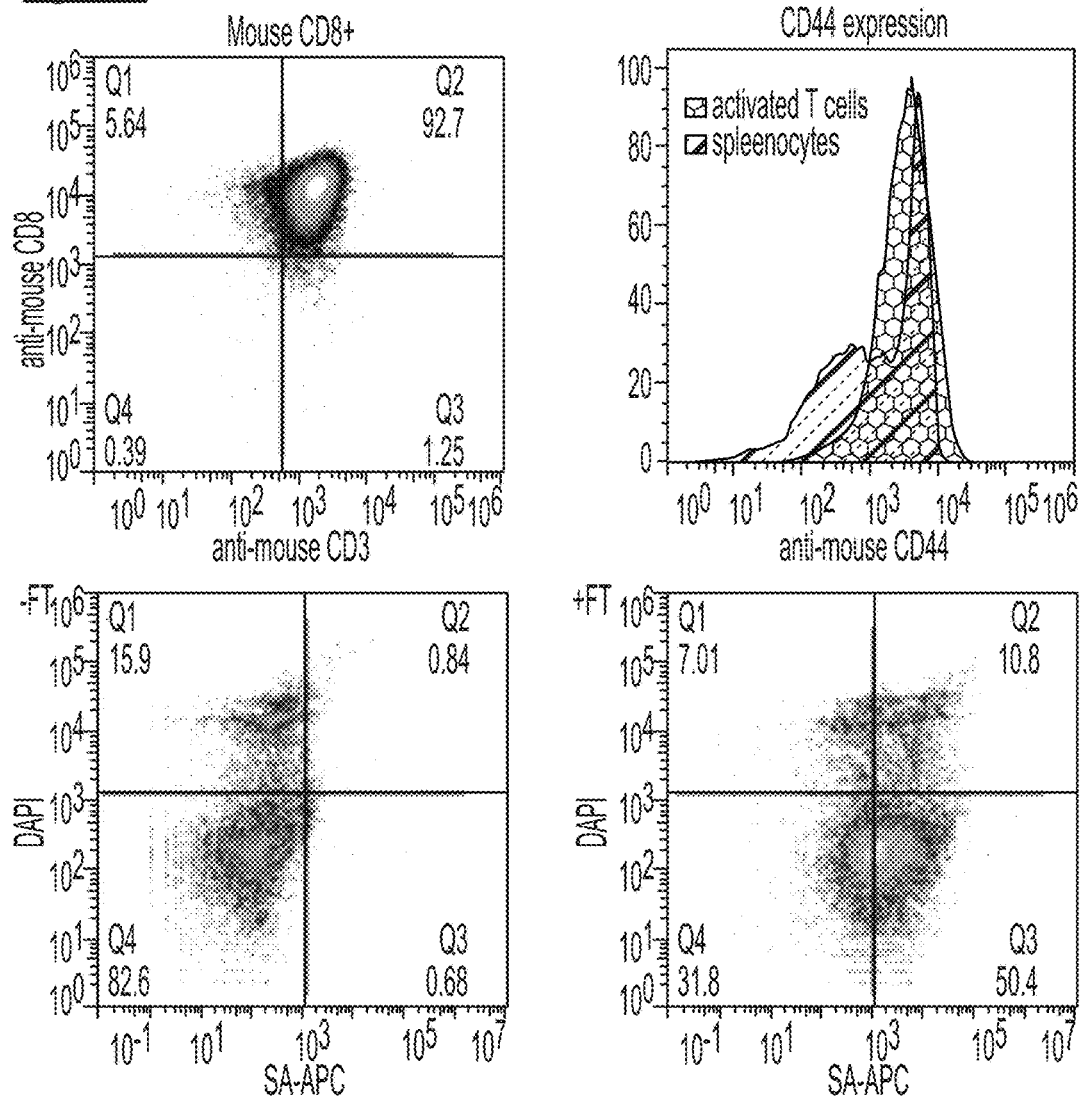
FIG. 10 depicts, in accordance with embodiments herein, modification of activated mouse CD8+ cells surface using crude one-pot GDP-fucose-biotin.

In one embodiment, FIG. 10 illustrates modification of activated mouse CD8+ cells surface using crude one-pot GDP-fucose-biotin. To further illustrate the general applicability, one-pot fucosylation reaction was used to modify activated mouse CD8+ T cells with biotin probe. The phenotype of the cells was characterized first (FIG. 10). Most of the cells are CD3+CD8+ cells. The CD44 high expression indicates the activation of the T cells. The cells were fucosylated and stained with SA-APC, and subsequently the samples were analyzed in flow cytometry. As shown in FIG. 10, the mouse CD8+ T cells were efficiently labeled with biotin.

Example 12

Figure 11:
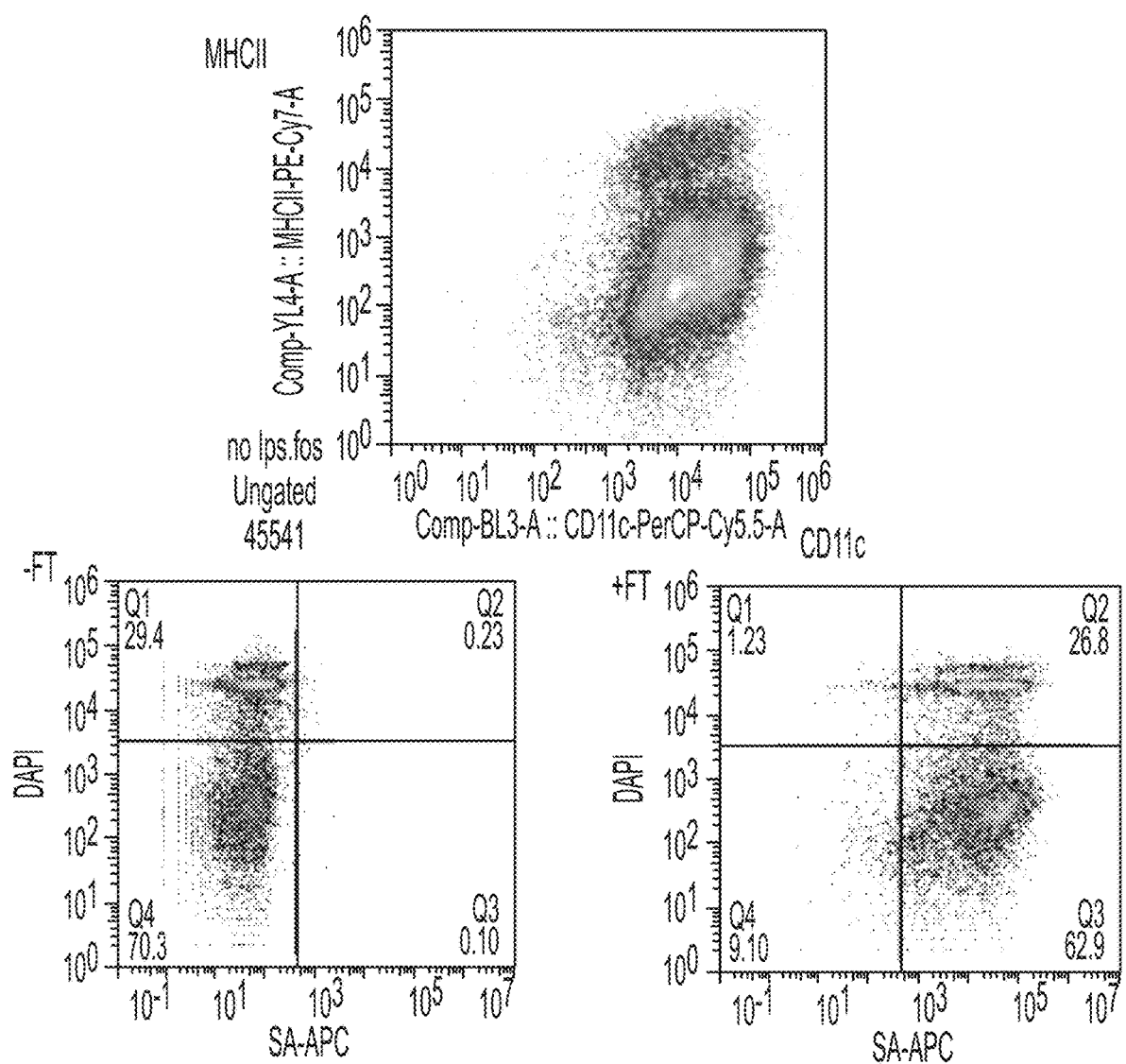
FIG. 11 depicts, in accordance with embodiments herein, modification of mouse dendritic cell (DC) surface using crude one-pot GDP-fucose-biotin.

In one embodiment, FIG. 11 illustrates modification of mouse dendritic cell (DC) surface using crude one-pot GDP-fucose-biotin. To further illustrate the general applicability, one-pot fucosylation reaction was used to modify mouse DC cells with biotin probe. The phenotype of the cells was characterized first (FIG. 11). Most of the cells are CD11c+ cells. After fucosylation and staining with SA-APC, the samples were analyzed in flow cytometry. As shown in FIG. 11, the DC cells were efficiently labeled with biotin.

Example 13

Figure 12:
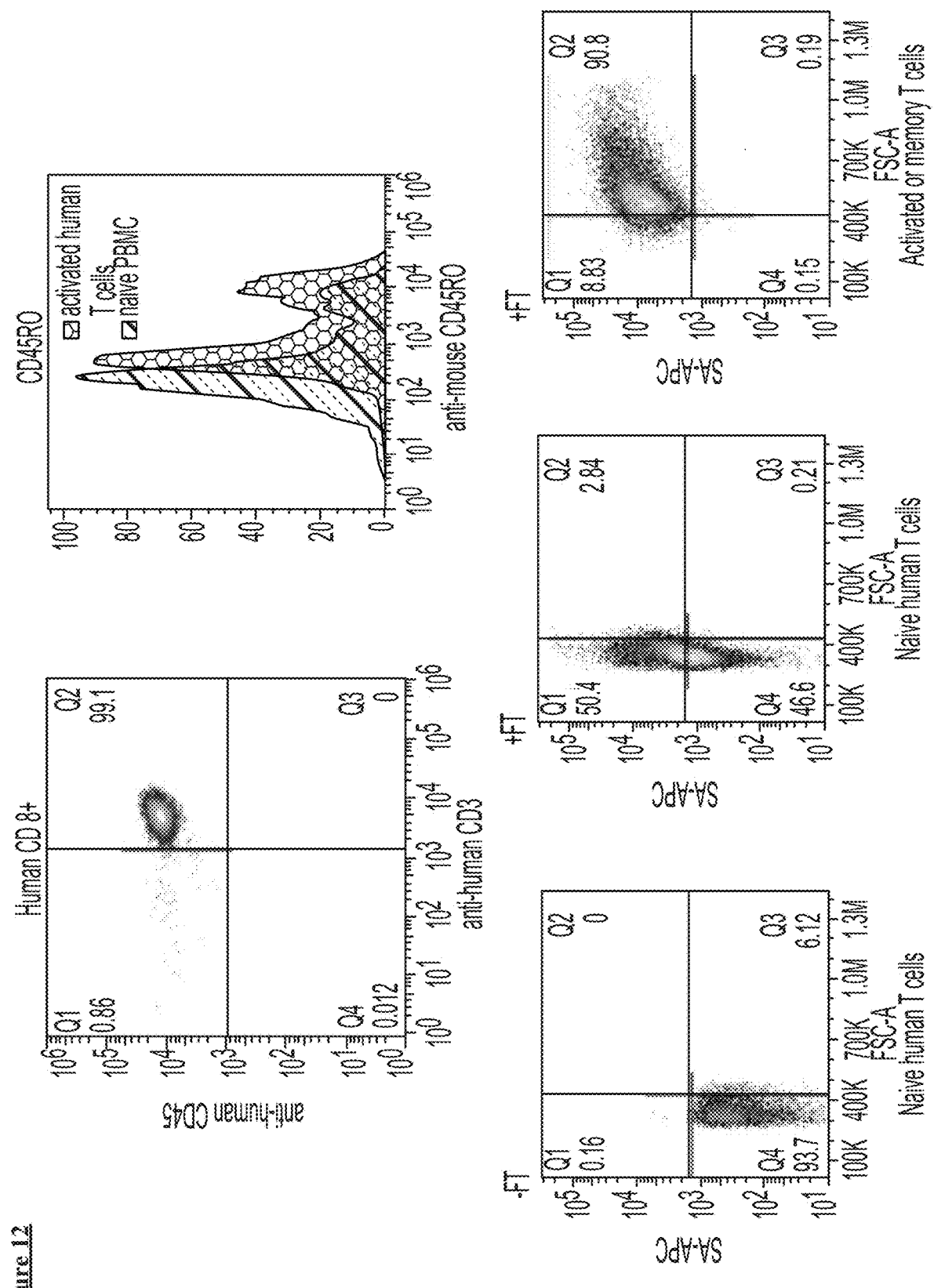
FIG. 12 depicts, in accordance with embodiments herein, modification of naïve or activated human CD8+ T cell surface using crude one-pot GDP-fucose-biotin.

In one embodiment, FIG. 12 illustrates modification of naïve or activated human CD8+ T cell surface using crude one-pot GDP-fucose-biotin. To further illustrate the general applicability, one-pot fucosylation reaction was used to modify human CD8+ T cells with biotin probe. The phenotype of the cells was characterized first (FIG. 12). Most of the cells were CD3+CD8+ cells. The CD45RO high expression indicates the activation of the T cells. After fucosylation and staining with SA-APC, the samples were analyzed in flow cytometry. As shown in FIG. 12, both the naïve and activated human CD 8+ T cells were labeled with biotin. The activated human CD8+ T cells have higher LacNAc level and were labeled more efficiently.

Example 14

Figure 13:
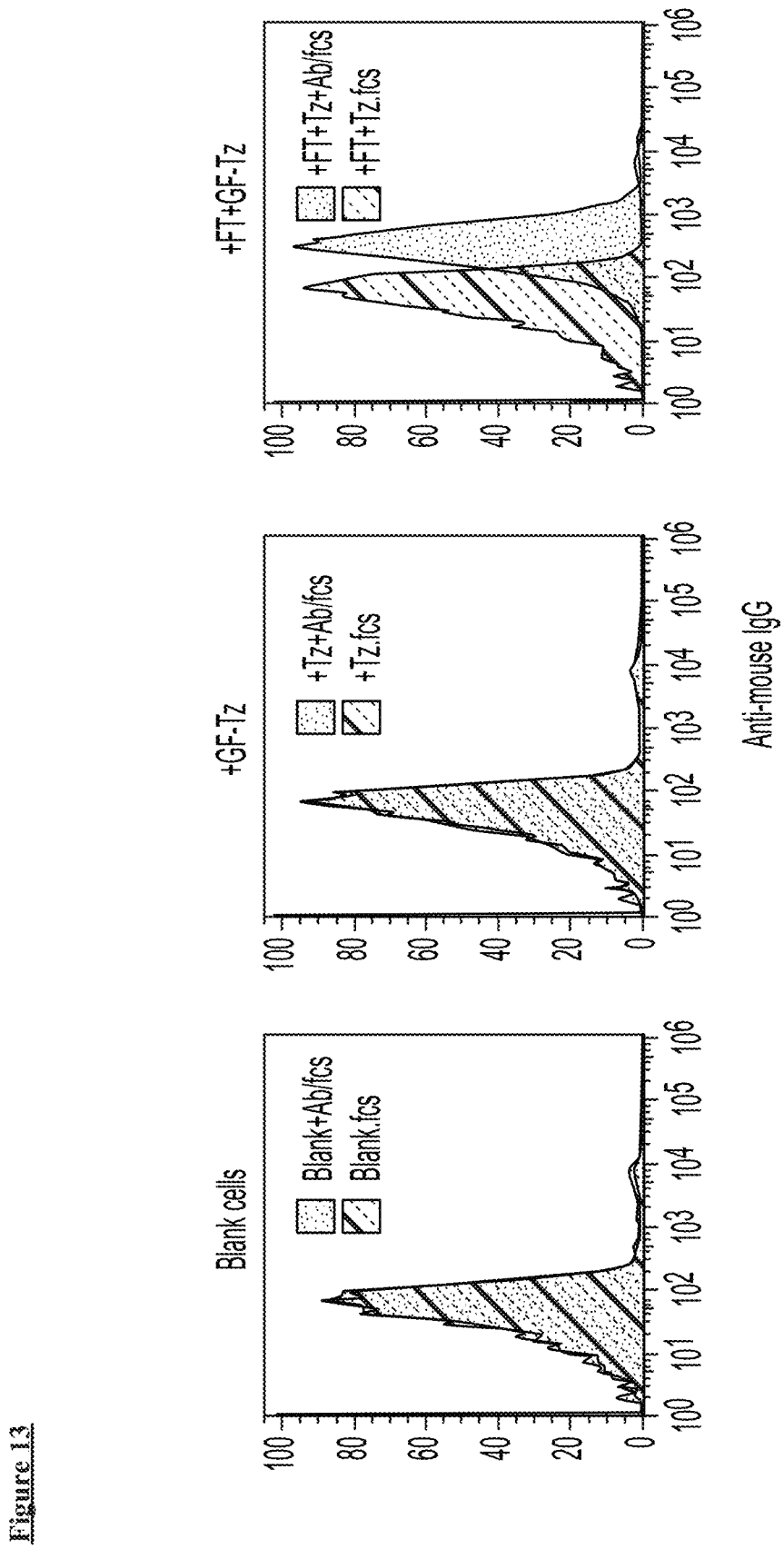
FIG. 13 depicts, in accordance with embodiments herein, modification of activated mouse CD8+ T cell surface using crude one-pot GDP-fucose-Tz and then conjugated with TCO-mouse IgG.

FIG. 13 illustrates one embodiment of the modification of activated mouse CD8+ T cell surface using crude one-pot GDP-fucose-Tz and then conjugated with TCO-mouse IgG. To illustrate the general applicability, one-pot fucosylation reaction was used to install IgG onto activated mouse CD8+ cells surface. The phenotype of the cells was characterized, followed by fucosylation. After fucosylation with GDP-fucose-Tz, the cells were then conjugated with TCO-mouse IgG. After that, the cells were staining with APC-anti-mouse IgG and then analyzed in flow cytometry. As shown in FIG. 13, the CD 8+ T cells were efficiently labeled with mouse IgG. Control experiments were also characterized without α-1,3 FucT (FIG. 13), which indicates that the labeling is based on unnatural fucosylation. The TCO-IgG does not have non-specific binding (FIG. 13).

Example 15

Figure 14:
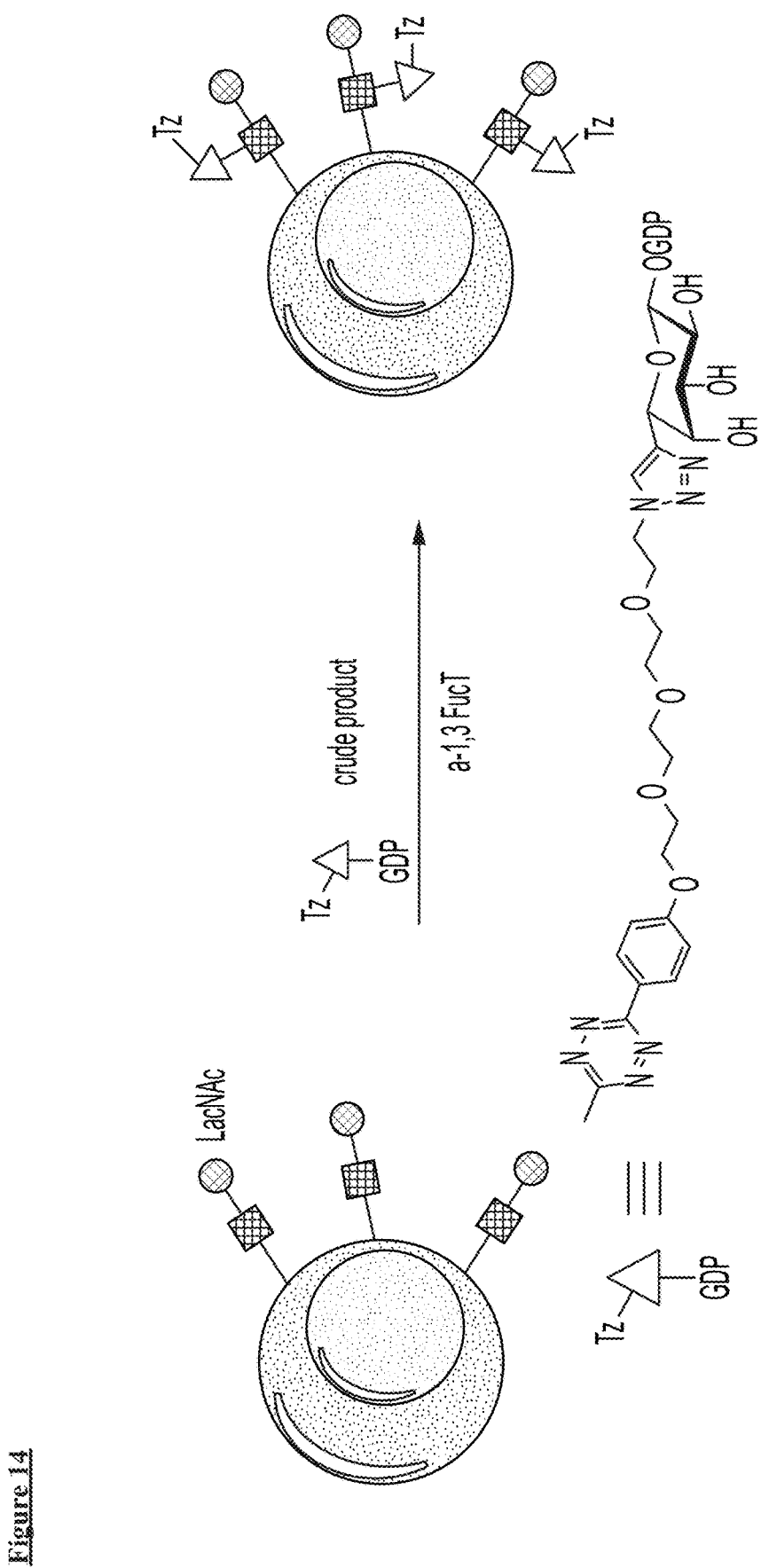
FIG. 14 depicts, in accordance with embodiments herein, modification of activated mouse CD8+ T cell surface using crude one-pot GDP-fucose-Tz and then conjugated with TCO-mouse IgG and TCO-rat IgG together.
Figure 14:
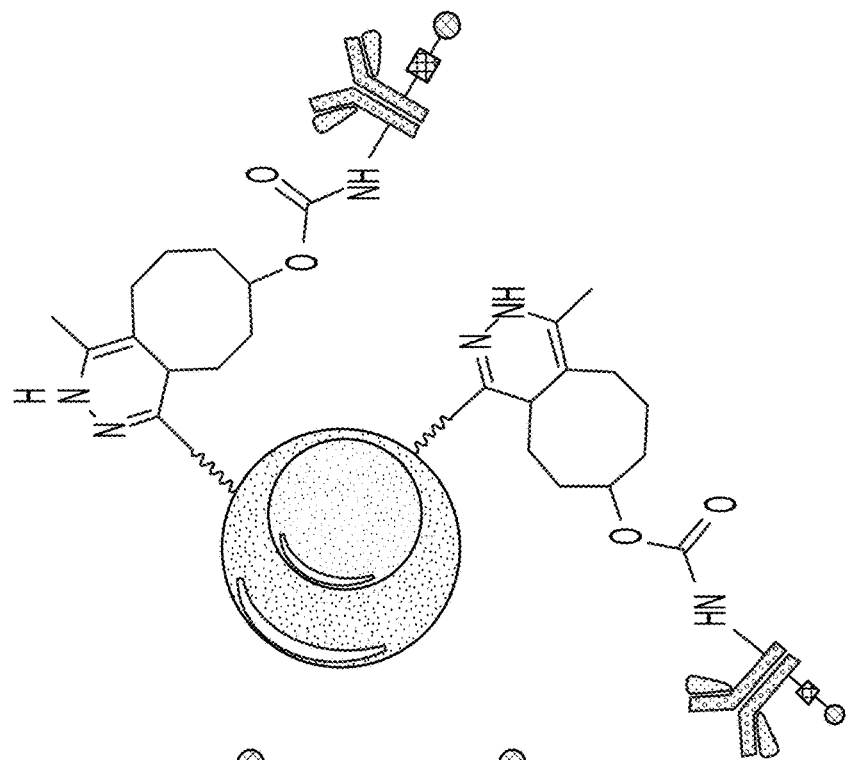
Figure 14:
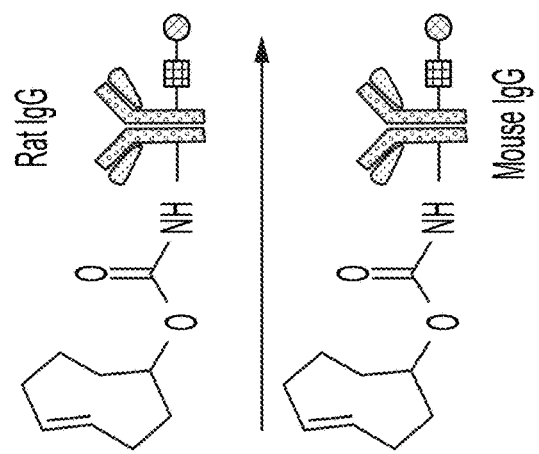
Figure 14:
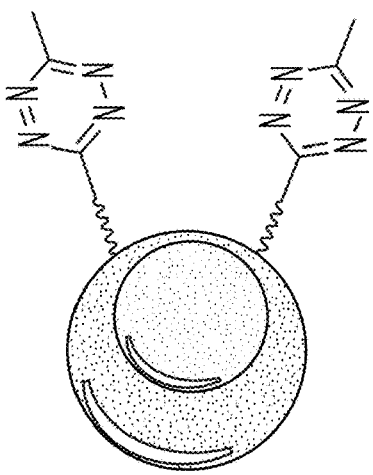
Figure 14:
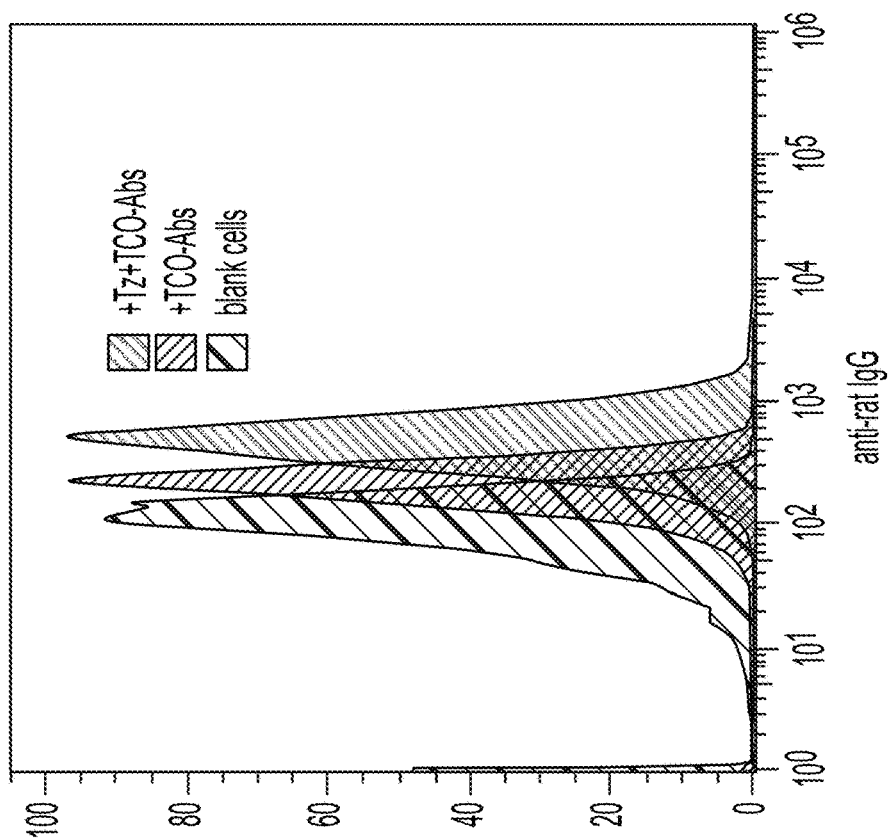
Figure 14:
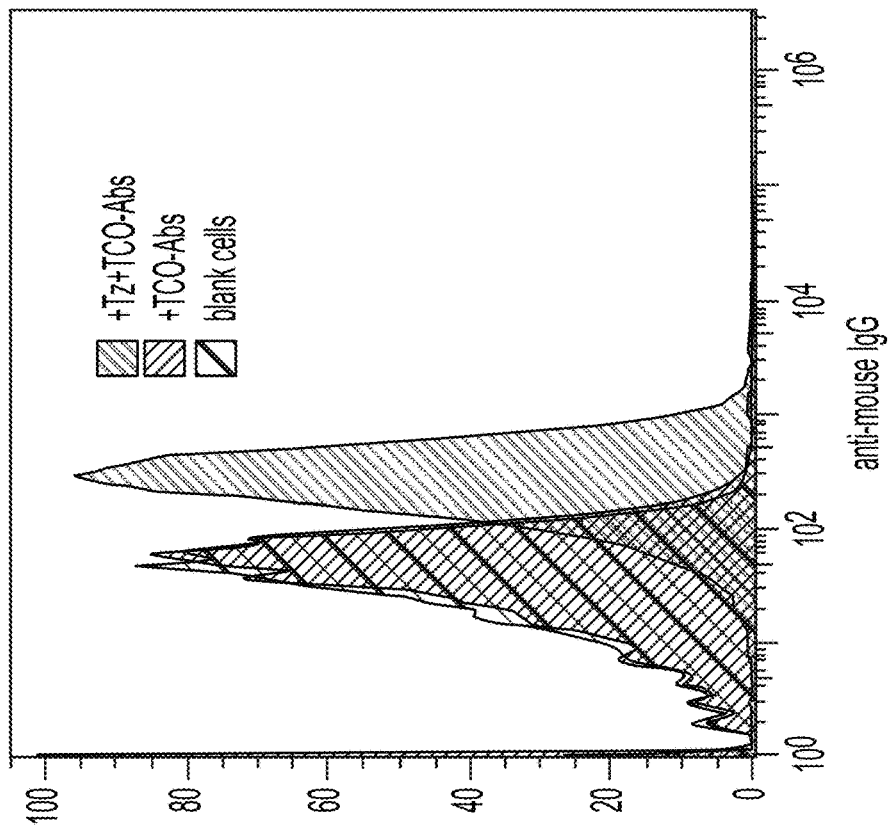

FIG. 14 illustrates one embodiment of the modification of activated mouse CD8+ T cell surface using crude one-pot GDP-fucose-Tz and then conjugated with TCO-mouse IgG and TCO-rat IgG together. Mouse T cell surface was functionalized with tetrazine group specifically on LacNAc. After fucosylation, the samples were reacted with 0.1 mg/ml TCO-mouse IgG and 0.1 mg/ml TCO-rat IgG together for 20 min in room temperature (FIG. 14). The TCO-IgG proteins were first prepared by label IgG with NHS-TCO group. After conjugated with IgG antibodies, the cells were stained with APC-anti-mouse IgG, FITC-anti-rat IgG and then analyzed by FACS. As shown in FIG. 14, the mouse CD8+ T cells were efficiently labeled with both mouse IgG and rat IgG. Control experiments were also characterized with only TCO-Abs (Rat IgG has some non-specific binding towards mouse T cells) (FIG. 14). This example shows that the cells functionalized with tetrazine can be easily modified with two different IgG antibodies bearing TCO group.

Example 16

Figure 15:
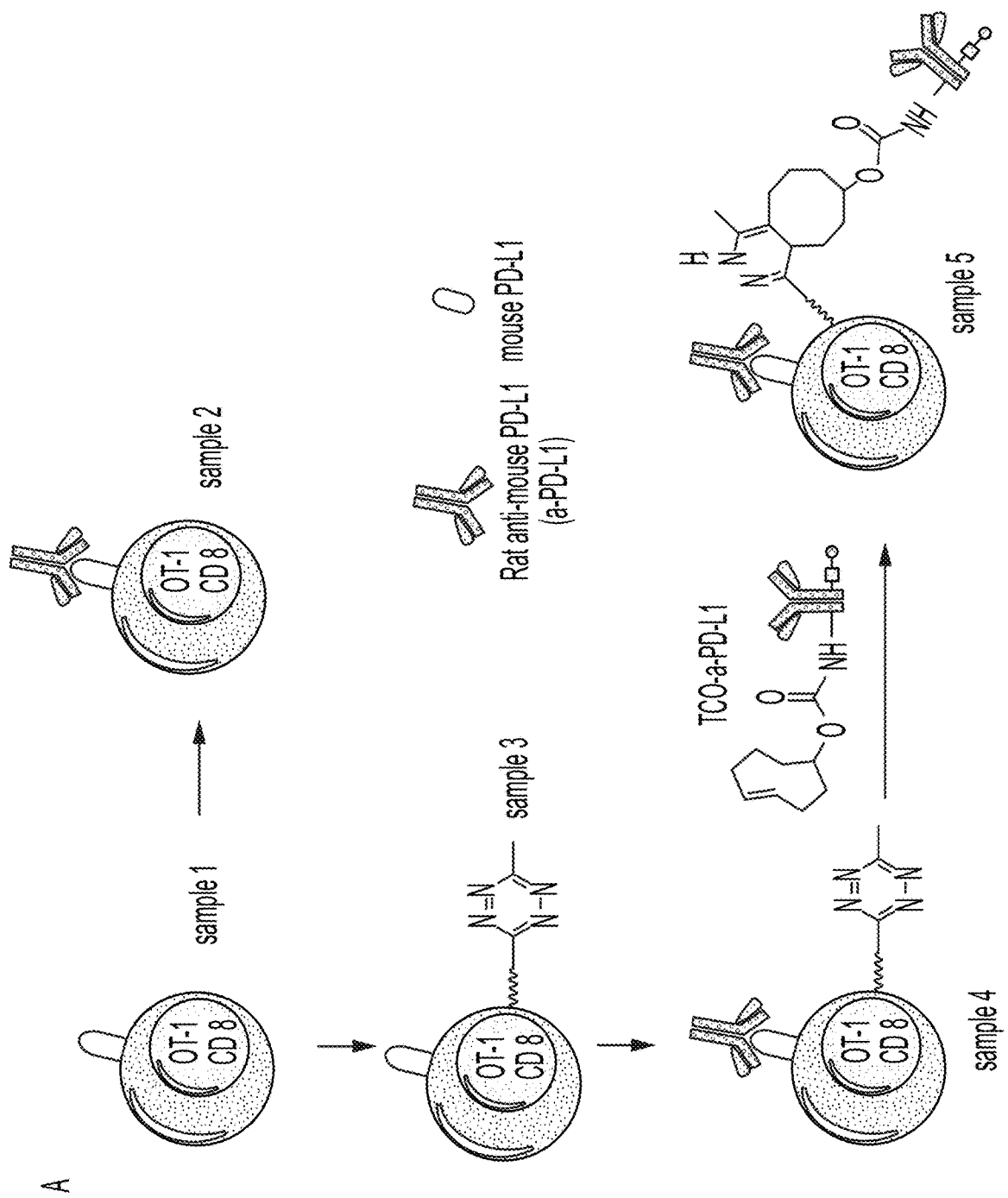
FIG. 15 depicts, in accordance with embodiments herein, installation of anti-PD-L1 antibody on OT-1 T cell surface.
Figure 15:
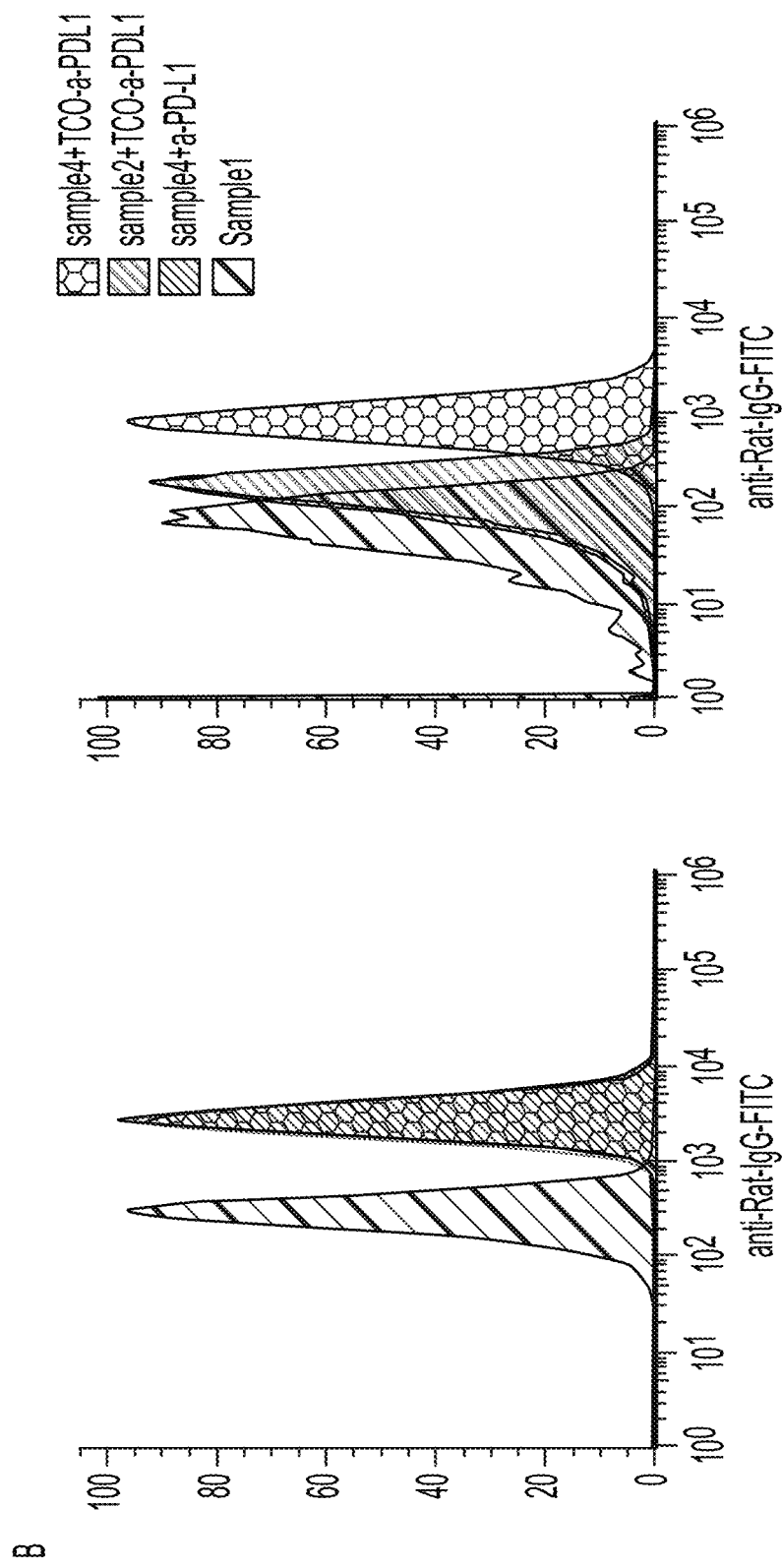

FIG. 15 illustrates one embodiment of installation of anti-PD-L1 antibody on OT-1 T cell surface. As described above in Examples 8 and 13, using GDP-fucose-Tz as substrate, cell surface may be modified with tetrazine group and then antibody is installed onto cell surface via inv DA reaction between Tz and TCO group. In this example, anti-PD-L1 antibody, which inhibits the immune checkpoint (PD-1/PD-L1 pathway), was covalently linked to cell surface LacNAc and sLacNAc via this approach. The OT-1 CD8+ T cells (sample 1) were fucosylated with GDP-fucose-Tz (sample 3) and then were incubated with anti-PD-L1 antibody to block the PD-L1 protein on T cell surface (sample 4). After that, the cells were stained with FITC-anti-rat IgG to mark the antibody that bind to native expressed PD-L1. Later, the cells were conjugated with TCO-anti-PD-L1 antibody through inv DA reaction (sample 5). At last, the cells were stained with APC-anti rat IgG to show the covalently linked anti-PD-L1 on cell surface. Control experiments were performed: sample 4 was mixed with anti-PD-L1, or sample 1 was directly blocked with PD-L1 (sample 2) and then mixed with TCO-anti-PD-L1. As shown in FIG. 15, only the Tz bearing cells were covalently conjugated with anti-PD-L1 (APC channel, control samples have a little background compared to the blank cells). And all the control samples only show positive signal in FITC channel, which indicates the binding of anti-PD-L1 with native expressed PD-L1 protein. This example shows that this method could be used to modify T cells surface with functional antibody.

Example 17

Figure 16:
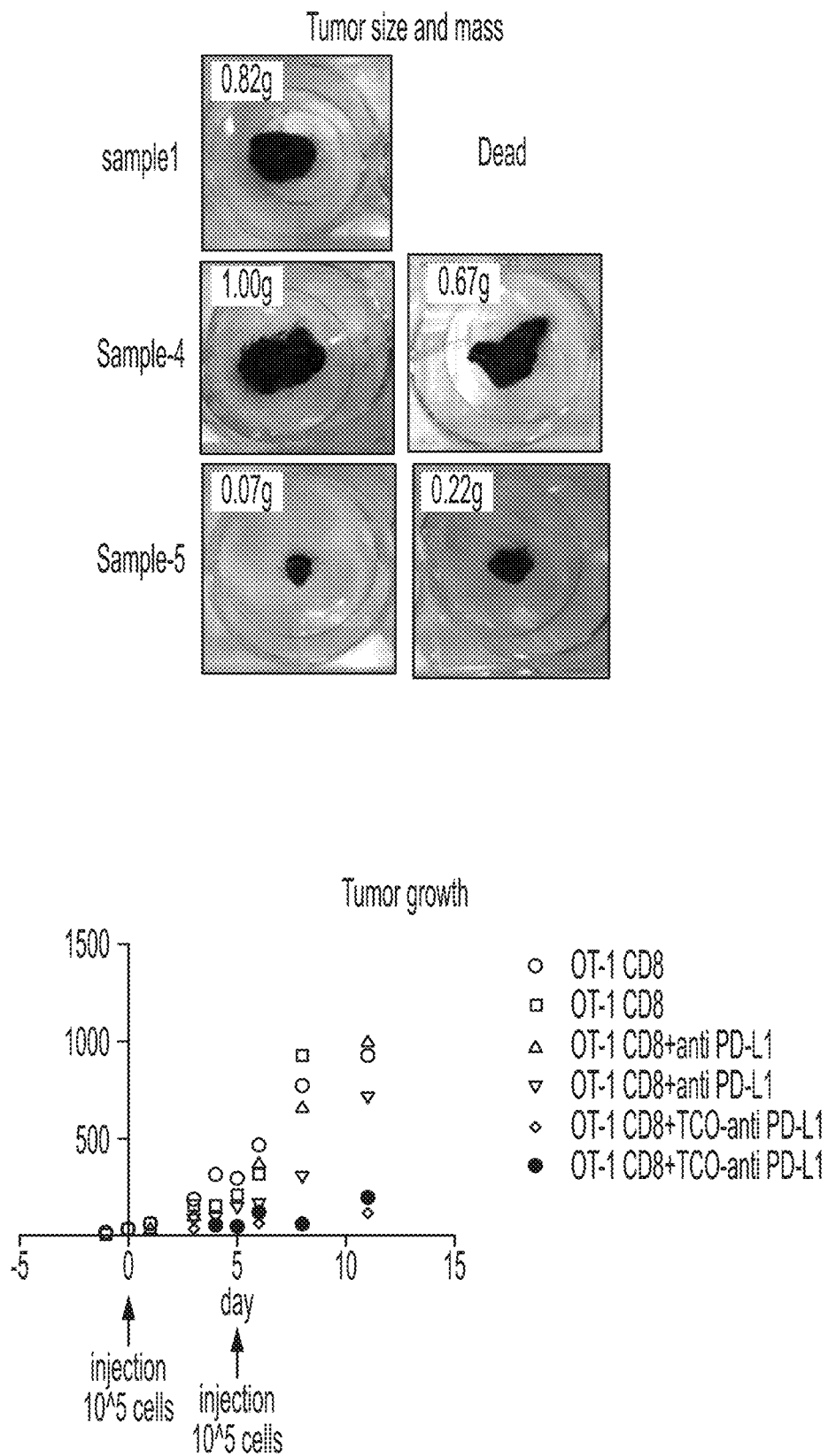
FIG. 16 depicts, in accordance with embodiments herein, installation of anti-PD-L1 antibody on OT-1 T cell surface boost the adoptive cell therapy (ACT).

FIG. 16 illustrates one embodiment of installation of anti-PD-L1 antibody on OT-1 CD8$^+$ T cell surface to boost the adoptive cell therapy (ACT). As shown in Example 14, anti-PD-L1 antibody could be covalently linked to the OT-1 cell surface. In this example, the OT-1 CD8+ T cells were also modified with anti-PD-L1 antibody after the native expressed PD-L1 protein was blocked (in this example, the samples were not stained after the PD-L1 antibody treatment). Murine B16-OVA melanoma cells ($5 \times 10^5$) were subcutaneously inoculated to the shaved flank of 8-week old C57BL/6 female WT mice. After 10 days, $10^5$ of OT-1 CD8+ T cells (with different modification, sample 1, 4 and 5) were adoptively transferred to those B16-OVA tumor bearing mice (day 0, n=2 in each group). Subsequently, $10^5$ (on day 5) of the same processed OT-1 CD8+ T cells were transferred in each experimental mouse. Tumor sizes were determined one or two days by caliper measurements. At day 11, one of the mice in sample 1 group died and all the other mice were euthanized and the tumor of each mouse was weighed (FIG. 16). The tumor mass and growth curve both indicate that adoptive transfer of T cells with covalently linked anti-PD-L1 antibody have significant improvement in the cancer therapy.

Example 18

Figure 17:
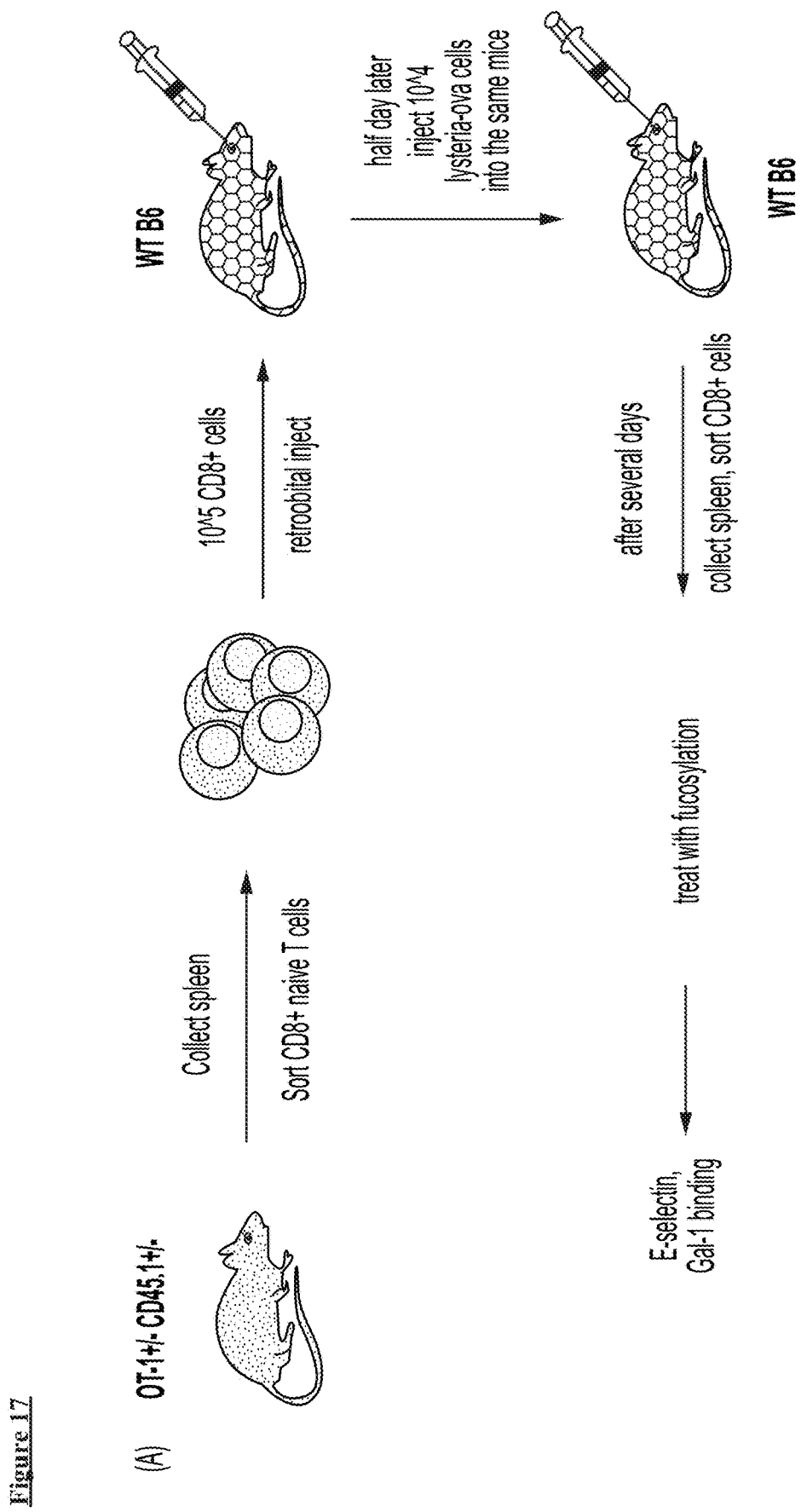
FIG. 17 depicts, in accordance with embodiments herein, in-situ one-pot fucosylation of in vivo expanded mouse CD8+ T cells increase E-selectin binding and suppress Gal-1 binding.
Figure 17:
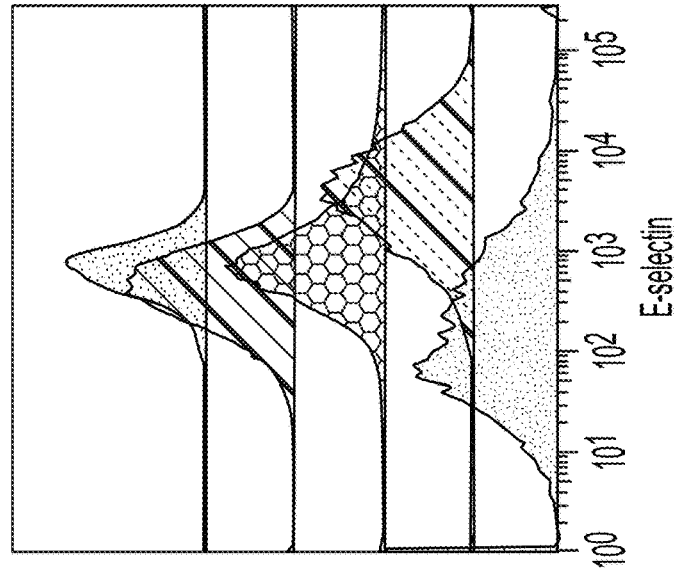
Figure 17:
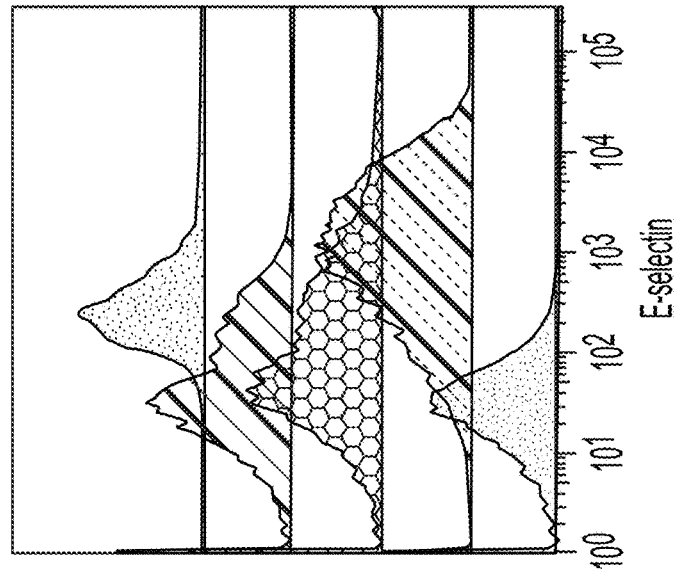
Figure 17:
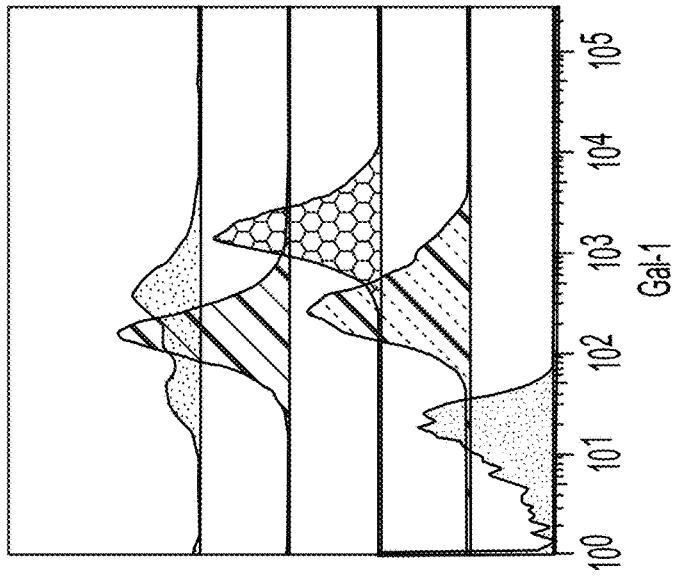
Figure 17:
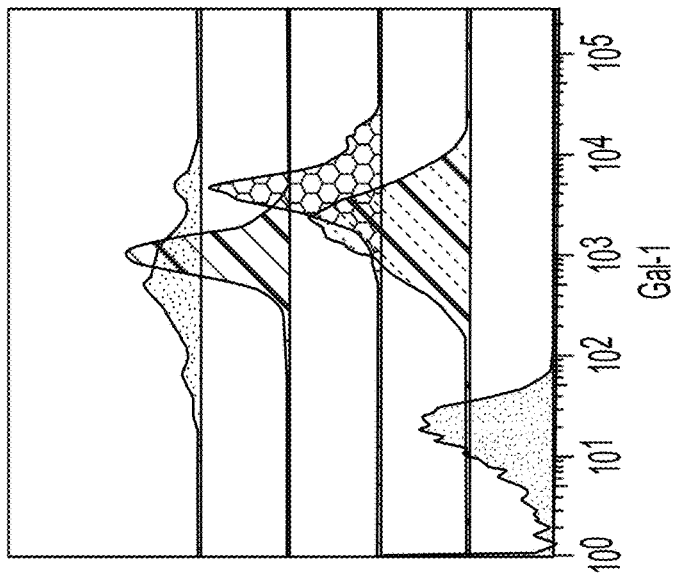

FIG. 17 illustrates one embodiment of in-situ one-pot fucosylation of in vivo expanded mouse CD8+ T cells increase E-selectin binding and suppress Gal-1 binding. As shown in FIG. 17A, splenocytes from OT-1+/−CD45.1+/− mice were collected and sorted to get pure CD8+ naïve T cells. $10^5$ of these fresh T cells were injected into wild type B6 mice retroobitally. Half day later, $10^4$ lysteria-ova cells were also retroobitally injected to these mice to activate those naïve OT-1 CD8+ T cells. After several days of expansion, CD8+ T cells from WT recipient mice were sorted and then fucosylated through one-pot reaction. After fucosyaltion, the cells were stained with E-selectin or Gal-1 protein, and then washed, stained with second antibody. After the staining process, the samples were analyzed by flow cytometry. CD45.1 congenic marker was used to track the OVA-antigen activated CD8+ T cells. As shown in FIG. 17B, the E-selectin binding on OVA-specific CD8+ T cells increases significantly after fucosylation in each time point. In day 14, the difference of E-selectin binding between fucosylated and unfucosylated is up to 10 fold. By contrast, the Gal-1 binding decreases after fucosylation (FIG. 17C).

Example 19

Figure 18:
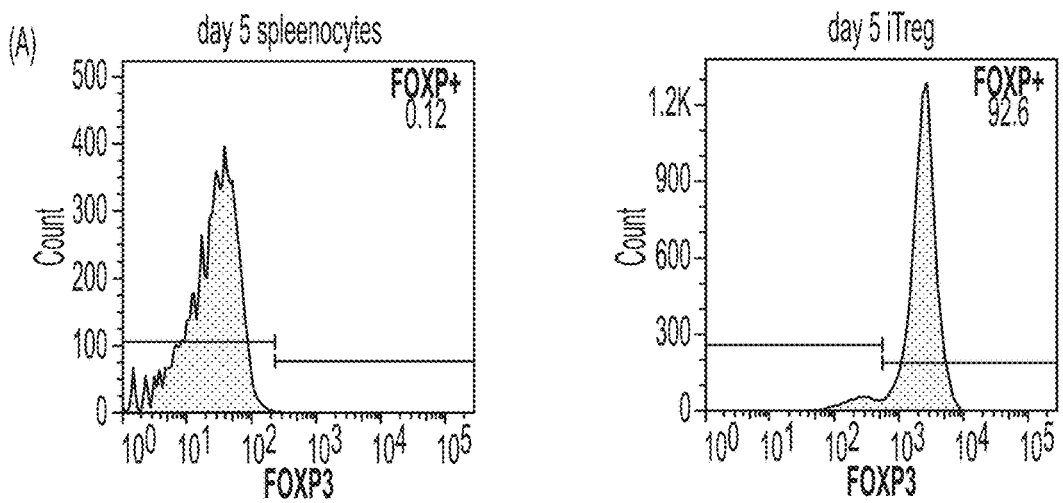
FIG. 18 depicts, in accordance with embodiments herein, in-situ one-pot fucosylation of induced mouse regulatory T cells (iTreg) increase E-selectin binding.
Figure 18:
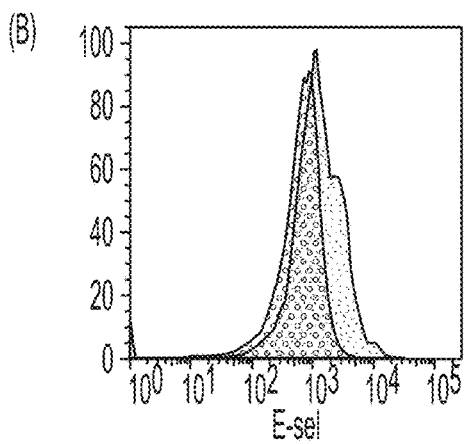
Figure 18:
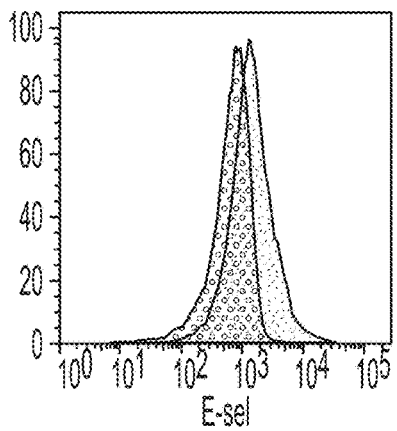

FIG. 18 illustrates one embodiment of in-situ one-pot fucosylation of induced mouse regulatory T cells (iTreg) increase E-selectin binding. Naïve CD4+ T cells were sorted from SAMP or AKR mice spleenocytes. These cells were then re-suspended in T cell culture media and induced in a pre-coated plate supplemented with 2 ug/ml α-CD28, 10 ng/ml IL 2, 20 ng/ml TGF-b, 10 nM RA. The concentration of cells were kept at $1^{\wedge}10^6$/ml by adding media with IL2 and TGF-b. After 5 days expansion, more than 80% of the viable cells were CD4+CD25+ T cells as determined by flow cytometry. The ratio of FOXP3+ cells in CD4+CD25+ was higher than 90%, which indicate that most of these cells are iTreg cells (FIG. 18A). On day 6 iTreg cells were then treated with one-pot fucosylation. After fucosylation, the E-selectin binding level was obviously improved (FIG. 18B).

Example 20

Figure 19:
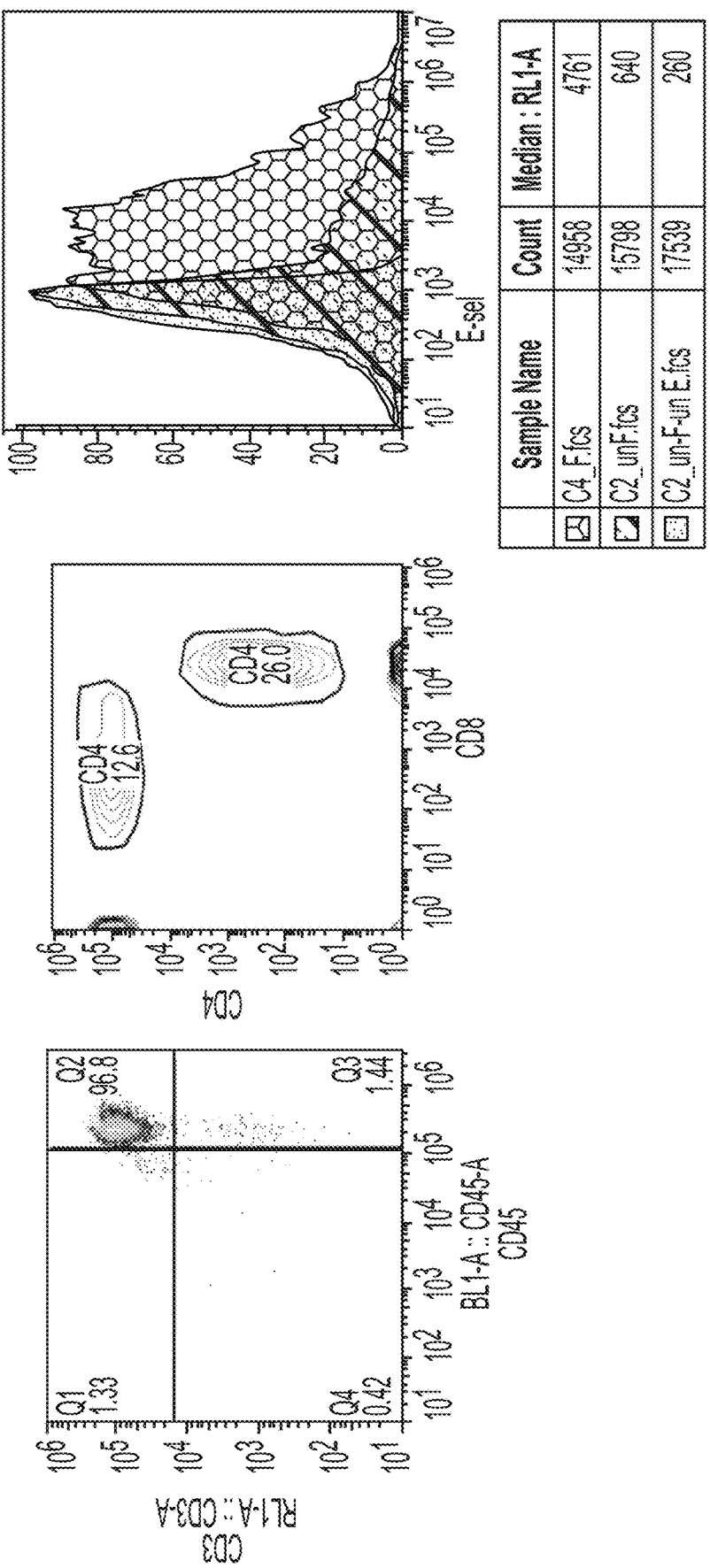
FIG. 19 depicts, in accordance with embodiments herein, in-situ one-pot fucosylation of human T cells increases E-selectin binding.

FIG. 19 illustrates one embodiment of in-situ one-pot fucosylation of human T cells that results in increased E-selectin binding. Human PBMCs were isolated by Ficoll density gradient centrifugation from human blood and then activated with plate bound anti-CD3 (5 ug/ml) and soluble anti-CD28 (2 ug/ml). Twenty-four hours after activation, media were changed and PBMCs were cultured in fresh T cell media with IL 2 and expanded for approximately 2 weeks (kept at $1^{\wedge}10^6$ cells/ml). After 14 days of expansion, more than 95% of the total cultured PBMCs were CD45+ CD3+ T cells, determined by flow cytometry, and about 60% of T cells expressed the CD8+ phenotype. The expanded human T cells were than fucosylated with one-pot fucosylation reagents. After fucosylation, the E-selectin binding level was increased about 8-fold (orange vs. blue FIG. 19).

Example 21

Figure 20:
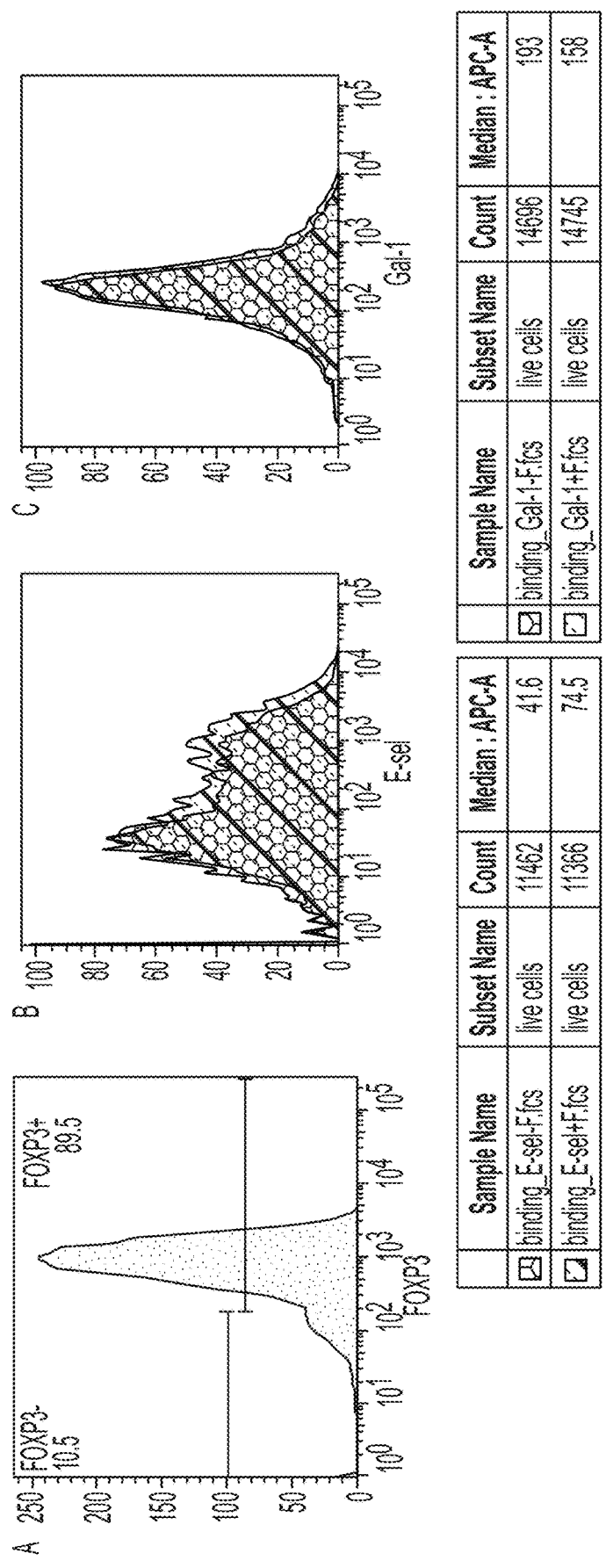
FIG. 20 depicts, in accordance with embodiments herein, in-situ one-pot fucosylation of human natural regulatory T (nTreg) cells increase E-selectin binding and inhibit Gal-1 binding.

FIG. 20 illustrates one embodiment of in-situ one-pot fucosylation of human natural regulatory T (nTreg) cells increase E-selectin binding and inhibit Gal-1 binding. Human PBMCs were isolated by Ficoll density gradient centrifugation from human blood. Human nTreg cells are sorted as CD4+CD127lowCD25+ cells. After sorting, nTreg cells were kept at $1^{\wedge}10^6$ cells/ml in T cell culture media with IL2. After 14 days expansion, ~90% cells are FOXP3+ cells (FIG. 20A). After one-pot fucosyaltion, the E-selectin binding was increased and Gal-1 binding was slightly decreased (FIGS. 20B and 20C).

Example 22

Figure 21:
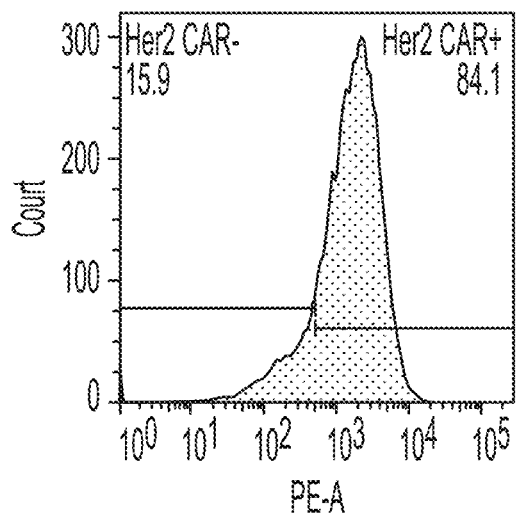
FIG. 21 depicts, in accordance with embodiments herein, in-situ one-pot fucosylation of Her2 specific human CAR-T cells increases E-selectin binding and inhibits Gal-1binding.
Figure 21:
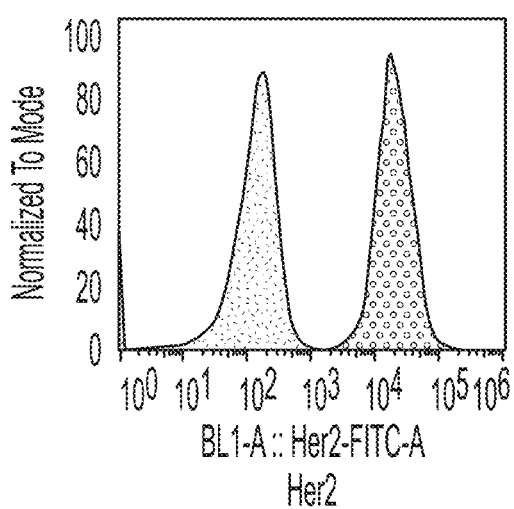
Figure 21:
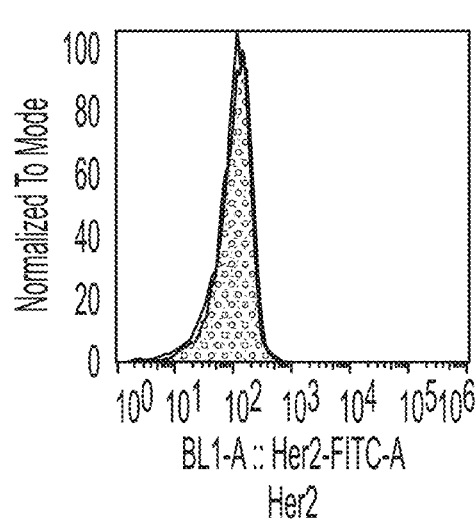
Figure 21:
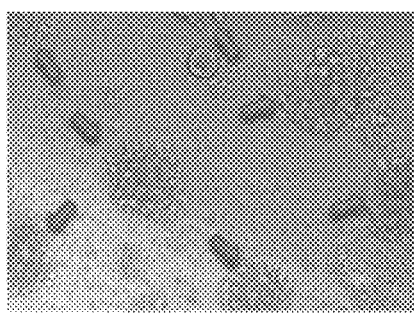
Figure 21:
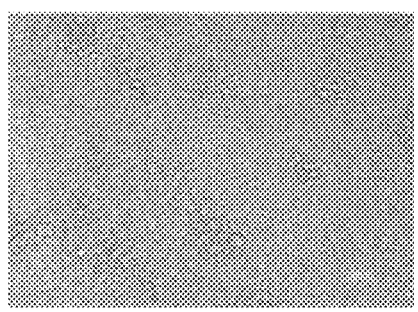
Figure 21:
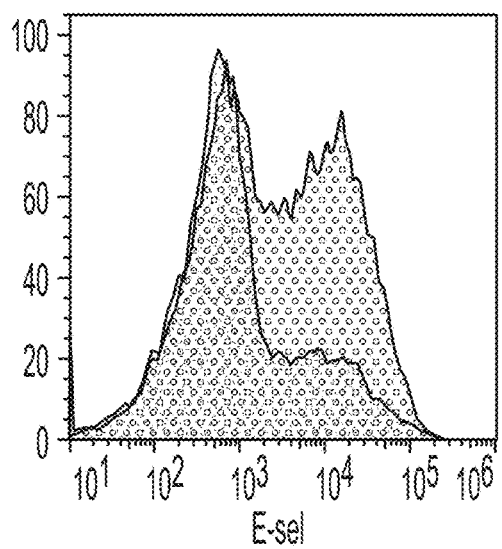
Figure 21:
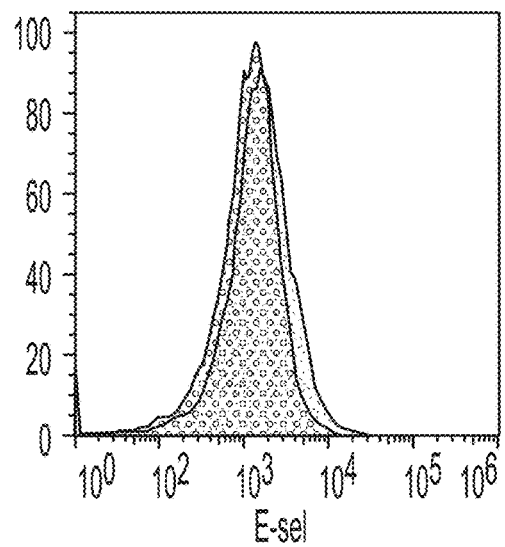

FIG. 21 illustrates one embodiment of in-situ one-pot fucosylation of Her2 specific human CAR-T cells increases E-selectin binding and inhibits Gal-1 binding. Human PBMCs were isolated by Ficoll density gradient centrifugation from human blood and then activated with plate bound anti-CD3 (5 ug/ml) and soluble anti-CD28 (2 ug/ml). Twenty-four hours after activation, PBMCs were transduced with lentiviral vectors at a multiplicity of infection of 5 and then cultured in fresh T cell media with IL 2 and expanded for approximately 2 weeks (kept at $1^\wedge 10^6$ cells/ml). After 14 days of expansion, more than 95% of the total cultured PBMCs were CD45+CD3+ T cells, determined by flow cytometry, and about 90% of T cells expressed Her2 specific CAR-T cells (FIG. 21A). These Her2 specific CAR T cells were then seeding into cultures of Her2+ SKBR3 cells or Her2-MDA-MB-468 cells. After 24 hours of T-cell seeding, formation of T-cell clusters and elimination of the cancer cell monolayer were only visible in Her2+ SKBR3 cells (FIG. 21B, 21C). These results indicate that Her2-specific T cells recognize and kill Her2+ cells in a Her2-specific manner. The expanded human CAR-T cells were then fucosylated with one-pot fucosylation reagents. After fucosylation, the E-selectin binding level was increased about 4 fold (FIG. 21D), while the Gal-1binding was only decreased slightly (FIG. 21E).

Example 23

Figure 22:
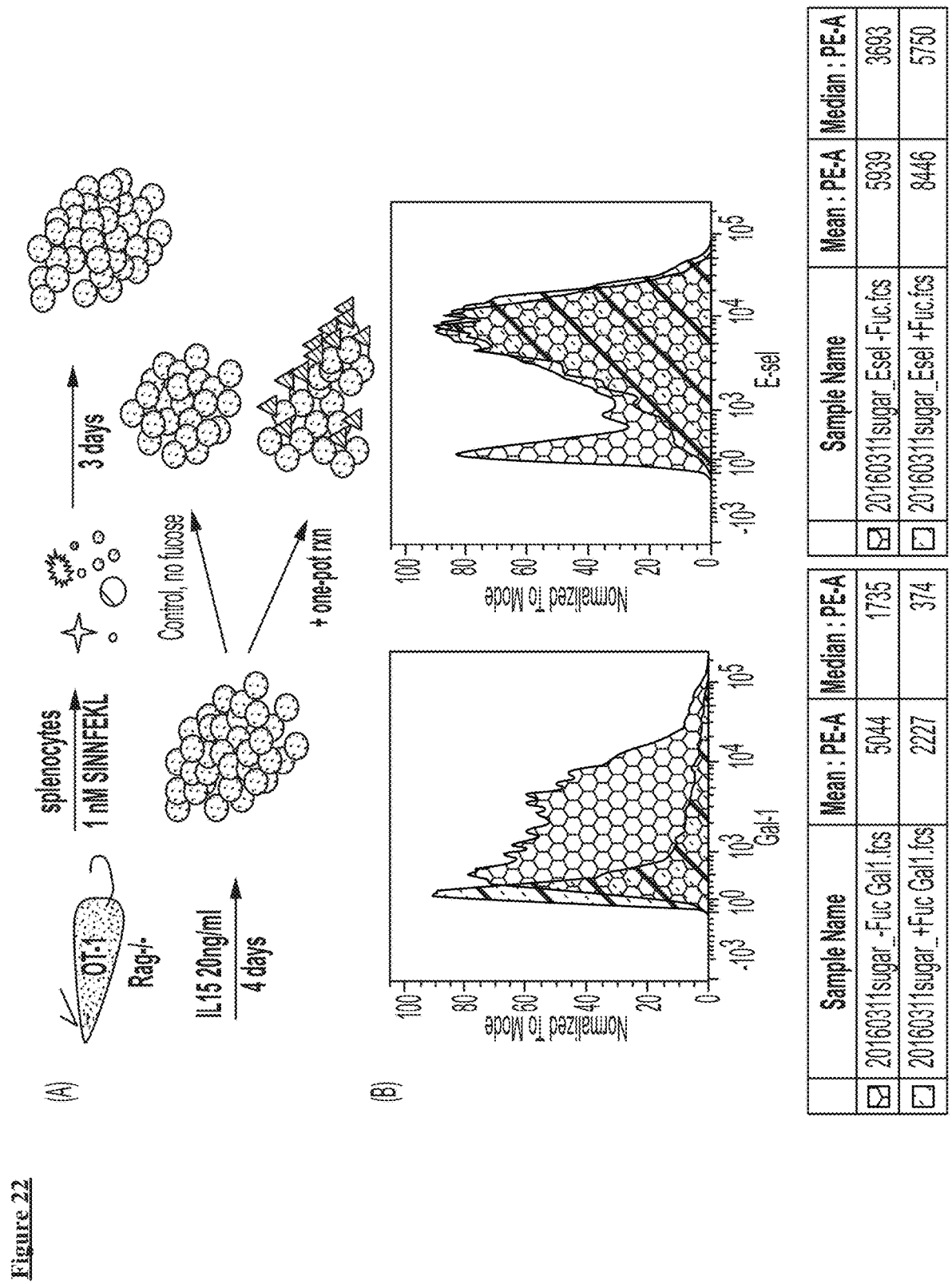
FIG. 22 depicts, in accordance with embodiments herein, in situ one-pot fucosylation of in vitro differentiated mouse CD8 T cells significantly enhanced E-selectin binding and decreased Gal-1 binding.

FIG. 22 illustrates one embodiment of in situ one-pot fucosylation of in vitro differentiated mouse CD8 T cells significantly enhanced E-selectin binding and decreased Gal-1 binding. (A) Splenocytes of OT-1+/+Rag−/− mice were incubated with 1 nM SIINFEKL peptide in growth media. Three days later, the cells were cultured in RPMI medium supplemented with IL-15 20 ng/ml and IL-7 10 ng/ml. Media were replaced and cytokines were added every 2 days. After 3 days of cytokine treatment, more than 95% of the viable cells were CD8+ T cells as determined by flow cytometry. Equal numbers of the CD8+ T cells were incubated in in situ fucosylation reaction buffer with fucose, GTP, ATP, FKP and *H. pylori* α-1,3-fucosyltransferase (one-pot reaction) or GTP, ATP, FKP and *H. pylori* α-1,3 fucosyltransferase without fucose (control) at 37° C. for 30 min. (B) Both the in situ fucosylated and non-fucosylated (as control) cells were stained with biotinylated Galectin-1 and human Fc-conjugated E-selectin, respectively, washed, then stained with streptavidin-PE and anti-human-Fc-PE, respectively, and analyzed using flow cytometry.

Example 24

Figure 23:
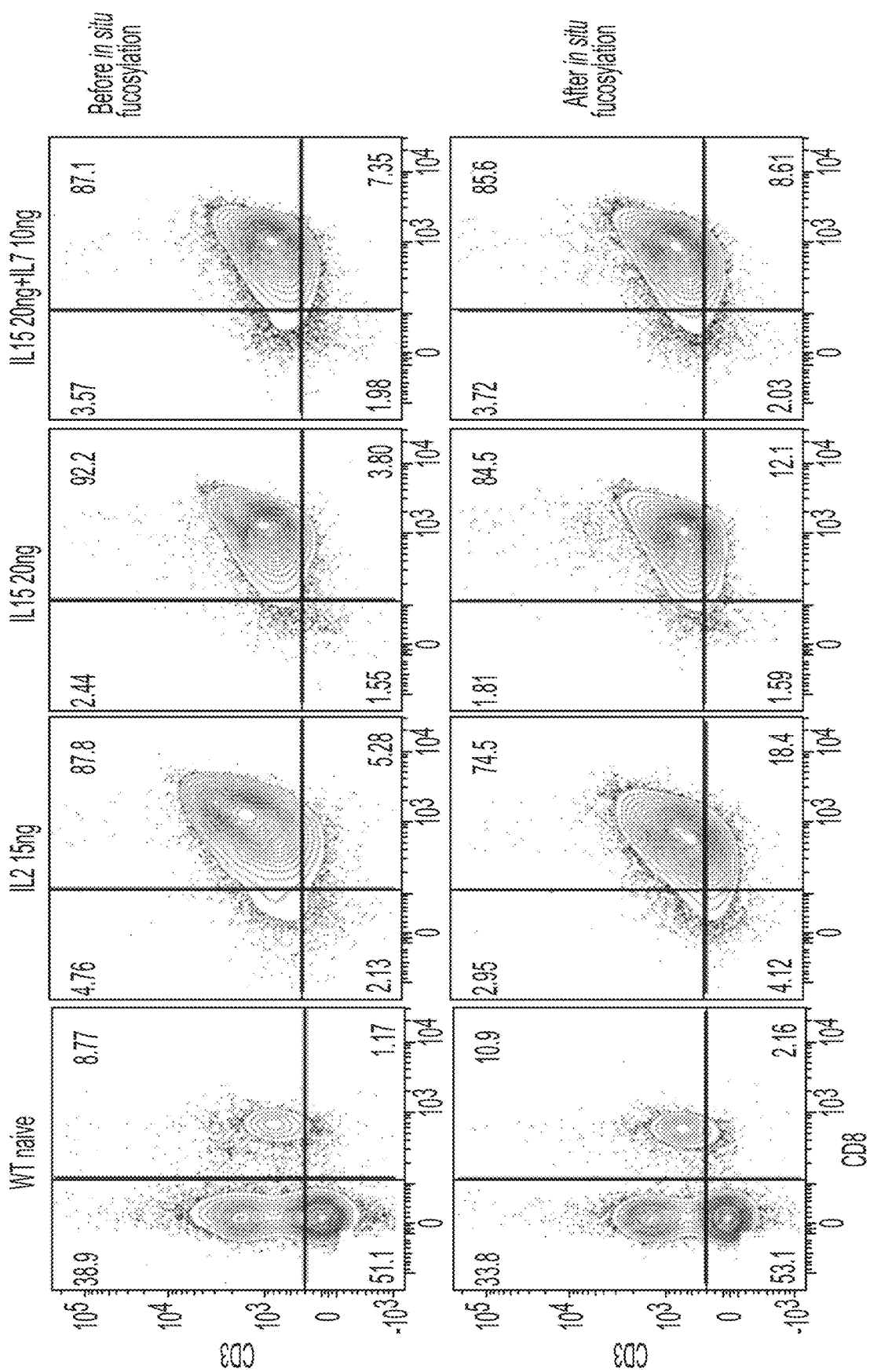
FIG. 23 depicts, in accordance with embodiments herein, in situ one-pot fucosylation of in vitro differentiated mouse OT-1 CD8 T cells had little impact on the expression of cell-surface markers.
Figure 23:
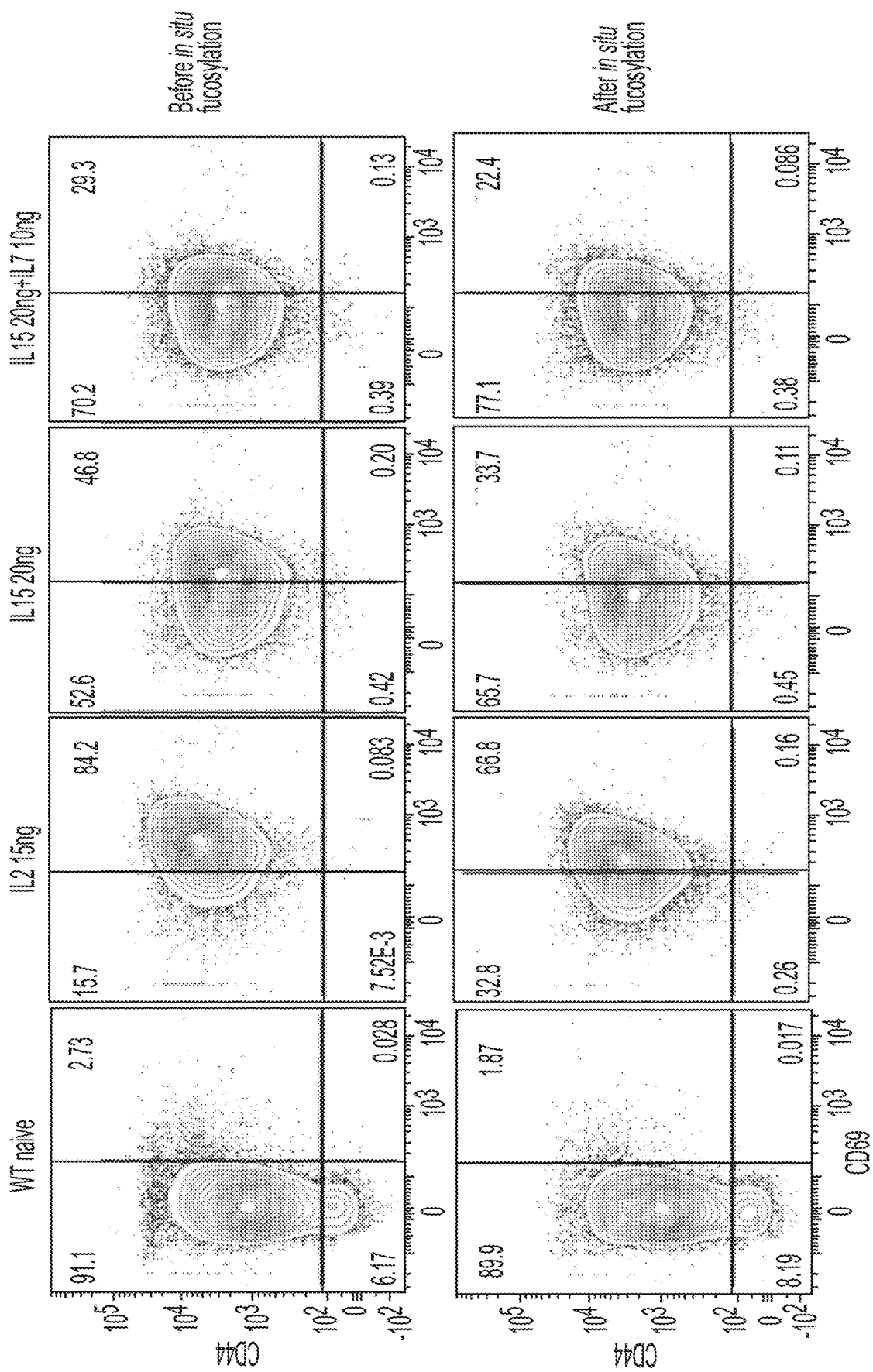

FIG. 23 illustrates one embodiment of in situ one-pot fucosylation of in vitro differentiated mouse OT-1 CD8 T cells had little impact on the expression of cell-surface markers. Splenocytes of OT-1+/+Rag−/− mice were incubated with 1 nM SIINFEKL peptide in growth media. Two days later, the cells were cultured in RPMI medium supplemented with IL-2 or IL-15 or IL-15+IL-7. After 3 days of cytokine treatment, more than 95% of the viable cells were CD8+ T cells as determined by flow cytometry. Equal numbers of the CD8+ T cells were incubated in in situ fucosylation reaction buffer with fucose, GTP, ATP, FKP and a 1,3 fucosyltransferase (one-pot reaction) at 37° C. for 30 min or untreated. Cell-surface markers were stained with corresponding antibodies and analyzed using flow cytometry.

Example 25

Figure 24:
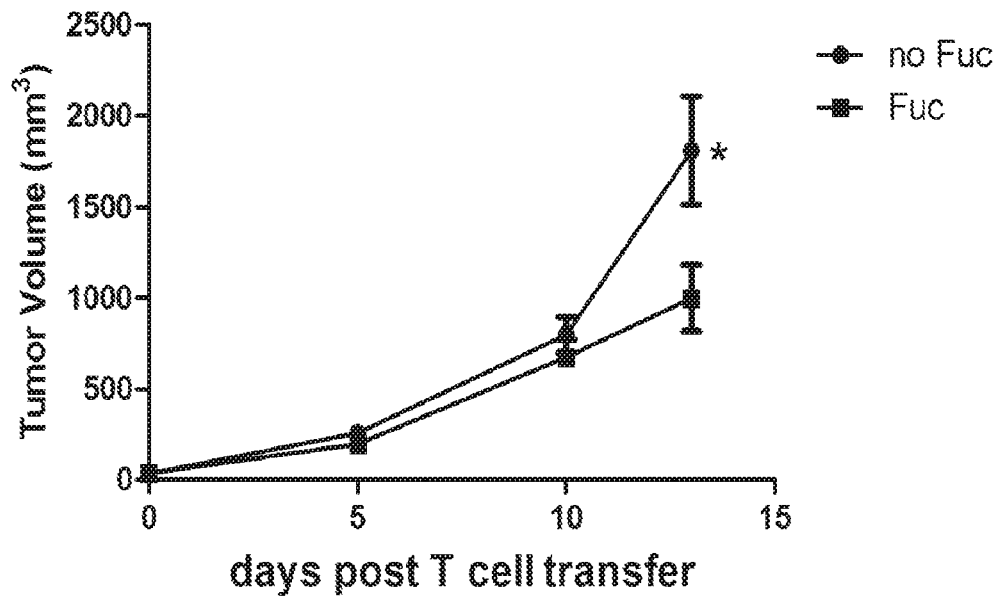
FIG. 24 depicts, in accordance with embodiments herein, treatment of B16-OVA-embedded mice with in vitro differentiated, glycan modified OT-1 T cells significantly decreased tumor growth.

FIG. 24 illustrates one embodiment of treatment of B16-OVA-embeded mice with in vitro differentiated, glycan modified OT-1 T cells significantly decreased tumor growth. Murine B16-OVA melanoma cells ($6 \times 10^5$) were subcutaneously inoculated to the shaved flank of 8-week old C57BL/6 female WT mice. After 8 days, $10^5$ of in situ fucosylated or non-fucosylated IL-15+IL-7 in vitro differentiated OT-1 CD8+ T cells were adoptively transferred to those B16-OVA tumor bearing mice (day 0, n=10 in each group). Subsequently, $2 \times 10^5$ (on day 6) and $5 \times 10^5$ (on day 9) of the same processed OT-1 CD8+ T cells were transferred in each experimental mouse. Tumor sizes were determined daily by caliper measurements. *P<0.05 (determined by non-parametric t-test).

Example 26

Figure 25:
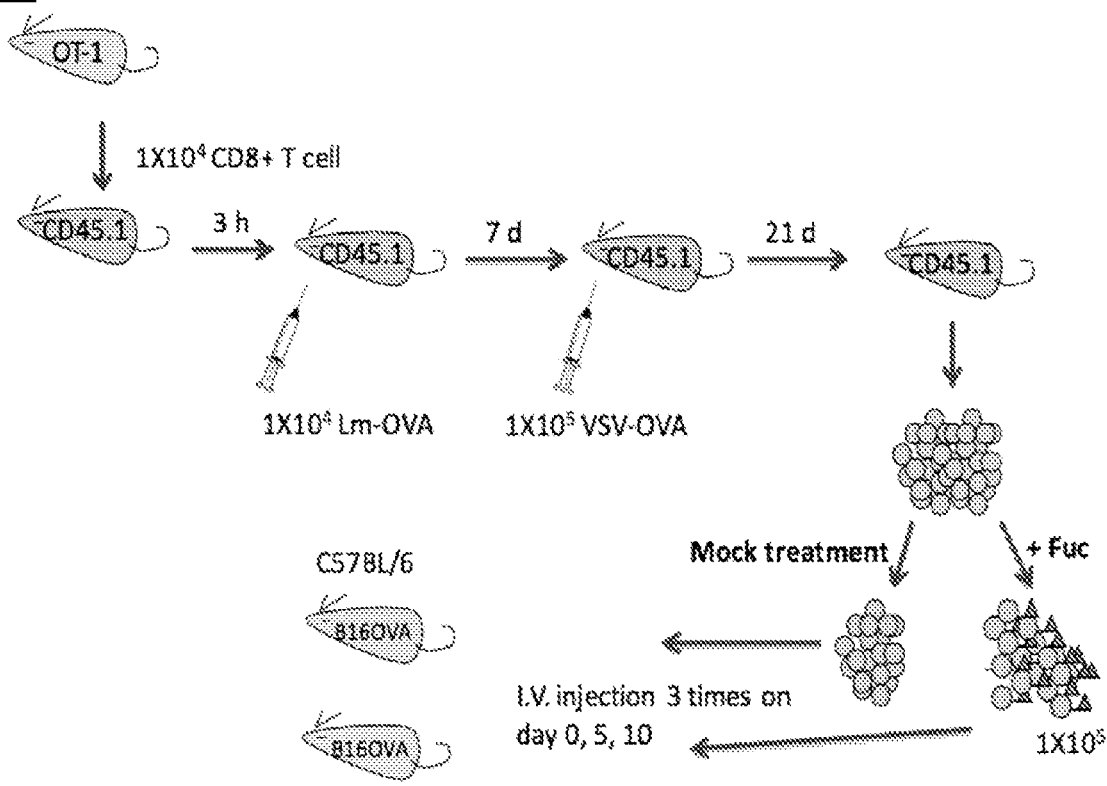
FIG. 25 depicts, in accordance with embodiments herein, treatment of B16-OVA-embedded mice with in vivo differentiated, glycan modified OT-1 T cells significantly decreased tumor growth and extended the life span of the tumor embedded mice.
Figure 25:
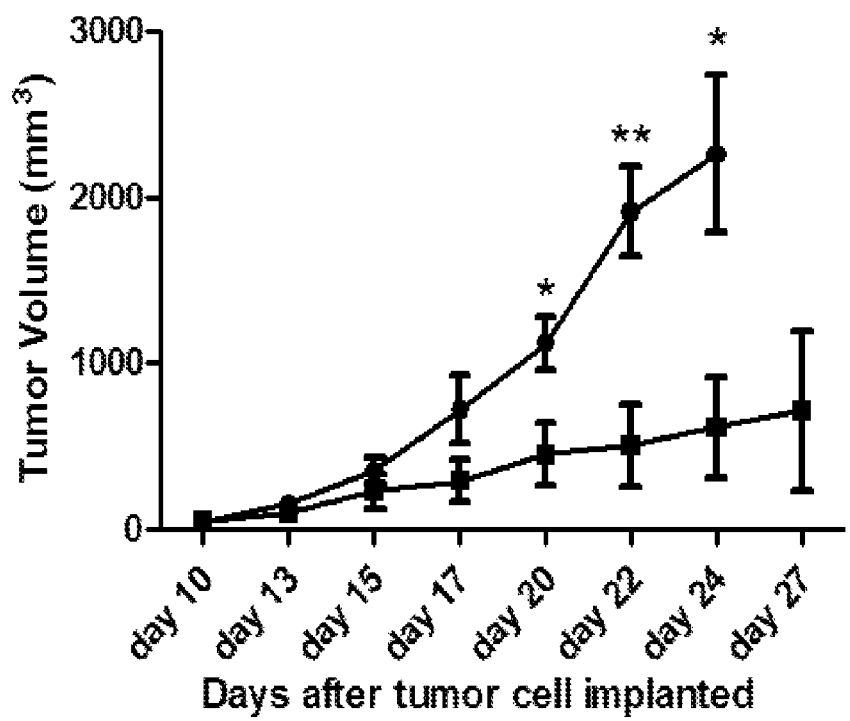
Figure 25:
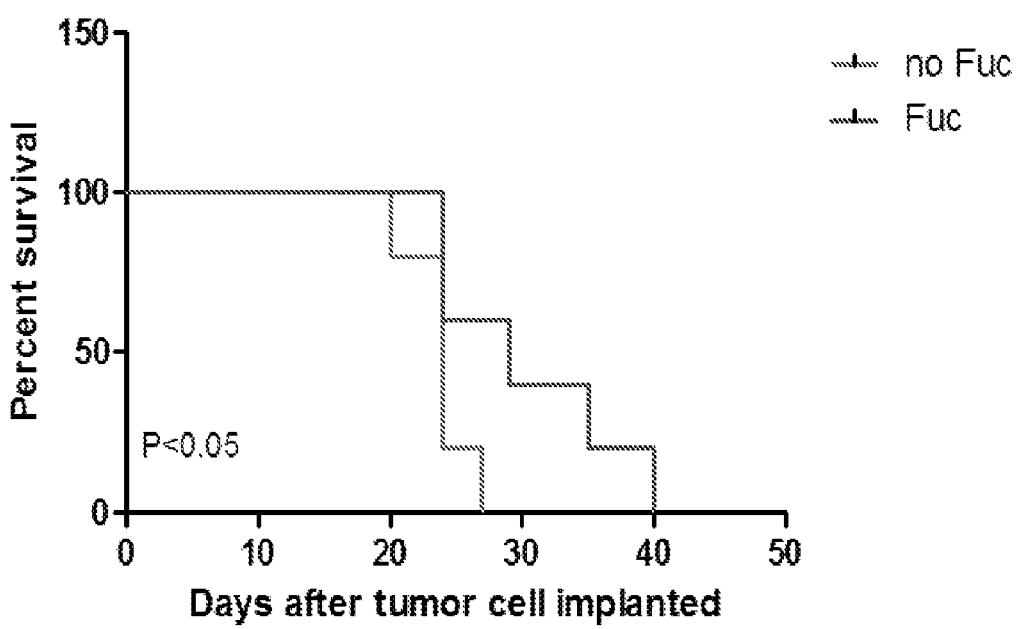

FIG. 25 illustrates one embodiment of treatment of B16-OVA-embedded mice with in vivo differentiated, glycan modified OT-1 T cells significantly decreased tumor growth and extended the life span of the tumor embedded mice. (A) To obtain OT-1 memory CD8+ T cells in vivo, $1 \times 10^4$ OT-1 naïve CD8 T cells were transferred to CD45.1+/+ mice followed by infection with $1 \times 10^4$ CFU of *Listeria monocytogenes* strain expressing OVA (Lm-OVA) after 3 hr. After 7 days, the recipient mice were infection with $1 \times 10^5$ vesicular stomatitis virus encoding ovalbumin (VSV-OVA) to boost OVA-specific immune responses. 21 days later, CD8 T cells containing about 3-5% OVA-specific OT-1 memory CD8 T cells can be harvested from CD45.1 mice splenocytes by negative selection. After in situ fucosylation or untreated, the CD8 T cells containing $1 \times 10^5$ OT1 memory CD8 T cells were i.v. injected to WT mice bearing B16-OVA tumor on their flanks, which were s.c. implanted at $5 \times 10^5$ for each mouse 10 days ago. The memory T cells were injected three times on day 0, day 5 and day 10. (B) OT-1 memory CD8+ T cell treated with in situ fucosylation or untreated as described above were adoptively transferred in to mice bearing B16-OVA tumors (n=5 in each group). Tumor size was monitored by caliper measurement every other day and mice were sacrificed when tumor size reached 1.8 cm. Data (mean+/−s.e.m.) are representative of three independent experiments. *p<0.05, **p<0.005 (analyzed by non-parametric t-test). (C) Mice survival rate was monitored over time. The survival rate was analyzed by Kaplan-Meier log rank test.

Example 27

Figure 26:
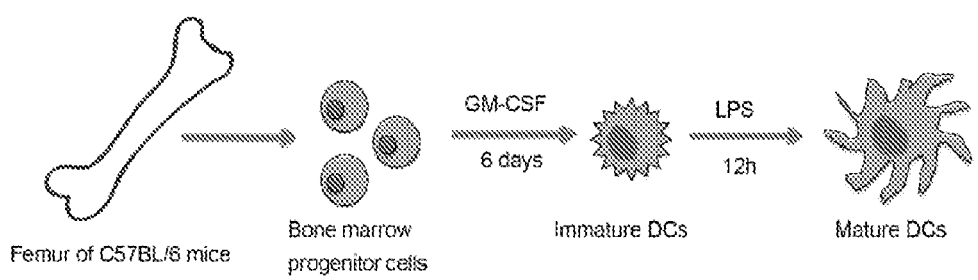
FIG. 26 depicts, in accordance with embodiments herein, in situ one-pot fucosylation of in vitro differentiated mouse dendritic cells (DCs) significantly enhanced E-selectin binding and decreased Galectin-1 binding.
Figure 26:
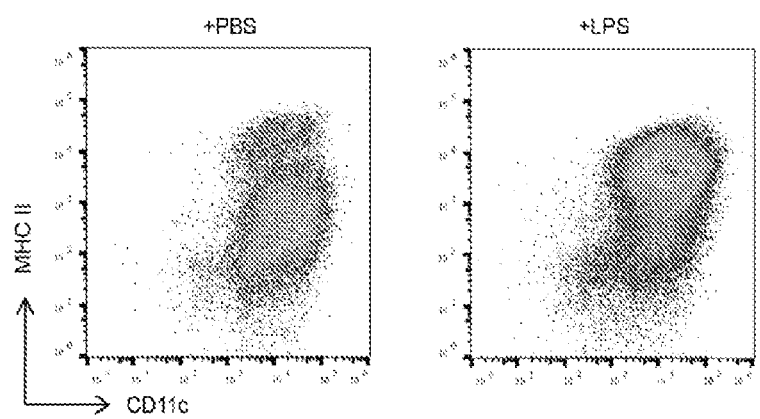
Figure 26:
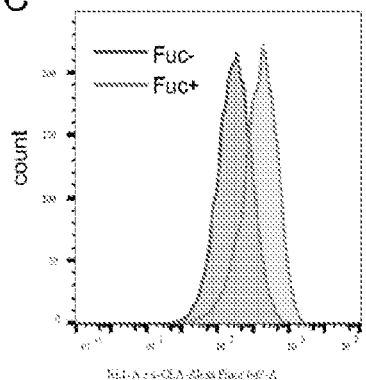
Figure 26:
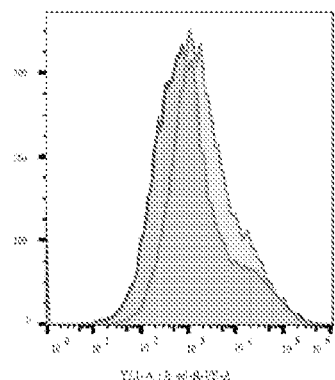
Figure 26:
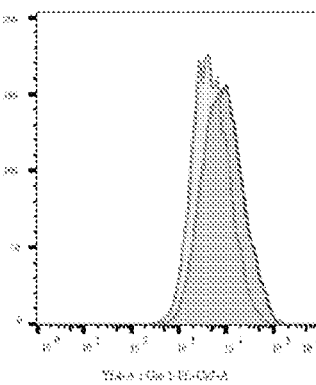
Figure 26:
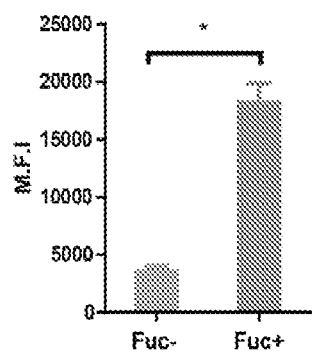
Figure 26:
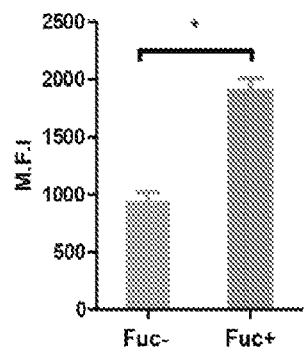
Figure 26:
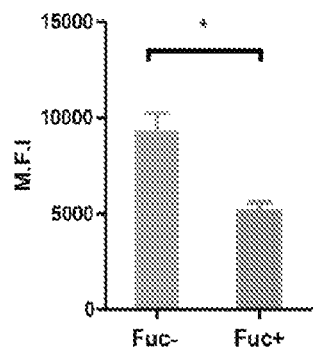

FIG. 26 illustrates one embodiment of in situ one-pot fucosylation of in vitro differentiated mouse dendritic cells (DCs) significantly enhanced E-selectin binding and decreased Galectin-1 binding. One-pot fucosylation reaction was used to modify mouse bone marrow derived dendritic cells according to the procedure disclosed herein. Mature BMDCs were made by culturing bone marrow progenitor cells with GM-CSF and stimulated with LPS, with high expression of CD11c and WIC II (FIGS. 26A and 26B). After fucosylation, the cell surface sLacNAc were converted into sLeX, which could be detected through Alexa Fluor 647 conjugated anti-CLA antibody (FIG. 26C). E-selectin binding was also increased (FIG. 26D). By contrast, the Galectin-1 binding decreases after fucosylation (FIG. 26E). (A). Scheme of differentiation and maturation of bone marrow derived dendritic cells (BMDCs). Briefly, bone marrow cells were collected, suspended in PBS by addition of red blood cell lysis buffer for depletion of erythrocytes, and then seeded in $1 \times 10^6$ cells/ml in the RPMI 1640 media with recombinant GM-CSF (20 ng/ml, Peprotech) in a humidified incubator with 5% CO2 at 37° C. The cells were fed once at the interval of 3 day with the identical dose of recombinant GM-CSF. Immature dendritic cells were harvested on day 6 with the purity of CD11c+ cells higher than 90%. Then the cells were stimulated with LPS for maturation. (B). Immature DCs were stimulated with LPS (100 ng/ml) for 12 h, expression of CD11c and WIC II were analyzed by flow cytometry. (C-E). Mature DCs were fucosylated using the one-pot strategy, then the cells were stained with anti-CLA antibody, E-selectin or Gal-1 protein, and then washed, stained with second antibody. After the staining process, the samples were analyzed by flow cytometry. M.F.I means "Medium of Fluorescence Intensity". Data are presented as mean±standard deviations and analyzed for statistical significance by two-tailed student's t test in Prism (GraphPad) software. Differences with P values<0.05 were considered statistically significant. *means P<0.05.

Example 28

Figure 27:
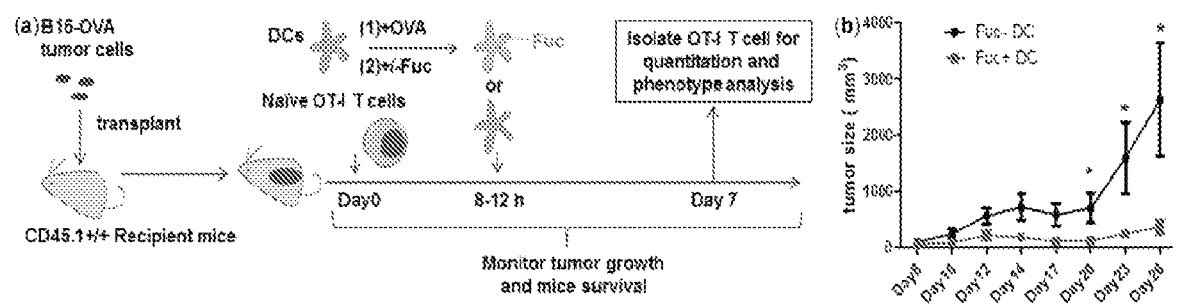
FIG. 27 depicts, in accordance with embodiments herein, fucosylation of antigen loaded DCs induces a significantly stronger anti-tumor immune response.

FIG. 27 illustrates one embodiment of fucosylation of antigen loaded DCs induces a significantly stronger anti-tumor immune response. To evaluate the effect of fucosylated DCs in inducing anti-tumor immune response, B16-OVA melanoma tumor model was used (FIG. 27A). Compared with unfucosylated DC vaccine group, fucosylated DCs vaccine was found to inhibit tumor growth more efficiently. (A). Scheme of fucosylated dendritic cell vaccine inhibiting tumor growth in vivo. C57BL/6 wild type recipient mice were inoculated subcutaneously with $5 \times 10^5$ B16-OVA melanoma cells in right flank, $5 \times 10^3$ naive OT-I T cells were inoculated into the mice through retrobulbar injection on day 6 post tumor cell inoculation. On day 8, mature DCs were incubated with 200 nM OVA257-264 (SIINFEKL) peptide for 1.5 h, washed and then fucosylated using the one-pot strategy. After fucosylation, $4 \times 10^5$ DCs were inoculated into the tumor bearing mice through subcutaneous injection in right flank. Then tumor growth was recorded. (B). Tumor sizes were measured by Vernier caliper and calculated. 8 mice were in each experimental group. Data are presented as mean±standard deviations and analyzed for statistical significance Mann-Whitney non-parametric test in Prism (GraphPad) software. Differences with P values<0.05 were considered statistically significant. *means P<0.05.

Example 29

Figure 28:
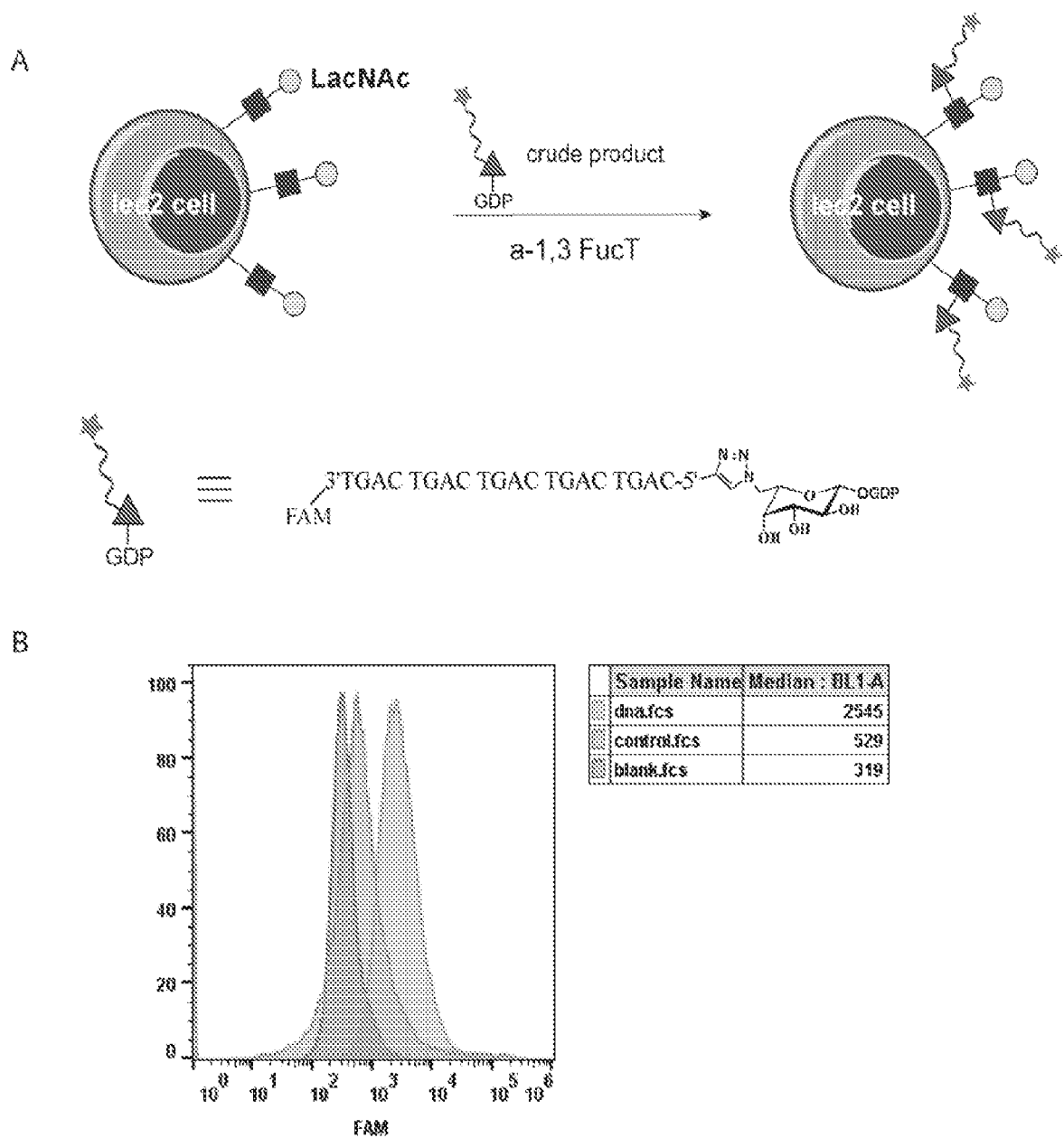
FIG. 28 depicts, in accordance with embodiments herein, modification of cultured Lec2 CHO cell surface using crude one-pot GDP-fucose-DNA-FAM.

FIG. 28 illustrates one embodiment of modification of cultured Lec2 CHO cell surface using crude one-pot GDP-fucose-DNA-FAM. One-pot fucosylation reaction was used to modify CHO-lec 2 cells with a polynucleotide (a single chain DNA). GDP-fucose-DNA-FAM was synthesized by the one-pot procedure according to the procedure in Example 1. The DNA substrate is a single chain DNA with a 5' alkyne group and a 3' FAM fluorophore. The term "FAM" or "6-FAM," as used herein, refers to the fluorescent dye 6-carboxyfluorescein. Using GDP-fucose-DNA-FAM as substrates, the cell surface was functionalized with a single chain DNA specifically on LacNAc, which could be confirmed by the fluorescent signal on the DNA (FIG. 28). The fucosylation protocol is the same as in Example 3. As shown in FIG. 28(B), the lec2 cells fucosylated with GDP-fucose-DNA-FAM shows a significant increase in the fluorescence of FAM. Control experiments were also characterized without 1,3 FucT (FIG. 28(B)), which indicates that the signal is from the fucosylation reaction.

Example 30

Figure 29:
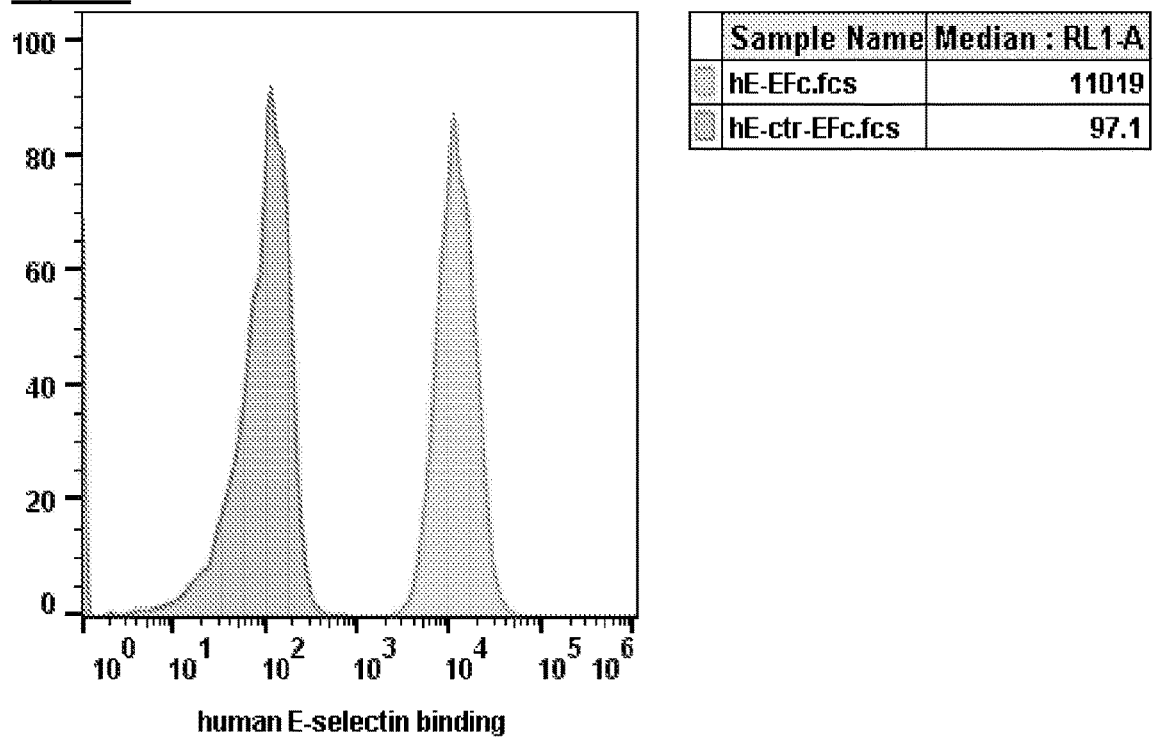
FIG. 29 depicts, in accordance with embodiments herein, anti-human E-selectin installed on cultured Lec2 CHO cell surface can bind to human E-selectin.

FIG. 29 illustrates one embodiment of anti-human E-selectin installed on cultured Lec2 CHO cell surface can bind to human E-selectin. Anti-human E-selectin antibody was installed on lec2 cell surface through protocol in Example 8. After that, cells labeled with anti-human E-selectin or its isotype antibody were incubated with the human E-selectin Fc protein. The result indicates that only the cells labeled with anti-human E-selectin can bind to E-selectin protein (FIG. 29), which was detected by staining with APC-anti-Fc antibody.

Example 31

Figure 30:
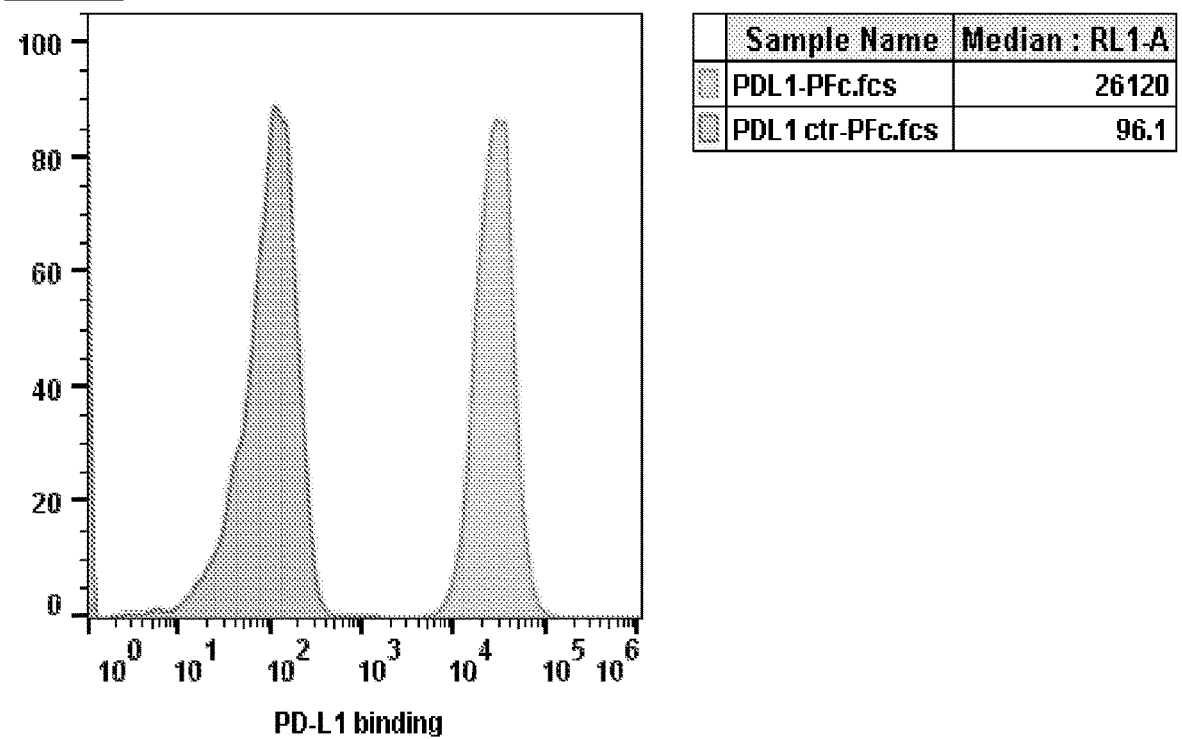
FIG. 30 depicts, in accordance with embodiments herein, anti-mouse PD-L1 installed on cultured Lec2 CHO cell surface can bind to mouse PD-L1

FIG. 30 illustrates one embodiment of anti-mouse PD-L1 installed on cultured Lec2 CHO cell surface can bind to mouse PD-L1. Anti-mouse PD-L1 was installed on Lec2 cell surface using the protocol described in Example 8. After that, cells labeled with anti-mouse PD-L1 or its isotype antibody were incubated with the mouse PD-L1 Fc fusion protein. The result indicates that only the cells labeled with anti-mouse PD-L1 can bind to mouse PD-L1 protein (FIG. 30), which was detected by staining with APC-anti-Fc antibody.

Example 32

Figure 31:
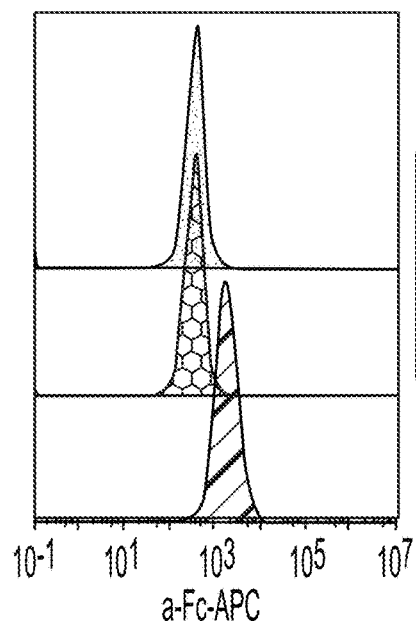
FIG. 31 depicts, in accordance with embodiments herein, anti-mouse CTLA4 installed on cultured CHO cell surface can bind to mouse CTLA4 protein.

FIG. 31 illustrates one embodiment of Anti-mouse CTLA4 installed on cultured CHO cell surface can bind to mouse CTLA4. Anti-mouse CTLA4 was installed on CHO cell surface using the protocol described in Example 8. After that, cells labeled with anti-mouse CTLA4 or its isotype antibody were incubated with the mouse CTLA4 Fc protein. The result indicates that only the cells labeled with anti-mouse CTLA4 can bind to mouse CTLA4 protein (FIG. 31), which was detected by staining with APC-anti-Fc antibody.

Example 33

Figure 32:
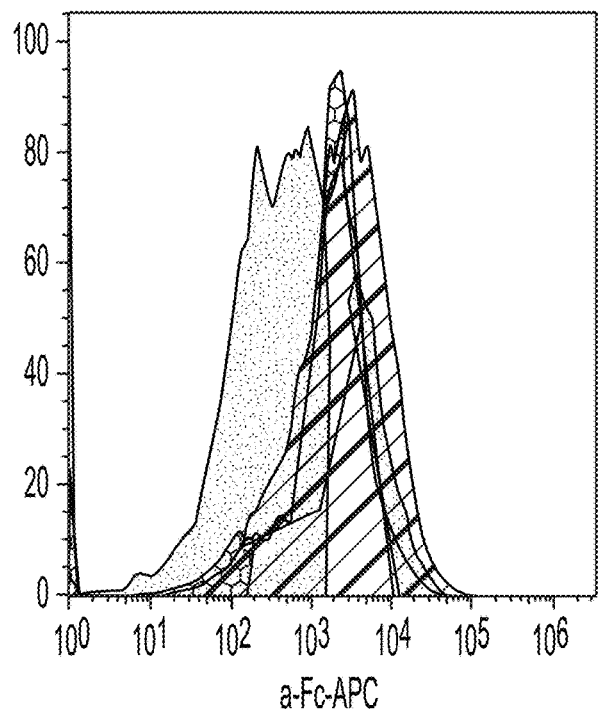
FIG. 32 depicts, in accordance with embodiments herein, anti-mouse CTLA4 installed on mouse dendritic cell surface can bind to mouse CTLA4 protein.

FIG. 32 illustrates one embodiment of Anti-mouse CTLA4 installed on mouse dendritic cell surface can bind to mouse CTLA4 protein. Mouse DC cells were first incubated with anti-CD16/32 to block Fc binding. Then anti-CTLA4 antibody was used to block the CTLA4 antigen on DC cell surface. After that, TCO-anti-CTLA4 antibody was installed on DC surface using the protocol described in Example 8. Cells labeled with anti-mouse CTLA4 or its isotype antibody were then incubated with the mouse CTLA4 Fc protein. The result indicates that the cells labeled with anti-mouse CTLA4 can bind more CTLA4 protein compared to the isotype conjugated cells, which was detected by staining with APC-anti-Fc antibody.

Example 34

Figure 33:
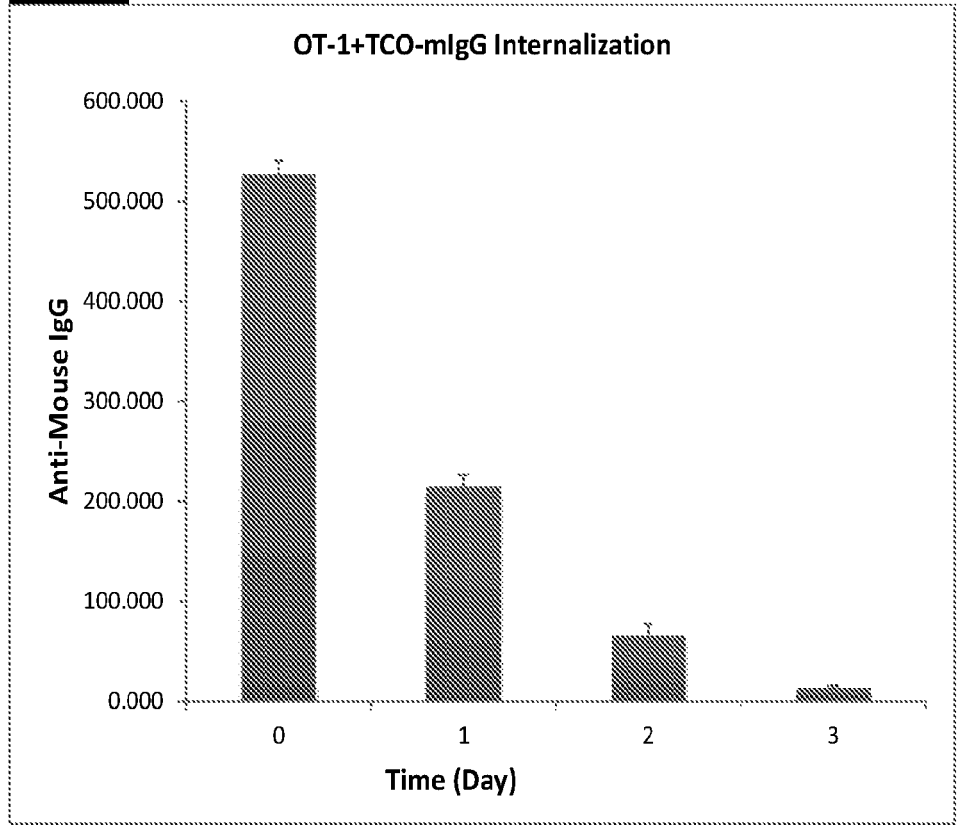
FIG. 33 depicts, in accordance with embodiments herein, mouse IgG installed on OT-1 CD8 T cell surface can stay on surface for more than 24 hours.

FIG. 33 illustrates one embodiment of Mouse IgG installed on OT-1 CD8 T cell surface can stay on surface for more than 24 hours. Mouse IgG antibodies were conjugated with OT-1 CD8 T cells as described in Example 13. Later, APC-anti mouse IgG was used to track the T cell surface covalently linked mouse IgG molecules. As shown in FIG. 33, the signal from mouse IgG can be obviously detected after 24 hours.

Example 35

Figure 34:
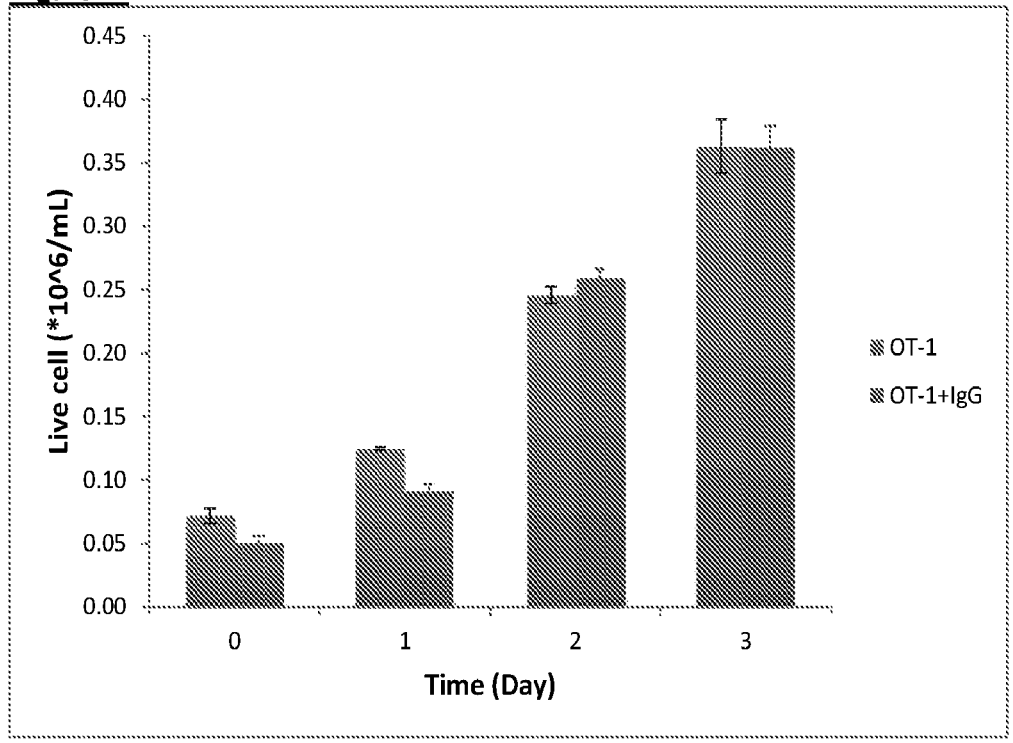
FIG. 34 depicts, in accordance with embodiments herein, conjugate OT-1 CD8 T cell with mouse IgG antibodies does not affect the proliferation rate of the modified cells.

FIG. 34 illustrates one embodiment of Conjugate OT-1 CD8 T cell with mouse IgG antibodies doesn't affect the proliferation. Mouse IgG antibodies were conjugated with OT-1 CD8 T cells as described in Example 13. Then the cells were cultured in T cell culture media with 10 ng/ml IL2. The cell counts were counted in three days. The data shows the proliferation rate of modified cells are similar as the unmodified cells.

Example 36

Figure 35:
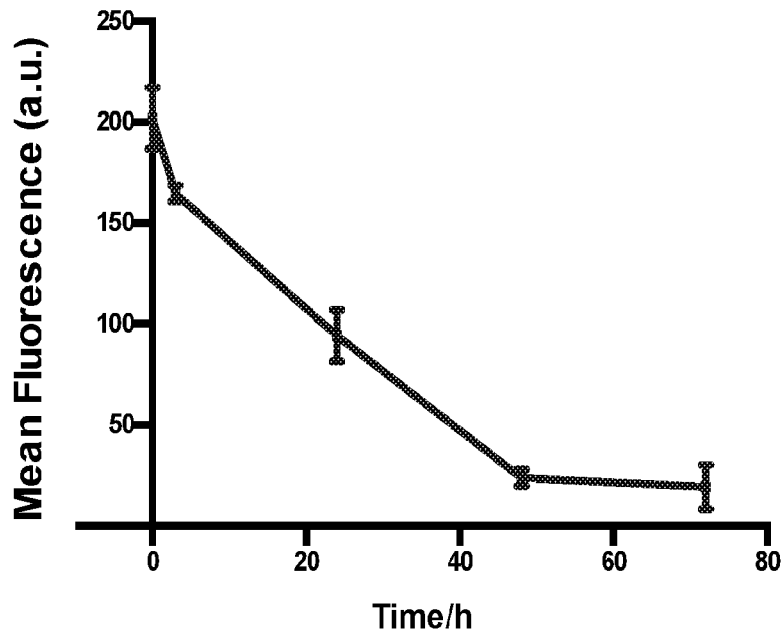
FIG. 35 depicts, in accordance with embodiments herein, anti-mouse PD-L1 installed on OT-1 CD8 T cell surface can stay on cell surface for more than 24 hours.

FIG. 35 illustrates one embodiment of Anti-mouse PD-L1 installed on OT-1 CD8 T cell surface can stay on cell surface for more than 24 hours. Anti-PD-L1 antibodies were conjugated with OT-1 CD8 T cells as described in Example 15 (after blocking with anti-PD-L1 antibodies, the cells were not stained with FITC-anti rat IgG in this example). Later, APC-anti rat IgG were used to track the T cell surface covalently linked anti-PD-L1 antibodies. As shown in FIG. 35, the signal from the conjugated anti-PD-L1 can be obviously detected after 24 hours.

Example 37

Figure 36:
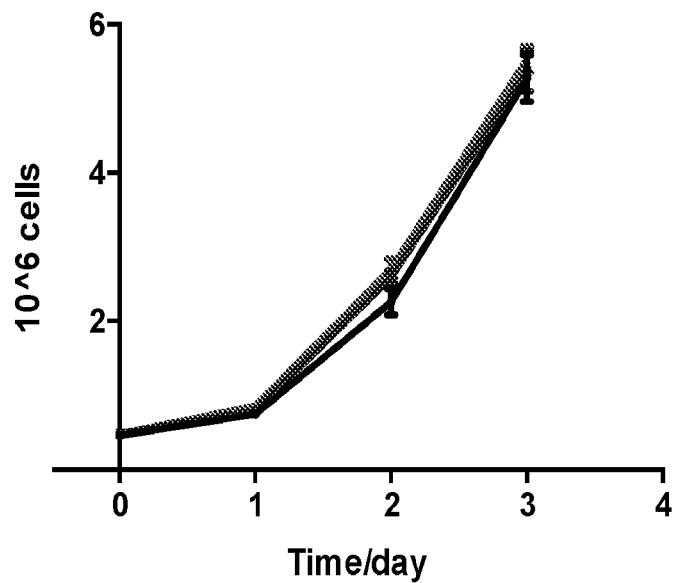
FIG. 36 depicts, in accordance with embodiments herein, conjugate OT-1 CD8 T cell with anti-PD-L1 antibodies doesn't affect the proliferation rate of modified cells.

FIG. 36 illustrates one embodiment of Conjugate OT-1 CD8 T cell with anti-PD-L1 antibodies doesn't affect the proliferation. Anti-PD-L1 antibodies were conjugated with OT-1 CD8 T cells as described in Example 16. Then the cells were cultured in T cell culture media with 10 ng/ml IL2. The cell counts were counted in three days. The data shows the proliferation rate of modified cells are similar as the unmodified cells.

Example 38

Figure 37:
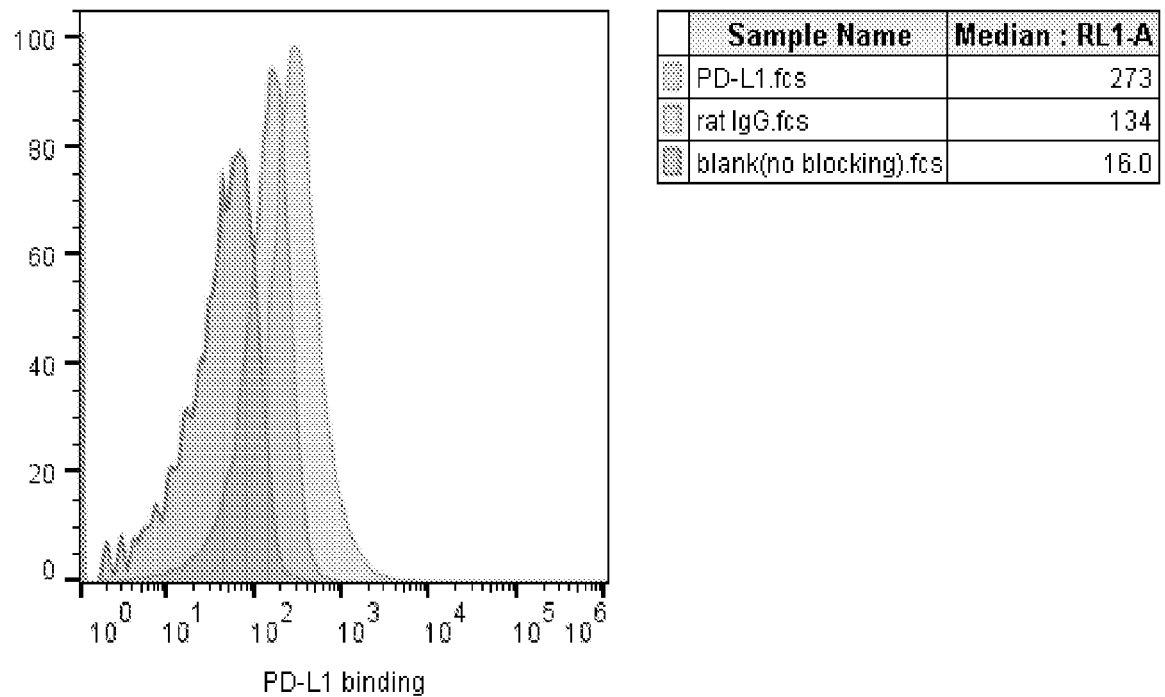
FIG. 37 depicts, in accordance with embodiments herein, anti-mouse PD-L1 installed on OT-1 CD8 T cell surface can bind to mouse PD-L1.

FIG. 37 illustrates one embodiment of Anti-mouse PD-L1 installed on OT-1 CD8 T cell surface can bind to mouse PD-L1. Anti-mouse PD-L1 or rat IgG isotype control was installed on OT-1 T cell surface through the protocol in Example 16 (cells were blocked by anti-PD-L1 before covalent reaction with TCO-antibodies). After that, cells labeled with anti-mouse PD-L1 or its isotype antibody were incubated with the mouse PD-L1 Fc protein. The result shows that the cells labeled with anti-mouse PD-L1 can bind more PD-L1 protein compared to the isotype conjugated cells (FIG. 37). The PD-L1 binding in the isotype control group comes from the blocking anti-PD-L1 antibodies on T cell surface.

Example 39

Figure 38:
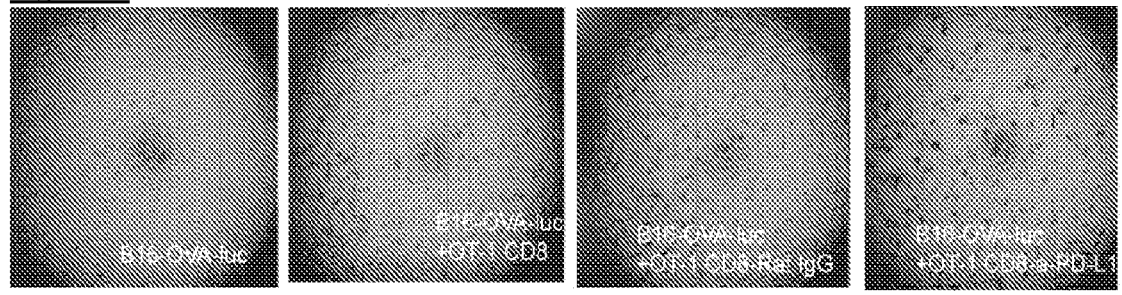
FIG. 38 depicts, in accordance with embodiments herein, anti-mouse PD-L1 installed on OT-1 CD8 T cell surface can improve T cells' killing function on cancer cells.
Figure 38:
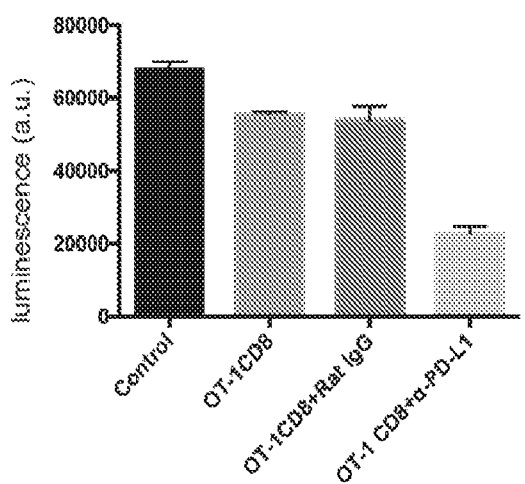

FIG. 38 illustrates one embodiment of Anti-mouse PD-L1 installed on OT-1 CD8 T cell surface can improve T cells' killing function on cancer cells. Anti-mouse PD-L1 or rat IgG isotype control was installed on OT-1 T cell surface through the protocol in Example 16. After that, OT-1 CD8 T cells with or without modifications were mixed with B16-OVA-luc cells (B16 melanoma cells with overexpressed OVA antigen and luciferase marker) and incubated for 2 days. According to the imaging and luciferase activity assay, OT-1 cells with covalently linked anti-PD-L1 antibody can induce more T clusters and kill more cancer cells compared to OT-1 CD8 T cells or isotype labeled T cells.

Example 40

Figure 44:
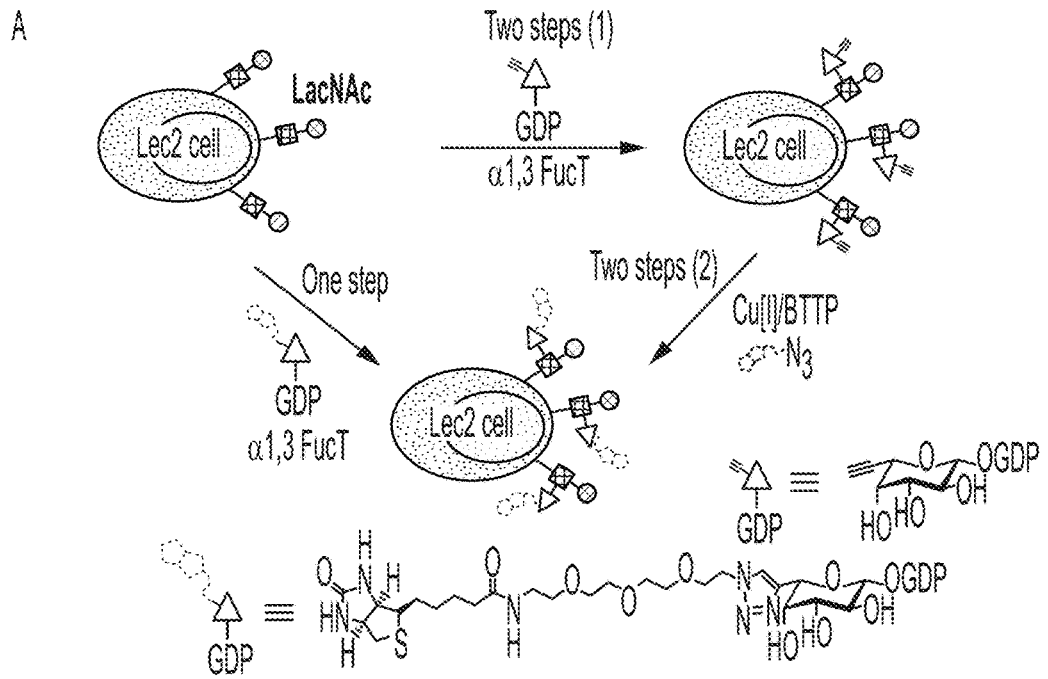
FIG. 44 depicts, in accordance with embodiments herein, one-step enzymatic labeling is more efficient and biocompatible than two-step. (A) Scheme of one-step and two-step labeling system. In one step labeling system, one-pot product of GF-Al-biotin was directly transferred to LacNAc epitope on Lec2 cell surface using α1,3-FucT. In contrast, the two-step labeling involved the first step of enzymatic transfer of GF-Al and a followed step of CuAAC reaction between surface alkyne and azide-biotin probe. (B) Flow cytometry analysis of biocompatibility in one-step or two-step labeling process. Lec2 cells after reaction were stained with DAPI. (C) Comparison of efficiency in one-step and two-step labeling process described in (A). Cells were stained by streptavidin-APC.
Figure 44:
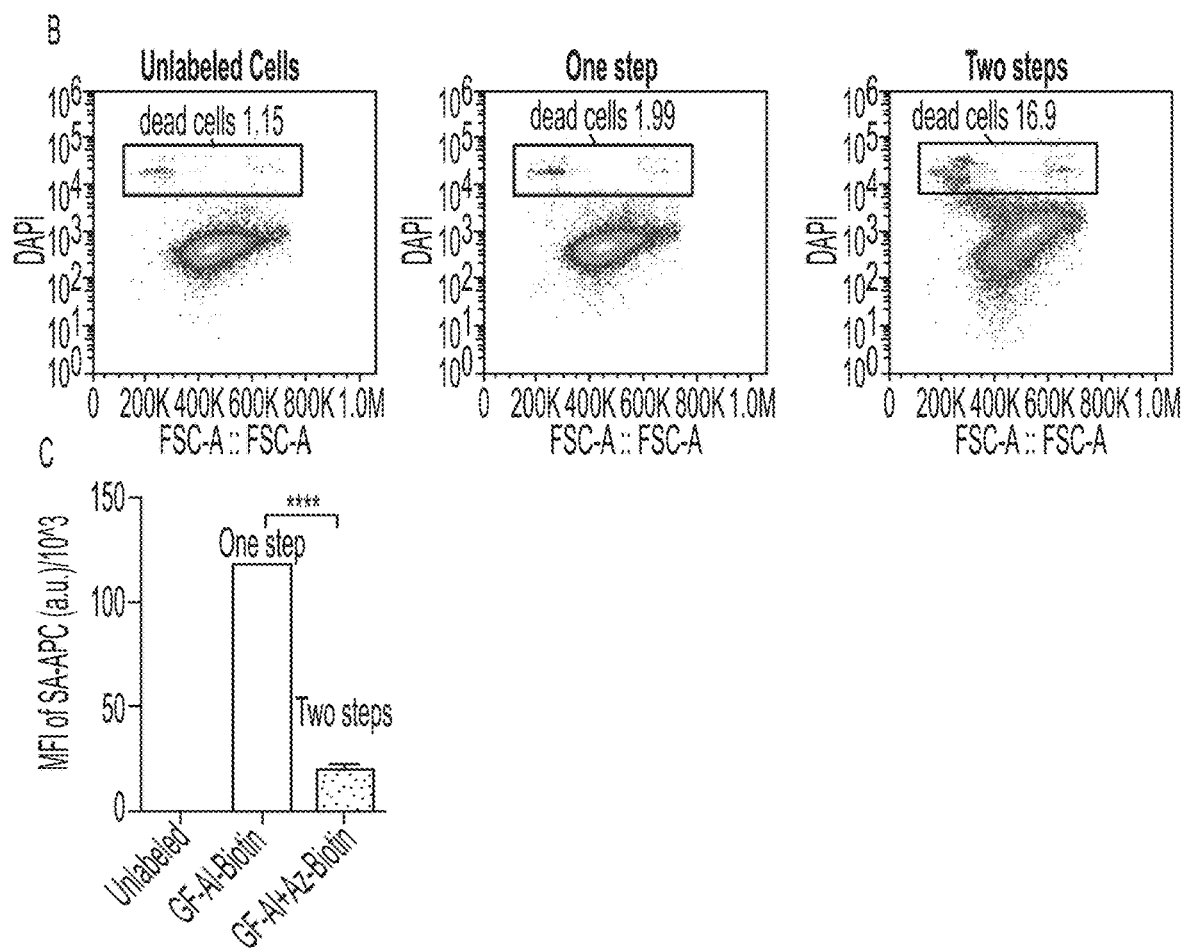
Figure 45:
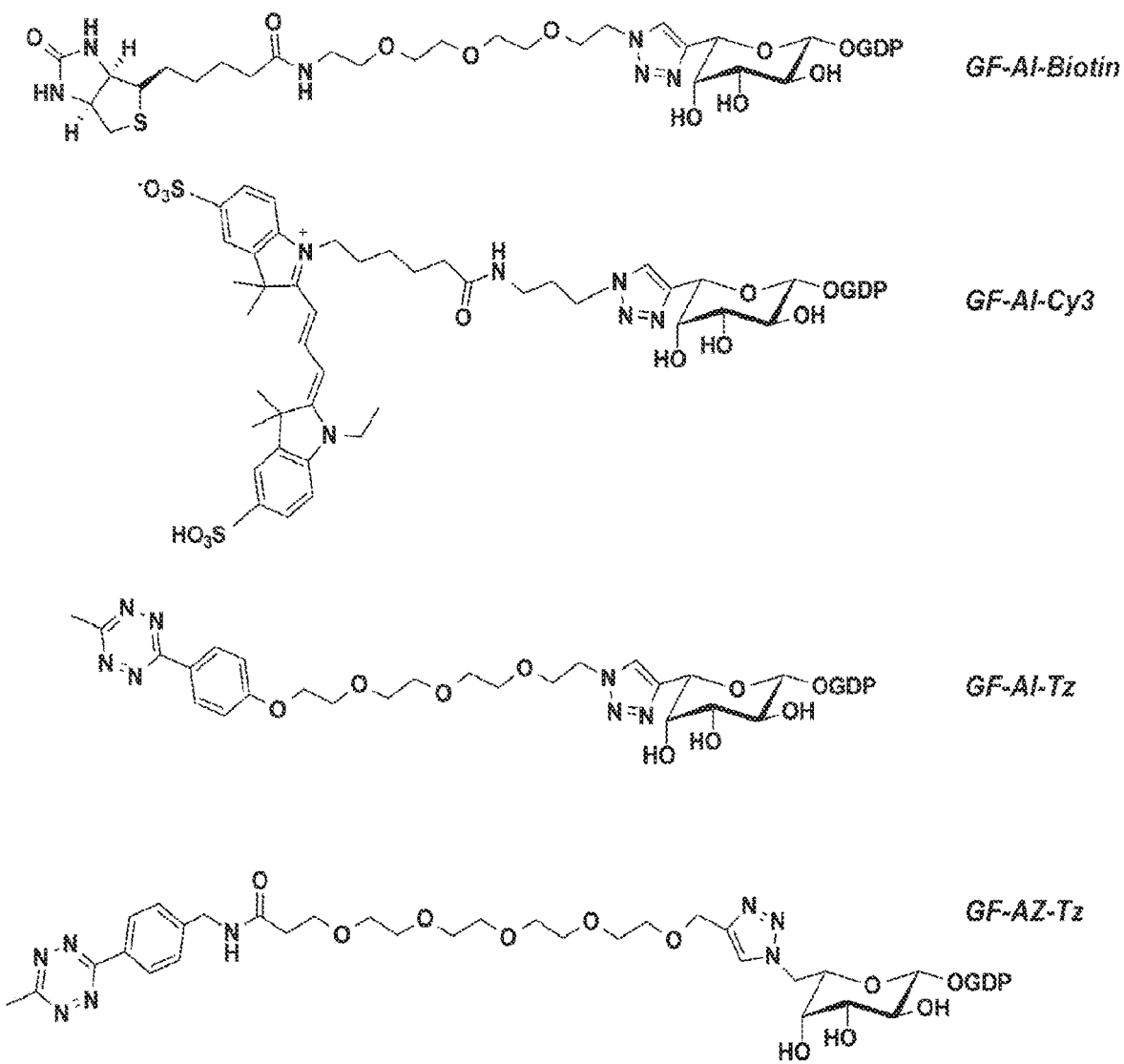
FIG. 45 depicts, in accordance with embodiments herein, chemical structures of GDP-Fuc derivatives including GF-Al-Biotin, GF-Al-Cy3, GF-Al-Tz and GF-Az-Tz.
Figure 46:
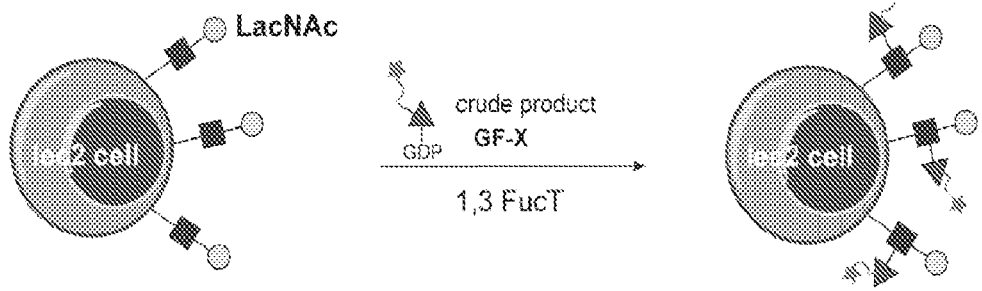
FIG. 46 depicts, in accordance with embodiments herein, one-step enzymatic transfer of one-pot GDP-Fuc derivatives to Lec2 cells. (A) Scheme of transferring one-pot GDP-Fuc derivatives using α1,3-FucT to LacNAc epitope on Lec2 CHO cell surface. (B) Lec2 cells were treated with FT and GF-Al-Cy3, FT alone, or GF-Al-Cy3 alone, or untreated. Then cells were analyzed by flow cytometry, which only showed successful labeling when treated with both FT and GF-Al-Cy3. (C) Lec2 cells were treated with FT and GF-Az-Tz, FT alone, or GF-Az-Tz alone, or untreated. Then the cells were reacted with TCO-Cy5 and analyzed by flow cytometry. Clear labeling is only shown in the group treated with FT and GF-Az-Tz. (D) GF-Al-Tz and GF-Az-Tz were compared in the FT mediated transfer reaction on Lec2 cells. Cells were reacted with TCO-Cy5 after enzymatic reaction and analyzed by flow cytometry. GF-Az-Tz group showed stronger signal than GF-Al-Tz. (E) Lec2 cells were treated with FT and GF-Az-ssDNA-FAM, or GF-Az-ssDNA-FAM alone, or untreated. Then the cells were analyzed by flow cytometry. The group treated with FT and GF-Az-ssDNA-FAM has the strongest FAM signal.
Figure 46:
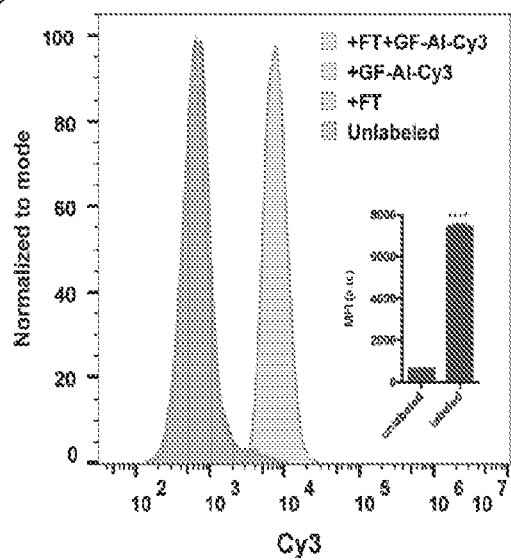
Figure 46:
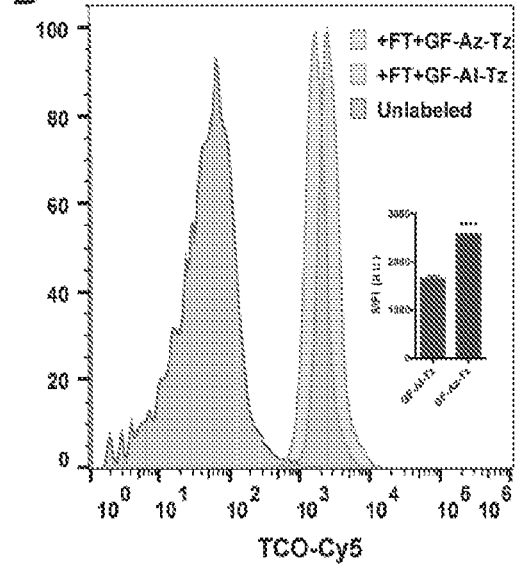
Figure 46:
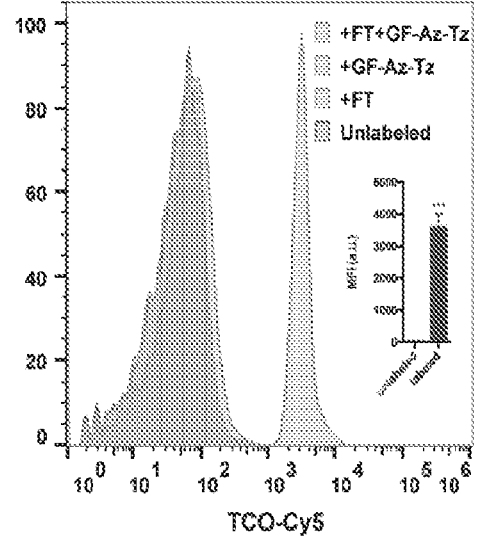
Figure 46:
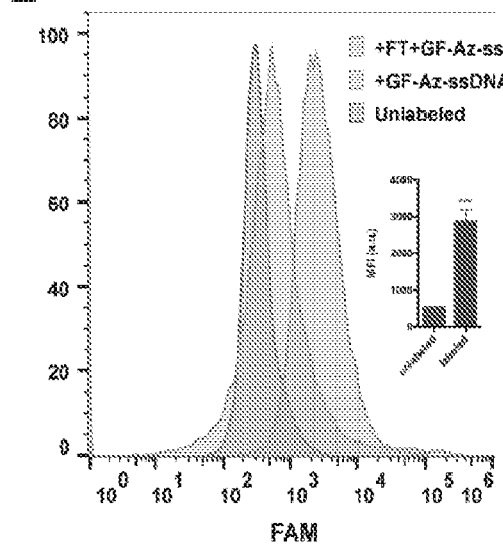
Figure 47:
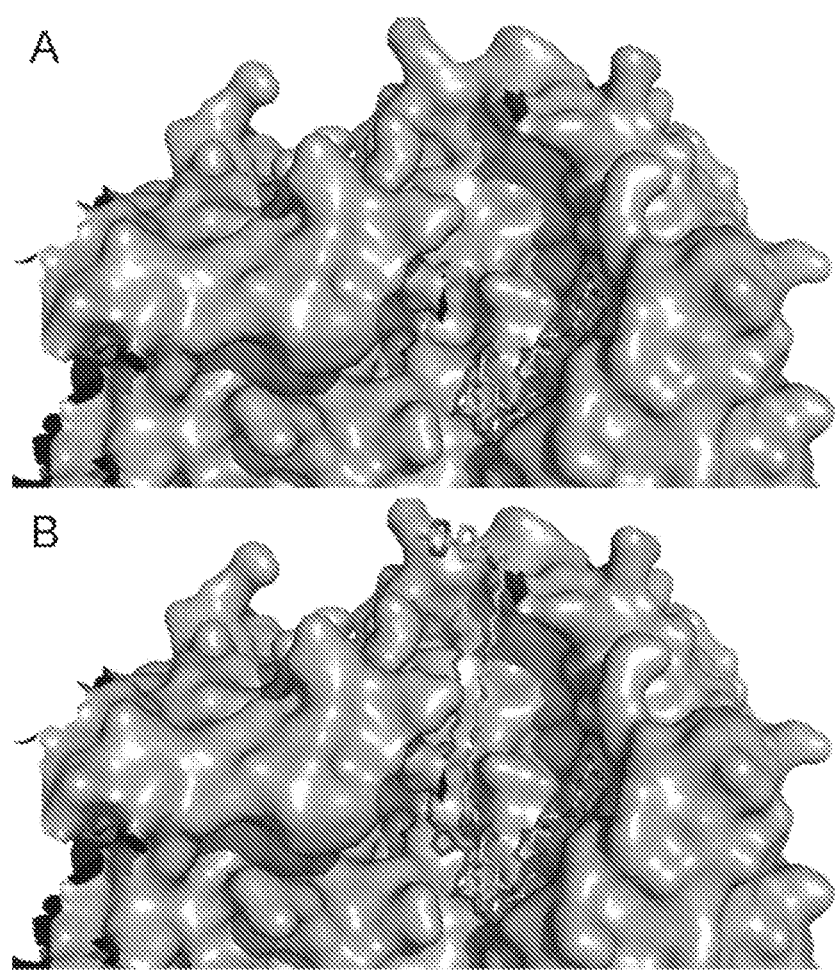
FIG. 47 depicts, in accordance with embodiments herein, molecular models of GDP-fucose (A) and GF-Az-Tz (B) in the active site of α1,3-FucT. Images are created from the previous reported crystal structure (PDB: 2NZY) of HP-FucT and GDP-fucose complex in PyMOL.

In one embodiment, disclosed herein is a one-pot method for producing GDP-Fuc derivatives efficiently and cost-effectively. The absence of facile methods for the synthesis and purification of versatile donor substrates in preparative scales has hindered the applications of enzymatic glycoengineering. In fact, the inventors have previously shown that FucT enzyme from *H. pylori* could accept GDP-Fuc derivatives with a functional group (e.g. fluorescein) larger than azide at the C6 position of the fucose. However, great loss of products in purifying one-step engineering substrates makes the two-step procedure more preferred in cell surface. To expand the scope and applications of one-step engineering enabled by FucT, all kinds of derivatives of GDP-Fuc should be easily prepared in large scale. Since the approach for GDP-Fuc analogues synthesis is nearly quantitative (>90%), it seems that purifications of products are not required for subsequent cell surface reactions if all the components after reactions are biocompatible. To test this hypothesis, the inventors prepared one-pot crude products of GDP-Fuc using biocompatible $Mg^{2+}$. The one-pot products are directly used without purification and the efficiency is the same as pure GDP-Fuc on cell surface (FIG. 44). To make this one-pot protocol compatible with versatile GDP-Fuc derivatives, one-pot products of GDP-Fuc alkyne (GF-Al) or GDP-Fuc azide (GF-Az) was directly modified with different moieties using ligand accelerated and biocompatible copper(I)-catalyzed alkyne-azide cycloaddition (CuAAC) previously developed (FIG. 39C). See, for example, Wang, W. et al, Proc. Natl. Acad. Sci. USA 2009, 106, 16096; Besanceney-Webler, C. et al Angew. Chem. Int. Ed. 2011, 50, 8051, the contents of each of which are incorporated by reference in its entirety, including the drawings. All the reactions were in great yields (>95%) after overnight and then quenched by the copper chelator (bathocuproine sulphonate, BCS) to make the one-pot products more biocompatible for direct use on cells. Compared to the conventional two-step protocol for cell surface LacNAc labeling (enzymatic transfer followed by cell surface click chemistry), one-step enzymatic labeling using one-pot GF-Al-biotin are more efficient and biocompatible (FIG. 45). Besides the biotin probe, a fluorescent probe Cy3, a bioorthogonal reaction handle tetrazine (Tz) and a dye (FAM) labeled single-strand DNA (ssDNA) were also conjugated with GF-Al or GF-Az through this one-pot protocol in high efficiency (FIG. 39C and FIG. 46). All these one-pot products were later efficiently transferred to cell surface via one-step enzymatic reactions using FucT (FIG. 47). These results demonstrate this one-pot protocol is robust and its products are general applicable in the subsequent cell surface reaction. Additionally, the one-pot Tz derivative made from GF-Az is more efficient than the one made from GF-Al (FIG. 46D). It is consistent with the inventor's previous result that GF-Az is a more favorable substrate of FucT.

Example 41

Figure 40:
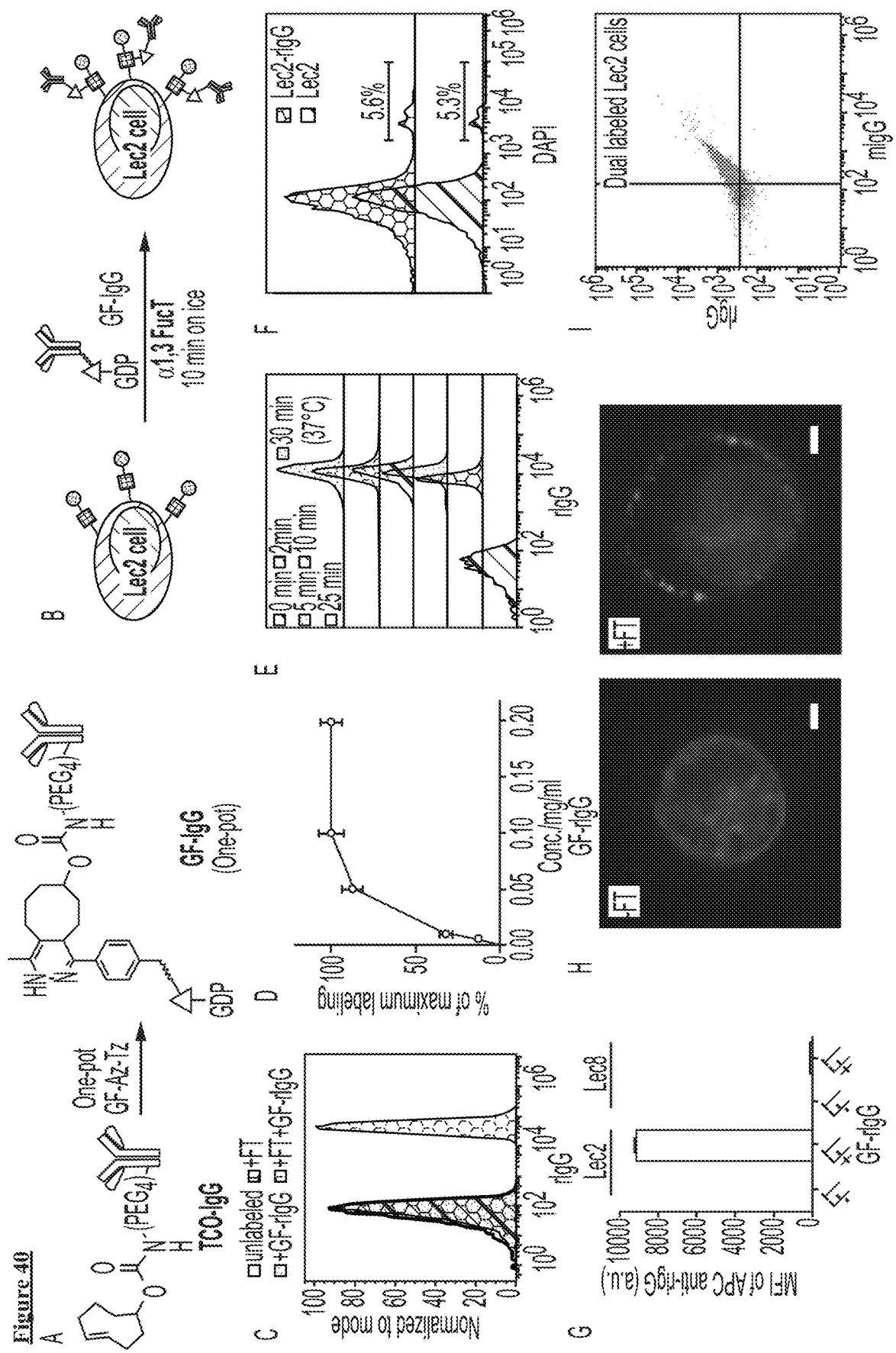
FIG. 40 depicts, in accordance with embodiments herein, enzymatic transfer of IgG to the cell surface of Lec2CHO cells. (A) Schematic representation of GDP-Fuc modified IgG (GF-IgG) synthesis. Chemical structures of bioorthogonal handles and linkers are shown. (B) Scheme of using FucT to transfer GF-IgG to CHO Lec2 cell surface. (C) Flow cytometry analysis of Lec2 cells treated with enzyme FT, substrates GF-rIgG or both. (D) Titration of GF-rIgG concentrations (from 0.005 mg/ml to 0.2 mg/ml) in enzymatic transfer. Each reaction used same amount of FT and was left in room temperature for 30 min. Mean±SD (error bars), representative graph from three independent experiments. (E) Time course of enzymatic transfer of GF-rIgG to Lec2 cells on ice. Reaction at 37° C. was a maximum labeling control. (F) Flow cytometry analysis of Lec2 cells viability before and after IgG labeling. (G) CHO Lec8 cells without LacNAc expression was compared with Lec2 cells in enzymatic IgG transfer as a negative control. Mean±SD (error bars), representative graph from three independent experiments. (H) Confocal microscopy images of Lec2 cells treated with or without FT when incubated with Alexa Fluor 647 labeled GF-rIgG. Nuclei were stained with Hoechst 33342. Scale bar: 2 μm. (I) Flow cytometry analysis of Lec2 cells labeled with rIgG and mIgG simultaneously.
Figure 48:
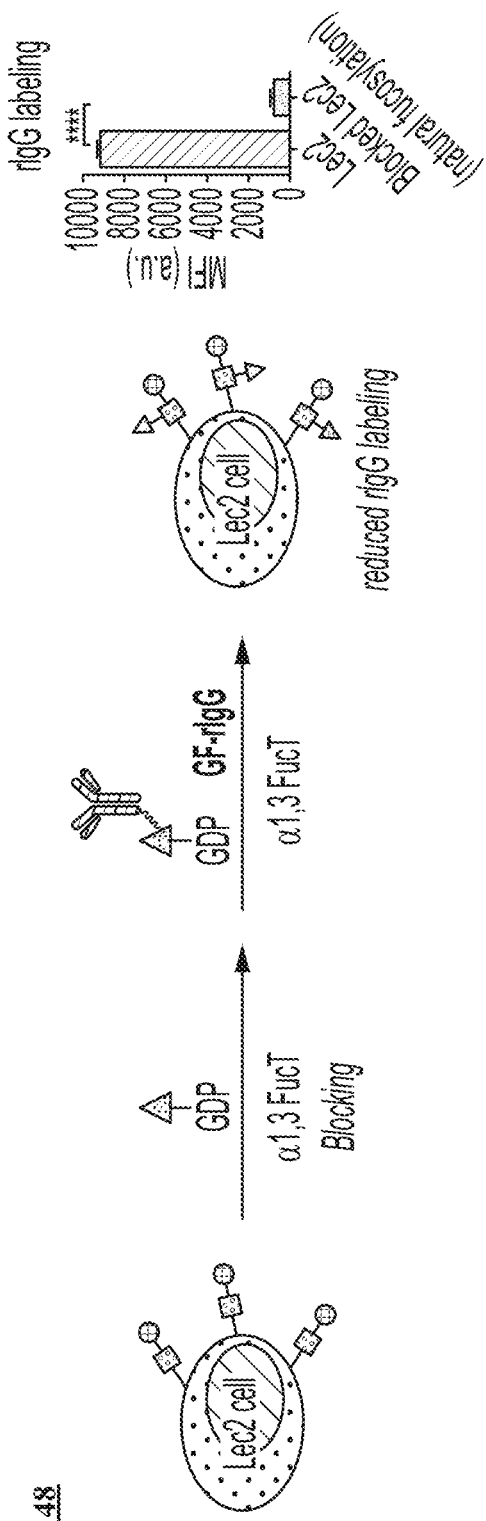
FIG. 48 depicts, in accordance with embodiments herein, the blockade of LacNAc epitope inhibits FT mediated GF-rIgG transfer to Lec2 cell surface. Lec2 cells were treated with FT and GDP-Fuc first, which could occupy almost all of the LacNAc epitope. After that, blocked cells were treated with FT and GF-rIgG. rIgG labeling were analyzed by flow cytometry. Compared to direct GF-rIgG transfer, the blocked Lec2 have a significantly reduced rIgG signal. Error bars, mean values±SD. ****P<0.0001.
Figure 49:
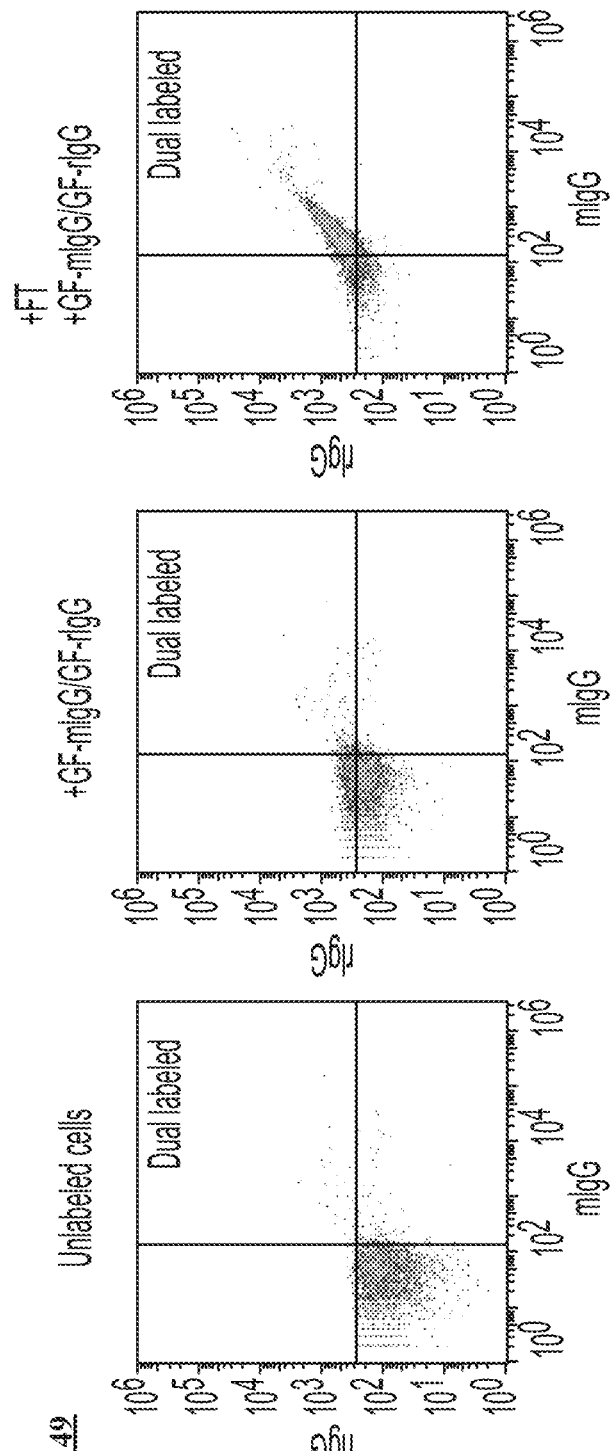
FIG. 49 depicts, in accordance with embodiments herein, dual labeling of two different IgG molecules on Lec2 cells. Lec2 cells were treated with GF-mIgG, GF-rIgG and FT. GF-mIgG and GF-rIgG treated was shown as a negative control. The labeled cells were stained with anti-mIgG and anti-rIgG fluorescent antibodies and analyzed by flow cytometry.

In one embodiment, disclosed herein is an enzymatic transfer method for transferring whole IgG molecules to cell surface using FucT. Through the one-pot protocol, GDP-Fuc derivatives could be easily diversified. Among them, GF-Az-Tz is an interesting derivative with a very powerful bioorthogonal handle (Tz), which could be further reacted with biomacromolecules bearing strained dienophiles. This type of reaction is the so-called inverse electron-demand Diels-Alder reaction (IEDDA) with extremely high efficiency and superior bioorthogonality. The inventors challenged the substrates limit of FucT from whole IgG, as it is one of the biggest therapeutic biomolecules. The bioorthogonal handle of trans-cyclooctene (TCO) with a PEG linker was installed onto mAbs or their isotype controls via standard amine-coupling procedures. The labeling reagent of TCO-PEG4-NHS ester is commercially available and the protocols are well studied. After that, mAbs bearing TCO moieties were directly reacted with one-pot GF-Az-Tz to generate GDP-Fuc modified IgG molecules (GF-IgG) (FIG. 40A). One-pot products of GDP-Fuc labeled rat IgG (GF-rIgG) were first employed in the enzymatic transfer using FucT on cell surface (FIG. 40B). Lec2 CHO cells with complex/hybrid N-glycans that mainly terminate in LacNAc units were chosen as mode cells due to its well-defined glycan complement. Surprisingly, the transfer of GF-rIgG to Lec2 surface was efficient and specific under normal ex vivo fucosylation conditions: the very positive signal of rIgG on cell surface analyzed by flow cytometer was only detected when both FucT (60 mU) and GF-rIgG (0.1 mg/ml) were added (FIG. 40C). Meanwhile, the labeling intensity is GF-rIgG concentration dependent, which reaches saturation at 0.1 mg/ml (FIG. 40D). Most notably, the reaction could finish in 10 minutes even on ice (FIG. 40E). The viability of rIgG labeled cells was similar as unlabeled cells, which further confirm the biocompatibility of reaction and one-pot substrates (FIG. 40F). Lec8 CHO cells, which do not express LacNAc, were used as a negative control to confirm the transfer is dependent on the reaction between GDP-Fuc moieties on IgG molecules and the LacNAc unit on cell surface. As expected, there was no increase of fluorescence displayed by Lec8 cells after reaction compared to Lec2 cells (FIG. 40G). A competition experiment using cells blocked by natural substrates of FucT, GDP-Fuc, was also conducted, in which the subsequent GF-rIgG labeling was almost abolished (FIG. 48). These results further confirmed the reaction sites of enzymatic transfer of GF-rIgG are almost the same as GDP-Fuc on cell surface, which have been demonstrated as LacNAc units in complex/hybrid N-glycans. Besides flow cytometry analysis, confocal microscopy images were taken to confirm most of the labeled rIgG stay on cell surface (FIG. 40H). To show the advantages of enzymatic engineering in introducing multiple functionalities, GF-rIgG and GF-mIgG (GDP-Fuc modified mouse IgG) were mixed at 1:1 ratio in the enzymatic reaction. Dual label of two different IgG molecules on Lec2 cell surface was clearly detected, which is hard to be achieved in genetic engineering (FIG. 40I and FIG. 49).

Example 42

Figure 41:
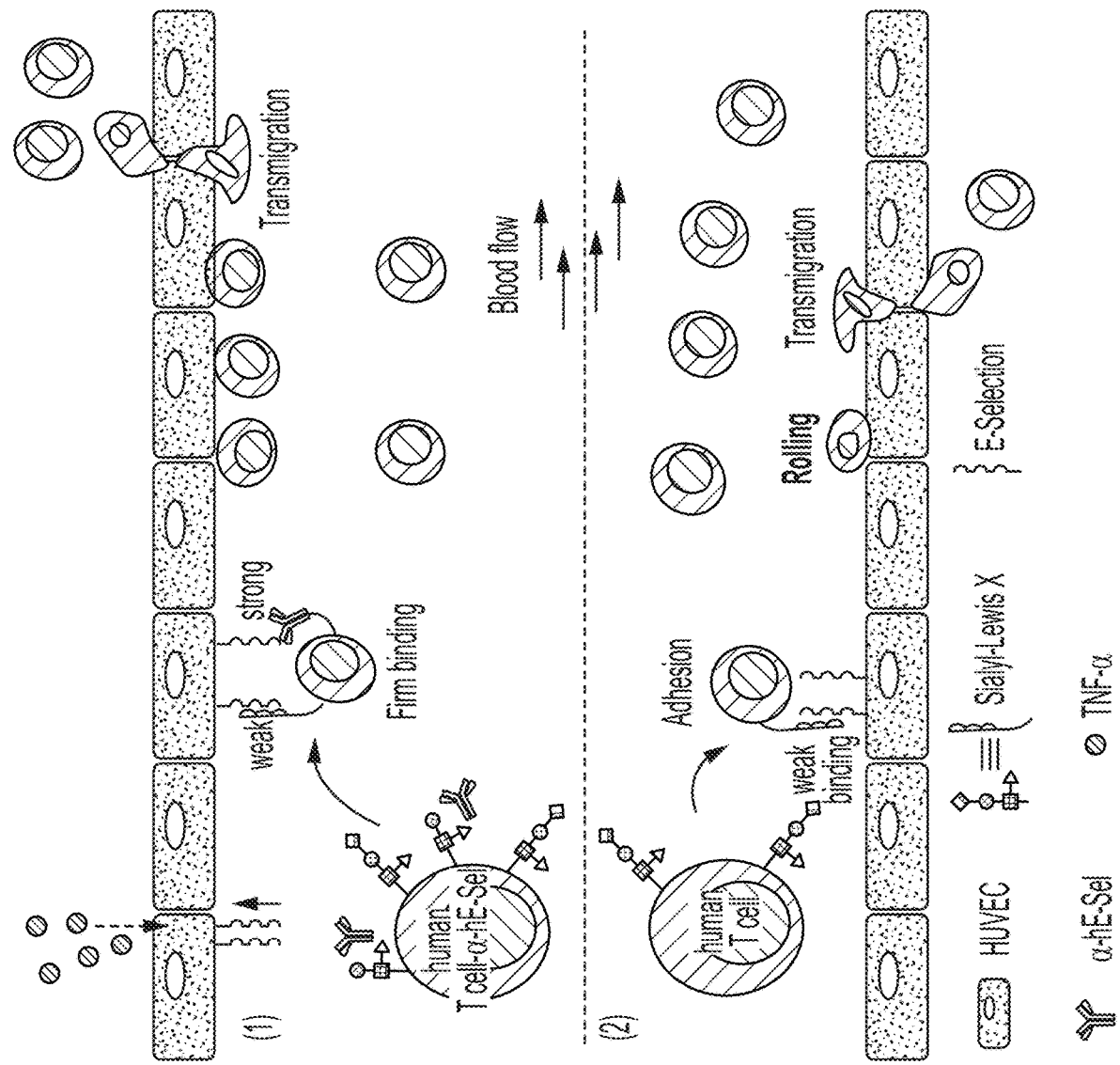
FIG. 41 depicts, in accordance with embodiments herein, enzymatic transfer of α-E-selectin to primary human T cells. (A) Schematic illustration of modified (1) and natural (2) process of human T cell binding and transmigration on HUVEC cells. (B) FT mediated GF-α-hE-Sel labeling on primary human T cells from three different donors. Mean±SD (error bars), representative graph from three independent experiments. (C) Binding of human E-selectin-Fc chimera on unlabeled T cells and T cells labeled with mIgG or α-hE-Sel. Mean±SD (error bars). (D) Analysis of flow chamber assay on human E-selectin-Fc coated slides under shear stress conditions. T cells labeled with mIgG or α-hE-Sel were compared with unlabeled T cells. Cell numbers (cells/mm$^2$) were quantified in ImageJ. Mean±SD (error bars). (E,F) Quantitative analysis and fluorescent microscopy images of human T cells binding on HUVEC. Human T cells were stained with CFSE (green) and HUVEC cells were stained with Hoechst 33342 (blue) and DiD (red). HUVEC were pretreated with TNF-α if indicated. Mean±SD (error bars), representative graph from three independent experiments. Scale bar: 50 μm. (G) Analysis of transmigration assay on HUVEC. Migrated T cells (LeukoTracker, Green) in the bottom layer were quantified by fluorescence signal. In all figures: ns, P>0.05; *P<0.05; P<0.01; **P<0.0001.
Figure 41:
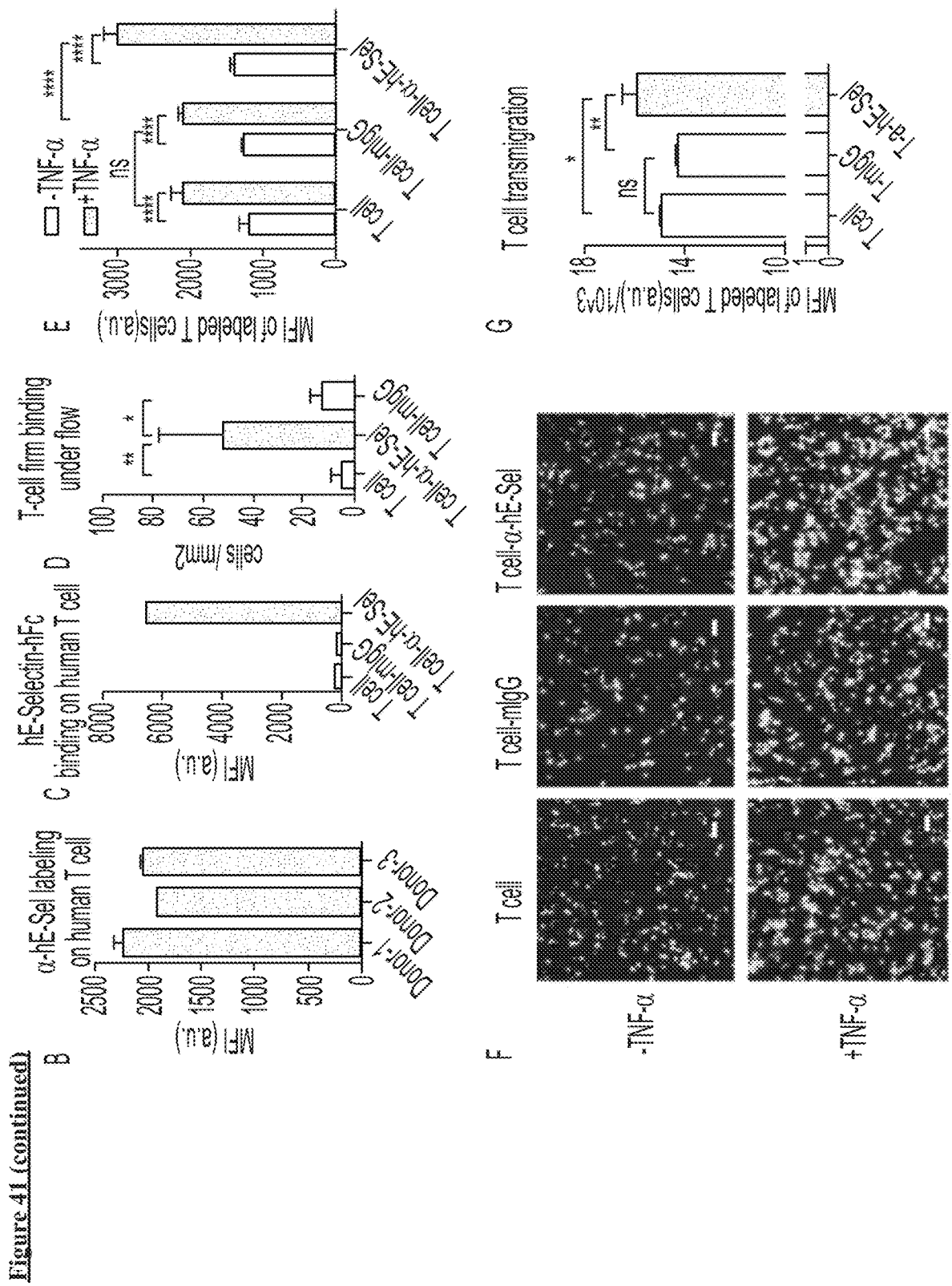

In one embodiment, disclosed herein is an enzymatic transfer method for transferring of α-E-Selectin to T cells which enables firm binding to inflamed sites. Cell homing to diseased tissues is the first important issue of a successful ACT. Briefly, the interaction between the glycan ligand sialyl Lewis X (sLeX) and the selectin family (e.g. E-selectin) mediates the tethering and rolling of circulating leukocytes on the vascular cell wall, which promotes subsequent extravasation and migration of leukocytes through the endothelium into the surrounding tissue (FIG. 41A). In patients, cytokines (e.g. TNF-α) from the inflamed sites, such as tumorous, infected or injured tissues, induces the over-expression of E-selectin on endothelial cells of nearby blood vessels, which could help to recruit immune cells for treatment. Therefore, targeting E-selectin to induce firm binding could help adoptive transferred cells homing to diseased tissues for an enhanced therapy. Unlike the conventional approach to increase the amount of sLeX on cell surface, in one embodiment, the inventors have proposed that installation of α-E-selectin on T cell surface could directly mediate firm binding of T cells on endothelial cells with high E-selectin expression level, which could bypass natural processes of tethering, rolling and firm adhesion (FIG. 41A).

Figure 50:
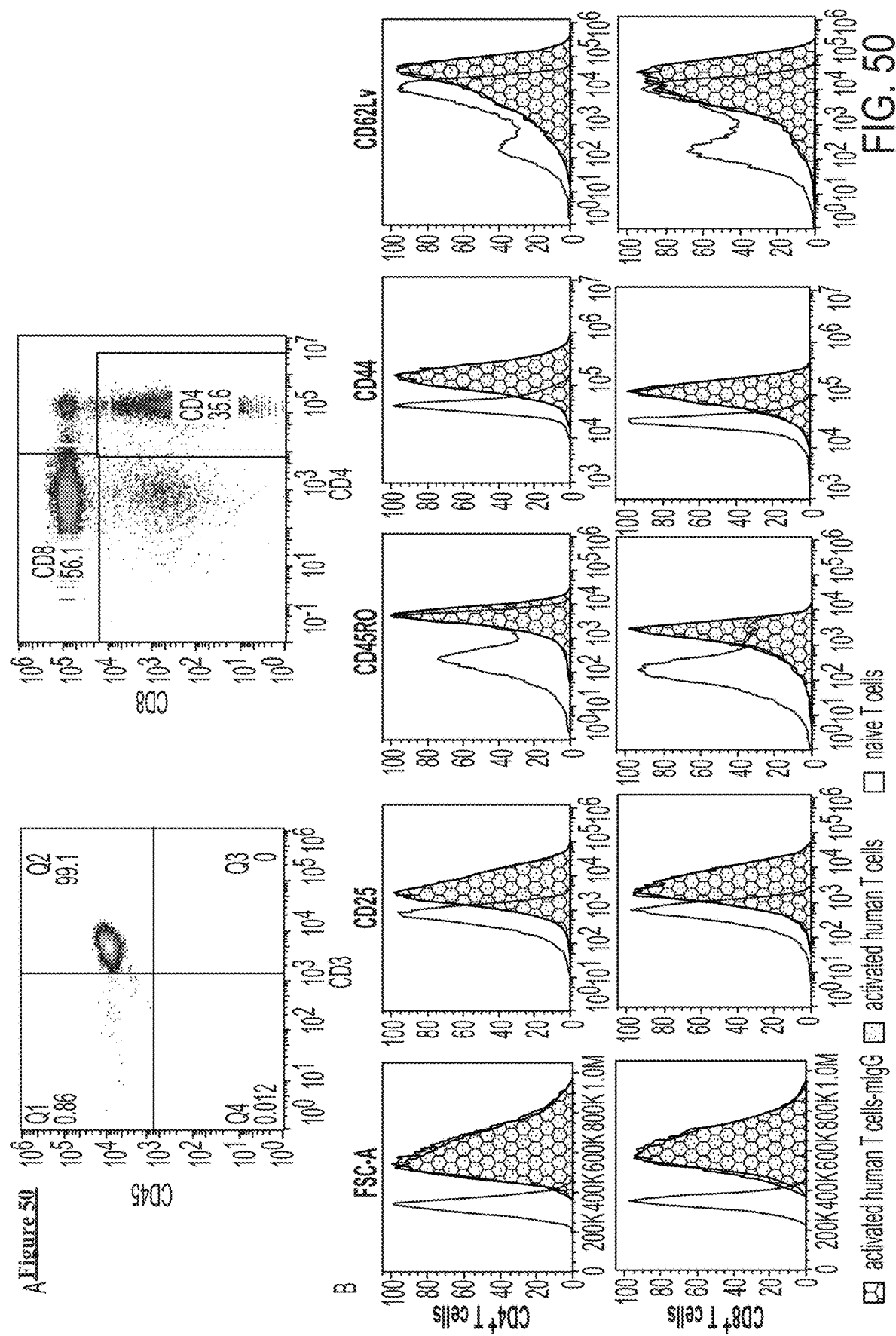
FIG. 50 depicts, in accordance with embodiments herein, phenotype of human T cells before and after mIgG labeling. (A) Human PBMC were activated by anti-CD3/CD28 antibody and expanded in vitro for about two weeks. The cells were stained with anti-CD3, anti-CD45, anti-CD4 and anti-CD8 fluorescent antibodies, and analyzed by flow cytometry. (B) Activated human T cells were treated with GF-IgG and FT. Labeled or unlabeled cells were stained with anti-CD4, anti-CD8, anti-CD25, anti-CD45RO, anti-CD44 and anti-CD62L fluorescent antibodies and analyzed by flow cytometry. Naïve T cells were used as control.
Figure 51:
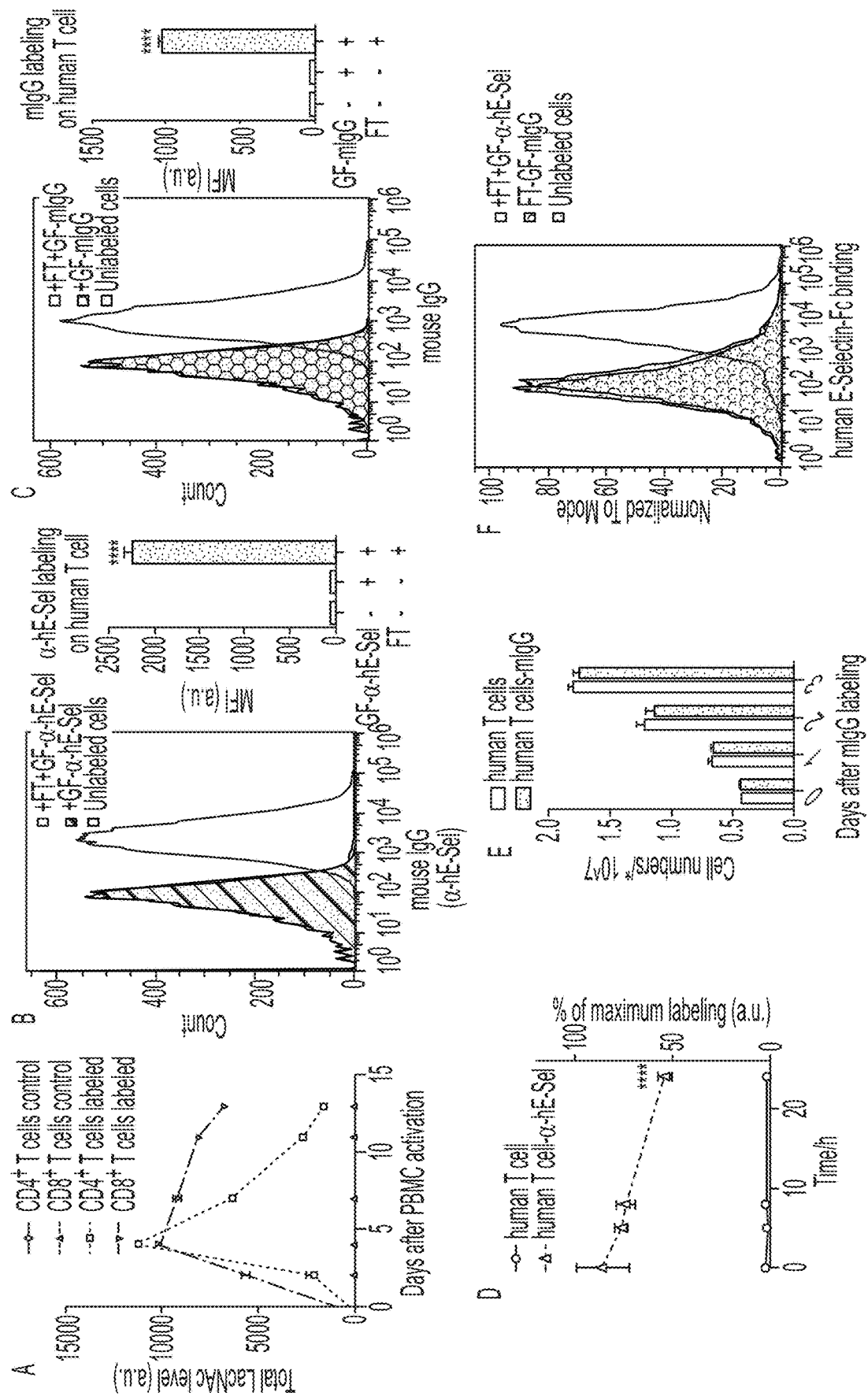
FIG. 51 depicts, in accordance with embodiments herein, transferring IgG molecules onto human T cells. (A) LacNAc on Human PBMC was labeled by GF-Biotin on different days after activation. Labeled cells were stained with streptavidin-APC, anti-CD4 and anti-CD8 fluorescent antibodies, and analyzed by flow cytometry. (B) Human T cells were treated with FT and GF-α-hE-Sel, or GF-α-hE-Sel alone, or untreated. The cells were stained with anti-mIgG fluorescent antibody and analyzed by flow cytometry. (C) Human T cells were treated with FT and GF-mIgG, or GF-mIgG alone, or untreated. The cells were stained with anti-mIgG fluorescent antibody and analyzed by flow cytometry. (D) Human T cells labeled with α-hE-Sel were stained with anti-mIgG fluorescent antibody and analyzed by flow cytometry at different time points after labeling. (E) Human T cells with or without mIgG labeling were cultured in T cell media and live cells in each group were counted on different days after labeling. (F) Human T cells with different modifications were incubated with E-selectin-Fc protein and then stained with anti-hFc fluorescent antibody for FACS analysis. Error bars, mean values±SD. In all figures: ****P<0.0001.

To demonstrate this possibility, the inventors used clinically relevant primary human T cells (in similar culture conditions of CAR-T). Freshly prepared human peripheral blood mononuclear cells (PBMC) were activated through anti-CD3/CD28 treatment and expanded ex vivo for around two weeks (characterization of phenotypes in FIG. 50). During the culture process, the LacNAc levels of human T cells were tracked via enzymatic labeling with GF-Al-biotin (FIG. 51A). Both CD4+ and CD8+ T cells have a great increase of LacNAc level after activation, which stay at a moderate level after two weeks (CD8+ is higher than CD4+). After confirming that ex vivo expanded human T cells have enough LacNAc for labeling, FucT was used to transfer GDP-Fuc modified anti-human E-selectin (GF-α-hE-Sel) to human T cells as well as an isotype control, GF-mIgG. Both of these two antibodies were specifically labeled to human T cells, while the labeling efficiency have negligible variations among three different donors (FIGS. 41B, 51B, 51C). After that, cells conjugated with mIgG were stained using several surface markers and compared with unlabeled cells. The results indicate that enzymatic transfer of IgG molecules to cell surface does not affect the surface markers (FIG. 50B). Whole IgG conjugated on human T cell surface stayed more than 24 hours (~50% left after 24 hours) and had no effect on cells proliferation (FIGS. 51D and 51E). Labeled or unlabeled human T cells were then mixed with hE-Selectin/human Fc Chimera protein (hE-Selectin-hFc). Compared to unlabeled cells or mIgG group, cells labeled with α-hE-Sel strongly bind to its antigen, hE-Selectin-hFc protein, which indicates the mAbs conjugated to cell surface still have functions (FIG. 41C, FIG. 51F). Meanwhile, in a flow chamber assay, T cells with different modifications were mixed with unlabeled cells separately and then flowed through hE-Selectin-hFc coated slides under certain shear stress. Firm binding to E-selectin on the slide was only achieved when T cells were conjugated with α-hE-Sel (FIG. 41D). To further confirm the results on cell surface, CFSE labeled human T cells (green) were modified with antibodies and then added to human umbilical vein endothelial cells (HUVEC) stimulated with or without TNF-α. After washing off unbound cells, T cells binding to HUVEC were quantified by plate reader via the fluorescence intensity of CFSE. The highest signal was shown when T cells conjugated with α-hE-Sel were added to TNF-α stimulated HUVEC (FIG. 41E). A parallel imaging experiment shown in FIG. 41F has similar results. Moreover, a transwell assay was performed to show that the transendothelial migration ability of human T cells over HUVEC monolayer was not affected by the antibody labeling (FIG. 41G). These results show that engineering human T cells via installation of α-hE-Sel lead to firm binding of T cells on TNF-α stimulated endothelial cell with unaffected transmigration ability, which indicate this engineering could potentially promote efficient T cells homing to diseased tissues.

Example 43

In one embodiment, disclosed herein is a method for enzymatic construction of conjugates between NK-92MI cells and Herceptin for enhanced cancer killing. Specific killing is the key step of ACT in cell based cancer immunotherapy. Human natural killer (NK) cells play a crucial role in innate immunity against malignant cells, yet being developed as an effective cancer killer in cancer immunotherapy. NK cells mediated specific killing of target cell involves several mechanisms, in which antibody-dependent cell-mediated cytotoxicity (ADCC) is one of the most important. However, one challenge of NK cell based therapy is difficult to obtain sufficient numbers of active NK cells from a patient's blood. NK-92, a highly cytotoxic natural killer (NK) cell line established from patients with clonal NK-cell lymphoma, can be employed to generate larger numbers of cytotoxic NK cells in GMP-grade, which is a so called "off-the-shelf therapeutic" for adoptive NK-based cancer immunotherapy. Currently, there are four phase I trials in US, Canada, and Germany for different malignancies conducted with normal NK-92 cells. However, specific targeting is a golden standard for a good cancer therapy. NK-92 cells do not express Fc receptors for ADCC effects to target specific cells, which limit its wide applications. In one embodiment, as described herein mAbs could be enzymatically transferred to cell surface much easier and more efficiently than genetic approaches. Thus, in on embodiment, construction of NK-92 cell-mAb conjugates would be a great technique to achieve specific targeting in therapy.

Figure 42:
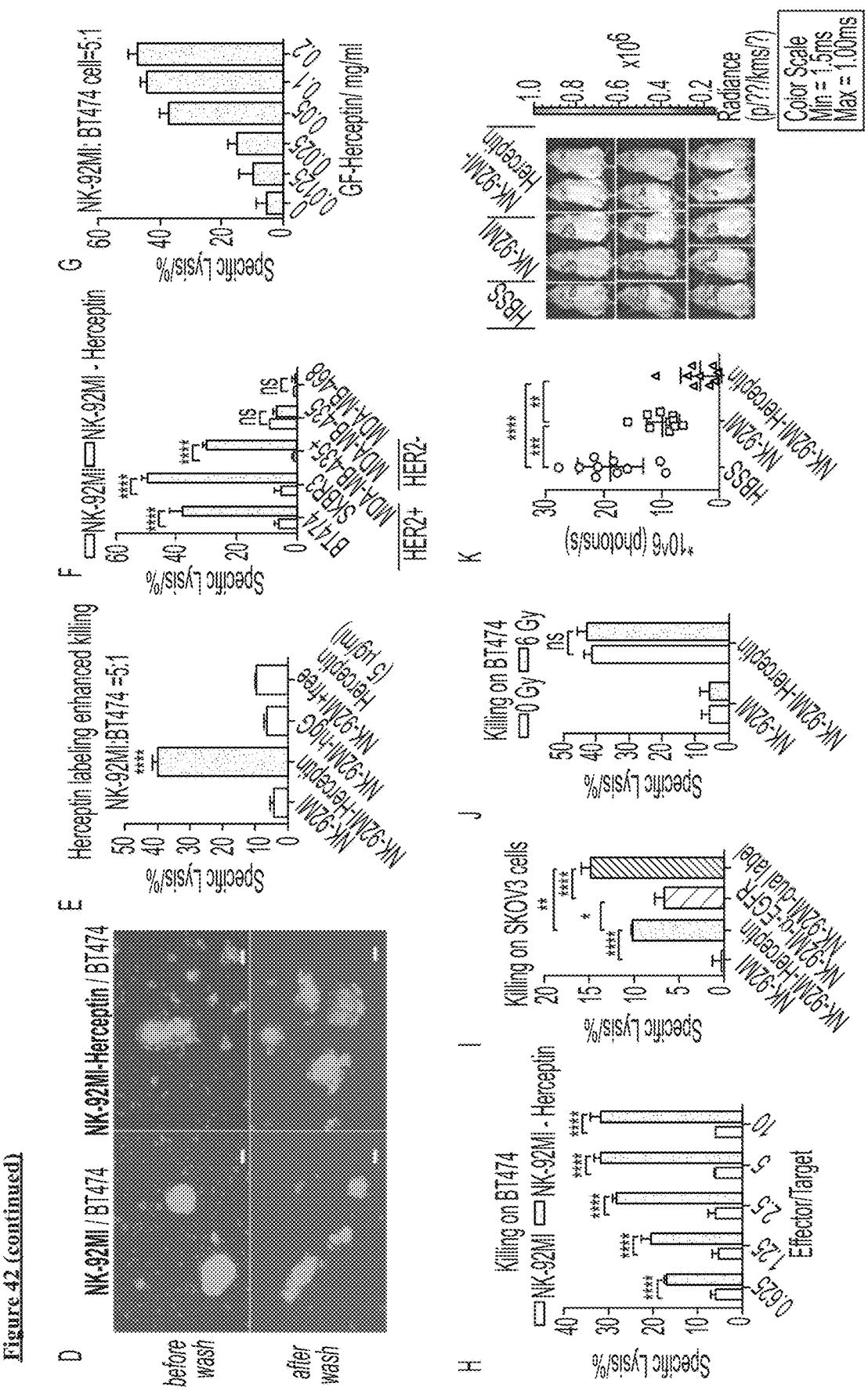
FIG. 42 depicts, in accordance with embodiments herein, construction of Herceptin and NK-92MI cells conjugates for HER2+ cancer therapy. (A) NK-92MI-Hercetin conjugates could specifically bind to HER2+ cancer cells and hence have enhanced killing effect due to proximity. (B) Analysis of specific HER2 antigen binding on NK-92MI-Hereceptin conjugates. Mean±SD (error bars). (C,D) Flow cytometry analysis and fluorescent microscopy images of specific binding between NK-92MI-Herceptin and BT474 (HER2+). NK-92MI cells are stained with CellTracker Orange (red) and BT474 cells are stained with CellTracker Green (green). Shown are merged channels of fluorescence and phase contrast. Green fields are clusters of BT474 cells. Scale bar: 50 μm. (E) LDH release assay of quantifying cell-mediated cytotoxicity of NK-92MI cells against BT474 cells. NK-92MI-Herceptin was compared with parental NK-92MI with or without additional added free Herceptin (5 μg/ml). NK-92MI-hIgG was used as a negative control. Mean±SD (error bars), representative graph from three independent experiments. (F) Comparison of NK-92MI and NK-92MI-Herceptin in killing different cancer cell lines with or without HER2 expression. Mean±SD (error bars), representative graph from three independent experiments. (G) Killing activity of NK-92MI-Herceptin in different GF-Herceptin concentrations for enzymatic transfer. Mean±SD (error bars). (H) Comparison of NK-92MI and NK-92MI-Herceptin in killing BT474 under different effector to target cell ratios. Mean±SD (error bars). (I) Herceptin and α-EGFR dual labeled NK-92MI cells were compared with NK-92MI-Herceptin and NK-92MI-α-EGFR in killing HER2+/EGFR+ SKOV3 cancer cells. Mean±SD (error bars). (J) Comparison of non-irradiated and irradiated (6 Gy) NK-92MI cells in killing BT474 cells. (K) In vivo antitumor activity of NK-92MI-Herceptin. NSG mice were intravenously injected with 0.5 million MDA-MB-435/HER2+/F-luc cells. Then, animals were treated once by i.v. injection of 5 million NK-92MI or NK-92MI-Herceptin cells at day 1 after tumor cell injection. Control mice received HBSS. Six days after tumor challenge, mice were injected with i.p. with D-luciferin and imaged by IVIS system. Tumor size of individual mice and mean values±SD are shown; n=10. Representative images are also shown. In all figures: ns, P>0.05; *P<0.05; P<0.01; *P<0.001; ****P<0.0001.
Figure 52:
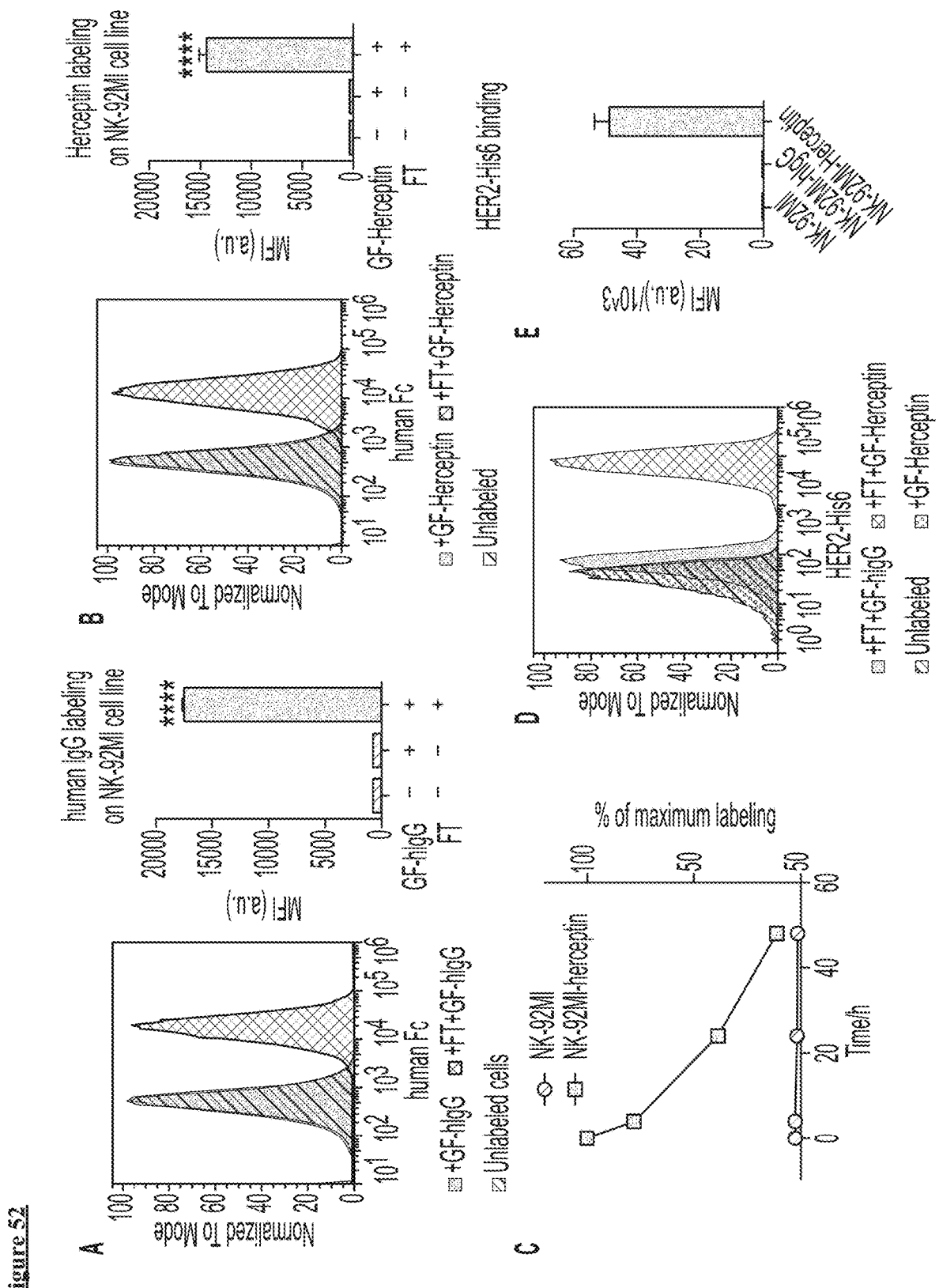
FIG. 52 depicts, in accordance with embodiments herein, transferring IgG molecules onto NK-92MI cells. (A) NK-92MI cells were treated with GF-hIgG and FT, or GF-hIgG alone, or untreated. The cells were stained with anti-hFc fluorescent antibody and analyzed by flow cytometry. (B) NK-92MI cells were treated with GF-Herceptin and FT, or GF-Herceptin alone, or untreated. The cells were stained with anti-hFc fluorescent antibody and analyzed by flow cytometry. (C) NK-92MI cells conjugated with Herceptin were stained with anti-hFc fluorescent antibody and analyzed by flow cytometry at different time points post labeling. (D) NK-92MI cells with different modifications were then incubated with HER2-His6 protein and then stained with anti-His6 fluorescent antibody for FACS analysis. (E) NK-92MI cells conjugated with or without Herceptin were co-cultured with BT474 at a ratio of 5:1 (Effector: Target) for 4 h. Granzyme B secretion in culture supernatant was analyzed by ELISA. Error bars, mean values±SD. In all figures: ns, P>0.05; ****P<0.0001.
Figure 53:
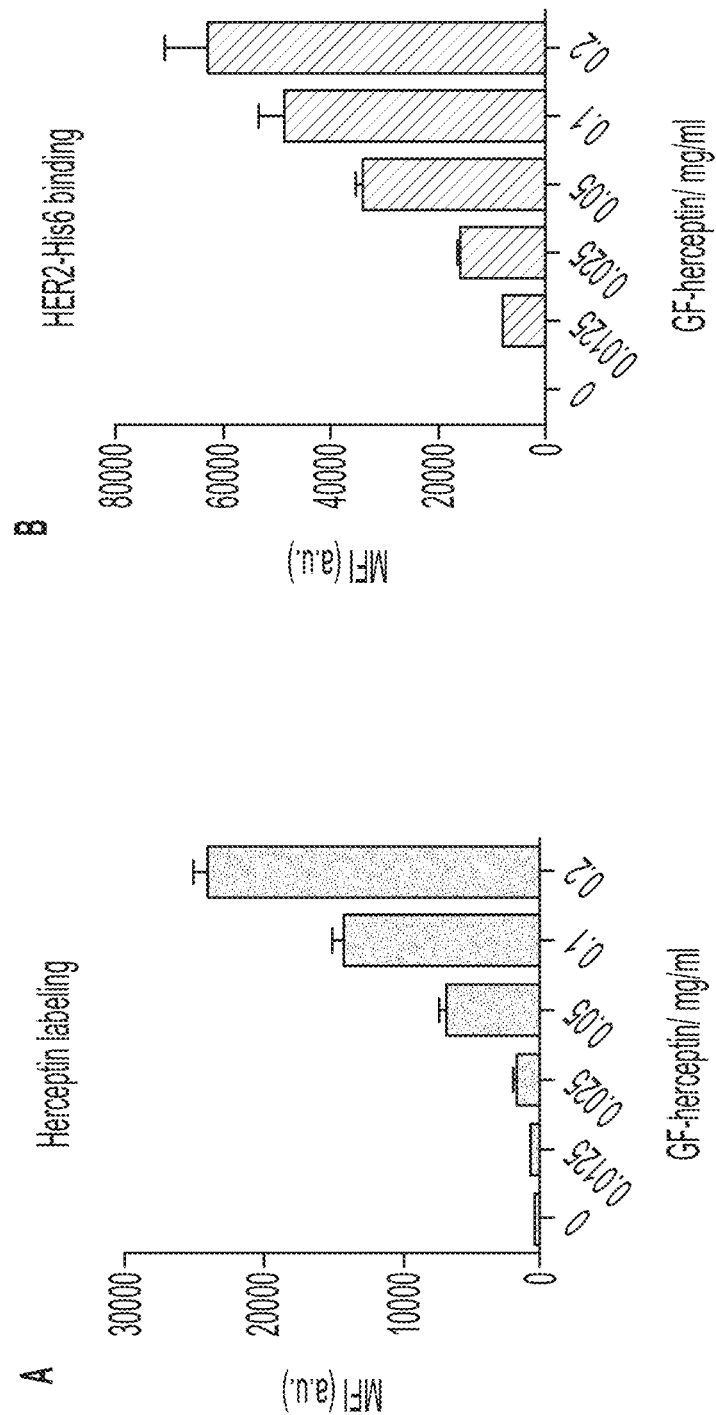
FIG. 53 depicts, in accordance with embodiments herein, titration of GF-Herceptin concentrations in enzymatic transfer. NK-92MI cells were treated with different concentrations of GF-Herceptin in a standard labeling condition. Labeled cells were directly stained with anti-hFc fluorescent antibody (A), or incubated with HER2-His6 and then stained with anti-His6 fluorescent antibody (B) before flow cytometry analysis.
Figure 54:
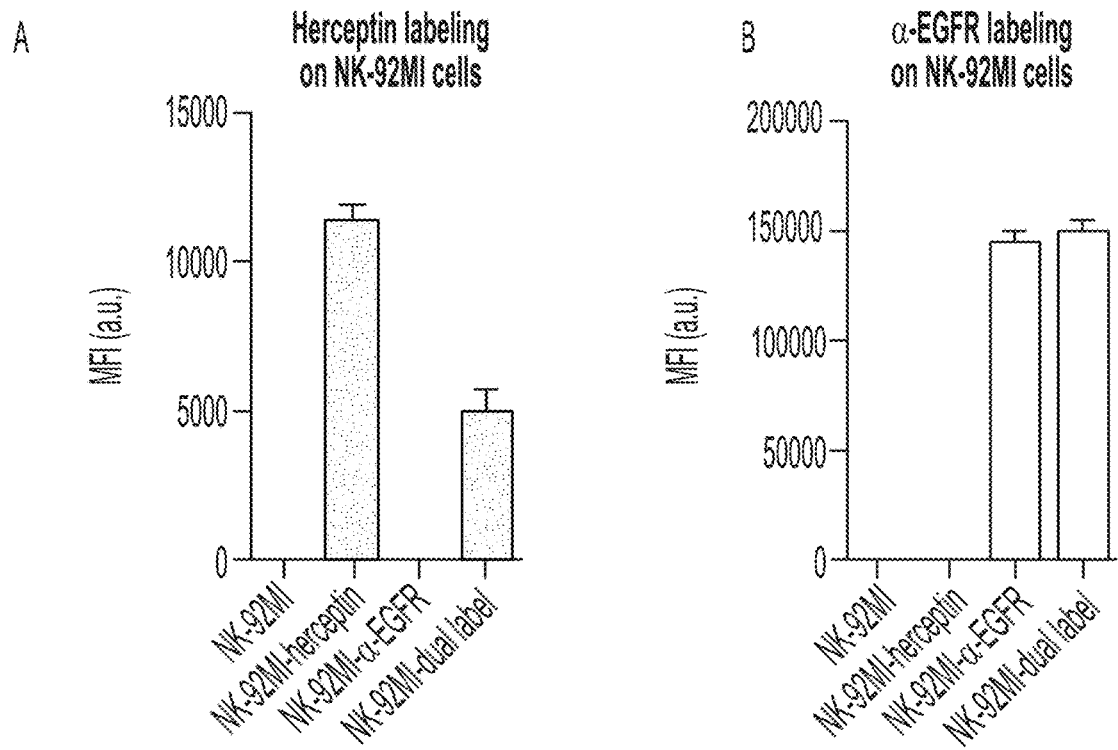
FIG. 54 depicts, in accordance with embodiments herein, dual antibody labeling on NK-92MI cells. NK-92MI cells were treated with FT and GF-Herceptin, and then treated with FT and GF-α-EGFR. Labeled cells were stained with anti-hFc fluorescent antibody (A), or stained with anti-mIgG fluorescent antibody (B) before flow cytometry analysis.

NK-92MI cells, an IL-2 independent variant of NK-92 cell line, constantly express high level of LacNAc, which is good for FucT based engineering. Expectedly, transfer of GDP-Fuc modified human IgG (GF-hIgG) to NK-92MI cells surface is efficient and specific under normal ex vivo fucosylation conditions (FIG. 52A). Herceptin, also named Trastuzumab, is a mAb for the treatment of human epidermal growth factor receptor 2-positive (HER2+) breast cancer. In one embodiment, NK-92MI cells conjugated with Herceptin could target HER2+ cancer cells to enable the proximity enhanced cancer killing (FIG. 42A). GF-Herceptin was successfully transferred to NK-92MI cells surface using FucT (FIG. 52B). The half-life of Herceptin displayed on cell surface is about 20 h (FIG. 52C). Herceptin conjugated to NK-92MI cells still exclusively bind to HER2 antigen (FIG. 42B, FIG. 52D, FIG. 52E). In addition, NK-92MI cells conjugated with Herceptin strongly bind to HER2+ breast cancer cell BT474 in a co-culture system, while unmodified NK-92MI cells weakly bind to BT474 (FIGS. 42C and 42D). Furthermore, Herceptin labeled NK-92MI cells killed BT474 cells more efficiently than unlabeled NK-92MI cells ex vivo (FIG. 42E). Neither control hIgG labeling nor free Herceptin co-treatment could enhance the killing activity of NK-92MI on BT474, which indicates that conjugation between Herceptin and NK-92MI cell surface is required (FIG. 42E). The enhanced killing effect of NK92-MI-Herceptin was later confirmed in other HER2+ cancer cells including SKBR3 and MDA-MB-435/HER2+, but not in HER2-cancer cells like MDA-MB-435 and MDA-MB-468 (FIG. 42F). This specificity further confirm Herceptin conjugated NK-92MI cells enhance killing through strong binding to HER2 antigens on cancer cell surface. Interestingly, the total secretion of granzyme B does not increase for the enhanced killing effect (FIG. 52E). This result tells us prolixity between NK-92MI cells and target cells could sufficiently induce the enhanced killing activity and specificity of NK-92MI cells. High concentration of GF-Herceptin in enzymatic reactions leads to more Herceptin conjugation as well as antigen binding on NK-92MI cells surface (FIGS. 53A and 53B). Thus, the killing efficiency of NK-92MI cells is also dependent on GF-Herceptin concentrations in labeling reactions (FIG. 42G). Similar to other cell mediated cytotoxicity, higher effector to target cell ratios also have better killing results, but only in Herceptin labeled NK-92MI group, which reaches saturation at 5:1 (FIG. 42H). Another important advantage of enzymatic engineering is that people can conjugate several antibodies onto cell surface at one time. To show the application, NK-92MI cells were labeled with both of Herceptin and α-EGFR (FIGS. 54A and 54B), which had better killing efficiency on SKOV3 cells (HER2+EGFR+) than either single mAb labeling (FIG. 42I).

Figure 55:
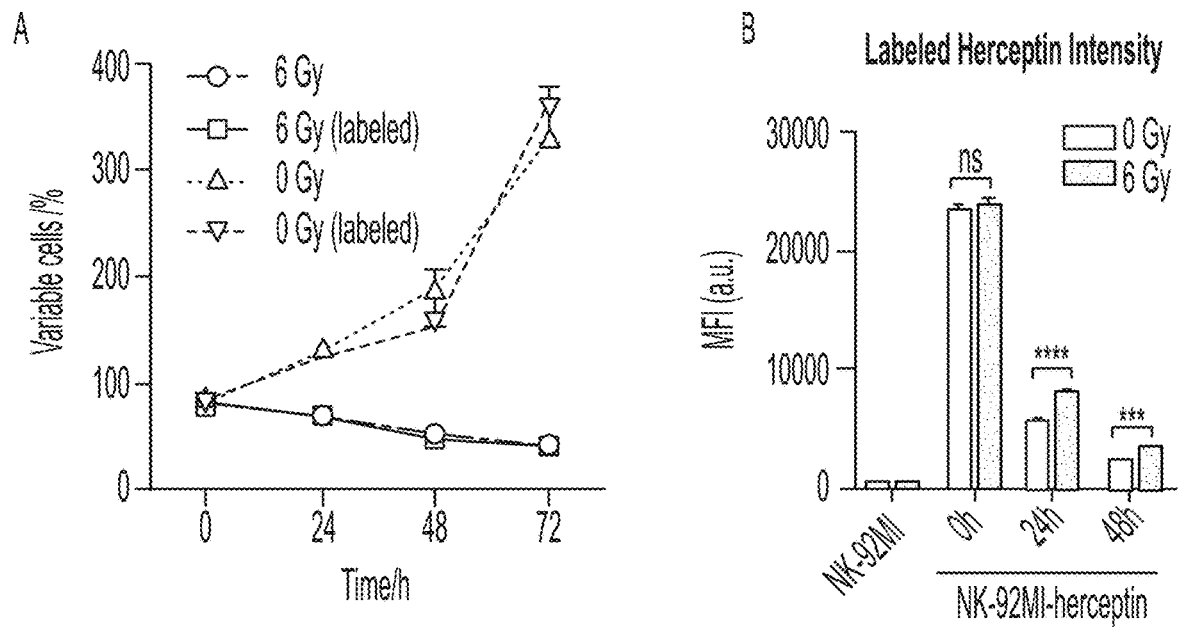
FIG. 55 depicts, in accordance with embodiments herein, growth and cytotoxic activity of NK-92MI cells upon γ-irradiation. NK-92MI cells were received with or without 6 Gy gamma irradiations before enzymatic reaction. Labeled and unlabeled NK-92MI cells were cultured for another three days. (A) Viable cells were counted by flow cytometry at different time points after irradiation and labeling. (B) Herceptin labeled cells were also stained with anti-hFc fluorescent antibody and analyzed by flow cytometry at different time points post labeling. Irradiated cells has a slower decay of Herceptin labeling. Error bars, mean values±SD. In all figures: ns, P>0.05; *P<0.001; **P<0.0001.
Figure 56:
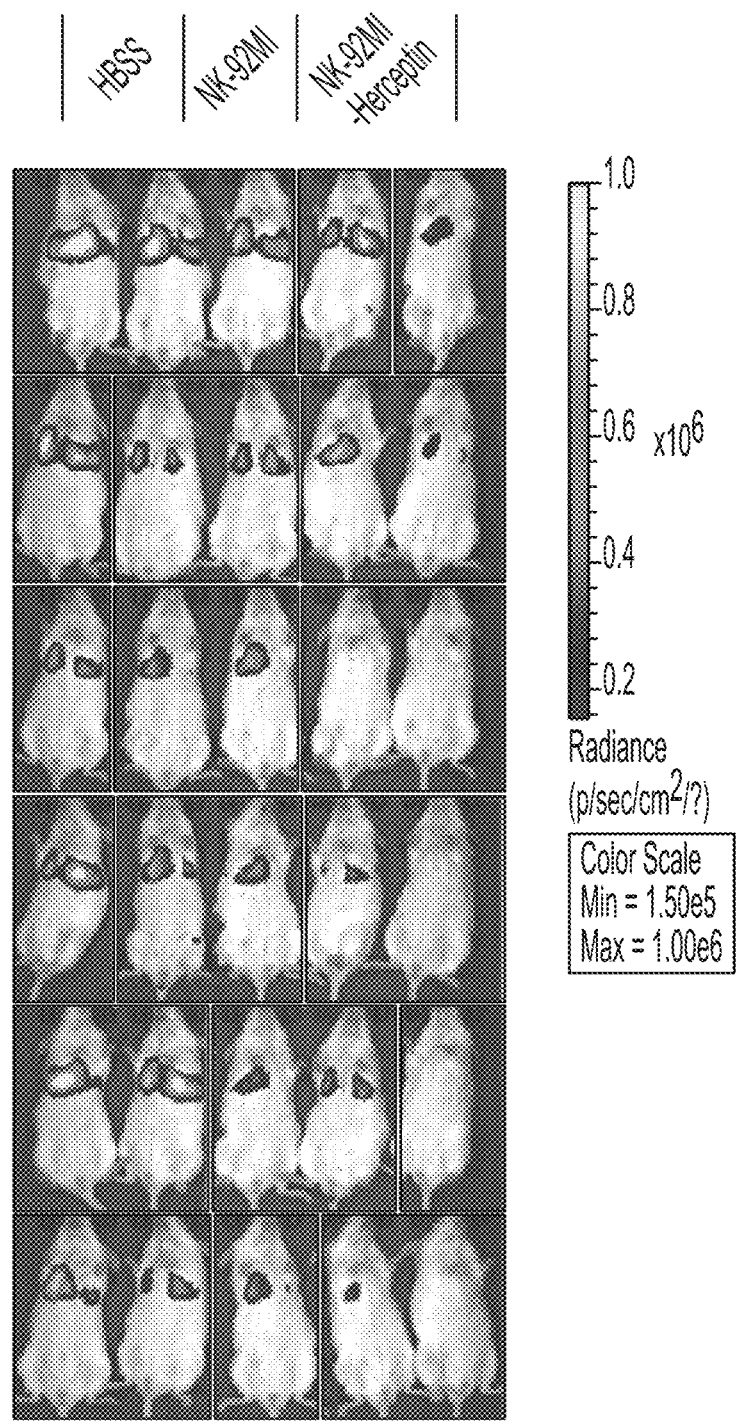
FIG. 56 depicts, in accordance with embodiments herein, images of NK-92MI-Herceptin showing enhanced antitumor activity in mice. Shown are images of 30 mice in three groups. The data is summarized and analyzed in FIG. 4K.
Figure 57:
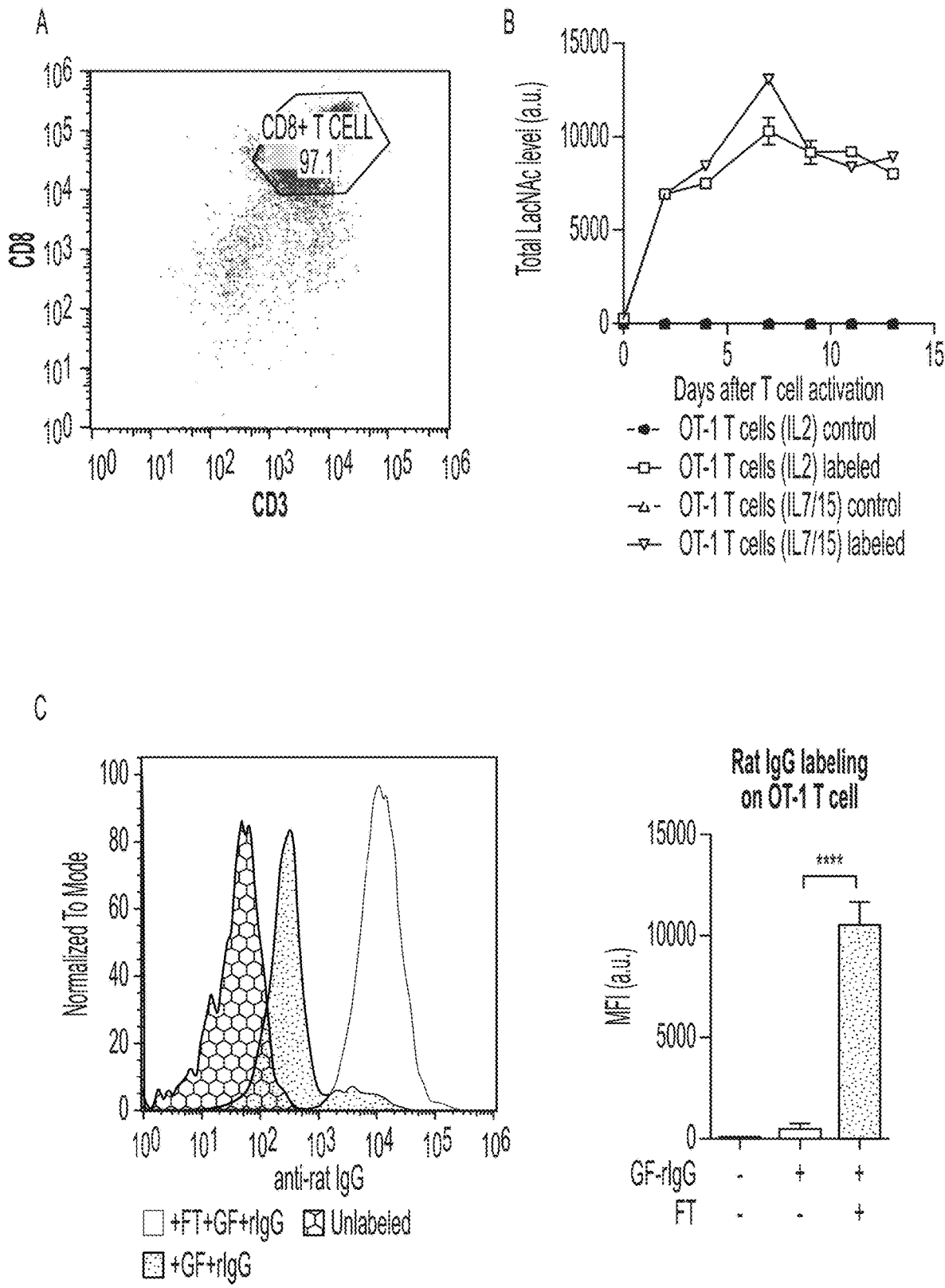
FIG. 57 depicts, in accordance with embodiments herein, enzymatic transfer of rIgG to OT-1 CD8+ T cells. (A-B) Splenocytes from OT-1 mice were activated by OVA peptides and in vitro expanded by adding IL2 or IL7/IL15. After four days expansion, the cells were stained with anti-CD3 and anti-CD8 fluorescent antibodies and analyzed by flow cytometry (A). The cells were also treated with GF-Al-Biotin and FT, and then stained with streptavidin-APC and analyzed by flow cytometry to track LacNAc level on different days after T cell activation (B). (C) OT-1 T cells were treated with GF-rIgG and FT, or GF-rIgG alone, or untreated. Then the cells were stained with anti-rIgG fluorescent antibody and analyzed by flow cytometry. (D) OT-1+/−CD45.1+/− T cells were first labeled with CFSE and then treated with GF-rIgG and FucT, or untreated. After fucosylation, the cells were co-cultured with OVA peptide pulsed WT B6 splenocytes for 48 h and T cell proliferation was analyzed by flow cytometry. Error bars, mean values±SD. In all figures: ns, P>0.05; ****P<0.0001.
Figure 57:
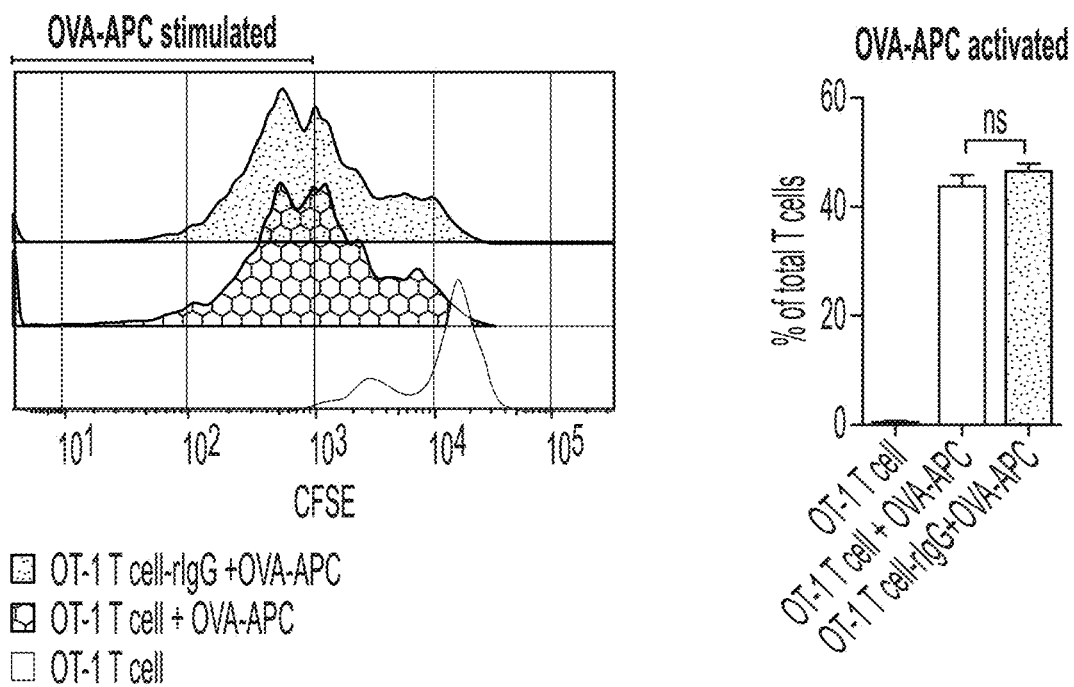

As developed from a patient with lymphoma, NK-92 should be irradiated for clinical use. Irradiation of NK-92MI cells with 6 Gy prevented its proliferation (FIG. 55A). Killing efficiency of irradiated NK-92MI cells is comparable with non-irradiated ones (FIG. 42J). in one embodiment, the half-life of Herceptin conjugated to irradiated NK-92MI was found to be slightly longer than non-irradiated group (FIG. 57B). The promising results of enhanced ex vivo killing effect let us try to test this system in vivo. In one embodiment, the inventors chose an experimental lung metastasis model as a proof of concept, in which NSG mice received intravenous injections of MDA-MB-435/HER2+/F-luc cells (stably transduced with firefly luciferase). After one day of tumor cell inoculation, mice were treated by i.v. injections of HBSS buffer, parental NK-92MI or NK-92MI-Herceptin cells (irradiated NK-92MI cells). Six days after tumor challenge, the lung tumor size of mice was determined by longitudinal noninvasive bioluminescence imaging. While treatment with parental NK-92MI cells moderately reduced lung tumor formation (~48% smaller than HBSS group), Herceptin labeled NK-92MI cells have significantly enhanced in vivo tumor killing activity (~83% smaller than HBSS group) (FIG. 42J and FIG. 56). Taken together, NK-92MI-Herceptin conjugates have significantly enhanced anti-tumor effect than parental NK-92MI cells both ex vivo and in vivo, which showed great potential to be translated to the clinical trial.

Example 44

In one embodiment, as disclosed herein α-PD-L1 conjugated on cell surface is capable of blocking PD-1/PD-L1 pathway and enhance T cell proliferation ex-vivo. Beyond the applications of enhancing or inducing cell-cell interactions, the present disclosure shows that mAbs conjugated to cell surface could specifically affect the signaling pathway to enhance the therapy. First of all, OT-1 CD8+ T cells were chosen as model cells since its transgenic T-cell receptor (TCR) only recognize $OVA_{257-264}$ peptide presented by the MHC I molecule, which is a good model to study CD8+ T cell response to specific antigen. The OT-1 splenocytes were activated by OVA peptides and ex vivo expanded by adding IL2 or IL7/IL15. After three days, most of the cells are CD8+ T cells (FIG. 57A), while their LacNAc level is high enough for labeling after activation (FIG. 57B). To exclude the possibility that large IgG molecules on cell surface would block TCR signaling nonspecifically, OT-1+/− CD45.1+/− T cells conjugated with rIgG were restimulated using OVA peptide-pulsed wild type B6 splenocytes (FIG. 57C). According to the results of CFSE dilution, IgG molecules do not block the interaction between TCR and MHC I since labeled T cells have similar proliferation rate as unlabeled (FIG. 57D).

Figure 43:
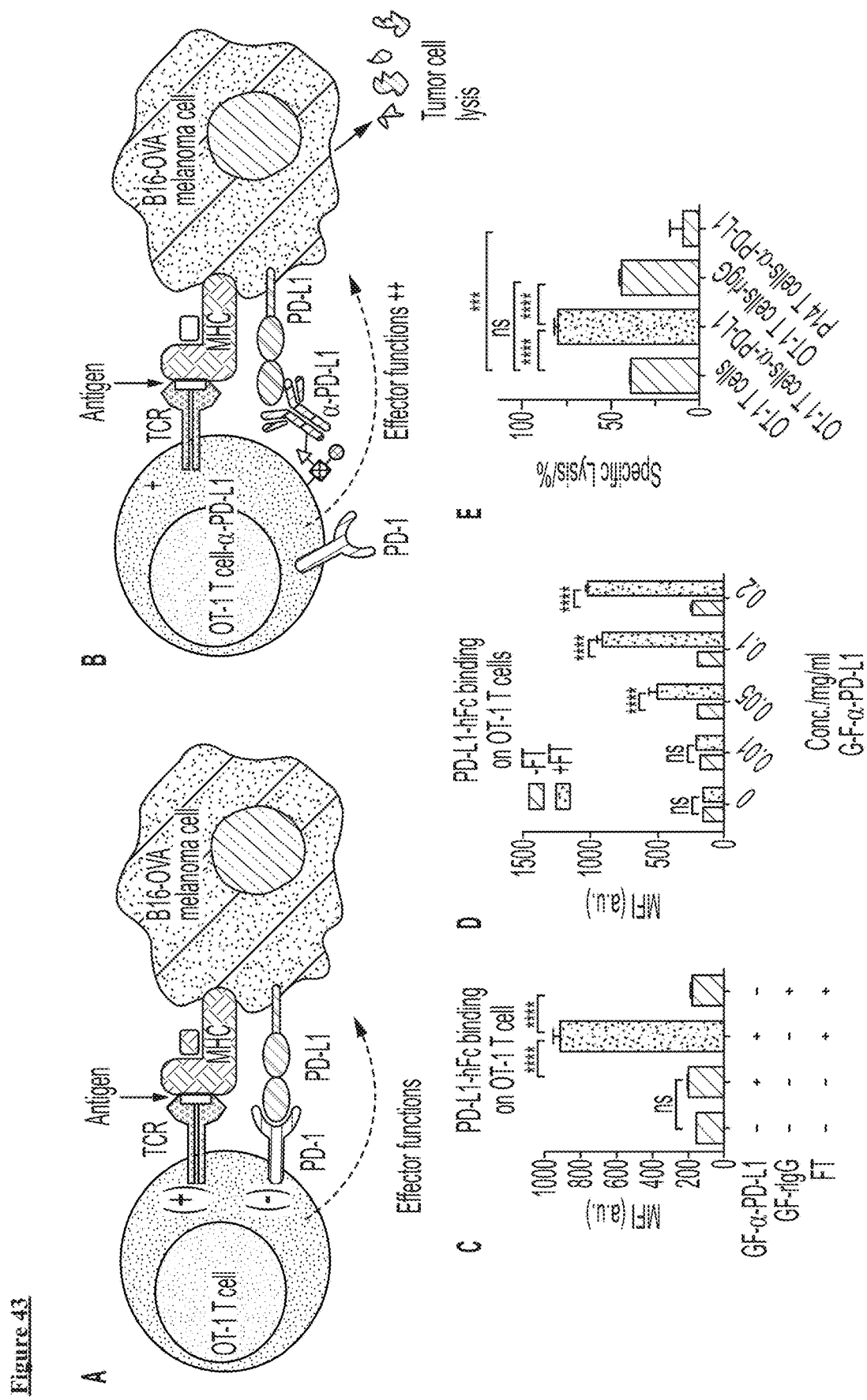
FIG. 43 depicts, in accordance with embodiments herein, enzymatic transfer of α-PD-L1 to OT-1 T cells for enhanced T cell activation in specific killing. (A) Scheme of the interaction between OT-1 T cells (TCR-T) and B16-OVA melanoma cells. MHC complex on B16-OVA present OVA antigen to specific TCR on OT-1 T cells to induce activation, while PD-L1 on B16-OVA interact with PD-1 on OT-1 T cells inhibit the activation signal. (B) Scheme of the blockade of PD-1/PD-L1 pathway via α-PD-L1 conjugated on OT-1 T cell surfaces. The in situ blockade could enhance T cell activation and killing on cancer cells. (C) Analysis of PD-L1 antigen binding on OT-1 T cells under different treatment. Mean±SD (error bars). (D) Analysis of PD-L1 antigen binding on different GF-α-PD-L1 concentrations in enzymatic transfer. Mean±SD (error bars). (E) Assay of quantifying cell-mediated cytotoxicity of OT-1 T cell-α-PD-L1 conjugates on B16-OVA cells. Mean±SD (error bars), representative graph from three independent experiments. OT-1 T cells conjugated with rIgG and P14 T cells conjugated with α-PD-L1 were shown as negative control. (F) Comparison of OT-1 T cells and OT-1 T cell-α-PD-L1 in killing B16-OVA under different effector to target cell ratios. Mean±SD (error bars). (G) Killing activity of OT-1 T cells and OT-1 T cell-α-PD-L1 in different GF-α-PD-L1 concentrations for enzymatic transfer. Mean±SD (error bars). (H) IFN-γ ELISA of OT-1 T cells mixed with B16-OVA under different treatment. P14 T cell conjugated with α-PD-L1 was shown as negative control. Only B16-OVA was background. Mean±SD (error bars), representative graph from three independent experiments. (I) Microscopy images of OT-1 T cells killing B16-OVA with or without α-PD-L1 labeling. Blue arrow indicates less cancer cells and purple arrow indicates bigger cluster of T cells. Scale bar: 50 μm. (J) Analysis of OT-1 T cell proliferation after the activation mediated by B16-OVA through CFSE dilution. Mean±SD (error bars). (K) Competition assay of comparing T cells frequency in blood, draining lymph nodes, and tumor with or without α-PD-L1 labeling. OT-1 T cells with CD45.1 or Thy1.1 congenic marker were labeled with α-PD-L1, which were later mixed with unlabeled OT-1 T cells with the other congenic marker. The OT-1 T cells mixture was i.v. injected into B16-OVA challenged mice and analyzed after 48 hours expansion. Relative ratio of individual mice and mean values±SD are shown; n=3. In all figures: ns, P>0.05; P<0.01; *P<0.001; ****P<0.0001.
Figure 43:
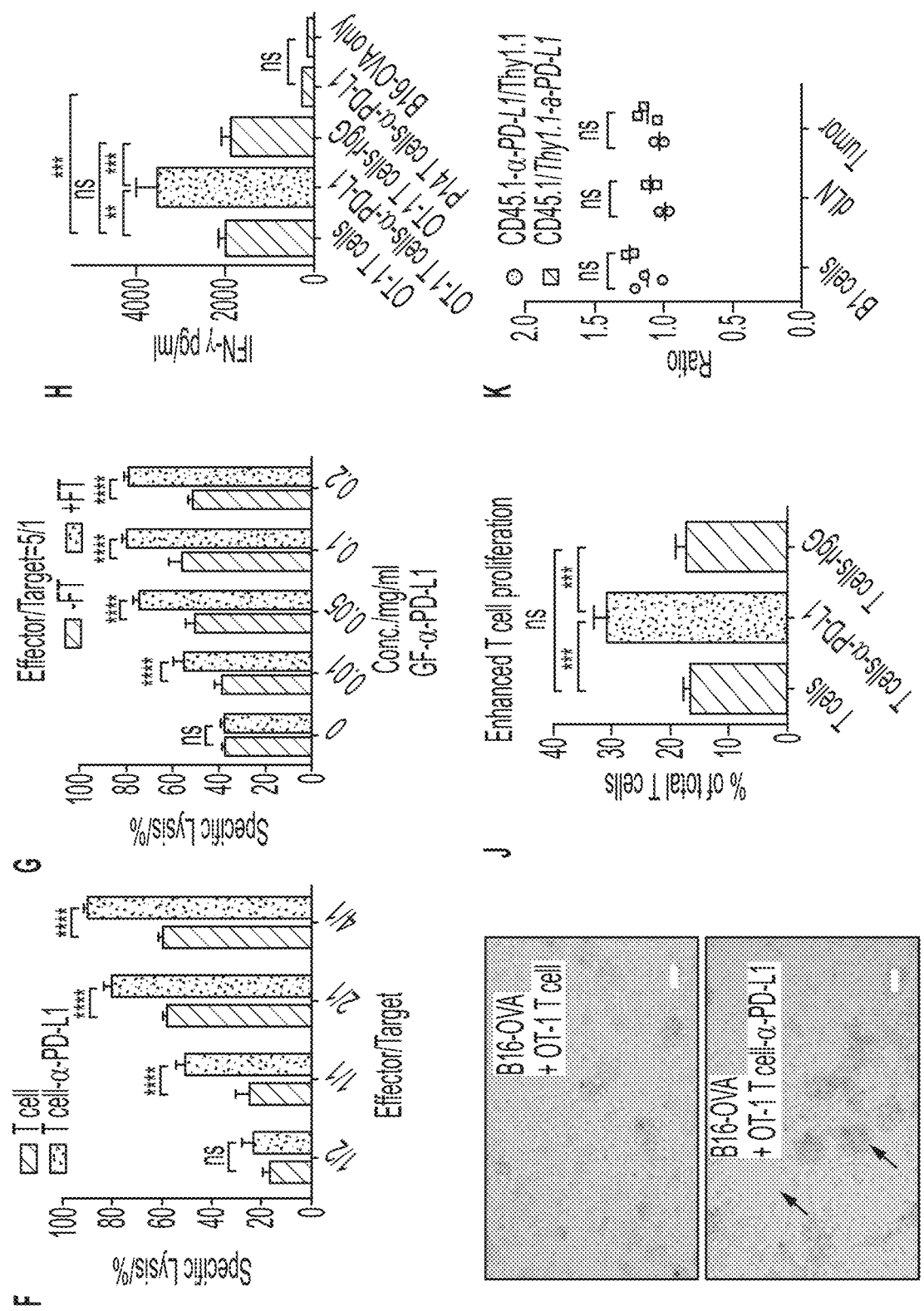
Figure 58:
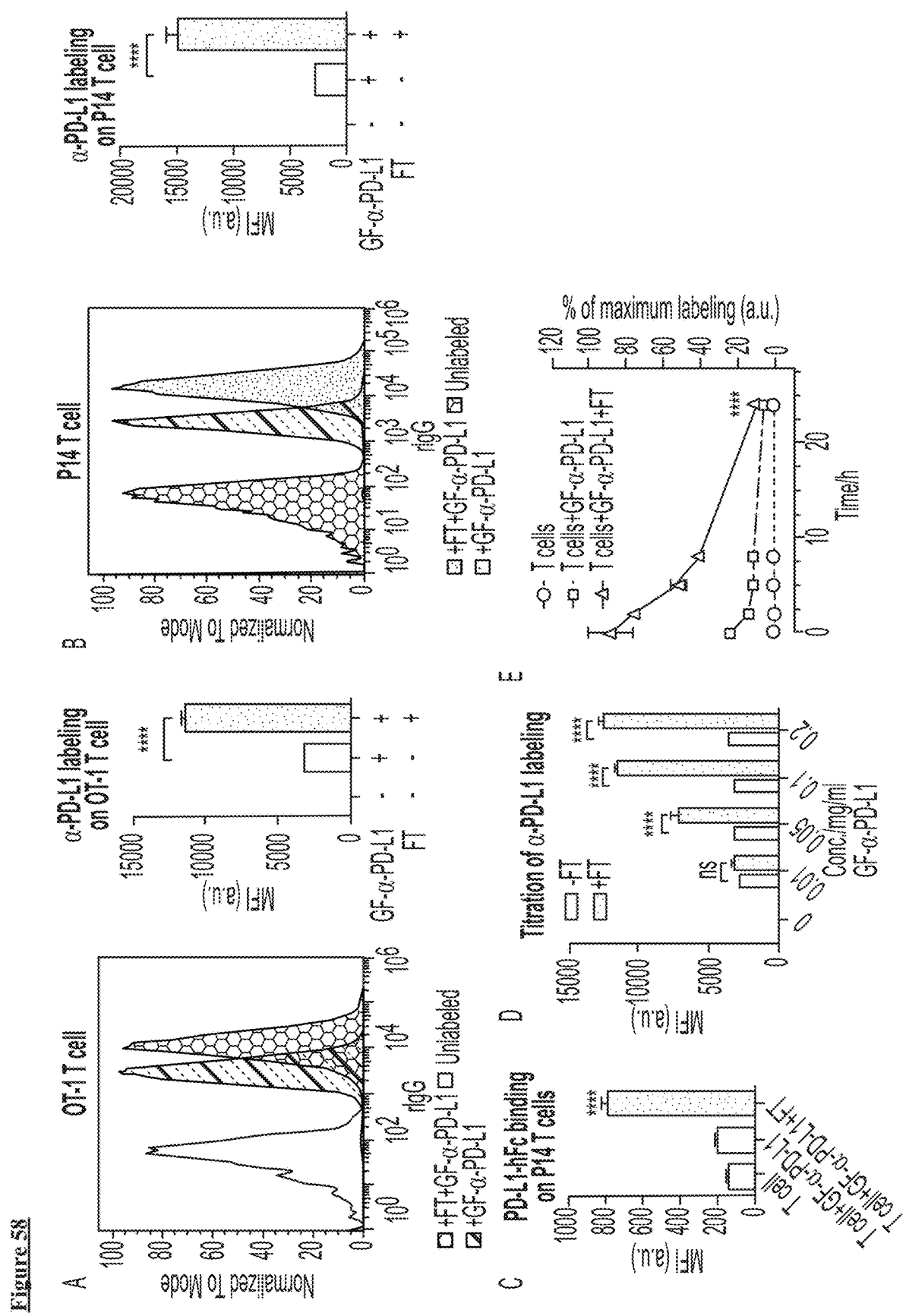
FIG. 58 depicts, in accordance with embodiments herein, transferring α-PD-L1 onto OT-1 CD8+ T cells. (A) OT-1 CD8+ T cells were treated with GF-α-PD-L1 and FT, or GF-α-PD-L1 alone, or untreated. The cells were then stained with anti-rIgG fluorescent antibody and analyzed by flow cytometry. (B-C) CD8+ T cells from P14 mice were treated with GF-α-PD-L1 and FT, or GF-α-PD-L1 alone, or untreated. The cells were stained with anti-rIgG fluorescent antibody (B), or incubated with PD-L1-hFc first and then stained with anti-hFc fluorescent antibody (C). After staining, these cells were analyzed by flow cytometry. (D) OT-1 T cells were labeled under different concentrations of GF-α-PD-L1 with or without FT. After labeling, cells were stained with anti-rIgG fluorescent antibody and analyzed by flow cytometry. (E) OT-1 T cells were treated with GF-α-PD-L1 and FT, or GF-α-PD-L1 alone, or untreated. The cells were then stained with anti-rIgG fluorescent antibody and analyzed by flow cytometry at different time points after reaction. Error bars, mean values±SD. In all figures: ns, P>0.05; ****P<0.0001.

While T cell activation depends on TCR signaling, additional co-stimulatory signals also fine-tune this response. For example, the interaction between programmed death 1 (PD-1) receptor and PD-Ligand (PD-L) pathway inhibit T cell activation (FIG. 43A), which is a reason of cancer immune evasion. Therefore, in one embodiment, installation of α-PD-L1 on T cell surface could specifically block the PD-1/PD-L1 interaction to enhance the activation of T cells and the subsequent cancer killing effect (FIG. 43B). TCR-T cells (OT-1 or P14) were labeled efficiently using FucT and GF-α-PD-L1 (FIGS. 58A and 58B). After that, the antigen binding capacity of α-PD-L1 on T cell surface was further confirmed (FIG. 43C and FIG. 58C). As expected, the intensities of labeling and antigen binding are both GF-α-PD-L1 concentrations dependent (FIG. 43D and FIG. 58D). Then OT-1 CD8+ T cells with different modifications were subjected to an ex vivo killing assay, in which a B6-derived melanoma cell line B16F10 expressed ovalbumin (B16-OVA) was used as antigen-specific cancer cells. After 20 hours of incubation, OT-1 T cells conjugated with α-PD-L1 showed a significantly enhanced cytotoxic activity on B16-OVA cells, while isotype rIgG labeling has similar results as unlabeled (FIG. 43E). Remarkably, another TCR-transgenic CD8+ T cells (P14) of irrelevant specificity were also conjugated with α-PD-L1 as a negative control (FIG. 43E), which showed that α-PD-L1 itself could not induce the killing without a specific TCR-T. This synergistic killing effect indicates that α-PD-L1 conjugated to CD8+ T cells improves the TCR specific cytotoxicity through the PD-1/PD-L1 pathway blockade. Moreover, in different effector to target cell ratios (>1:1), the enhanced killing effect (FIG. 43F) could be seen. Unlike the antigen binding saturated at ~0.1 mg/ml GF-α-PD-L1 (FIG. 43D), the enhanced killing effect reached the maximum at ~0.05 mg/ml GF-α-PD-L1 (FIG. 43G), which indicates that only half of the maximum labeling could efficiently block the PD-1/PD-L1 pathway.

Figure 59:
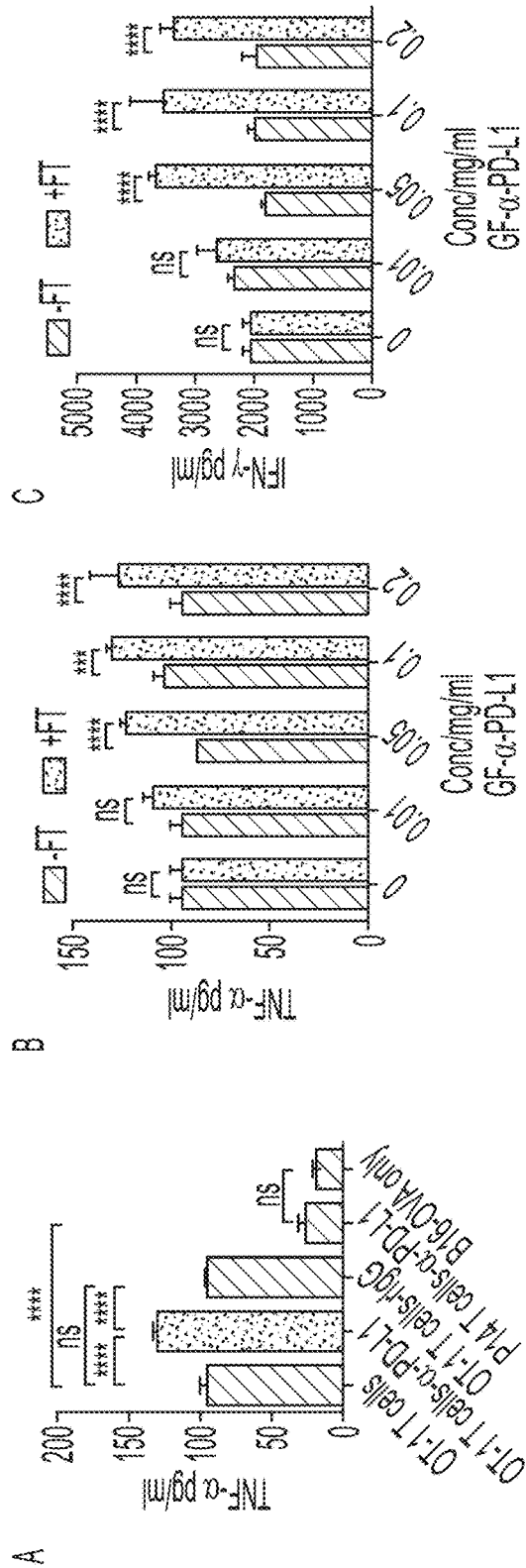
FIG. 59 depicts, in accordance with embodiments herein, transferring α-PD-L1 onto OT-1 T cell surface enhance the cytokine secretion during killing cancer cells. (A) OT-1 T cells and P14 T cells were treated with GF-α-PD-L1 and FT, or GF-rIgG and FT, or untreated. T cells were then co-cultured with B16-OVA cells for 9 hours. TNF-α concentrations in culture supernatant were quantified via ELISA kit. (B-C) OT-1 T cells were treated under different concentrations of GF-α-PD-L1 with or without FT, and then co-cultured with B16-OVA cells for 9 hours. TNF-α and IFN-γ in culture supernatant were analyzed by ELISA. Error bars, mean values±SD. In all figures: ns, P>0.05; *P<0.001; **P<0.0001.
Figure 60:
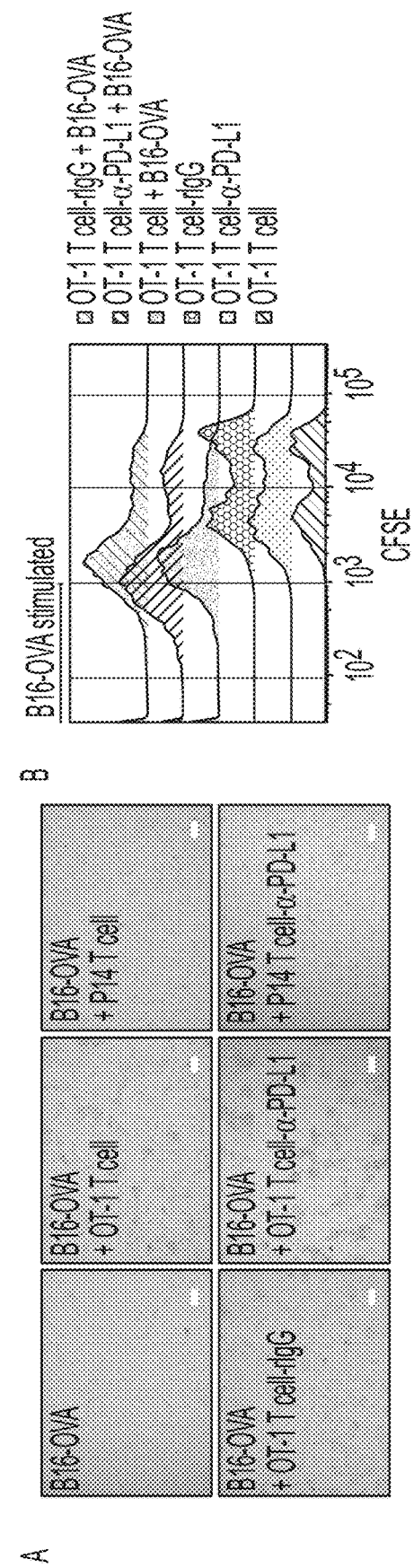
FIG. 60 depicts, in accordance with embodiments herein, transferring α-PD-L1 onto T cell surface increase the size of T cell cluster and T cell proliferation during killing. (A) OT-1 T cells and P14 T cells were treated with GF-α-PD-L1 and FT, or GF-rIgG and FT, or untreated. The cells were then co-cultured with B16-OVA cells for 20 hours. T cell cluster during killing were imaged using microscope. Scale bar: 50 µm. (B) OT-1 T cells were stained with CFSE and treated with GF-α-PD-L1 and FT, or GF-rIgG and FT, or untreated. Then the cells were cultured with or without B16-OVA cells for 72 hours. Proliferations of OT-1 T cells were analyzed through CFSE signal dilution.

To further confirm these α-PD-L1/CD8+ T cell conjugates could escape from the PD-1/PD-L1 coinhibitory signaling, the inventors measured cytokine secretions of OT-1 T cells when mixed with B16-OVA cells. The enhanced IFN-γ and TNF-α secretion were only observed in T cells conjugated with α-PD-L1, which were also α-PD-L1 labeling intensity dependent (FIG. 43H and FIG. 59). The blockade of co-inhibitory signaling promotes the T cell activation that leads to more cytokine secretion. This kind of enhanced T cell activation also could be directly observed in the microscopy, as the clusters of T cells were much bigger than others in the α-PD-L1 labeling group (FIG. 43I and FIG. 60A). Furthermore, the enhanced T cell activation also promoted T cell proliferations, which is confirmed by a CFSE dilution assay of re-stimulating OT-1 T cells with B16-OVA (FIG. 43J and FIG. 60B). After confirming the α-PD-L1 labeling could last more than 24 hours (FIG. 58E), a competition assay was designed to test if α-PD-L1/CD8+ T cell conjugates could have a better proliferation rate than unlabeled cells in vivo. OT-1 CD8+ T cells with a congenic marker (OT-1+/−CD45.1+/−) were conjugated with α-PD-L1 and then mixed with another congenic marker labeled OT-1 CD8+ T cells (OT-1+/−Thy1.1+/−) in a ratio around 1:1. Similarly, OT-1+/−Thy1.1+/− T cells were conjugated with α-PD-L1 and then mixed with unmodified OT-1+/−CD45.1+/− T cells. These two groups of OT-1 T cells were injected into B16-OVA challenged B6 mice through tail vein separately. After 48 hours of expansion, the ratio of two different congenic markers labeled OT-1 cells in two groups were analyzed. However, the ratios in blood, draining lymph nodes (dLN) and tumor have no significant difference between two groups (FIG. 43K), which indicates the co-inhibitory signaling in tumor microenvironment are much more complicated than ex vivo.

Example 45

Figure 61:
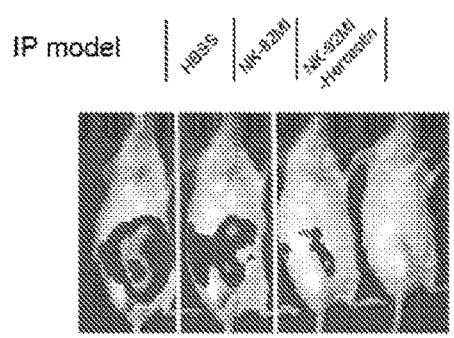
FIG. 61 depicts, in accordance with embodiments herein, in vivo antitumor activity of NK-92MI-Herceptin in intraperitoneal cancer model. NSG mice were intraperitoneally injected with 1 million MDA-MB-435/HER2+/F-luc cells. Then, animals were treated once by i.v. injection of HBSS, 5 million NK-92MI or NK-92MI-Herceptin cells at day 5 and day 10 after tumor cell injection. On day 4, day 12, day 17 after tumor challenge, mice were injected with i.p. with D-luciferin and imaged by IVIS system. (A) Representative images on day 12 after tumor inoculation showing enhanced antitumor activity in mice in Herceptin labeled group. (B) Luciferin signal on day 4, day 12 and day 17 were analyzed and calculated. (C) Luciferin signal on day 12 were analyzed and compared. (D) Luciferin signal on day 17 were analyzed and compared. Tumor size of individual mice and mean values±SD are shown; n=8. Representative images are also shown. In all figures: ns, P>0.05; *P<0.05; P<0.01; *P<0.001; ****P<0.0001.
Figure 61:
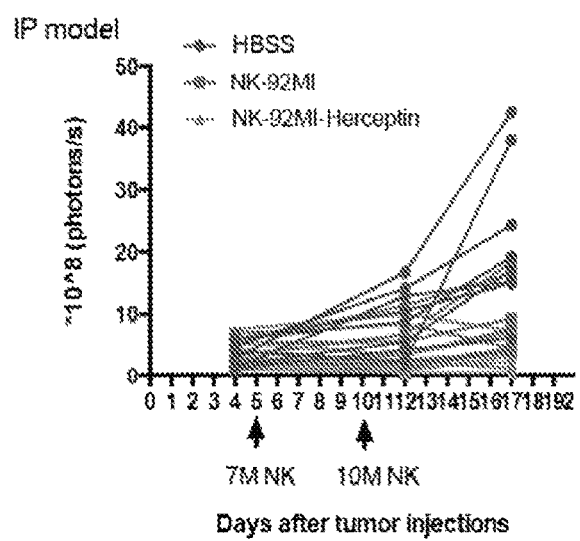
Figure 61:
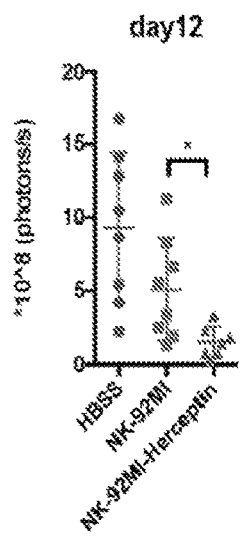
Figure 61:
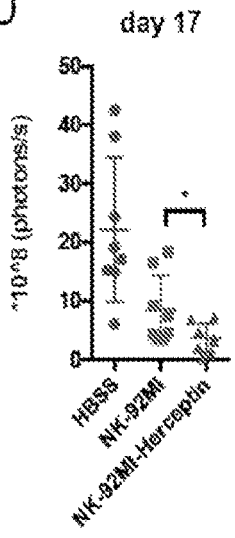

In one embodiment, as disclosed herein, enzymatic construction of conjugates between NK-92MI cells and Herceptin enhances cancer killing by NK cells in intraperitoneal cancer model in vivo. An intraperitoneal tumor model was set up by injecting MDA-MB-435/HER2+/F-luc cells through i.p injection. On day 7 and day 10 post tumor inoculation, mice were treated by i.p. injections of HBSS buffer, parental NK-92MI or NK-92MI-Herceptin cells (irradiated NK-92MI cells). Tumor growth was monitored by longitudinal noninvasive bioluminescence imaging (FIG. 61A). Herceptin labeled NK-92MI cells enhanced killing of tumor significantly compared with NK-92MI cells treatment group (FIGS. 61B, 61C and 61D). Taken together, NK-92MI-Herceptin conjugates have significantly enhanced anti-tumor effect than parental NK-92MI cells both ex vivo and in vivo, which showed great potential to be translated to the clinical trial.

Example 46

Figure 62:
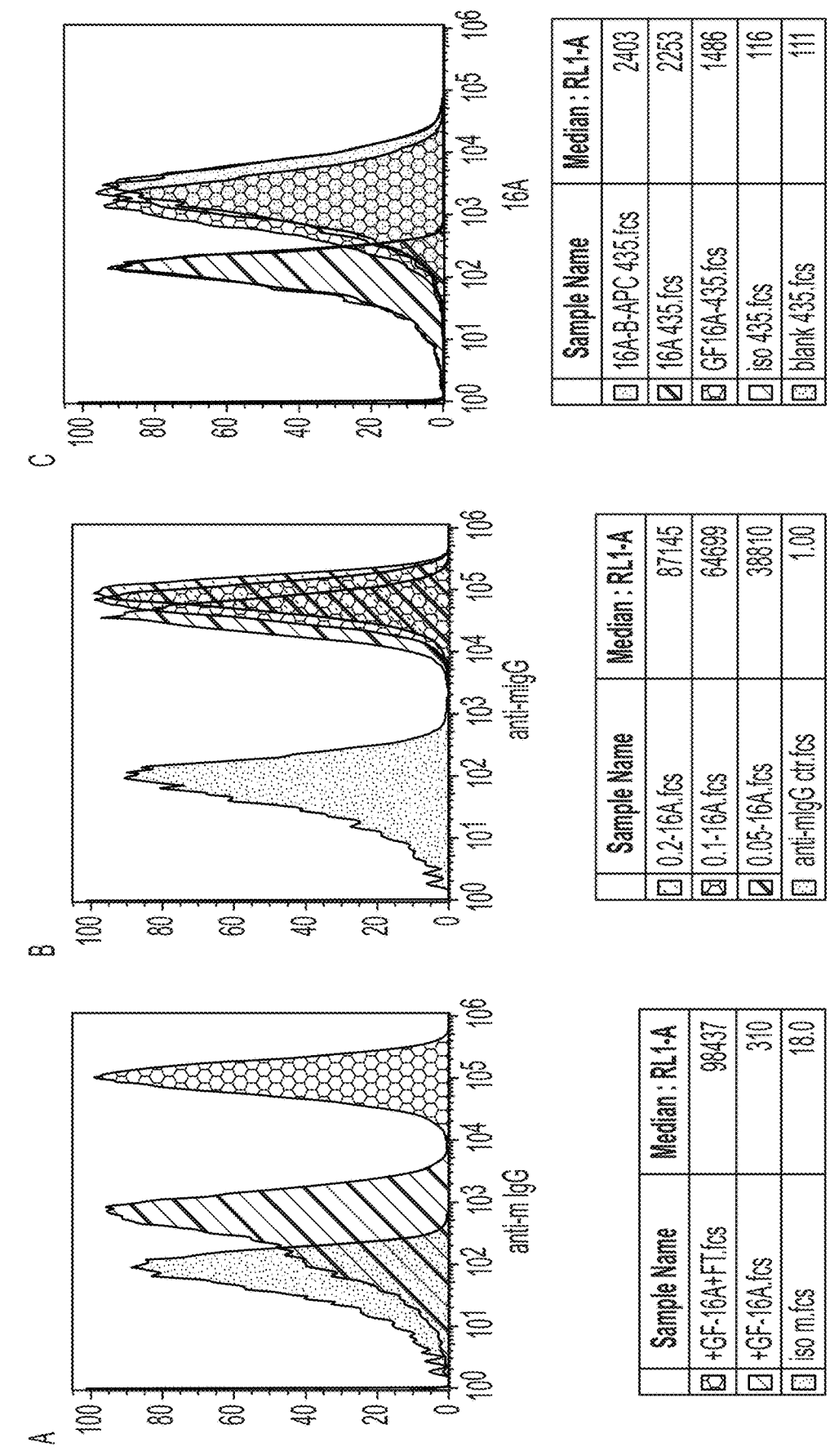
FIG. 62 depicts, in accordance with embodiments herein, another Antibody Cell Conjugate (ACC) strategy. (A), Flow cytometry analysis of NK-92 cells treated with GF-16A (anti-MUC1), or GF-16A and FT. (B), Titration of GF-16A concentrations ranging from 0.05 mg/ml to 0.2 mg/ml in the reaction buffer; each reaction used the same amount of FT and proceeded at room temperature for 30 min. (C) and (D), Flow cytometry analysis of MUC1 expression on MDA-MB-435 and SKBR3 cancer cells. (E) and (F), Luciferase assay of quantifying cell-mediated cytotoxicity of NK-92MI cells against SKBR3-luc and MDA-MB-435-luc cells; 16A-NK-92MI conjugates were compared with parental NK-92MI with or without additional added free 16A (5 µg/ml). 16A and NK-92MI cells only treated with GF-16A in labeling were used as negative controls. Mean±SD (error bars), representative graph from three independent experiments. ns, P>0.05; **P<0.01.
Figure 62:
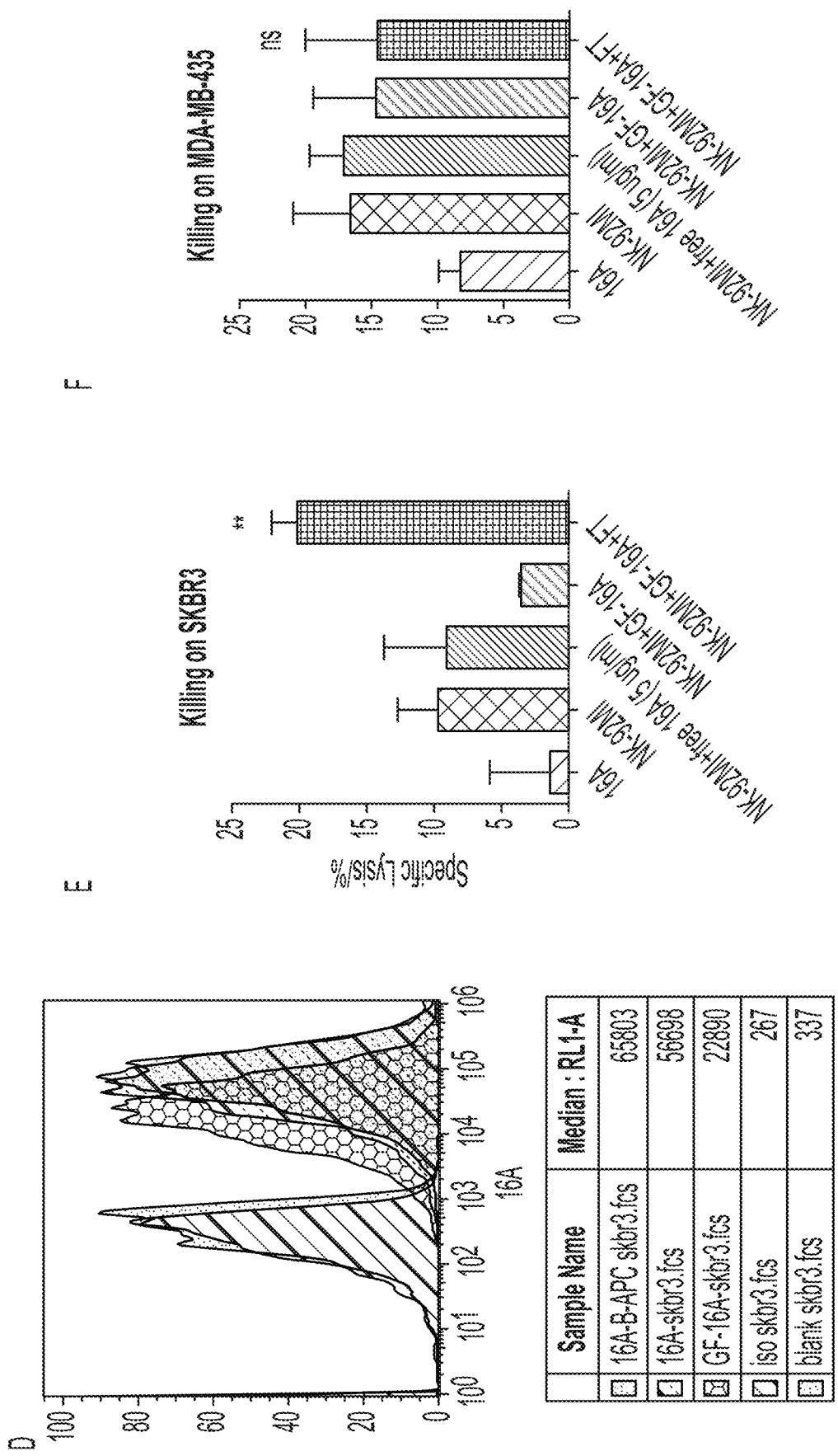

In one embodiment, as disclosed herein, the cancer-associated antigen MUC1, a large (>250 kDa) heavily glycosylated type 1 transmembrane protein, is overexpressed and modified by tumor cells in over half of all cancer cases. The 16A antibody (mouse) reacts with human MUC1. In one embodiment, 16A-NK-92MI conjugates were constructed through the one-pot fucosylation method as disclosed herein. 16A was conjugated to NK-92MI cells only when treated with GF-16A and FT, which is also GF-16A concentration dependent (FIGS. 62A and 62B). Breast cancer cell line SKBR3 has more MUC-1 antigens on cell surface than MDA-MB-435 (FIGS. 62C and 62D). NK-92MI cells modified with 16A induced the lysis of SKBR3 cells more effectively than unmodified NK-92MI cells (FIG. 62E). Neither treated with GF-16A without FT nor co-treatment with excess free 16A (5 μg/ml) could enhance the killing activity of NK-92MI on SKBR3 cells, indicating that covalent conjugation of Herceptin to the surface of NK-92MI cells is required (FIG. 62E). By contrast, there are no enhanced killing effects of 16A-NK-92MI conjugates on MDA-MB-435 cells since its MUC1 expression is low. In all killing experiments, NK-92MI cells were treated with 0.2 mg/ml GF-16A. Cancer cells were mixed with NK-92MI cells or its conjugates for 4 hours in the ratio of 1/2. This experiment demonstrated the ACC strategy for enhanced killing activity of NK-92 MI cells could be extended to other antigens beyond HER2.

Example 47

Figure 63:
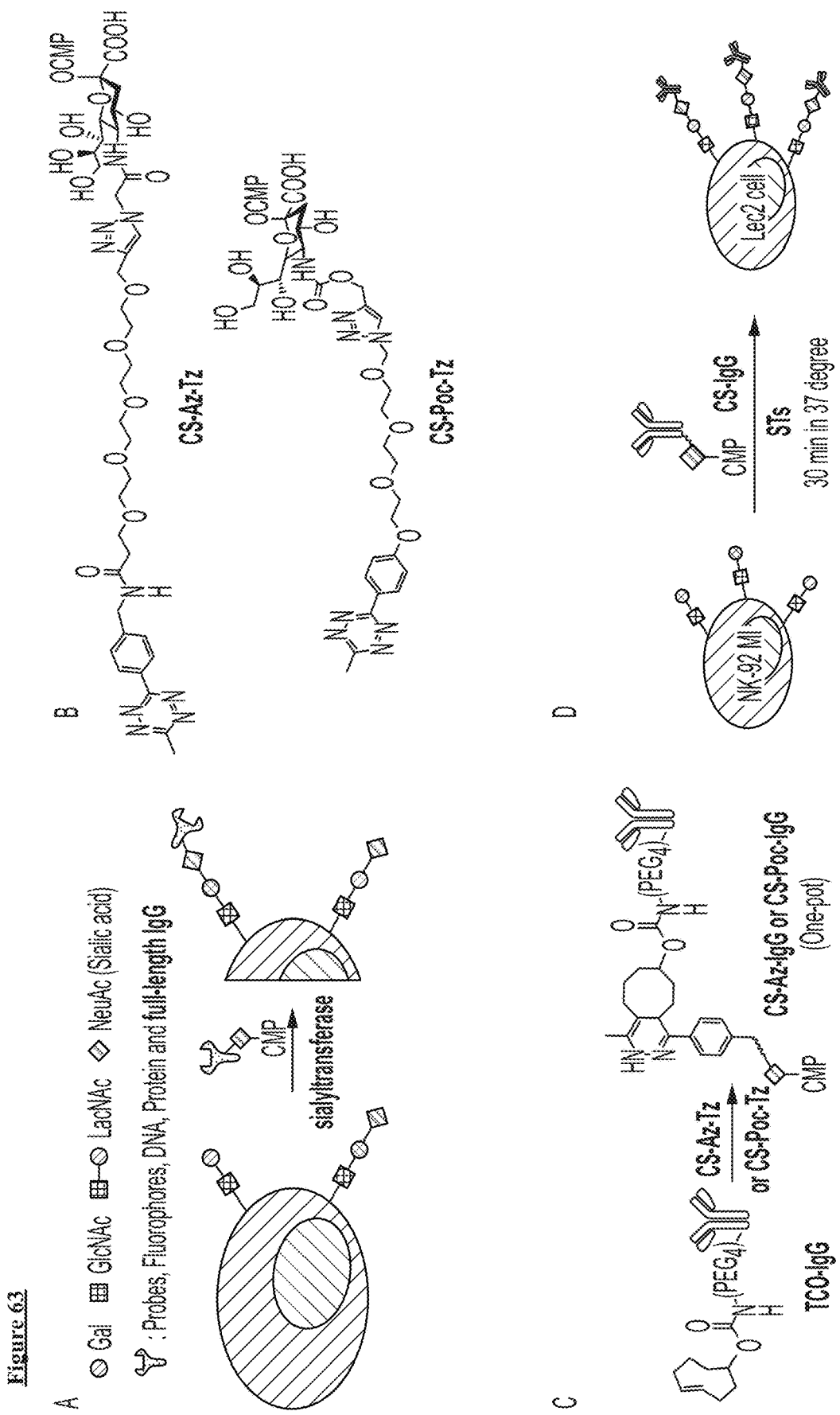
FIG. 63 depicts, in accordance with embodiments herein, enzymatic bio-macromolecule transfer using a sialylation strategy. (A), Sialyltransferase enables enzymatic transferring a variety of functional molecules to the surfaces of cells in one step. (B), Chemical structures of CMP-sialic acid-azide-tetrazine (CS-Az-Tz) and CMP-sialic acid-propargyl carbamate-tetrazine (CS-Poc-Tz). (C), Schematic representation of the synthesis of a CMP-Sialic acid conjugated IgG (CS-IgG). (D), Workflow of the ST-catalyzed transfer of CS-IgG to the surface of NK-92MI cells. (Three different sialyltransferases were tested here). (E), Flow cytometry analysis of NK-92MI cells treated with enzyme STs, substrates CS-Az-mIgG, or both. (F), Flow cytometry analysis of NK-92MI cells treated with enzyme STs, substrates CS-Poc-mIgG, or both.
Figure 63:
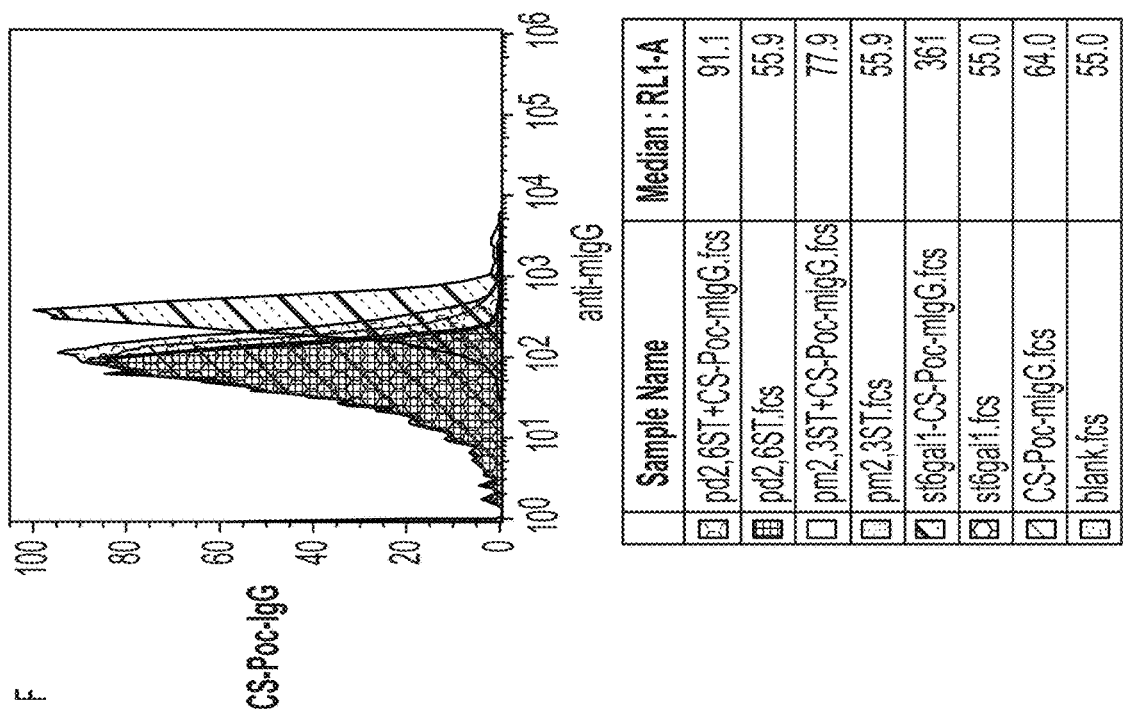
Figure 63:
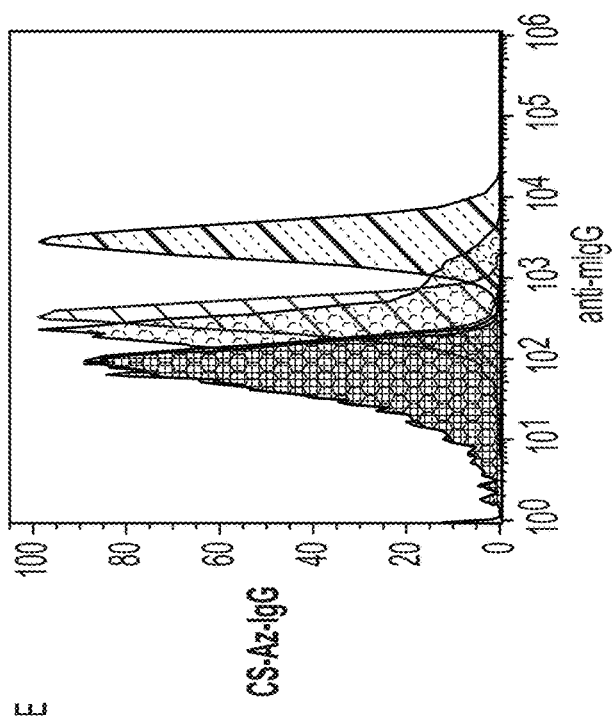

In one embodiment, the enzymatic biomacromolecules transfer as disclosed herein was extended from fucosylation to sialylation (FIG. 63A). Several sialyltransferases have been demonstrated by other groups that could transfer CMP-sialic acid derivatives to cell surface. However, CMP-sialic acid conjugated to proteins, like whole IgG molecules, are not in the previous substrate scopes of these enzymes. We first synthesized CMP-sialic acid-azide-tetrazine (CS-Az-Tz) and CMP-sialic acid-propargyl carbamate-tetrazine (CS-Poc-Tz) using one-pot click chemistry (FIG. 63B). Then, mouse IgG2a antibodies bearing TCO moieties were reacted with CS-Az-Tz or CS-Poc-Tz via the inverse electron-demand Diels-Alder reaction (IEDDA) to generate CMP-Sialic acid-conjugated IgG molecules (CS-IgG) (FIG. 63C). The one-pot product of CMP-Sialic acid conjugated mouse IgG (CS-mIgG) was then incubated with NK-92 MI cells that express abundant terminal LacNAc units in the presence of sialyltransferases (STs) (FIG. 63D). We tested three STs, including recombinant ST6Gal1, *Pasteurella mul-* tocida α(2,3) sialyltransferase M144D mutant (Pm2,3 ST-M144D), *Photobacterium damsel* α(2,6) sialyltransferase (Pd2,6ST). According to the results, all of these three enzymes could transfer CS-mIgG to cell surface (FIGS. 63E and 63F). In general, CS-Az-IgG is a more favorable substrate of these STs than CS-Poc-IgG. ST6Gal1 is the most efficient ST in these three enzymes (FIGS. 63E and 63F). Taken together, ST6Gal1 and CS-Az-IgG is the best pair to transfer IgG to cell surface through sialylation (FIG. 63E). This example demonstrates cell surface engineering through glycan to install biomacromolecules could also be achieved using sialyltranferases. All the applications in this disclosure using FucT would be similarly achieved through ST.

Example 48

In one embodiment, the present disclosure provides a one-step enzymatic ACC construction method through cell surface glycoengineering on LacNAc, which is fast and easy to use. This method is also cost effective due to the one-pot synthesis protocol of GDP-Fuc derivatives, as disclosed herein. This method is demonstrated in at least three different immune cells including primary cells and cell line, which shows its general applicability. Moreover, reagents of FucT and GDP-Fuc modified biomolecules (e.g. GF-IgG) used in this method are stable at 4° C. for more than one month. In one embodiment, this method would be widely used in cell surface engineering due to these attractive properties. In one embodiment, enzymatic engineering cell surface with whole IgG molecules in one step is a breakthrough because it shows more possibilities of non-genetic cell surface engineering using biomacromolecules (e.g. enzymes, proteins, virus and even cells), especially in therapeutic applications.

Although mAbs conjugated on cell surface would be diluted because of proliferations and internalizations (half decay time: 8-24 h in experiments), these transient modifications could have a lot of applications and serve as complements to the permanent genetic engineering approach. Other advantages, such as multiple mAbs installations at one time, making the instant enzymatic method more appealing in many cases than genetic engineering. In one embodiment, the inventors have applied the new methods disclosed herein to easily construct three ACCs, which have potentials to enhance ACT in three different stages: homing, targeting and signaling. Among these, NK-92MI-Herceptin conjugates stand out since it has been demonstrated in killing HER2+ cancer cells both ex vivo and in vivo. As NK-92MI cells are in clinical trials and Herceptin is a commercial drug, the NK-92MI-Herceptin conjugates disclosed herein would be easier in clinical translation. Moreover, NK-92MI cells could be easily conjugated with other therapeutic mAbs via this method, which may find broad applications in cancer therapy. In one embodiment, growing mAbs and cell-based therapies could be easily combined to get synergistic effect using the methods disclosed herein.

Example 49

Materials and Reagents:

All chemical reagents and solvents were obtained from Sigma-Aldrich and used without further purification unless otherwise noted. All cell culture materials are listed in cell culture methods. ImmunoCult human CD3/CD28 T cell activator was purchased from STEMCELL Technologies, Inc. Recombinant mouse IFN-γ, recombinant mouse PD-L1-human Fc Chimera (PD-L1-hFc), CFSE cell division tracker kit, APC Streptavidin, anti-mouse CD3 (17A2)-FITC, anti-mouse CD8 (53-6.7)-PE, anti-mouse CD45.1 (A20)-Pacific blue, anti-mouse Thy1.1 (OX7)-Alexa Fluor 700, anti-mouse IgG (Poly4060)-APC, anti-human Fc (HP6017)-APC, anti-rat IgG (Poly4050)-APC, anti-His Tag (J095G46)-PE, anti-human CD3 (HIT3a)-APC, anti-human CD45 (HI30)-FITC, anti-human CD4 (RPA-T4)-PE/Cy7, anti-human CD8 (SK1)-Pacific Blue, anti-human CD25 (M-A251)-PerCP/Cy5.5, anti-human CD44 (BJ18)-FITC, anti-human CD45RO (UCHL1)-Alexa Fluor 700, anti-human CD62L (DREG-56)-PE and human Fc Receptor blocking solution were purchased from Biolegend. Bulky monoclonal antibodies including anti-human E-selectin (α-hE-Sel, CL2), isotype mouse IgG2a (C1.18.4), anti-mouse PD-L1 (α-PD-L1, 10F.9G2), isotype rat IgG2b (LTF-2) and anti-human EGFR (528) were purchased from Bio X Cell. Therapeutic Herceptin were from Genentech. The control human IgG was obtained from Athens Research and Technology. Recombinant human E-Selectin/CD62E Fc chimera protein (hE-Selectin-hFc) and recombinant human TNF-α protein were purchased from R&D systems, Inc. Recombinant human HER2/ErbB2 Protein with His Tag (HER2-His) was purchased from Sino Biological, Inc. Click reagents including biotin-PEG3-azide (AZ-104, MW: 444.5), methyltetrazine-PEG4-azide (1014, MW: 389.40), methyltetrazine-PEG4-alkyne (1013-old, MW: 487.5, a discontinued product in their website), TCO-PEG4-NHS Ester (A137, MW: 514.6) and Cy5-TCO (1089, MW: 959.20) were purchased from Click Chemistry Tools LLC. Cy3-Azide (MW: 712.8) is a gift from Prof. Xing Chen's lab (PKU, China). (5OctdU)-5'-CAGTCAGTCAGTCAGTCAGT-3'(6-FAM) was ordered from Integrated DNA Technologies, Inc. D-Luciferin (monosodium salt), TNF-α mouse ELISA kit, IFN-γ mouse ELISA kit, Granzyme B human ELISA kit, DiD' solid, Hoechst 33342, DAPI, Alexa Fluor 647 NHS Ester, cell tracker green (CMFDA) and orange (CMTMR) were purchased from Thermo Fisher Scientific. CytoSelect™ Leukocyte Transmigration Assay kit and 5×RIPA buffer kit were purchased from Cell Biolabs, Inc. CytoTox 96® non-radioactive cytotoxicity assay and Bright-Glo™ luciferase assay system were purchased from Promega Corporation. Inorganic pyrophosphatase, FKP and FucT were expressed in endotoxin free bacteria (ClearColi® BL21-DE3, Lucigen) and purified as previously reported. Pure GDP-Fuc, GF-Al and BTTP were synthesized as previously described.

Equipments:

All of the flow cytometry analyses were performed on an Attune NxT Flow Cytometer. Images of protein gels including coomassie SDS-PAGE gel and western blotting membrane were taken on ChemiDoc XRS+ (Bio-Rad). Absorbance, fluorescence intensity and luminescence were monitored in a Multi-Mode Microplate Reader (Synergy™ H4, Bio-Tek). Confocal images were taken on a Nikon spinning disk confocal microscope (TE2000). Fluorescent and phase contrast microscope images were taken on an All-In One fluorescence microscope (Keyence, BZ-X700). Bioluminescence imaging of live mice were acquired using an IVIS Spectrum system.

Cells:

Cell lines are all from ATCC unless otherwise specified. CHO cell lines (WT, Lec2 and Lec8, from Prof. Pamela Stanley lab) were grown as monolayer in alpha-Minimum Essential medium (a-MEM) (GIBCO) supplemented with 10% fetal bovine serum (FBS) (Omega Scientific, Inc). HUVEC cell line was cultured in RPMI 1640 (GlutaMAX, GIBCO) with 20% heat-inactivated FBS (Omega Scientific, Inc), 40 µg/mL endothelial cell growth supplement (Corning), 100 µg/mL heparin (Sigma-Aldrich), 50 µM β-ME (GIBCO), and 10 mM HEPES (GIBCO). HUVEC culture dish was pre-coated with 0.1% gelatin solution (ATCC) at 4° C. overnight. NK-92MI cell line was grown in MyeloCult™ H5100 (STEMCELL Technologies, Inc). Cancer cell lines including BT474, SKBR3, MDA-MB-435 (HER2+ and HER2−), MDA-MB-468, SKOV3 and mouse B16-OVA (from Prof. Gregoire Lauvau lab) are all grown in grown in DMEM (Dulbecco's modified Eagle's medium, GlutaMAX, GIBCO) supplemented with 10% FBS. Human blood samples were collected from healthy donors under the TSRI Normal Blood Donor Services program (#IRB 15-6710). Peripheral blood mononuclear cells (PBMCs) were obtained by Ficoll (Ficoll-Paque Plus, GE) density centrifugation. PBMC, activated human T cells and mouse T cells were all cultured in RPMI 1640 (GlutaMAX) with 10% heat-inactivated FBS, 1 mM sodium pyruvate, 50 µM β-ME, 10 mM HEPES and 1×MEM NEAA (GIBCO) (referred as T cell culture media later). Cytokines in T cell culture media were added as indicated (rhIL2, rhIL7 and rhIL15 are all from NIH program). All cells cultures were incubated at 37° C. under 5% $CO_2$.

Mice:

All mice were bred or housed under specific pathogen free (SPF) conditions. All animal experiments were approved by TSRI Animal Care and Use Committee. OT-1 mice are purchased from Taconic Biosciences. CD 45.1 and Thy 1.1 mice from C57BL/6J (B6) genetic background were purchased from the Jackson Laboratory. Strains of OT-1+/−/CD 45.1+/− and OT-1+/−/Thy 1.1+/− were generated by cross breeding. Six female B6 background P14 mice were gifts from Prof. John Teijaro lab. 176 female NSG mice are gifts from Prof. Philippe A. Gallay lab. Both male and female mice of 8-12 weeks of age were used for most experiments.

One Pot Protocol for Producing GDP-Fuc Derivatives:

Reactions were typically carried out in a 15 mL corning tube with 5 mL 100 mM HEPES buffer (pH 7.5) containing L-fucose analogues (final concentration, 10 mM), ATP (10 mM), GTP (10 mM), $MgSO_4$ (10 mM), KCl (50 mM), inorganic pyrophosphatase (90 units, ~0.17 g/L, endotoxin free), and FKP (9 units, ~0.6 g/L, endotoxin free). The reaction mixture was incubated at 37° C. for 5-6 h with shaking (225 rpm). After the reaction finished (monitored by TLC analysis), enzymes were precipitated by adding 5 mL cold EtOH into the crude product. After the precipitates were removed through centrifuge (8000×g, 5 min), the crude products (containing ~10 mM GDP-Fuc analogues) could be directly used. For GF-Al and GF-Az, further modification could be achieved through CuACC reaction. Crude GF-Al/GF-Az sample (5 mM, in HEPES buffer) were reacted with azide/alkyne probes (5 mM) in the presence of Cu/BTTP (1/2, 500 µM) and sodium ascorbate (2 mM) at 30° C. for 6 h (For Tz substrates, add one volume of MeOH in reaction mixture). After reaction finished (monitored by TLC and LC-MS analysis), BCS (bathocuproine sulphonate, 2 mM) were added to quench the reaction. Following this protocol, one-pot products of GF-Al-Biotin, GF-Al-Cy3, GF-Al-Tz and GF-Az-Tz were made. Their structures are shown in FIG. 45.

General Procedure for Enzymatic Transfer of GDP-Fuc Derivatives to Cell Surface:

Live cells (10~20 million) were resuspended in 100 µL HBSS buffer containing 20 mM $MgSO_4$, 3 mM HEPES, 0.5% FBS, 100 µM GDP-Fuc derivatives and 30 mU FucT (~0.02 mg/mL). After the incubation for 20 minutes (works from on ice to 37° C.), the cells were washed with PBS and ready for further application or analysis. For biotin detection, the cells were stained with APC Streptavidin after reaction. For Tz detection, the cells were reacted with 20 µM TCO-Cy5 on ice for 30 minutes and washed three times.

Preparation of GDP-Fuc Modified Antibodies:

All of the antibodies (full-length IgG, MW: ~150 KDa) for conjugation were first desalted into PBS and concentrated to a 6 mg/mL solution. TCO group was first introduced onto antibodies according to the standard labeling protocol of TCO-PEG4-NHS ester and a previous report about its application on IgG labeling. Briefly, fresh 10 mM stock of TCO-PEG4-NHS reagent in DMSO was prepared, and added it to the IgG sample (final concentration 6 mg/mL) at a final concentration of 0.5 mM. The reactions were incubated at room temperature for 30 minutes and quenched by adding Tris buffer (pH 8.0) to a final concentration of 50 mM Tris. The quenched reaction mixtures were incubated at room temperature for 5 minutes and then desalted into PBS using desalting column (GE). The concentrations of desalted TCO-IgGs were around 4.5 mg/mL (~4 TCO per IgG). After that, ~10 mM one-pot products of GF-Az-Tz were added to TCO-IgGs with a final concentration at 0.15 mM (5 eq of IgG). After 30 minutes of incubation at room temperature, these one-pot GF-IgG products were ready to use and could be kept at 4° C. for up to 2 months. For Alexa Fluor 647 labeled GF-rIgG used in confocal imaging, the rIgG molecule was first labeled with Alexa Fluor 647 probes following the manual and then subjected to this protocol. According to the reference, these mAbs modified by NHS ester and subsequent IEDDA reaction have similar antigen binding affinity as unmodified mAbs.

General Procedure for Enzymatic Transfer of GF-IgG to Cell Surface:

Live cells (10~20 million) were resuspended in 100 µL HBSS buffer containing 20 mM $MgSO_4$, 3 mM HEPES, 0.5% FBS, 0.1 mg/mL one-pot GF-IgG (different concentrations were used in titration) and 60 mU FucT (~0.04 mg/mL). After the incubation for 20 minutes (works from on ice to 37° C.), the cells were washed with PBS and ready for further application or analysis. For labeling detection, IgG labeled cells were stained with DAPI and fluorescent secondary antibody against labeled IgG (1/50-1/200 dilution) on ice for 30 minutes. For confocal imaging, Lec2 cells plated on a chamber cover glass (Nunc) were treated with 0.1 mg/mL Alexa Fluor 647 labeled GF-rIgG in the same fucosylation condition as described above. After conjugation, live cells were washed and stained with Hoechst 33342 for 30 minutes on ice and then washed for imaging. To confirm the binding activity of cell surface conjugated antibodies, labeled cells were allowed to bind with 10 µg/mL antigen (hE-sel-hFc, PD-L1-hFc or HER2-His) in binding buffer (HBSS with 5 mM HEPES, 2 mM $CaCl_2$, and 1 mM $MgCl_2$) on ice for 30 minutes. After binding, cells were washed twice with PBS and stained with DAPI and APC-anti-human Fc (1/50 dilution) or PE-anti His (1/100 dilution).

Primary Human T Cells Preparation and IgG Labeling on their Surface:

Fresh PBMCs were freshly prepared as described above. 4 million per mL PBMCs were cultured in T cell culture media with 15 ng/mL rhIL2 and activated with human CD3/CD28 T cell activator for two days. After that, activated human T cells were kept under $4*10^6$ cells/mL in T cell culture media (fresh media with cytokine were added every two days). Phenotypes were characterized after two weeks expansion (>95% are human T cells). LacNAc levels on CD4+ and CD8+ T cells were tracked through fucosylation with GF-biotin on day 0 (naïve T cells), day 2, day 4, day 7, day 11 and day 13. Activated human T cells were labeled with α-hE-Sel and mIgG control using the general procedure for enzymatic GF-IgG transfer. After that, the labeling detection and the antigen (hE-sel-hFc) binding were both confirmed. Labeled human T cells were then cultured in T cell culture media at a start cell density of $0.5*10^6$ cells/mL. The decay of cell surface mIgG molecule was tracked in 24 hours after labeling (anti-mouse IgG staining). The cell proliferation rate of labeled T cells was compared with unlabeled human T cells in three days (live cell counting).

Flow Chamber Assay on E-Selectin Coating Slides:

Sterile cover glass slides (catalog #12-545M, Fisher Scientific) were coated with recombinant human E-selectin-Fc (2 μg/mL) for 2 h at room temperature, followed by blocking with casein for at least 30 min. Ibidi sticky-Slides I 0.1 Luer (H: 150 μm, W: 5 mm, ibidi) were mounted on the coated glass slides and connected with inlet and outlet tubing. Two groups of human T cells were mixed (unmodified human T cells stained with cell tracker green and mIgG or α-hE-Sel conjugated human T cells stained with cell tracker orange) and then perfused through the inlet tube at a concentration of $2\times10^6$ cells/mL. The outlet tube was connected to a syringe pump (Harvard Apparatus). Wall shear stress was determined as described before (Abadier et al., 2015, Coisne et al., 2013). First the cells were allowed to settle down for 1 min at 1 dyn/cm$^2$ for accumulation in the field of view (FOV) and started imaging acquisition. The shear stress was then enhanced to 10 dyn/cm$^2$ for 3 min. To study the behavior of T cells, image acquisition was performed at 10× magnification with an inverted Zeiss Axiovert 200M (Zeiss, Feldbach, Switzerland). The numbers of firm binding cells (unmoved during the 2 min acquisition after shear increase at 10 dyn/cm$^2$) was quantified by ImageJ software (National Institute of Health, Bethesda, Md.).

Analysis of Human T Cells Binding on HUVEC Surface:

2,000 HUVEC were seeded in each well of a gelatin-coated 96-well plate and grown to confluence. HUVEC were either untreated or stimulated with 200 U/mL TNF-α for 4 h. Human T cells stained with CFSE were labeled with mIgG or α-hE-Sel using general GF-IgG transfer protocol. Labeled cells were washed with PBS and resuspended to $10^6$ cells/mL in serum free RPMI 1640. After media in HUVEC was removed, 100 μl CFSE stained human T cells ($10^6$ cells/mL) of three groups (unlabeled, mIgG and α-hE-Sel) were added to untreated or treated with TNF-α. The cells were allowed to attach for 20 minutes at 37° C. Unbound human T cells were removed and each well was gently washed with warm RPMI twice. Attached CFSE stained human T cells were lysed using RIPA buffer. The attached T cell numbers in each well were quantified through the CFSE fluorescence signal (ex 492 nm/em 517 nm) using a plate reader. For imaging analysis, HUVEC were stained prior to T cells binding (5 μg/mL DiD and 2 μg/mL Hoechst 33342 in culture media, 37° C. for 20 minutes). HUVEC were washed with warm PBS three times before adding CFSE stained T cells. After binding, attached cells were replenished in live cell imaging solution and imaged with a fluorescence microscope.

Transmigration Assay of Human T Cells:

Following the provided protocol, Leukocyte Transmigration Assay Kit was employed to perform transwell assay. In brief, 50,000 HUVEC cells in 300 μL HUVEC growth medium were added to the insert of a 24-well plate with 500 μL growth medium in bottom. Cells were grown to confluence and treated with 200 U/mL TNF-α for 4 h. $10^6$/mL human T cells were stained with LeukoTracker in serum free medium (RPMI with 0.5% BSA, 2 mM CaCl$_2$, and 2 mM MgCl$_2$) for 1 h at 37° C. and washed three times with serum free medium. Stained T cells were labeled with mIgG or α-hE-Sel and resuspended at $10^6$ cells/mL in serum free medium. Transwell inserts were moved to new wells containing 500 μL of fresh T cell medium in the bottom, and medium in the insert was replaced with 300 μL of T cells suspension. After incubation at 37° C. for 4 hours, migrated T cells in the bottom were lysed and the resulting fluorescence signal was measured using a plate reader (ex 480 nm/em 520 nm).

IgG Labeling on NK-92M1 Cells:

NK-92MI cells or irradiated NK-92MI cells (6 Gy) were labeled with Herceptin or control human IgG according to the general protocol. After labeling, the labeling detection and the antigen (HER2-His) binding were both confirmed. NK-92MI cells with or without IgG conjugation were then cultured in T cell media with a start cell density of $0.5*10^6$ cells/mL. The decay of ell surface conjugated Herceptin were tracked at day 0, day 1 and day 2 (anti-human Fc staining). The proliferation rates of cells were tracked at day 0, day 1, day 2 and day 3 (DAPI staining and FACS counting). For dual antibodies labeling, NK-92MI cells were conjugated with GF-α-EGFR first and then conjugated with GF-Herceptin after washing.

Flow and Imaging Analysis of Binding Between NK-92MI and BT474:

For flow cytometry analysis, NK-92MI cells were stained with CFSE and then labeled with Herceptin or not according to the general protocol. BT474 cells were stained with DiD first and then mixed with Herceptin labeled or unlabeled NK-92MI cells at the ratio of 1:1. Two hours later, the cells mixture was analyzed by flow cytometry. For fluorescence imaging, BT474 cells were stained with CFSE and cultured in glass bottom petri dish overnight. NK-92MI cells were then stained with cell tracker orange and then labeled with Herceptin or not. NK-92MI cells were added to BT474 culture at ratio of 1:1. Two hours later, the co-cultured cells were imaged by fluorescent microscope before and after PBS wash.

Analysis of NK-92MI Cells-Mediated Cytotoxicity Against HER2+ Cancer Cells:

Labeled or unlabeled NK-92MI cells were co-cultured with different type of cancer cells at indicated effector/target ratios for 4 hours in a 96-well plate. In most of the experiments, the effector/target ratio is 5/1. Free Herceptin were added at a final concentration of 5 μg/mL if indicated. Specific cancer cell lysis was detected by LDH secretion in supernatant (CytoTox 96, Promega). Set-up of control groups and calculations of specific lysis were according to manufactory's instruction. Supernatant of each group were also collected and subjected to granzyme B ELISA kit for quantification.

Mice Model of NK-92MI Mediated Killing of HER2+ Cancer:

Thirty female NSG mice (6-8 weeks old) were inoculated with $5*10^5$ MDA-MB-435 HER2+/F-luc cells through tail vein injection. One day later, mice were randomly divided into three groups (10 mice per group). Each group were treated with HBSS, NK-92MI or Herceptin labeled NK-92MI cells through tail vein injection ($3*10^6$ NK cells each mice). Six days after tumor challenge, mice were injected with 200 μL D-luciferin (15 mg/mL) through i.p. injection. Twelve minutes later, the bioluminescence signal in mice were analyzed by PerkinElmer IVIS system. The total photons indicating the tumor mice were quantified by IVIS software.

Primary OT-1 CD8+ T Cells Preparation and IgG Labeling on their Surface:

Splenocytes from OT-1 mice were activated by 1 nM OVA peptides in T cell media for two days. After that, activated cells were in vitro expanded in fresh T cell media with 15 ng/mL rhIL2 or 10 ng/mL rhIL7 and 20 ng/mL rhIL15 for several days (kept under $8*10^6$ cells/mL, fresh media with cytokine were added every two days). Phenotypes were characterized (>95% are OT-1 CD8+ T cells). LacNAc levels on OT-1 T cells (cultured with two different cytokines) were tracked through fucosylation with GF-biotin on day 0 (naïve T cells), day 2, day 4, day 7, day 9, day 11 and day 13. Activated OT-1 T cells were labeled with α-PD-L1 and mIgG control using the general procedure for enzymatic GF-IgG transfer. After that, the labeling detection and the antigen (PD-L1-hFc) binding were both confirmed. Labeled OT-1 T cells were then cultured in T cell culture media at a start cell density of $0.5*10^6$ cells/mL. The decay of cell surface α-PD-L1 molecule was tracked in 24 hours after labeling (anti-rat IgG staining).

OT-1 T Cells Re-Stimulation Using OVA Pulsed Splenocytes:

Splenocytes from B6 WT mice were pulsed with SIINFEKL (OVA) peptide (1 µg/mL, in T cell media) for 2 h. After that, cells were washed three times before use. OT-1 T cells with CD45.1 congenic marker were stained with CFSE and then labeled with rIgG. $10^5$ OT-1 T cells (labeled or unlabeled) were mixed with $10^6$ OVA-pulsed splenocytes in 500 µL T cell media. Control groups were also set up without splenocytes. The cell mixtures were cultured for 3 days. After that, cells were stained with APC anti-CD45.1 and DAPI. The CFSE dilution signals were analyzed on live CD45.1 positive cells.

Analysis of OT-1 CD8+ T Cells Mediated Cytotoxicity Against B16-OVA:

B16-OVA cells (stably transduced with firefly luciferase) were seeded in 96-well plate and treated with 10 ng/mL IFN-γ overnight (B16-OVA cells were all treated with IFN-γ to induce high expression level of PD-1 in this work). Labeled or unlabeled OT-1 cells were co-cultured with B16-OVA cancer cells at indicated effector/target ratios for 20 hours in a 96-well plate. In most of the experiments, the effector/target ratio is 5/1. Phenotype of T cell clusters was imaged before cell number quantification. B16-OVA cell numbers were quantified through the luciferase activity according to the reference. The detection reagent was directly added to medium in each well according to the manufactory's manual (Bright-Glo, Promega). For cytokine secretion quantification, cells were cultured for 9 hours and supernatant were collected and subjected to TNF-α and IFN-γ ELISA kit. For OT-1 T cells proliferation in killing B16-OVA, OT-1 cells were stained by CFSE before IgG labeling. Modified cells were mixed with B16-OVA cells in the effector/target ratio of 2/1. After 72 hours, the cell mixtures were stained with APC-anti CD8 and DAPI. CFSE dilution signal was analyzed on CD8+ cells.

Competition Assay for Analyzing OT-1 T Cells In Vivo Proliferation Against B16 Tumor:

Splenocytes from OT-1+/−CD45.1+/− and OT-1+/−Thy1.1+/− mice were activated by 1 nM OVA peptides and in vitro expanded by adding 10 ng/mL IL7 and 20 ng/mL IL15 for 4 days. OT-1 T cells with different congenic markers were treated with or without GF-α-PD-L1 and FT. CD45.1+OT-1 T cells labeled with α-PD-L1 were mixed with Thy1.1+OT-1 T cells at ratio of 1:1. Similarly, unlabeled CD45.1+OT-1 T cells were mixed with Thy1.1+OT-1 T cells labeled with α-PD-L1 at ratio of 1:1. The ratio of two different populations as well as successful labeling of α-PD-L1 was analyzed by flow cytometry. The mixed T cells ($10*10^6$) were injected through tail vein into B16-OVA melanoma tumor (tumor size: ~5 mm*5 mm) bearing mice, which were inoculated with $10^6$ B16-OVA cells through subcutaneous injection on the right flank 10 days ago. After 48 hours of T cells injection, blood, draining lymph node (dLN) and tumor tissue of recipient mice were collected. Single cells from each tissue were acquired, stained with anti-CD3, anti-CD8, anti-Thy1.1, anti-CD45.1 fluorescent antibody and analyzed by flow cytometry. The ratio of Thy1.1+/−OT1 T cell and CD45.1+/−OT-1 T cells in these tissues were calculated.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps, some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. An engineered cell, comprising:
an antibody covalently bound to a N-acetylglucosamine (GlcNAc) cell surface glycan through a GDP-fucose via a $\alpha$-1,3 linkage.

2. The engineered cell of claim 1, wherein the engineered cell is a T-cell or a natural killer (NK) cell, or a Dendritic Cell (DC).

3. The engineered cell of claim 1, wherein the antibody is a single chain variable fragment (scFv), fragment antigen binding (Fab) fragment, or a full length antibody.

4. The engineered cell of claim 1, wherein the antibody is an immunoglobulin G (IgG) antibody.

5. The engineered cell of claim 4, wherein the IgG is a full length IgG.

6. The engineered cell of claim 1, wherein the engineered cell is a chimeric antigen receptor (CAR)-T cell.

7. The engineered cell of claim 6, wherein the CAR-T cell comprises a genetically modified T-cell with the cell surface GlcNAc covalently bound to a GDP-Fucose bearing a new motif.

* * * * *